US008563523B2

(12) United States Patent
Boons

(10) Patent No.: US 8,563,523 B2
(45) Date of Patent: Oct. 22, 2013

(54) SYNTHETIC LIPID A DERIVATIVE

(75) Inventor: Geert-Jan Boons, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 391 days.

(21) Appl. No.: 12/676,253

(22) PCT Filed: Sep. 5, 2008

(86) PCT No.: PCT/US2008/010394
§ 371 (c)(1),
(2), (4) Date: Apr. 19, 2010

(87) PCT Pub. No.: WO2009/035528
PCT Pub. Date: Mar. 19, 2009

(65) Prior Publication Data
US 2010/0221269 A1 Sep. 2, 2010
US 2011/0280893 A9 Nov. 17, 2011

Related U.S. Application Data

(60) Provisional application No. 60/967,876, filed on Sep. 7, 2007, provisional application No. 61/135,666, filed on Jul. 23, 2008.

(51) Int. Cl.
*A01N 43/04* (2006.01)
*A61K 31/70* (2006.01)
*C07H 17/02* (2006.01)
*C07H 15/06* (2006.01)
*C07C 59/147* (2006.01)
*C07C 59/185* (2006.01)

(52) U.S. Cl.
USPC ............ 514/25; 536/17.2; 536/18.2; 554/115

(58) Field of Classification Search
None
See application file for complete search history.

(56) References Cited

U.S. PATENT DOCUMENTS

| | | | |
|---|---|---|---|
| 4,673,574 A | 6/1987 | Anderson | |
| 4,761,283 A | 8/1988 | Anderson | |
| 4,885,256 A | 12/1989 | Alving et al. | |
| 4,902,506 A | 2/1990 | Anderson et al. | |
| 5,097,020 A | 3/1992 | Anderson et al. | |
| 5,360,897 A | 11/1994 | Anderson et al. | |
| 5,393,878 A | 2/1995 | Leumann | |
| 5,530,113 A * | 6/1996 | Christ et al. ............. | 536/123.13 |
| 6,635,261 B2 | 10/2003 | LaPosta et al. | |
| 6,953,850 B1 | 10/2005 | Dekany et al. | |
| 2002/0018808 A1 | 2/2002 | Alving et al. | |
| 2002/0025330 A1 | 2/2002 | LaPosta et al. | |

FOREIGN PATENT DOCUMENTS

| | | | |
|---|---|---|---|
| WO | WO 2009/035528 A2 | 3/2009 | |
| WO | WO 2009/035528 A3 | 3/2010 | |

OTHER PUBLICATIONS

Zhang et al., Journal of the American Chemical Society, vol. 129, No. 16, 2007, pp. 5200-5216.*
Schmidt et al., Angew. Chemie Int Ed. 27:1178-1180, 1998.*
Akira et al., "Toll-like receptors: critical proteins linking innate and acquired immunity," 2001*Nat. Immunol.* 2:675-680.
Alexander and Zahringer, "Chemical Structure of Lipid A—The Primary Immunomodulatory Center of Bacterial Lipopolysaccharides," 2002 *Trends Glycosci. Glycotechnol.* 14:69-86.
Beutler, "Innate immunity: an overview," 2004 *Mol. Immunol.* 40:845-859.
Boons, Geert-Jan, "Synthetic Oligosaccharides for Probing Infection and Innate Immunity," Grant Abstract, Grant No. R01GM061761. National Institute of General Medical Sciences, National Institutes of Health, project dates Jul. 1, 2000 to Jul. 31, 2015. Available online; retrieved on Apr. 24, 2012. Retrieved from the Internet: <http://projectreporter.nih.gov/project_info_description.cfm?aid=8108827&icde=12257443&ddparam=&ddvalue=&ddsub=&cr=1&csb=efault&cs=ASC>; 2 pgs.
Boons, Geert-Jan, "Modulation of Innate Immune Responses With Synthetic Lipid A Derivatives," Grant Abstract, Grant/Project No. 5P41RR005351-20, Sub-Project ID 7741. National Center for Research Resources/National Institutes of Health, project dates Feb. 1, 2009 to Jan. 31, 2010. Available online; retrieved on Apr. 24, 2012. Retrieved from the Internet: <http://projectreporter.nih.gov/project_info_description.cfm?aid=7957528&icde=12257592>; 1 pg.
Boons, Geert-Jan, "Modulation of Innate Immune Responses With Synthetic Lipid A Derivatives," Grant Abstract, Grant/Project No. 2P41RR005351-21, Sub-Project ID 8674. National Center for Research Resources/National Institutes of Health, project dates Apr. 10, 2010 to Jan. 31, 2011. Available online; retrieved on Apr. 24, 2012. Retrieved from the Internet: <http://projectreporter.nih.gov/project_info_description.cfm?aid=8168857&icde=12257592>; 1 pg.
Caroff et al., "Structural and functional analyses of bacterial lipopolysaccharides," Jul. 2002 *Microbes Infect.* 4:915-926.
Chatterjee et al., "A general model for selectivity in olefin cross metathesis," Sep. 17, 2003 *J. Am. Chem. Soc.*, 125:11360-11370.
Chow et al., "Toll-like receptor-4 mediates lipopolysaccharide-induced signal transduction," Apr. 16, 1999 *J. Biol. Chem.* 274:10689-10692.
Christ et al., "E5531, a pure endotoxin antagonist of high potency," Apr. 7, 1995 *Science*, 268:80-83.
Coats et al., "MD-2 mediates the ability of tetra-acylated and penta-acylated lipopolysaccharides to antagonize *Escherichia coli* lipopolysaccharide at the TLR4 signaling complex," Oct. 1, 2005 *J. Immunol.*, 175:4490-4498.
Crawford et al., "The role of 3' poly(A) tail metabolism in tumor necrosis factor-alpha regulation," Aug. 22, 1997 *J. Biol. Chem.*, 272:21120-21127.

(Continued)

*Primary Examiner* — Traviss C McIntosh, III
(74) *Attorney, Agent, or Firm* — Mueting Raasch & Gebhardt, P.A.

(57) ABSTRACT

The invention provides functionalized monosaccharides and disaccharides suitable for use in synthesizing a lipid A derivative, as well as methods for synthesizing and using a synthetic lipid A derivative.

4 Claims, 14 Drawing Sheets

(56) References Cited

OTHER PUBLICATIONS

Darveau et al., "*Porphyromonas gingivalis* lipopolysaccharide contains multiple Lipid A species that functionally interact with both toll-like receptors 2 and 4," Sep. 2004 *Infect. Immun.*, 72:5041-5051.

Dixon and Darveau, "Lipopolysaccharide heterogeneity: innate host responses to bacterial modification of lipid a structure," Jul. 2005 *J. Dent. Res.*, 84:584-595.

Erridge et al., "Lipopolysaccharides of *Bacteroides fragilis, Chlamydia trachomatis* and *Pseudomonas aeruginosa* signal via toll-like receptor 2," Aug. 2004 *J. Med. Microbiol.*, 53:735-740.

Fujimoto et al., "Synthesis and bioactivity of fluorescence- and biotin-labeled lipid A analogues for investigation of recognition mechanism in innate immunity," 2006 *Tetrahedron Lett.* 47(4):539-543.

Fujimoto et al., "Synthesis of immunoregulatory *Helicobacter pylori* lipopolysaccharide partial structures," 2007 *Tetrahedron Lett.* 48(37):6577-6581.

Galanos et al., "Synthetic and natural *Escherichia coli* free Lipid A express identical endotoxic activities," Apr. 1, 1985 *Eur. J. Biochem.* 148:1-5.

Gamian et al., "Structure of the L2 lipopolysaccharide core oligosaccharides of *Neisseria meningitidis*," Jan. 15, 1992 *J. Biol. Chem.* 267:922-925.

Girard et al., "Lipopolysaccharides from *Legionella* and *Rhizobium* stimulate mouse bone marrow granulocytes via Toll-like receptor 2," Jan. 15, 2003 *J. Cell Sci.* 116:293-302.

Golenbock et al., "Lipid A-like molecules that antagonize the effects of endotoxins on human monocytes," Oct. 15, 1991 *J. Biol. Chem.* 266:19490-19498.

Guo et al., "Regulation of lipid A modifications by *Salmonella typhimurium* virulence genes phoP-phoQ," Apr. 11, 1997 *Science* 276:250-253.

Hiramoto et al., "Stimulation of apolipoprotein E secretion in human hepatoma Hep G2 cells by a cyclic acylpeptide, N-4909," Sep. 1996 *J. Antibiot.* 49:949-952.

Kanegasaki et al., "Structure-activity relationship of lipid A: comparison of biological activities of natural and synthetic lipid A's with different fatty acid compositions," Apr. 1986 *J. Biochem.* 99:1203-1210.

Kawai et al., "Various kinds of lipoamino acids including a novel serine-containing lipid in an opportunistic pathogen *Flavobacterium*. Their structures and biological activities on erythrocytes," Jan. 15, 1988 *Eur. J. Biochem.* 171:73-80.

Kawasaki et al., "3-O-deacylation of lipid A by PagL, a PhoP/PhoQ-regulated deacylase of *Salmonella typhimurium*, modulates signaling through Toll-like receptor 4," May 7, 2004 *J. Biol. Chem.* 279:20044-20048. Available online on Mar. 10, 2004.

Kulshin et al., "Structural characterization of the Lipid A component of pathogenic *Neisseria meningitidis*," Mar. 1992 *J. Bacteriol.* 174:1793-1800.

Kumada et al., "Structural study on the free Lipid A isolated from lipopolysaccharide of *Porphyromonas gingivalis*," Apr. 1995 *J. Bacteriol.* 177:2098-2106.

Kusumoto et al., "Synthesis of endotoxic principle of bacterial lipopolysaccharide and its recognition by the innate immune systems of hosts," 2006 *Chemical Record* 6:333-343.

Lam et al., "Immunostimulatory, but not antiendotoxin, activity of lipid X is due to small amounts of contaminating N,O-acylated disaccharide-1-phosphate: in vitro and in vivo reevaluation of the biological activity of synthetic lipid X," Jul. 1991 *Infect. Immun.* 59:2351-2358.

Mijatovic et al., "Tumor necrosis factor-alpha mRNA remains unstable and hypoadenylated upon stimulation of macrophages by lipopolysaccharides," Oct. 2000 *Eur. J Biochem.* 267:6004-6011.

Muroi and Tanamoto, "The polysaccharide portion plays an indispensable role in *Salmonella* lipopolysaccharide-induced activation of NF-kappaB through human toll-like receptor 4," Nov. 2002 *Infect. Immun.* 70:6043-6047.

Nakahata et al., "The Preparation of Optically Pure 3-Hydroxyalkanoic Acid. The Enantioface-differentiating Hydrogenation of the C=O Double Bond with Modified Raney Nickel," 1982 *Bull. Chem. Soc. Jpn.* 55:2186-2189.

Ogawa et al., "Cell activation by *Porphyromonas gingivalis* Lipid A molecule through Toll-like receptor 4- and myeloid differentiation factor 88-dependent signaling pathway," Nov. 2002 *Int. Immunol.* 14:1325-1332.

Ogura et al., "The inflammasome: first line of the immune response to cell stress," Aug. 25, 2006 *Cell* 126:659-662.

Pasare and Medzhitov, "Toll-dependent control mechanisms of CD4 T cell activation," Nov. 2004 *Immunity* 21:733-741.

Que-Gewirth et al., "A methylated phosphate group and four amide-linked acyl chains in leptospira interrogans lipid A. The membrane anchor of an unusual lipopolysaccharide that activates TLR2," Jun. 11, 2004 *J. Biol. Chem.* 279:25420-25429. Available online on Mar. 24, 2004.

Raetz and Whitfield, "Lipopolysaccharide endotoxins," Jul. 2002 *Annu. Rev. Biochem.* 71:635-700. Available online on Nov. 9, 2001.

Reife et al., "*Porphyromonas gingivalis* lipopolysaccharide lipid A heterogeneity: differential activities of tetra- and penta-acylated lipid A structures on E-selectin expression and TLR4 recognition," May 2006 *Cell. Microbiol.* 8:857-868. Available online on Jan. 13, 2006.

Rice and Bernard, "Therapeutic intervention and targets for sepsis," 2005 *Annu. Rev. Med.* 56:225-248. Available online on Aug. 30, 2004.

Rose et al., "Agonistic and antagonistic activities of bacterially derived *Rhodobacter sphaeroides* lipid A: comparison with activities of synthetic material of the proposed structure and analogs," Mar. 1995 *Infect. Immun.* 63:833-839.

Saitoh et al., "Lipid A antagonist, lipid IVa, is distinct from lipid A in interaction with Toll-like receptor 4 (TLR4)-MD-2 and ligand-induced TLR4 oligomerization," Jul. 2004 *Internatl. Immunol.* 16:961-969. Available online on Jun. 7, 2004.

Sawada et al., "Toll-like receptor 4-dependent recognition of structurally different forms of chemically synthesized lipid As of *Porphyronionas gingivalis*," Jun. 2007 *Clin. Exp. Immunol.* 148:529-536. Available online on Mar. 5, 2007.

Schmidt et al., "Anomeric O-alkylation. 6. Simple synthesis of KDO-α-glycosides by anomer-selective O-alkylation," 1988 *Angew. Chemie* 100(9):1234-1236.

Swartz et al., "Antibodies to cholesterol," Mar. 1988 *Proc. Nat. Acad. Sci. USA* 85:1902-1906.

Tsukamoto et al., "Synthesis of novel 25-substituted Milbemycin A4 derivatives and their acaricidal activity against *Tetranychus urticae*," 1997 *Biosc. Biotech. Biochem.* 61:1650-1657.

van Amersfoort et al., "Receptors, mediators, and mechanisms involved in bacterial sepsis and septic shock," Jul. 2003 *J. Clin. Microbiol. Rev.* 16:379.

van der Ley et al., "Modification of lipid A biosynthesis in *Neisseria meningitidis* 1pxL mutants: influence on lipopolysaccharide structure, toxicity, and adjuvant activity," Oct. 2001 *Infect. Immun.* 69:5981-5990.

van Deuren et al., "Update on meningococcal disease with emphasis on pathogenesis and clinical management," Jan. 2000 *Clin. Microbiol. Rev.* 13:144-166.

Wolfert et al., "The origin of the synergistic effect of muramyl dipeptide with endotoxin and peptidoglycan," Oct. 18, 2002 *J. Biol. Chem.* 277:39179-39186. Available online on Jul. 31, 2002.

Yamamoto et al., "ASC is essential for LPS-induced activation of procaspase-1 independently of TLR-associated signal adaptor molecules," Nov. 2004 *Genes Cells* 9:1055-1067.

Yanai and Hiramoto, "First total synthesis of N-4909 and its diastereomer; a stimulant of apolipoprotein E secretion in human hepatoma Hep G2 cells," Feb. 1999 *J. Antibiot.* 52:150-159.

Yin et al., "Synthesis of lipid A derivatives and their interactions with polymyxin B and polymyxin B nonapeptide," Mar. 5, 2003. *J. Am. Chem. Soc.* 125:2426-2435.

Yoshimura et al., "Lipopolysaccharides from periodontopathic bacteria *Porphyromonas gingivalis* and *Capnocytophaga ochracea* are antagonists for human toll-like receptor 4," Jan. 2002 *Infect. Immun.* 70:218-225.

(56) References Cited

OTHER PUBLICATIONS

Yoshizaki et al., "First total synthesis of the Re-type lipopolysaccharide," Apr. 17, 2001 *Angew. Chemie Int. Ed.* 40:1475-1480.
Zhang et al., "Modulation of innate immune responses with synthetic lipid A derivatives," 2007 *J. Am. Chem. Soc.* 129:5200-5116. Available online on Mar. 29, 2007.
Zhang et al., Apr. 2007 *J. Am. Chem. Soc.* 129:5200-5216; Supporting Information, available online at the American Chemical Society website at: <pubs.acs.org/subscribe/journals/jacsat/suppinfo/ja068922a/ja068922asi20070228_031652.pdf>; 52 pages.
Zhang et al., "Innate immune responses of synthetic lipid A derivatives of *Neisseria meningitides*," Jan. 7, 2008 *Chem. Eur. J.* 14:558-569. Available online on Oct. 17, 2007.
Zhang et al., 2008 *Chemistry—A Eur. J.* 14:558-569; Supporting Information, available online at the Wiley Interscience website at: <wiley-vch.de/contents/jc_2111/2008/f701165_s.pdf>; 43pages.
Zhang et al., "Synthetic tetra-acylated derivatives of lipid A from *Porphyromonas gingivalis* are antagonists of human TLR4," 2008 *Org. Biomol. Chem.* 6:3371-3381. Available online on Jul. 25, 2008.
Zhang et al., 2008 *Org. Biomol. Chem.* 6:3371-3381; Supplementary Information available at the RSC Publishing website at: <rsc.org/suppdata/OB/b8/b809090d/b809090d.pdf>; 56 pages.
Zughaier et al., "*Neisseria meningitidis* lipooligosaccharide structure-dependent activation of the macrophage CD14/Toll-like receptor 4 pathway," Jan. 2004 *Infect. Immun.* 72:71-380.
Zughaier et al., "Differential induction of the toll-like receptor 4-MyD88-dependent and -independent signaling pathways by endotoxins," May 2005 *Infect. Immun.* 73:2940-2950.
Alving et al., "Chapter 11. Preparation and Use of Liposomes in Immunological Studies," in *Liposome Technology, vol. II Incorporation of Drugs, Proteins, and Genetic Material*. Gregoriadis (Ed.), CRC Press: Boca Raton FL; 1984. Cover page, publisher's page, and pp. 157-175.
Alving et al., "Chapter 21. Preparation and Use of Liposomes in Immunological Studies," in *Liposome Technology, 2nd Edition, vol. III Interactions of Liposomes with the Bioplogical Milieu*. Gregoriadis (Ed.), CRC Press: Boca Raton FL; 1984. Cover page, publisher's page, and pp. 317-343.
Bevan, "Helping the CD8(+) T-cell response," 2004 *Nat. Rev. Immunol.* 4:595-602.
Brandtzaeg et al., "Plasma endotoxin as a predictor of multiple organ failure and death in systemic meningococcal disease," 1989 *J. Infect. Dis.* 159:195-204.
Brandtzaeg et al., "Compartmentalization of lipopolysaccharide production correlates with clinical presentation in meningococcal disease," 1992 *J. Infect. Dis.* 166:650-652.
Chatterjee et al., "Synthesis of symmetrical trisubstituted olefins by cross metathesis," May 30, 2002 *Org. Lett.*, 4:1939-1942.
Christ et al., "Total Synthesis of the Proposed Structure of *Rhodobacter* sphaeroides Lipid A Resulting in the Synthesis of New Potent Lipopolysaccharide Antagonists," 1994 *J. Am. Chem. Soc.*, 116:3637-3638.
Dabbagh and Lewis, "Toll-like receptors and T-helper-1/T-helper-2 responses," Jun. 2003 *Curr. Opin. Infect. Dis.* 16:199-204.
Darveau, "Lipid A diversity and the innate host response to bacterial infection," Feb. 1998 *Curr. Opin. Microbiol.* 1:36-42.
Darveau, "Chapter 4: Oral Innate Host Defense Responses: Interactions with Microbial Communities and their Role in the Development of Disease," in *Oral Bacterial Ecology: The Molecular Basis*. Kuramitsu and Ellen (Eds.), Horizon Scientific Press: Wymondham, Norfolk, England; 2000. Title page, publisher's page, and pp. 169-218.
Demchenko (Ed.), *Handbook of Chemical Glycosylations: Advances in Stereoselectivity and Therapeutic Relevance*. Wiley-VCH: printed in the Federal Republic of Germany; 2008, ISBN 978-3-527-31780-6. Title page, publisher's page, and table of contents; 12 pages.
Demchenko et al., "Synthesis and biological evaluation of *Rhizobium sin*-1 lipid A derivatives," May 21, 2003 *J. Am. Chem. Soc.*, 125:6103-6112.

Dick and Burret, "Glycoconjugates of bacterial carbohydrate antigens. A survey and consideration of design and preparation factors," in *Conjugate Vaccines. Volume 10: Contributions in Microbiology and Immunology*. Cruse et al. (Eds.), Karger: Basel, Switzerland; 1989. Title page, publisher's page, and pp. 48-114.
Duffy et al., "The ADAMs family of proteins: from basic studies to potential clinical applications," Apr. 2003 *Thromb. Haemost.* 89:622-631.
Eisele et al., "Synthesis of carbon-bridged *N*-acetyl-C-lactosamine and derivatives," Nov. 23, 1995 *Liebigs Ann.* 1995:2113-2121.
Erridge et al., "Structure and function of lipopolysaccharides," Jul. 2002 *Microbes Infect.* 4:837-851.
Finlay and Hancock, "Can innate immunity be enhanced to treat microbial infections?" Jun. 2004 *Nat. Rev. Microbiol.* 2:497-504.
Fukase et al., "Synthetic route for $^{14}$C-labeling of a bioactive Lipid A analogue," Nov. 20, 1995 *Tetrahedron Lett.* 36:8645-8648.
Fukase et al., "Divergent synthesis and biological activities of Lipid A analogues of shorter acyl chains," Apr. 16, 1998 *Tetrahedron* 54:4033-4050.
Garegg et al., "A novel, reductive ring-opening of carbohydrate benzylidene acetals," Oct. 1, 1982 *Carbohyd. Res.* 108:97-101.
Imoto et al., "Total synthesis of *Escherichia coli* Lipid A," 1985 *Tetrahedron Lett.* 26:1545-1548.
Imoto et al., "Preparation of novel pyranosyl fluorides of 3-deoxy-D-*manno*-2-octulosonic acid (KDO) feasible for synthesis of KDO α-glycosides," 1987 *Tetrahedron Lett.* 28:6277-6280.
Jennings et al., "The R-type lipopolysaccharides of *Neisseria meningitidis*," Feb. 1980 *Can. J. Biochem.* 58:128-136.
Jiang and Chan, "BoraneBu2BOTf: A mild reagent for the regioselective reductive ring opening of benzylidene acetals in carbohydrates," Jan. 29, 1998 *Tetrahedron Lett.* 39:355-358.
Joklik et al. (eds.), *Zinsser Microbiology, 20th Edition*. W. K. Appleton & Lange Publishing Division of Prentice Hall: Norwalk, CT; 1992. Title page, publisher's page, and table of contents; 5 pages.
Jongeneel, "Transcriptional regulation of the tumor necrosis factor alpha gene," Jul. 1995 *Immunobiology* 193:210-216.
Karaghiosoff et al., "Central role for type I interferons and Tyk2 in lipopolysaccharide-induced endotoxin shock," May 2003 *Nat. Immunol.* 4:471-477. Available online on Apr. 7, 2003.
Katoh et al., "Application of microbial enantiofacially selective hydrolysis in natural product synthesis," Oct. 1994 *Tetrahedron: Asymmetry* 5:1935-1944.
Kawata et al., "Chapter 10. Specfic Lipid A Analog Which Exhibits Exclusive Antagonism of Endotoxin," in *Novel Therapeutic Strategies in the Treatment of Sepsis*. Morrison and Ryan (Eds.), Marcel Dekker: New York, NY; 1995. Title page, publisher's page, and pp. 171-186.
Keegan et al., "Efficient asymmetric synthesis of (R)-3-hydroxy- and alkanoyloxytetradecanoic acids and method for the determination of enantiomeric purity," Dec. 1996 *Tetrahedron: Asymmetry* 7:3559-3564.
Kubasch and Schmidt, "Synthesis of Muramyl Peptides Containing meso-Diaminopimelic Acid," Aug. 2002 *Eur. J. Org. Chem.* 2002:2710-2726.
Kusumoto, "Chapter 4. Chemical Synthesis of Lipid A," in *Bacterial Endotoxin Lipopolysaccharides; vol. I: Molecular Biochemistry and Cellular Biology*. CRC Press: Boca Raton, FL; 1992. Title page, publisher's page, and pp. 81-105.
Kusumoto et al., "Chapter 14. The Chemical Synthesis of Lipid A," in *Endotoxin in Health and Disease*. Brade et al. (Eds.), Marcel Dekker, New York, NY; 1999. Title page, publisher's page, and pp. 243-256.
Lee et al., "The 2-Aminogluconate Isomer of *Rhizobium sin*-1 Lipid A Can Antagonize TNF-α Production Induced by Enteric LPS," Jan. 9, 2005 *ChemBioChem* 7:140-148. Available online on Nov. 30, 2005.
Libshutz et al, "Tandem olefin metathesis—elimination reactions. A new route to doubly unsaturated carbonyl derivatives," Jul. 14, 2008 *Tetrahedron* 64:6949-6954. Available online on Apr. 11, 2008.
Loewe et al., "Glycosidation Route to 4"-epi-(Methylamino)-4"-Deoxyavermectin B1 (MK-244, Emamectin Benzoate)," Dec. 1, 1994 *J. Org. Chem.* 59:7870-7875.

(56) References Cited

OTHER PUBLICATIONS

Mathiak et al., "Lipopolysaccharides from different bacterial sources elicit disparate cytokine responses in whole blood assays," Jan. 2003 *Int. J. Mol. Med.* 11:41-44.

Netea et al., "Lethal *Escherichia coli* and *Salmonella typhimurium* endotoxemia is mediated through different pathways," Sep. 2001 *Eur. J Immunol.* 31:2529-2538.

Ogawa, "Chemical structure of lipid A from *Porphyromonas* (*Bacteroides*) *gingivalis* lipopolysaccharide," Oct. 11, 1993 *FEBS Lett.* 332:197-201.

Ogawa et al., "Chemical structure and immunobiological activity of *Porphyromonas gingivalis* Lipid A," May 1, 2007 *Front. Biosc.* 12:3795-3812.

Oikawa et al., "Synthesis of $^{13}$C-Labeled Biosynthetic Precursor of Lipid A and Its Analogue with Shorter Acyl Chains," 1999 *Bull. Chem. Soc. Jpn.* 72:1857-1867.

Pasare and Medzhitov, "Toll-like receptors and acquired immunity," Feb. 2004 *Seminars Immunol.* 16:23-26.

Patil, "A simple access to trichloroacetimidates," Feb. 26, 1996 *Tetrahedron Lett.* 37:1481-1484.

Peri et al., "Inhibition of Lipid A Stimulated Activation of Human Dendritic Cells and Macrophages by Amino and Hydroxylamino Monosaccharides," Apr. 27, 2007 *Angew. Chem. Int. Ed.* 46:3308-3312. Available onine on Mar. 23, 2007.

Pittet et al., "Nosocomial bloodstream infection in critically ill patients. Excess length of stay, extra costs, and attributable mortality," May 25, 1994 *J. Am. Med. Assoc.* 271:1598-1601.

Rembold et al., "Synthesis of KDO α-glycosides of lipid A derivatives," Aug. 17, 1993 *Carb. Res.* 246:137-159.

Robbins and Freeman, "Obstacles to developing vaccines for the Third World," Nov. 1988 *Sci. Am.* 259:126-133.

Rossignol et al., "Chapter 47. Synthetic Endotoxin Antagonists," in *Endotoxin in Health and Disease*. Brade et al. (Eds.), Marcel Dekker, New York, NY; 1999. Title page, publisher's page, and pp. 699-717.

Sakagami and Hamana, "A selective ring opening reaction of 4,6-O-benzylidene acetals in carbohydrates using trialkylsilane derivatives," Jul. 15, 2000 *Tetrahedron Lett.* 41:5547-5551.

Santhanam et al., "Synthesis and biological evaluation of a lipid A derivative that contains an aminogluconate moiety," Oct. 4, 2004 *Chem.-Eur. J.* 10:4798-4807.

Schmidt and Stumpp, "Glycosylimidate, 8. Synthese von 1-Thioglycosiden," Jul. 15, 1983 *Liebigs Ann. Chem.* 1983:1249-1256. English language abstract included.

Schmidt, "New Methods for the Synthesis of Glycosides and Oligosaccharides—Are There Alternatives to the Koenigs-Knorr Method?" Mar. 1986 *Angew. Chem. Int. Ed.* 25:212-235.

Schmidt et al., "Simple synthesis of KDO-α-glycosides by anomerically selective O-alkylation," Sep. 1988 *Angew. Chemie Int. Ed.* 27:1178-1180.

Sherris et al. (Eds.), *Medical Microbiology: An Introduction to Infectious Diseases*, Second Edition. Elsevier Science Publishing Co., Inc.: New York, NY; 1984. Title page, publisher's page, and table of contents; 5 pages.

Shioiri et al., "Synthesis of topostins B567 and D654 (WB-3559D, flavolipin), DNA topoisomerase I inhibitors of bacterial origin," Dec. 17, 1998 *Tetrahedron* 54:15701-15710.

Shiozaki et al., "Stereocontrolled synthesis of all stereoisomers of the proposed flavolipin," May 27, 1996 *Tetrahedron Lett.* 37:3875-3876.

Shiozaki et al., "Revised structure and synthesis of flavolipin," Sep. 24, 1998 *Tetrahedron* 54:11861-11876.

Skotnicki and Levin, "Chapter 16. TNF-αconverting enzyme (TACE) as a therapeutic target," in *Annual Reports in Medicinal Chemistry vol. 38*. Doherty (Ed.), 2003. pp. 153-162.

Socransky et al., "Microbial complexes in subgingival plaque," Feb. 1998 *J. Clin. Periodontol.* 25:134-144.

Ubukata et al., "Structure elucidation of liposidomycins, a class of complex lipid nucleoside antibiotics," Nov. 1992 *J. Org. Chem.* 57:6392-6403.

Unger et al., "The anomeric configurations of the two ammonium (methyl 3-deoxy-d-manno-2-octulopyranosid)onate salts (methyl α- and β-ketopyranosides of KDO)," 1980 *Carbohydr. Res.* 80:191-195.

van der Klein et al., "An efficient route to 3-deoxy-d-manno-2-octulosonic acid (KDO) derivatives via a 1,4-cyclic sulfate approach," 1989 *Tetrahedron Lett.* 30:5477-5480.

Vasan et al., "Agonistic and antagonistic properties of a *Rhizobium sin*-1 lipid A modified by an ether-linked lipid," Jul. 7, 2007 *Org. Biomol. Chem.* 5:2087-2097. Available online on May 29, 2007.

Watanabe et al., "An efficient phosphorylation method using a new phosphitylating agent, 2-diethylamino-1,3,2-benzodioxaphosphepane," 1990 *Tetrahedron Lett.* 31:255-256.

Wens et al., "Leptospiral lipopolysaccharide activates cells through a TLR2-dependent mechanism," Apr. 2001 *Nat. Immunol.* 2:346-352.

Wick, "Living in the danger zone: innate immunity to *Salmonella*," Feb. 2004 *Curr. Opin. Microbiol.* 7:51-57.

Yoshizaki et al., "First Total Synthesis of the Re-Type Lipopolysaccharide," Apr. 17, 2001 *Angew. Chem.* 113:1523-1528.

Zhang et al., "The influence of the long chain fatty acid on the antagonistic activities of *Rhizobium sin*-1 lipid A," Jul. 15, 2007 *Bioorg. Med. Chem.* 15:4800-4812. Available online on May 6, 2007.

Zughaier et al., "Hexa-acylation and KDO(2)-glycosylation determine the specific immunostimulatory activity of *Neisseria meningitidis* lipid A for human monocyte derived dendritic cells," Feb. 27, 2006 *Vaccine* 24:1291-1297. Available online on Oct. 4, 2005.

International Preliminary Report on Patentability (Form PCT/IB/373) mailed Mar. 9, 2010, in regard to International Patent Application No. PCT/US2008/010394, filed Sep. 5, 2008; 13 pages.

International Search Report (Form PCT/ISA/210) mailed Feb. 4, 2010, in regard to International Patent Application No. PCT/US2008/010394, filed Sep. 5, 2008; 5 pages.

Written Opinion of the International Search Authority (Form PCT/ISA/237) mailed Feb. 4, 2010, in regard to International Patent Application No. PCT/US2008/010394, filed Sep. 5, 2008; 12 pages.

\* cited by examiner 1. hexa-acylated
   *E. coli* lipid A

2. *E. coli* lipid A
   w/ shorter lipids 3. hepta-acylated
   *S. typhimurium* lipid A 4. R = P(O)(OH)$_2$
   *S. typhimurium* lipid A
   w/ shorter lipids
5. R = H 51. *N. meningitidis* lipid A 52. hexa-acylated *E. coli* lipid A 53. *N. meningitidis* lipid A with KDO 54. *E. coli* lipid A with shorter lipids

US 8,563,523 B2

SYNTHETIC LIPID A DERIVATIVE

CONTINUING APPLICATION DATA

This application is national stage application of International Application No. PCT/US2008/010394, filed Sep. 5, 2008, which claims the benefit of U.S. Provisional Applications Ser. Nos. 60/967,876, filed Sep. 7, 2007, and 61/135,666, filed Jul. 23, 2008, each of which is incorporated herein by reference.

GOVERNMENT FUNDING

The present invention was made with government support under Grant No. GM061761, awarded by the Institute of General Medicine of the National Institute of Health. The Government has certain rights in this invention.

BACKGROUND

The innate immune system is an evolutionarily ancient system designed to detect the presence of microbial invaders and activate protective reactions (Beutler, *Mol. Immunol.* 2004, 40, 845-859). It responds rapidly to compounds that are integral parts of pathogens that are perceived as danger signals by the host. Recognition of these molecular patterns is mediated by sets of highly conserved receptors (van Amersfoort et al., *J. Clin. Microbiol. Rev.* 2003, 16, 379), whose activation results in acute inflammatory responses. These responses include the production of a diverse set of cytokines and chemokines, directing local attacks against the invading pathogen, and initiation of responses that activate and regulate the adaptive component of the immune system (Dabbagh and Lewis, *Curr. Opin. Infect. Dis.* 2003, 16, 199-204; Bevan, *Nat. Rev. Immunol.* 2004, 4, 595-602; Pasare and Medzhitov, *Seminars Immunol.* 2004, 16, 23-26; Finlay and Hancock, *Nat. Rev. Microbiol.* 2004, 2, 497-504; Akira et al., *Nat. Immunol.* 2001, 2, 675-680; Pasare and Medzhitov, *Immunity* 2004, 21, 733-741).

Evidence is emerging that innate immune responses can be exploited for therapeutic purposes such as the development of adjuvants for vaccines and the treatment of a wide range of diseases including asthma, infections, and cancer. An important concern of such therapies is, however, that over-activation of innate immunity may lead to the clinical symptoms of septic shock (Pittet et al., *J. Am. Med. Assoc.* 1994, 271, 1598-1601; Rice and Bernard, *Annu. Rev. Med.* 2005, 56, 225-248). Thus, an important issue for the design of safe immune modulators is a detailed knowledge of structure-activity relationships to harness beneficial effects without causing toxicity.

Lipopolysaccharides (LPS) are structural components of the outer membrane of Gram-negative bacteria and offer great promise for the development of immuno-modulators. LPS consists of a hydrophobic domain known as lipid A, a non-repeating core oligosaccharide and a distal polysaccharide (or O-antigen) (Caroff et al., *Microbes Infect.* 2002, 4, 915-926; Raetz and Whitfield, *Annu. Rev. Biochem.* 2002, 71, 635-700). The lipid A moiety of *Escherichia coli* consists of a hexa-acylated bis-1,4'-phosphorylated glucosamine disaccharide, which has (R)-3-hydroxymyristyl residues at C-2, C-2', C-3, and C-3'. Both of the primary (3)-hydroxyacyl chains in the distal glucosamine moiety are esterified with lauric and myristic acids, and the primary hydroxyl at the C-6 position is linked to the polysaccharide through a dimeric 3-deoxy-D-manno-oct-2-ulosonic acid (KDO) carbohydrate moiety. It has been proposed that microbial components such as LPS can induce inflammatory responses resulting in tissue damage and alveolar bone loss (Darveau, in *Oral Bacterial Ecology The Molecular Basis*, ed. Kuramitsu and Ellen, Horizon Scientific Press, Wymond Norfolk, 2000, pp. 169-218).

Recent structural studies have demonstrated that the carbohydrate backbone, degree of phosphorylation, and fatty acid acylation patterns vary considerably among bacterial species (Caroff et al., *Microbes Infect.* 2002, 4, 915-926; Raetz and Whitfield, *Annu. Rev. Biochem.* 2002, 71, 635-700; Darveau, *Curr. Opin. Microbiol.* 1998, 1, 36-42; Erridge et al., *Microbes Infect.* 2002, 4, 837-851; Alexander and Zahringer, *Trends Glycosci. Glycotechnol.* 2002, 14, 69-86). Structurally different lipid As may differentially induce proinflammatory responses (Zughaier et al., *Infect. Immun.* 2005, 73, 2940-2950; Netea et al., *Eur. J. Immunol.* 2001, 31, 2529-2538; Mathiak et al., *Int. J. Mol. Med.* 2003, 11, 41-44; van der Ley et al., *Infect. Immun.* 2001, 69, 5981-5990). For example, in one study, LPS from *E. coli* O55:B5 induced the production of mediators such as tumor necrosis factor alpha (TNF-α), interleukin 1 beta (IL-1β), monocyte chemoattractant protein 1 (MCP-1), and macrophage inflammatory protein 3alpha (MIP-3α) arising from the MyD88-dependent pathway, but caused less production of mediators such as interferon-beta (IFN-β), nitric oxide, and interferon-inducible protein 10 (IP-10) arising from the TRIF-dependent pathway. In contrast, LPS from *S. typhimurium* invoked strong production of mediators associated with the TRIF-dependent pathway, but caused only minimal production of TNF-α, IL-1↑, MCP-1, and MIP-3α. Heterogeneity in the structure of lipid A within a particular bacterial strain and possible contamination with other inflammatory components of the bacterial cell-wall complicate the use of either LPS or lipid A isolated from bacteria to dissect the molecular mechanisms responsible for the biological responses to specific lipid A molecules. Chemical synthesis of lipid A derivatives has been reported (Erridge et al., *Microbes Infect.* 2002, 4, 837-851).

*Neisseria meningitidis* is a Gram-negative bacterium that causes fulminant, rapidly fatal sepsis, and meningitis (Robbins and Freeman, *Sci. Am.* 1988, 259, 126-133). The morbidity and mortality of meningococcal bacteremia has been linked to a systematic inflammatory response to lipooligosaccharides (LOS) of affected patients (Brandtzaeg et al., *J. Infect. Dis.* 1989, 159, 195-204; Brandtzaeg et al., *J. Infect. Dis.* 1992, 166, 650-652; van Deuren et al., *Clin. Microbiol. Rev.* 2000, 13, 144-166). LOS, a major component of the outer membrane of *N. meningitidis*, initiates the production of multiple host-derived inflammatory mediators.

Meningococcal LOS lacks the repeating O-antigen of enteric LPS but has a conserved inner core region composed of L-glycero-D-manno-heptosides and a KDO moiety linked to lipid A (Jennings et al., *Can. J. Biochem.* 1980, 58, 128-136; Gamian et al., *J. Biol. Chem.* 1992, 267, 922-925). The lipid A of *N. meningitidis* is hexa-acylated in a symmetrical fashion whereas enteric bacteria have an asymmetrically hexa-acylated lipid A (Darveau, *Curr. Opin. Microbiol.* 1998, 1, 36-42; Kulshin et al., *J. Bacteriol.* 1992, 174, 1793-1800; Alexander and Zahringer, *Trends Glycosci. Glycotechnol.* 2002, 14, 69-86; Erridge et al., *Microbes Infect.* 2002, 4, 837-851). Also, a number of the fatty acids of *N. meningitidis* are shorter compared to those of *E. coli*. At low concentrations meningococcal LOS is a potent inducer of MyD88- and TRIF-dependent cytokines, whereas at the same picomole concentrations *E. coli* LPS induced comparable levels of TNF-α, IL-1β, and MIP-3α but significantly less IFN-β, nitric oxide, and IP-10 (Zughaier et al., *Infect. Immun.* 2005, 73, 2940-2950).

*Porphyromonas gingivalis* is a Gram-negative bacterium implicated in chronic periodontal diseases (Socransky et al., *J. Clin. Periociontol.*, 1998, 25, 134-144). It releases large amounts of outer membrane vesicles containing lipopolysaccharides (LPS), which can penetrate periodontal tissue. Early studies have indicated that *P. gingivalis* LPS can activate murine macrophages in a TLR2- and TLR4-dependent manner (Darveau et al., *Infect. Immun.*, 2004, 72, 5041-5051). However, it has been suggested that the TLR2 responses maybe due to contaminations with lipoproteins (Ogawa et al., *Int. Immunol.*, 2002, 14, 1325-1332; Ogawa et al., *Front. Biosc.*, 2007, 12, 3795-3812). It has also been found that LPS of *P. gingivalis* can inhibit IL-6 and IL-1β secretion and ICAM expression induced by enteric LPS by U373 and human peripheral mononuclear cells and human gingival fibroblasts, respectively (Yoshimura et al., *Infect. Immun.*, 2002, 70, 218-225). Another study found that a purified tetra-acylated monophosphoryl lipid A structure can antagonize E-selectin expression in human cells exposed to enteric or *P. gingivalis* LPS (Reife et al., *Cell. Microbiol.*, 2006, 8, 857-868). It appears that MD2 represents the principle molecular component used by these LPS derivatives for inhibition (Coats et al., *J. Immunol.*, 2005, 175, 4490-4498).

The lipid A moiety of the LPS of *P. gingivalis* displays considerable heterogeneity and the structures of four compounds have been elucidated, which differ in fatty acid substitution pattern (Ogawa, *FEBS Lett.*, 1993, 332, 197-201; Kumada et al., *J. Bacteriol.*, 1995, 177, 2098-2106). A common structural feature of these derivatives is, however, the presence of unusual branched fatty acids such as R-(3)-hydroxy-13-methyltetradecanic acid and R-(3)-hydroxy-15-methyl hexadecanic acid. The presence of multiple lipid A structures has made it difficult to interpret innate immune responses elicited by *P. gingivalis* LPS, which in turn has hindered a thorough understanding of the contributions of *P. gingivalis* LPS to periodontal diseases.

It has long been thought that the inflammatory properties of LPS and LOS reside in the lipid A moiety (Erridge et al., *Microbes Infect.* 2002, 4, 837-851; Kusumoto, in *Molecular Biochemistry and Cellular Biology*, Vol. 1, Bacterial Endotoxin Lipopolysaccharides; Chapter 9, Chemical Synthesis of Lipid A, CRC Press, Boca Raton, 1992, pp. 81-105; Kusumoto et al., in *Endotoxin in Health and Disease* (Ed.: H. Brade), Marcel Dekker, New York, 1999, pp. 243-256; Imoto et al., *Tetrahedron Lett.* 1985, 26, 1545-1548; Galanos et al., *Eur. J. Biochem.* 1985, 148, 1-5). Lipid A triggers innate immune responses through Toll-like receptor 4 (TLR4), a member of the TLR family that participates in pathogen recognition. Immediately distal to TLR4 activation are two intracellular cascades that regulate signal transduction processes, gene expression, and production of proinflammatory mediators (Akira et al., *Nat. Immunol.* 2001, 2, 675-680). One of these cascades requires a specific intracellular adaptor protein called MyD88, while the other cascade utilizes the TRIF adaptor protein. The MyD88-dependent pathway leads to up-regulation of cytokines and chemokines such as TNF-α, IL-1β, IL-6, and MCP-1, whereas the TRIF-dependent pathway leads to the production of IFN-β, which in turn activates the STAT-1 pathway resulting in the production of mediators such as IP-10 and nitric oxide (Karaghiosoff et al., *Nat. Immunol.* 2003, 4, 471-477).

However, recent studies have shown that lipid A expressed by meningococci with defects in KDO biosynthesis or transfer has significantly reduced bioactivities compared to $KDO_2$ containing meningococcal LOS (Zughaier et al., *Infect. Immun.* 2004, 72, 371-380). Removal of the KDO moieties of wild type LOS by mild acetic acid treatment also attenuated cellular responses. Interestingly, dendritic cells stimulated with $KDO_2$-lipid A from meningococci but not lipid A alone stimulated naïve allogeneic CD4+ cells to secrete enhanced levels of IFN-γ relative to T-cells primed with immature dendritic cells (Zughaier et al., *Vaccine* 2006, 24, 1291-1297).

Several other studies have suggested that the KDO moiety of LPS or LOS contributes to inflammatory responses. For example, it has been found that *salmonella* lipid A is inactive whereas the parent LPS is a potent activator of NF-κB in a TLR4-dependent manner in a human monocytic cell line (Muroi and Tanamoto, *Infect. Immun.* 2002, 70, 6043-6047). In addition, a synthetic enteric lipid A containing a di-KDO moiety was a more potent elicitor of TNF-α and IL-6 compared to its parent lipid A (Yoshizaki et al., *Angew. Chem. Int. Ed.* 2001, 40, 1475-1480; Yoshizaki et al., *Angew. Chem.* 2001, 113, 1523-1528). Furthermore, LPS from a nitrogen-fixing symbiont, *Rhizobium sin*-1 is able to significantly inhibit the *E. coli* LPS-dependent synthesis of TNF-α by human monocytic cells (Demchenko et al., *J. Am. Chem. Soc.* 2003, 125, 6103-6112; Santhanam et al., *Chem.-Eur. J.* 2004, 10, 4798-4807; Lee et al., *Chembiochem* 2006, 7, 140-148; Zhang et al., *Bioorg. Med. Chem.* 2007, 15, 4800-4812; Vasan et al., *Org. Biomol. Chem.* 2007, 5, 2087-2097). A comparison of the biological responses of synthetic and isolated lipid A derivatives and *R. sin*-1 LPS indicated that the KDO moieties are important for optimal antagonistic properties. Thus, it is probable that the cell surface receptors that recognize LPS bind to the lipid A as well as to the KDO moiety of LPS.

Several studies have reported compounds that can antagonize cytokine production induced by enteric LPS (Rossignol et al., in *Endotoxin in Health and Disease*, eds. Brade et al., Marcel Dekker, Inc., New York, 1999, vol. 1, pp. 699-717). Most efforts have been directed towards the synthesis of analogs of lipid A of *Rhodobacter sphaeroides* (Christ et al., *J. Am. Chem. Soc.*, 1994, 116, 3637-3638; Christ et al., *Science*, 1995, 268, 80-83) and derivatives of lipid X (Golenbock et al., *J. Biol. Chem.*, 1991, 266, 19490-19498; Lam et al., *Infect. Immun.*, 1991, 59, 2351-2358; Kawata et al., in *Novel Therapeutic Strategies in the Treatment of Sepsis*, ed. Morrison and Ryan, Marcel Dekker, New York, 1995, pp. 171-186; Peri et al., *Angew. Chem. Int. Ed.*, 2007, 46, 3308-3312). Analogs of the lipid A moiety of *Helicobacter pylori* have also been shown to inhibit IL-6 secretion by human whole blood cells (Fujimoto et al., *Tetrahedron Lett.*, 2007, 48, 6577-6581). Recently, it was reported that synthetic lipid As derived from *Rhizobium sin*-1 can prevent the induction of TNF-α by *E. coli* LPS in human monocytic cells (Demchenko et al., *J. Am. Chem. Soc.*, 2003, 125, 6103-6112; Santhanam et al., *Chem.-Eur. J.*, 2004, 10, 4798-4807; Lee et al., *Chembiochem*, 2006, 7, 140-148; Zhang et al., *Bioorg. Med. Chem.*, 2007, 15, 4800-4812; Vasan et al., *Org. Biomol. Chem.*, 2007, 5, 2087-2097).

Although studies with LOS isolated from meningococci have indicated that it possesses unique immunological properties, heterogeneity in the structure of lipid A and possible contaminations with other inflammatory components of the bacterial cell wall have made it difficult to confirm these results (Zughaier et al., *Infect. Immun.* 2005, 73, 2940-2950; Zughaier et al., *Infect. Immun.* 2004, 72, 371-380; Zughaier et al., *Vaccine* 2006, 24, 1291-1297). Furthermore, the acylation patterns, as well as fatty acid length, differ between meningococcal and *E. coli* lipid A. Hence, it has been impossible to establish which structural feature is responsible for the unique inflammatory properties.

SUMMARY OF THE INVENTION

The invention provides compounds suitable for use in synthesizing a lipid A derivative, as well as methods for synthesizing and using a synthetic lipid A derivative.

In one aspect, the invention provides a functionalized disaccharide having protecting groups at three, four, five, six, seven, or all eight positions C-1, C-2, C-3 and C-4 on the proximal ring, and C-2', C-3', C-4' and C-6' on the distal ring, as shown in formula I:

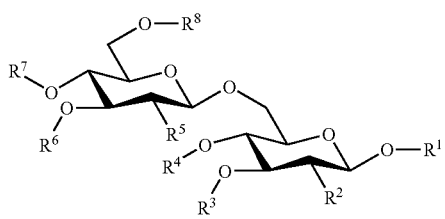

(I)

wherein:
$R^1$ at the C-1 position is an anomeric protecting group, preferably TDS or TBS;
$R^2$ at the C-2 position is azido or $NHR^{10}$, where $R^{10}$ is an amino protecting group, preferably Fmoc;
$R^3$ at the C-3 position is H, acyl, or a hydroxyl protecting group, preferably Alloc;
$R^4$ at the C-4 position is a hydroxyl protecting group, preferably Bn;
$R^5$ at the C-2' position is azido or $NHR^{11}$, where $R^{11}$ is acyl or an amino protecting group, preferably Fmoc;
$R^6$ at the C-3' position is acyl or a hydroxyl protecting group, preferably Alloc or Lev; and
$R^7$ and $R^8$ at the C-4' and C-6' positions, respectively, are each independently H, a phosphate or substituted phosphate, or a hydroxyl protecting group, preferably Bn; or together form a ring, preferably an acetal, more preferably an isopropylidine acetal or a benzylidene acetal.

In a preferred embodiment of the disaccharide of formula I, $R^2$ is azido. In another preferred embodiment of the disaccharide of formula I, $R^2$ is azido and $R^5$ is $NHR^{11}$ where $R^{11}$ is an amino protecting group or acyl. Preferably, the amino protecting group is Fmoc.

In another aspect, the invention provides a functionalized monosaccharide suitable for use in synthesizing the functionalized disaccharide of the invention.

In one embodiment of the functionalized monosaccharide of the invention, the monosaccharide has protecting groups at two, three or all four positions C-1, C-2, C-3 and C-4 as shown in formula II:

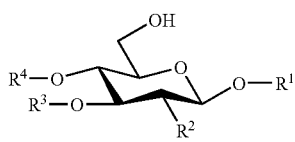

(II)

wherein:
$R^{11}$ at the C-1 position is an anomeric protecting group, preferably TDS or TBS;
$R^2$ at the C-2 position is azido or $NH R^{10}$, where $R^{10}$ is an amino protecting group, preferably Fmoc;
$R^3$ at the C-3 position is H, acyl, or a hydroxyl protecting group, preferably Alloc; and
$R^4$ at the C-4 position is a hydroxyl protecting group, preferably Bn.
In a preferred embodiment of the monosaccharide of formula II, $R^2$ is azido.

In another embodiment of the functionalized monosaccharide of the invention, the monosaccharide has a protecting group at three, four, or all five positions C-1, C-2, C-3, C-4, and C-6 as shown in formula III:

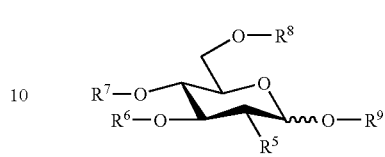

(III)

wherein:
$R^5$ at the C-2 position is azido or $NHR^{11}$, where $R^{11}$ is an amino protecting group, preferably Fmoc;
$R^6$ at the C-3 position is acyl or a hydroxyl protecting group, preferably Alloc or Lev; and
$R^7$ and $R^8$ at the C-4 and C-6 positions, respectively, are each independently H, a phosphate or substituted phosphate, or a protecting group, preferably Bn; or together form a ring structure, preferably an acetal, more preferably an isopropylidine acetal or a benzylidene acetal; and
$R^9$ at the C-1 position is an anomeric protecting group, preferably TDS or TBS, or a leaving group, preferably trichloroacetimidate.

In another aspect, the invention includes methods for making a functionalized disaccharide or monosaccharide, including compounds having formula I, formula II, or formula III, as well as methods of making a lipid A derivative that include selective acylation of compounds having formulas I, II or III at any or all of C-2, C-3, C-2' and C-3'. Optionally the method for making a lipid A derivative further includes phosphorylating the compound of formula I or II at the C-1 position. Additionally or alternatively, the method for making a lipid A derivative optionally further includes phosphorylating the compound of formula I or III at the C-4' or C-4 position, respectively. Additionally or alternatively, the method of making a lipid A derivative further includes, either before, in between, or after the successive acylation steps, contacting the compound having formula I or III, wherein $R^7$ is preferably H or a protecting group, with a KDO donor in a glycosylation reaction at the C-6 or C-6' position of the compound having formula I or III to yield a KDO glycoside.

In another aspect, the invention provides a method of preparing a fatty acid, a fatty acid precursor or a fatty acid derivative. In one embodiment, the method encompasses preparation of a 3-hydroxy fatty acid having a terminal isopropyl group. In another embodiment, the method encompasses preparation of a 3-hydroxy fatty acid precursor or fatty acid ester having a terminal isopropyl group.

In yet another aspect, the invention provides an isolated, synthetic lipid A derivative. Examples of lipid A derivatives include compounds 1, 2, 3, 4, 5, 51, 53, 101, 102, 103 and 104 (see FIGS. 1, 6 and 8).

In a further aspect, the invention provides methods for using a synthetic lipid A derivative, including but not limited to the novel synthetic lipid A derivatives described herein. In one embodiment, a synthetic lipid A derivative can act as antagonist or inhibitor of cytokine activity or secretion, as for example induced by enteric LPS, and thus is useful for treatment or prevention of conditions characterized by over-activation of a subject's immune system, such as Gram-negative septicemia or septic shock. In another embodiment, a synthetic lipid A derivative can activate the immune system of a subject, thereby having potential for use as an immune modulator. Accordingly the invention provides a method for treating a subject in need of immune system activation, modulation or inhibition, which method includes administering an effective amount of a synthetic lipid A derivative to the subject.

Synthetic lipid A derivatives are also useful in scientific studies, such as those designed to elucidate the innate immune responses elicited by Gram-negative bacteria and consequently their contributions to various diseases. Methods for using the synthetic lipid A derivative of the invention in scientific, laboratory or animal studies are also contemplated.

As used herein, the words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Further, the term "comprises" and variations thereof do not have a limiting meaning where these terms appear in the description and claims.

Unless otherwise specified, "a," "an," "the," and "at least one" are used interchangeably and mean one or more than one.

For any method disclosed herein that includes discrete steps, the steps may be conducted in any feasible order. And, as appropriate, any combination of two or more steps may be conducted simultaneously.

Abbreviations used herein include the following: Alloc, allyloxycarbonate; Bn, benzyl; Fmoc, 9-fluorenylmethoxycarbamate; KDO, 3-deoxy-D-manno-oct-2-ulosonic acid; Lev, levulinate; LPS, lipopolysaccharide; TBS, tert-butyldimethylsilyl; TDS, dimethylthexylsilyl.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
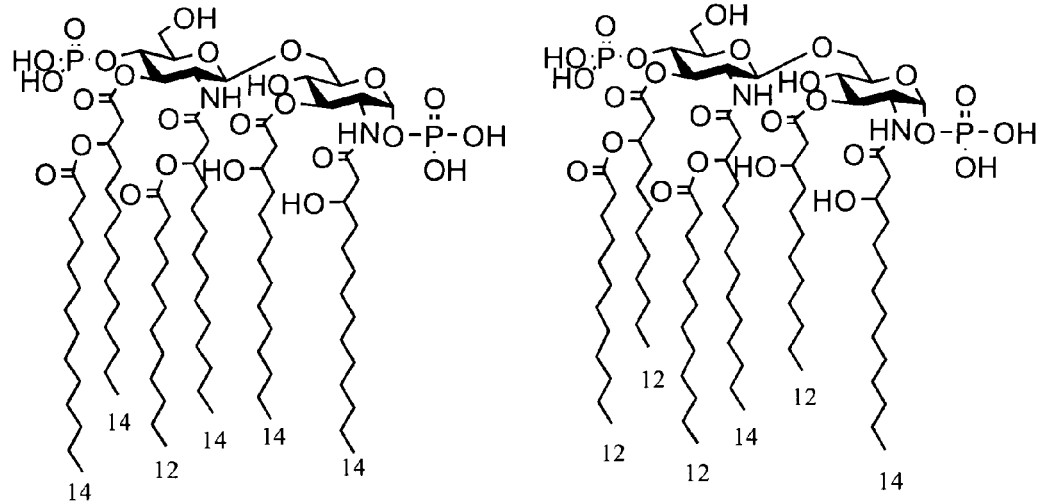
FIG. 1 shows the chemical structures of lipid A derivatives 1-5.
Figure 1:
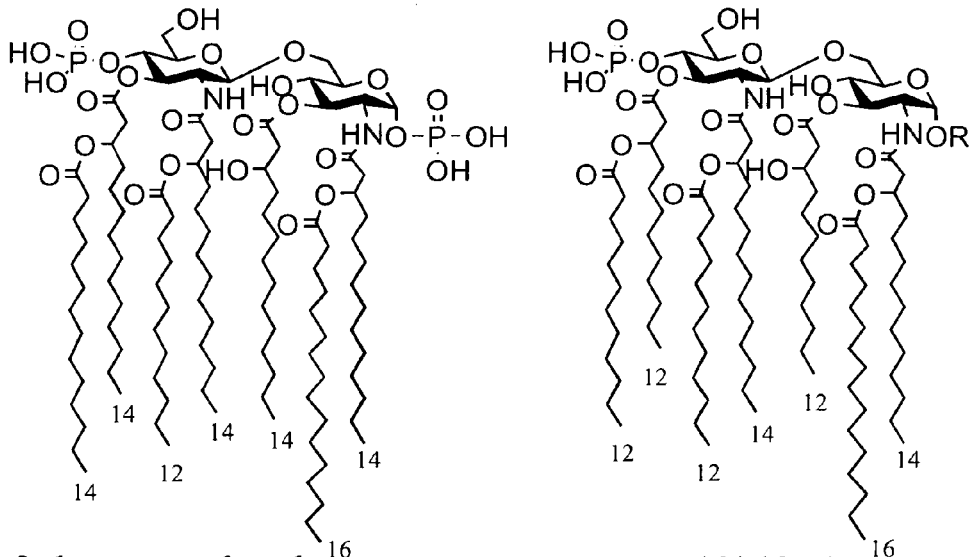

Lipopolysaccharides (LPS) consist of a hydrophobic domain known as lipid A, a non-repeating core oligosaccharide, and a distal polysaccharide (or O-antigen). The lipid A component of LPS initiates innate immune responses in mammals and can thereby initiate the production of a wide range of cytokines.

The invention provides a highly convergent chemical synthesis of lipid A molecules that utilizes an orthogonal protection strategy and a highly functionalized disaccharide intermediate. The synthetic process involves selectively removing or unmasking multiple amino and/or hydroxyl protecting groups in a sequential manner. This novel approach to lipid A synthesis provides easy access to a wide range of lipid A derivatives having different structural features, such as fatty acid acylation patterns, acyl chain length, degree of phosphorylation, KDO content and the like. The synthetic lipid As are useful for therapeutic applications as well as structure/activity relationship (SAR) studies. The invention is to be understood to include all intermediate and product compounds as well as the synthetic methods relating thereto.

The functionalized disaccharide of the invention, as shown in formula I, has protecting groups at three, four, five, six, seven, or all eight positions C-1, C-2, C-3 and C-4 on the proximal ring, and C-2', C-3', C-4' and C-6' on the distal ring. In a preferred embodiment of the disaccharide of formula I, $R^2$ is azido. In another preferred embodiment of the disaccharide of formula I, $R^2$ is azido and $R^5$ is $NHR^{11}$ where $R^{11}$ is an amino protecting group or acyl. Preferably, the amino protecting group is Fmoc.

The functionalized monosaccharides of the invention are suitable for use in synthesizing the functionalized disaccharide having formula I. Examples of functionalized monosaccharides of the invention are illustrated by compounds having formulas II and III. A compound having formula II functions the precursor for the proximal saccharide in the disaccharide having formula I, and a compound having formula III functions as the precursor for the distal saccharide in the disaccharide having formula I.

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—. An acyl group can be derived from an organic acid by removal of the hydroxy group. Examples of acyl groups include acetyl, propionyl, dodecanoyl, tetradecanoyl, isobutyryl, and the like. A preferred acyl group at positions C-2, C-3, C-2' and C-3' of the functionalized monosaccharides and disaccharides of the invention is an acyl group derived from fatty acid. A fatty acid can be branched or non-branched, and preferably contains from 4 to 28 carbon atoms. A "short chain fatty acid" as that term is used herein contains fewer than 14 carbon atoms. For example, a short chain fatty acid may contain 13, 12, 11, 10, 9 or 8 carbon atoms.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C1-C10 means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Typically, an alkyl group will have from 1 to 24 carbon atoms. A "lower alkyl" or is a shorter chain alkyl group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

Each of the above terms (e.g., "alkyl," "acyl") are meant to include both substituted and unsubstituted forms of the indicated radical.

The term "protecting group" refers to any group which, when bound to one or more hydroxyl group(s) or amine group(s) of a compound of the invention, prevents reactions from occurring at these hydroxyl or amine group(s) and which can be removed by chemical or enzymatic steps to reestablish the hydroxyl or amine group(s). The particular removable protecting group employed is determined by the nature of the compounds and chemical processes being utilized. Removable hydroxyl and amino protecting groups include, without limitation, substituents such as allyl, benzyl, acetyl, chloroacetyl, trifluoroacetyl, thiobenzyl, benzylidene, phenacyl, t-butyldimethylsilyl (TBS), dimethylthexylsilyl (TDS) and trialkylsilyls such as triethylsilyl, triisopropylsilyl, trimethylsily, tributylsilyl and the like, as well as azido, allyloxycarbonate (Alloc), 9-fluorenylmethoxycarbamate (Fmoc), levulinate (Lev), allyloxycarbonyl, 2,2-trichloroethoxycarbonyl, phthalimido, and any other group that can be introduced chemically onto a hydroxyl or amino functionality and later selectively removed either by chemical or enzymatic methods in mild conditions compatible with the nature of the product.

Methods for making a functionalized disaccharide or monosaccharide, including compounds having formula I, formula II, or formula III are also included in the invention. One embodiment of the method of making the disaccharide of formula I involves reacting the monosaccharide having formula III with tetrabutylammonium fluoride ($Bu_4NF$) under acid conditions to remove the anomeric protecting group at C-1, such as TBS or TDS, to yield a lactol. Alternatively, the anomeric protecting group (typically TDS or TBS) can be removed using HF/pyridine. The resulting lactol can be reacted with trichloroacetonitrile in the presence of sodium hydride to yield a trichloroacetimidate, which possesses trichloroacetimidate as leaving group at the anomeric C-1 carbon. The leaving group is not limited to trichloroacetimidate; any suitable leaving group can be used. Other suitable leaving groups that can be utilized at the anomeric center in accordance with the synthetic method of the invention include thioglycosides, glycosyl halides, anomeric sulfoxides, anomeric vinyl ethers, n-pentenyl glycosides, glycosyl phosphites, glycosyl phosphates, selenoglycosids (see, e.g., Handbook of Chemical Glycosylations, Edited by Alexei V. Demchenko, Wiley-VCH, 2008, ISBN 978-3-527-31780-6). Leaving groups are generally known in sugar chemistry; see for example, leaving group described in U.S. Pat. No. 5,393,878, issued Feb. 28, 1995. The resulting compound, which is activated at C-1 by inclusion of the leaving group, e.g., trichloroacetimidate, at the anomeric center, is reacted with a monosaccharide having formula II in an acid-mediated glycosylation reaction to yield a disaccharide having formula I.

Examples of the methods for making compounds of formulas I, II and III are found in the following Examples. Advantageously, compounds of formulas II and III can be synthesized from a common intermediate, e.g. compound 121 in Example III.

In a preferred embodiment of the functionalized disaccharide having formula I or the functionalized monosaccharides having formulas H or III, each of the plurality of protecting groups that are present at positions C-1 (the anomeric center), C-2, C-3, C-2', C-3' and/or C-4' is different from the others;

taken together, they constitute a set of orthogonal protecting groups, in that deprotection of the functional groups at each of those positions can proceed independently of the others. This allows the monosaccharide and disaccharide compounds of the invention to be selectively and sequentially modified with any lipid at C-2, C-3, C-2' and C-3'.

The invention accordingly includes a method for making a lipid A derivative that includes selective acylation of compounds having formulas I, II and III at any or all of C-2, C-3, C-2' and C-3'. An acylation step is accomplished by deprotecting the functionalized disaccharide or monosaccharide at one ring position, followed by acylating the ring at that position with the desired acyl group, typically a fatty acid or other lipid. Deprotection typically precedes acylation (i.e., they are accomplished in two successive steps) but they can in some instances be effected in a single chemical step. Successive acylations can generally be performed in any order. The skilled artwork can readily determine an order for the steps based upon the protection groups used and the acyl groups to be linked to the functionalized disaccharide or monosaccharide. It should be noted that in some instances introduction of an acyl chain at the C-3' position has been observed to lead to side products; therefore, it is preferred that the C-3' acyl chain be introduced at an earlier stage in the syntheses rather than a later stage.

Optionally the method for making a lipid A derivative further includes phosphorylating the compound of formula I or II at the C-1 position, which can be done either before, in between, or after the successive acylation steps but is preferably accomplished after completion of the acylation steps. Additionally or alternatively, the method for making a lipid A derivative optionally further includes phosphorylating the compound of formula I or III at the C-4' or C-4 position, respectively, either before, in between, or after the successive acylation steps. Preferably, phosphorylation at position C-4' (formula I) or C-4 (formula III) is accomplished after installing a fatty acid at the adjacent C-3'/C-3 position, respectively, because of the tendency of a 4-phosphate to migrate to the 3-hydroxyl. Preferably, the C-4' (formula I) or C-4 (formula III) position is protected, for example using an acetal that links the C-4'/C-4 position to the C-6'/C-6 position, until late in the synthetic process, at which point the phosphorylation step can be successfully accomplished. The resulting lipid A derivative can accordingly be unphosphorylated, monophosphorylated or bis-phosphorylated.

Additionally or alternatively, the method of making a lipid A derivative further includes, either before, in between, or after the successive acylation steps, contacting the compound having formula I or III, wherein $R^7$ is H, with a KDO donor in a glycosylation reaction at the C-6 or C-6' position of the compound having formula I or III to yield a KDO glycoside. The KDO donor molecule can be a monosaccharide or a disaccharide (KDO2). It should be understood that the invention includes the resulting intermediates and products formed in practicing the synthetic methods of the invention.

Also provided by the invention is a method for preparing a fatty acid, a fatty acid precursor or a fatty acid derivative. The fatty acid synthesis method utilizes an efficient cross metathesis to produce a fatty acid molecule terminating in an isopropyl group. Advantageously, the fatty acid molecules produced in accordance with the method can be used to acylate the functionalized monosaccharide and disaccharide of the invention to yield a desired lipid A derivative.

One embodiment of the fatty acid synthesis method encompasses the preparation of a 3-hydroxy fatty acid precursor having a terminal isopropyl group. The method includes: combining a compound of the formula $R=CHR^1$ (formula IV) with a compound of the formula $CH_2=CH(CH_2)_nC(O)CH_2C(O)OR^2$ (formula V) under conditions effective to form a cross metathesis product of the formula $R=CH(CH_2)_nC(O)CH_2C(O)OR^2$ (formula VI), wherein: R represents $(CH_3)_2C$ or $(CH_3)_2CH(CH_2)_mCH$; $R^1$ is hydrogen, methyl, or ethyl; $R^2$ is a C1-C10 alkyl (e.g., methyl or ethyl); m=0-12 (preferably O-2, and more preferably 1); and n=0-16 (preferably 4-12, more preferably 6-10, and even more preferably 8). In preferred embodiments, conditions effective to form a cross metathesis product can include the presence of a cross metathesis catalyst, which can be a transition metal complex (e.g., a ruthenium metal complex). In preferred embodiments, ruthenium carbene complexes such as those described in Libshutz et al, *Tetrahedron*, 64:6949-6954 (2008) can be used as cross metathesis catalysts.

Another embodiment of the fatty acid synthesis method encompasses the preparation of a 3-hydroxy fatty acid or fatty acid ester having a terminal isopropyl group. The method includes: providing a compound of the formula $R=CH(CH_2)_nC(O)CH_2C(O)OR^2$ (formula VI); reducing the ketone to an alcohol; reducing the double bond; and optionally hydrolyzing the ester to an acid; wherein: R represents $(CH_3)_2C$ or $(CH_3)_2CH(CH_2)_mCH$; $R^1$ is hydrogen, methyl, or ethyl; $R^2$ is a C1-C10 alkyl (e.g., methyl or ethyl); m=0-12 (preferably 0-2, and more preferably 1); and n=0-16 (preferably 4-12, more preferably 6-10, and even more preferably 8). In preferred embodiments, reducing the ketone is carried out under conditions effective to enantioselectively reduce the ketone. Exemplary conditions include reducing the ketone in the presence of an optically active catalyst and/or an optically active solvent. Exemplary optically active catalysts include, but are not limited to, ruthenium compounds such as those of the formula [(R)-2,2'-bis(diphenylphosphino)-1,1'-binaphthyl]RuCl$_2$. The steps of reducing the double bond and optionally hydrolyzing the ester to an acid can be carried out using conventional reagents under standard conditions.

Figure 8:
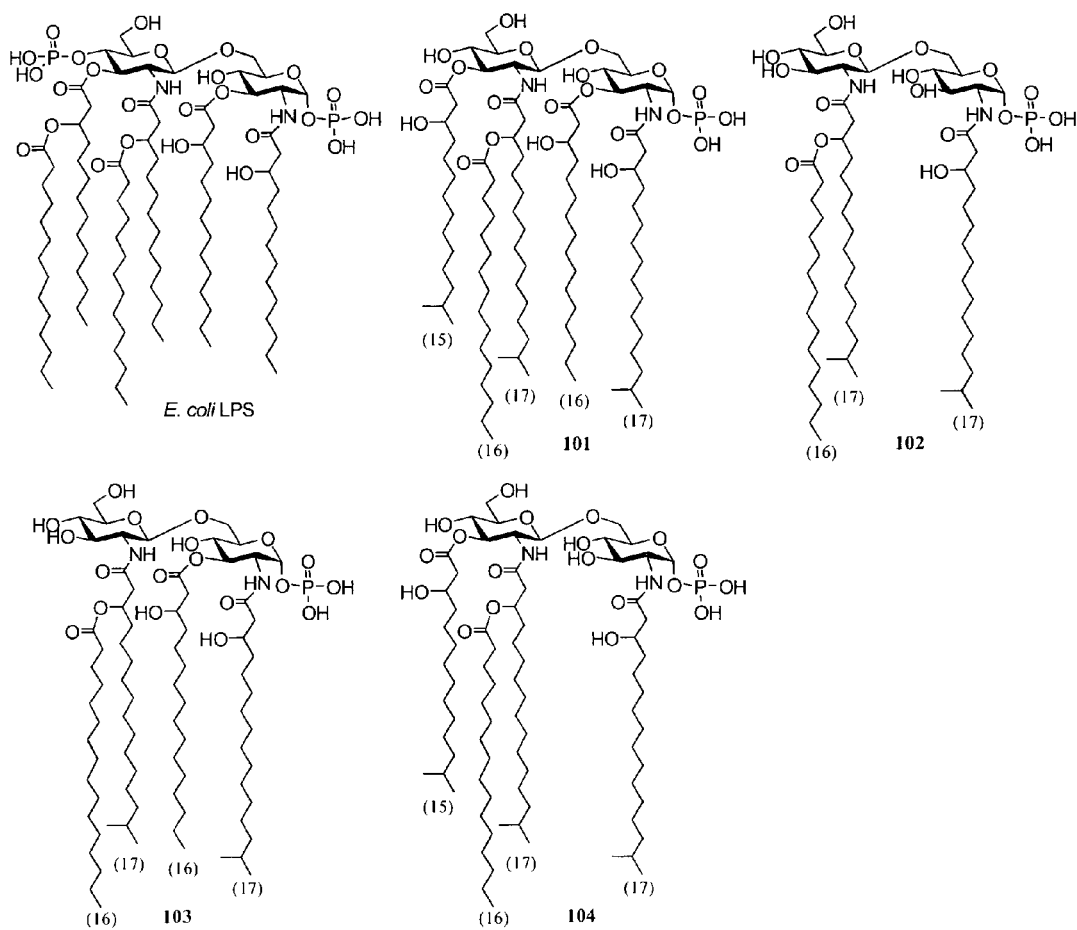
FIG. 8 shows structures of *E. coli* and *P. gingivalis* lipid A derivatives. The number of acyl chain carbon atoms, plus the terminal methyl group, where present, are shown in parentheses.

The invention further provides an isolated, synthetic lipid A derivative. As used herein, the term "lipid A derivative" encompasses a disaccharide of glucosamine derivatized with between two and eight fatty acyl chains. A lipid A derivative can be naturally occurring or non-naturally occurring. That is, the term "lipid A derivative" is inclusive of synthetic lipid As that are chemically identical to lipid As that are naturally occurring, and it also includes non-naturally occurring lipid A structures such as those obtainable by chemical or enzymatic synthesis. Acylation is present at positions C-2, C-3, C-2' and/or C-3' of the disaccharide. A lipid A may contain up to 8 fatty acyl chains due to the presence of a branched fatty acid at any or all of the four acylation positions on the disaccharide backbone. See, for example, *E. coli* lipid A (1, FIG. 1) which is hexa-acylated. The fatty acyl chains can vary in the number of carbons. The number of carbons in a fatty acyl chain typically falls between four and 28 carbons per chain. The number of carbon atoms in a fatty acyl chain is typically an even number, however a fatty acyl chain can contain an odd number of carbons if, for example, it terminates in an isopropyl group (see, for example, FIG. 8). Preferably the fatty acyl chains contain between 8 and 18 carbon atoms. The fatty acyl chains are preferably saturated, but they may be monounsaturated or polyunsaturated. Optionally, a lipid A derivative is phosphorylated. Phosphorylation preferably occurs at either of both of the C-1 position of the C-4' position. Also optionally, a lipid A derivative includes at least one 3-deoxy-D-manno-oct-2-ulosonic acid (KDO) moiety. The KDO moiety, or KDO$_2$ moiety, if present, is preferably positioned at the C-6' position. A preferred lipid A derivative is one that contains only one KDO moiety (i.e., a KDO monomer) at position C-6'.

Examples of lipid A derivatives include compounds 1, 2, 3, 4, 5, 51, 53, 101, 102, 103 and 104.

The invention further provides methods for using synthetic lipid A derivatives. For example, synthetic lipid A derivatives can be used in medical applications, which may be prophylactic or therapeutic. In one embodiment, a synthetic lipid A derivative can act as antagonist or inhibitor of cytokine production or secretion, as for example induced by enteric LPS. The invention accordingly provides a method for administering an effective amount of an antagonistic lipid A to a subject to treat or prevent conditions characterized by overactivation of a subject's immune system, such as Gram-negative septicemia or septic shock. Structurally, an antagonistic or inhibitory lipid A derivative preferably contains one or more longer fatty acyl chains (preferably more than 14 carbon atoms, more preferably more than 16 carbon atoms). Additionally or alternatively, an antagonistic or inhibitory lipid A derivative preferably contains at least one branched fatty acid. Examples of antagonistic lipid A derivatives having at least one longer fatty acyl chain and at least one branched fatty acid are compounds 103 and 104 in Example III.

In another embodiment, a synthetic lipid A derivative can activate or stimulate the immune system of a subject, thereby having potential for use as an immune modulator. In this embodiment, the lipid A derivative functions as an agonist which induces cytokine production or secretion. The invention therefore further encompasses the use of a lipid A derivative to treat disease or as a component of a therapeutic or prophylactic vaccine. The synthetic lipid A derivative can be used a primary therapeutic to treat a wide range of diseases or it can be included in a vaccine as an adjuvant. As illustrated in Example II, a synthetic lipid A with one or more shorter fatty acyl chains, compared to a naturally occurring lipid A, exhibits increased potency and immune stimulation activity. In this context, a shorter fatty acyl chain is a fatty acyl chain that contains less than 14 carbon atoms, preferably a fatty acyl chain that contains 8, 10 or 12 carbon atoms. Also as illustrated in Example II, it has been discovered that only one KDO moiety (i.e., a KDO monomer) at position C-6' is needed for robust induction of cytokine activity, such as TNF-α and IFN-β activity, even if the corresponding naturally occurring lipid A includes a KDO dimer at that ring position.

The invention accordingly provides a pharmaceutical composition that contains, as the active agent, a lipid A derivative in a therapeutically effective amount. Examples of lipid A derivatives that can be included in the pharmaceutical composition include compounds 103 and 104 as described herein. Alternatively or additionally, the pharmaceutical composition can include one or more other antagonistic lipid A molecules including lipid IVa (e.g., Saitoh et al., *Internat'l. Immunol.* 16(7) 961-969, 2004) and synthetic analogs based on the lipid A of *Rhodobacter sphaeroides* or *R. capsulatus* (e.g., Rose et al., Infect Immun. 63(3): 833-839, 1995). Optionally the pharmaceutical composition includes a pharmaceutically acceptable carrier. The potency of the lipid A derivative, when used as an active agent to inhibit or antagonize cytokine production induced, for example, by a pathogenic agent or an internal condition such as an autoimmune or autoinflammatory response in the subject, can be described by its $IC_{50}$ value. The $IC_{50}$ of a lipid A derivative is the concentration of the lipid A derivative that produces a 50% inhibition of cytokine production induced by *E. coli* LPS. The $IC_{50}$ value for a lipid A derivative can be determine using, for example, an assay as described in the following examples. When administered as an inhibitor or agonist, the lipid A derivative preferably exhibits an $IC_{50}$ of less than about 10 micromolar (μM). An effective amount of a lipid A derivative administered to subject as an active agent is an amount of compound expected to produce a therapeutic response in the subject. For example, an effective amount can be the amount needed to obtain serum levels of the lipid A derivative sufficient to induce or inhibit cytokine production, as desired. The total daily dose administered to a subject in single or divided doses is readily determined by a skilled clinician and may be in amounts, for example, from 0.001 to 10 mg/kg body weight daily and more usually 0.01 to 1 mg. Dosage unit compositions may contain such amounts or submultiples thereof to make up the daily dose.

Also provided by the invention is a pharmaceutical composition that includes, as a first component, an effective amount of an active agent other than a lipid A derivative and, as a second component, a lipid A derivative. Optionally the pharmaceutical composition includes a pharmaceutically acceptable carrier. In this embodiment of the pharmaceutical composition, the lipid A derivative is administered as an adjuvant. The first component, i.e., the active agent, can include any therapeutic agent, or multiple therapeutic agents, without limitation, since the function of the lipid A derivative in this embodiment of the pharmaceutical composition is that of an auxiliary, immune-stimulating compound. In a preferred embodiment, the active agent is an antigen or an immunogen. Pharmaceutical compositions that include an antigen or immunogen as the active agent are referred to herein as vaccines. Suitable antigen or immunogens for the vaccine compositions of the invention include any entity capable of producing an antibody or cell-mediated immunological response directed specifically against that entity in a subject exposed to the antigen or immunogen. One or more antigens or immunogens may be employed. An effective amount of antigen or immunogen is an amount of antigen that, when administered to a subject such as an animal or a human, evokes an immune response as measured by production of specific antibodies or cell-mediated effector mechanisms. Immunologically effective amounts of antigens or immunogens are in general from about 1 μg or less to 5 mg. The antigen or immunogen may be derived from pathogenic micro-organisms including viruses, bacteria, mycoplasmas, fungi, protozoa and other parasites. Further, the antigen or immunogen may be derived from sources other than microorganisms, for example, cancer cells or allergens. The antigen may constitute all or part of a pathogenic microorganism, or all or part of a protein, glycoprotein, glycolipid, polysaccharide or lipopoly-saccharide which is associated with the organism, or the antigen or antigens may be a polypeptide or other entity which mimics all or part of such a protein; glycoprotein, glycolipid, polysaccharide or lipopolysaccharide. Pathogenic microorganisms from which antigens or immunogens may be produced or derived for vaccine purposes are well known in the field of infectious diseases, as listed in, for example, Medical Microbiology, Second Edition, (1990) J. C. Sherris (ed.), Elsevier Science Publishing Co., Inc., New York, and Zinsser Microbiology, 20th Edition (1992), W. K. Joklik et al. (eds.), Appleton & Lange Publishing Division of Prentice Hall, Englewood Cliffs, N.J. Examples of organisms of interest for human vaccines include *Chlamydia*, Nontypeable *Haemophilus influenzae*, *Helicobacter pylori*, *Moraxella catarrhalis*, *Neisseria gonorrhoeae*, *Neisseria meningitidis*, *Salmonella typhi*, *Streptococcus pneumoniae*, Group A *Streptococcus*, Group B *Streptococcus*, Herpes Simplex Virus, Human Immunodeficiency Virus, Human Papilloma Virus, Influenza, Measles, Parainfluenza, Respiratory Syncytial Virus, Rotavirus, Norwalk Virus, and others. The antigen or immunogen may include glycoconjugates which comprise polysaccharide antigen or antigens, for example, bacterial capsular polysaccharide or fragment thereof, chemically linked to a protein carrier molecule in order to enhance immunogenicity. Methods for preparing conjugates of bacterial capsular polysaccharide and protein carrier molecules are well known in the art and can be found, for example, in Dick and Burret, Contrib Microbiol Immunol. 10:48-114 (Cruse J M, Lewis R E Jr., eds; Basel Kruger (1989). Suitable conjugates, including pneumococcal glycoconjugate, are described in greater detail in U.S. Pat. Nos. 4,673,574, 4,761,283, 4,902,506, 5,097,020 and U.S. Pat. No. 5,360,897.

The potency of the lipid A derivative, when used as an adjuvant or agonist to stimulate cytokine production, can be described by its $EC_{50}$ value. The $EC_{50}$ of a lipid A derivative is the concentration of the lipid A derivative at which 50% of the activity is produced. The $EC_{50}$ value for a lipid A derivative can be determine using, for example, an assay as described below, in the examples. When administered to stimulate cytokine production (e.g., as an adjuvant or agonist), the lipid A derivative preferably exhibits an $EC_{50}$ of less than about 100 nanomolar (100 nM). In a vaccine composition, an effective amount of a lipid A derivative adjuvant is an amount that, when added to the vaccine, will enhance the magnitude or quality or duration of the immune response to the antigen(s) or immungen(s) in the vaccine. An effective amount of lipid A derivative for use as an adjuvant is in the range of about 1 μg to about 1 mg. See, e.g., LaPosta et al., *US Pat Pub* 20020025330 published Feb. 28, 2002.

The pharmaceutical composition of the invention optionally further includes, in addition to the lipid A derivative, any adjuvant or mixture of adjuvants known to one skilled in the art that capable of boosting or enhancing the immune response in the subject. Examples of other adjuvants are well known to those skilled in the art and include, without limitation, nonionic block polymers, aluminum hydroxide or aluminum phosphate adjuvant, and mixtures thereof.

The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts. Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V). In addition, if desired, the pharmaceutical composition may contain minor amounts of auxiliary substances such as wetting or emulsifying agents, pH buffering agents, and/or adjuvants which enhance the effectiveness of the immune-stimulating composition.

In a preferred embodiment of the pharmaceutical composition of the invention, the lipid A derivative is incorporated into a delivery vehicle. Useful delivery vehicles include, but are not limited to, biocompatible-biodegradable, or biocompatible-nonbiodegradable liposomes, liposphere, polymers, and slow release devices such as microspheres or microcapsules, and combinations thereof. Methods of manufacturing and using liposomes are found, for example, in Alving et al. (Preparation and Use of Liposomes in Immunological Studies, Liposome Technology, Vol. II, pages 157-175 (1984)), and Alving et al. (Preparation and Use of Liposomes in Immunological Studies, Liposome Technology, 2nd Edition, Vol. III, pages 317-343 (1993)). Liposomes can be prepared for injection as taught by Swartz et al. (Antibodies to cholesterol. Proc. Nat. Acad. Sci. 85:1902-1906, 1988) and Alving et al. (U.S. Pat. No. 4,885,256 issued Dec. 5, 1989). See Alving et al. US Pat. Pub. 20020018808, published Feb. 14, 2002.

The pharmaceutical composition of the invention can be administered to a plant or an animal, preferably a vertebrate, more preferably a mammal. Suitable subjects include a human subject as well as veterinary subjects such as a primate, horse, cow, pig, sheep, goat, dog, cat, bird and rodent. The term "subject", as used herein, includes any plant or animal. The pharmaceutical composition is administered to a subject, such as a human, in a variety of forms adapted to the chosen route of administration. The formulations include those suitable for oral, rectal, vaginal, topical, nasal, ophthalmic or parenteral (including subcutaneous, intramuscular, intraperitoneal and intravenous) administration. Formulations suitable for parenteral administration conveniently comprise a sterile aqueous preparation of the active compound, or dispersions of sterile powders comprising the active compound, which are preferably isotonic with the blood of the recipient. Isotonic agents that can be included in the liquid preparation include sugars, buffers, and sodium chloride. Solutions of the active compound can be prepared in water, optionally mixed with a nontoxic surfactant. Dispersions of the active compound can be prepared in water, ethanol, a polyol (such as glycerol, propylene glycol, liquid polyethylene glycols, and the like), vegetable oils, glycerol esters, and mixtures thereof. The ultimate dosage form is sterile, fluid and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active compound, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active compounds over a prolonged period can be achieved by including agents for delaying, for example, aluminum monostearate and gelatin.

Synthetic lipid A derivatives are also useful in scientific studies, such as those designed to elucidate the innate immune responses elicited by Gram-negative bacteria and consequently their contributions to various diseases, such as periodontal disease caused by *P. gingivalis*. The convergent synthesis and orthogonal protection strategies provide easy access to a wide range of lipid A derivatives for structure/activity relationship (SAR) studies.

The present invention is illustrated by the following examples. It is to be understood that the particular examples, materials, amounts, and procedures are to be interpreted broadly in accordance with the scope and spirit of the invention as set forth herein.

EXAMPLES

Example 1

Modulation of Innate Immune Responses with Synthetic Lipid A Derivatives

The lipid A moiety of lipopolysaccharides (LPS) initiates innate immune responses by interacting with Toll-like receptor 4 (TLR4) which results in the production of a wide range of cytokines. Derivatives of lipid A show potential for use as immuno-modulators for the treatment of a wide range of diseases and as adjuvants for vaccinations. Development to these ends requires a detailed knowledge of patterns of cytokines induced by a wide range of derivatives. This information is difficult to obtain by using isolated compounds due to structural heterogeneity and possible contaminations with other inflammatory components. To address this problem, we have developed a synthetic approach that provides easy access to a wide range of lipid As by employing a common disaccharide building block functionalized with a versatile set of protecting groups. The strategy was employed for the preparation of lipid As derived from *E. coli* and *S. typhimurium* (Zhang et al., April 2007 *J. Am. Chem. Soc.* 129:5200-5216; Supporting Information for Zhang et al., April 2007 *J. Am. Chem. Soc.* 129:5200-5216 available at the American Chemical Society site on the World Wide Web at pubs.acs.org/subscribe/journals/jacsat/suppinfo/ja068922a/ja068922asi20070228_031652.pdf) Mouse macrophages were exposed to the synthetic compounds and *E. coli* 055:B5 LPS and the resulting supernatants examined for tumor necrosis factor alpha (TNF-α), interferon beta (IFN-β), interleukin 6 (IL-6), interferon-inducible protein 10 (IP-10), RANTES, and IL-1β It was found that for each compound, the potencies ($EC_{50}$ values) for the various cytokines differed by as much as 100-fold. These differences did not follow a bias towards a MyD88- or TRIF-dependent response. Instead, it was established that the observed differences in potencies of secreted TNF-α and IL-1β were due to differences in the processing of respective pro-proteins. Examination of the efficacies (maximum responses) of the various cytokines showed that each synthetic compound and *E. coli* 055:B5 LPS induced similar efficacies for the production of IFN-β, and IP-10. However, lipid As 1-4 gave lower efficacies for the production of RANTES and IL-6 compared to LPS. Collectively, the presented results demonstrate that cytokine secretion induced by LPS and lipid A is complex, which can be exploited for the development of immuno-modulating therapies.

We have developed an efficient synthetic approach whereby an advanced synthetic disaccharide can easily be converted into lipid A analogs that differ in phosphorylation and acylation pattern. This strategy has been employed for the preparation of lipid As derived from *E. coli* and *S. typhimurium*. Mouse macrophages were exposed to the synthetic compounds and *E. coli* 055:B5 LPS and the resulting supernatants examined for mouse TNF-α, IFN-β, IL-6, IP-10, RANTES, and IL-1β. It has been found that particular modifications had different effects on the potencies and efficacies of induction of the various cytokines. However, no bias towards a MyD88- or TRIF-dependent response was observed. Thus, for the first time, it has been shown that lipid A derivatives can modulate innate immune responses in a complex manner.

Results and Discussion

Chemical Synthesis of Lipid As. To determine whether the structure of lipid A can modulate innate immunological responses, we have synthesized derivatives 1-5 (FIG. 1) by a highly convergent approach. Compound 1 is a prototypical lipid A from *E. coli*, and is hexa-substituted in an asymmetrical fashion. Compound 2 is derived from compound 1, but several of its acyl groups have been shortened. Compounds 3, 4, and 5 are hepta-acylated lipid As derived from *S. typhimurium* LPS that differ in lipid length and phosphorylation pattern (Kawasaki et al., *J. Biol. Chem.* 2004, 279, 20044-20048; Wick, *Curr. Opin. Microbiol.* 2004, 7, 51-57; Guo et al., *Science* 1997, 276, 250-253; Kanegasaki et al., *J. Biochem.* 1986, 99, 1203-1210).

Previously reported approaches for lipid A synthesis employed strategies whereby monosaccharides were functionalized with lipids and phosphates, which were then used as glycosyl donors and acceptors for disaccharide synthesis, which after anomeric phosphorylation and deprotection provided target compounds (Erridge et al., *Microbes Infect.* 2002, 4, 837-851; Kusumoto, In *Molecular Biochemistry and Cellular Biology*; CRC Press: Boca Raton, 1992; Vol. 1, Bacterial Endotoxin Lipopolysaccharides; Chapter 9, Chemical Synthesis of Lipid A, p 81-105; Kusumoto, S.; Fukase, K.; Oikawa, M. In *Endotoxin in Health and Disease*; Brade, H., Ed.; Marcel Dekker: New York, 1999, p 243-256). Although this approach is attractive for one-compound-at-a-time synthesis, detailed structure-activity relationship studies require a synthetic approach that offers in a straightforward manner a panel of lipid As. The strategy that we have developed employs the advanced disaccharide intermediate 13, which can selectively be modified with any lipid at C-2, C-3, C-2' and C-3'. A key feature of 13 is the use of the allyloxycarbonate (Alloc), the anomeric t-butyldimethyl silyl ether (TBDMS), and the (9-fluorenylmethoxycarbamate (Fmoc) and azido as a set of functional groups that in a sequential manner can be deprotected or unmasked to allow selective lipid modification at each position. It was envisaged that disaccharide 13 could easily be prepared by a regio- and stereoselective glycosylation of trichloroacetimidate 12 with glycosyl acceptor 8. In this glycosylation, the higher glycosyl accepting reactivity of the primary C-6 hydroxyl of 8 compared to its secondary C-3 hydroxyl, and the ability of the Fmoc carbamate of 12 to control the β-anomeric configuration by neighboring group participation (Fukase et al., *Tetrahedron Lett.* 1995, 36, 8645-8648), was exploited.

Scheme 1[a]

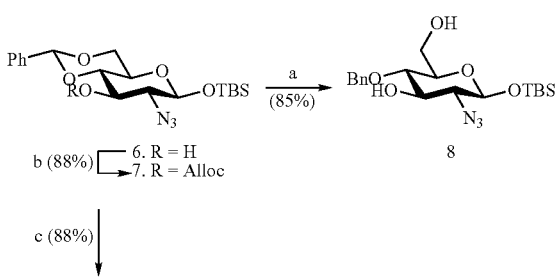

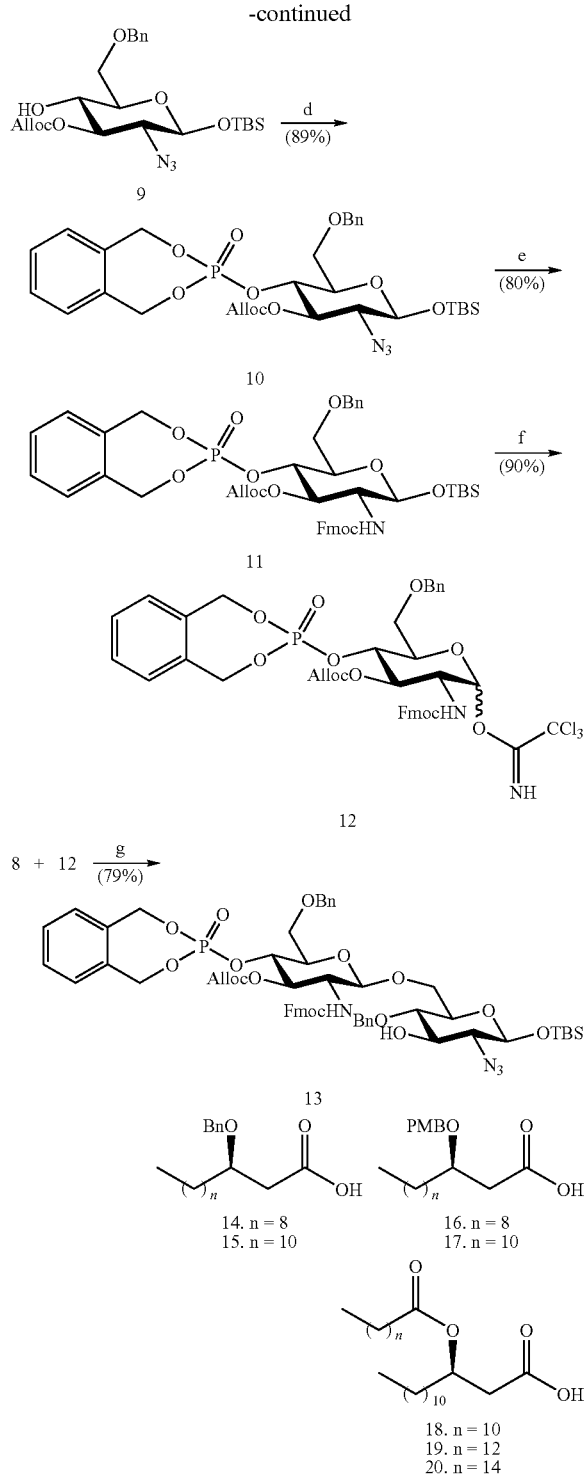

Glycosyl acceptor 8 and donor 12 could easily be prepared from common intermediate 6 (Scheme 1). Thus, a regioselective reductive opening of the benzylidene acetal of 6 using borane-THF complex in the presence of the bulky Lewis acid Bu$_2$BOTf gave glycosyl acceptor 8 as the only regio-isomer. Alternatively, the C-3 hydroxyl of 6 (Lee et al., *ChemBioChem* 2006, 7, 140-148) could be protected by an Alloc group by treatment with Alloc chloride in the presence of N,N,N',N'-tetramethylethylenediamine (TMEDA) in DCM to give 7 in a yield of 88%. Regioselective reductive opening of the benzylidene acetal of 7 using NaCNBH$_3$ and HCl in diethyl ether gave 9 (Garegg et al., *Carbohyd. Res.* 1982, 108, 97-101), which after phosphitylation with N,N-diethyl-1,5-dihydro-2,3,4,-benzodioxaphosphepin-3-amine in the presence of 1H-tetrazole followed by in-situ oxidation with m-chloroperoxybenzoic acid (mCPBA) (Watanabe et al., *Tetrahedron Lett.* 1990, 31, 255-256), provided the phosphotriester 10. Next, the azido function of 10 was reduced using activated Zn in a mixture of acetic acid and DCM to give an amine, which was immediately protected as an Fmoc carbamate by reaction with 9-fluorenylmethyl chloroformate (FmocCl) in the presence of N,N-diisopropylethylamine (DIPEA) in DCM to give fully protected 11. Removal of the anomeric TBDMS ether of 11 by treatment with HF in pyridine followed by conversion of the resulting anomeric hydroxyl into a trichloroacetimidate by reaction with trichloroacetonitrile in the presence of a catalytic amount of NaH (Patil, *Tetrahedron Lett.* 1996, 37, 1481-1484), afforded glycosyl donor 12 in an overall yield of 90%. A trimethylsilyl trifluoromethanesulfonate (TMSOTf)-mediated glycosylation of the trichloroacetimidate 12 with glycosyl acceptor 8 in dichloromethane gave the selectively protected disaccharide 13 in a yield of 79% as only the β-anomer. The alternative regioisomer resulting from glycosylation of the C-3 hydroxyl or the trisaccharide arising from glycosylation of both hydroxyls of 8 was not observed. The acyloxy- and acyloxyacyl lipids 14-20 were prepared by a reported procedure (Keegan et al., *Tetrahedron: Asymmetry* 1996, 7, 3559-3564).

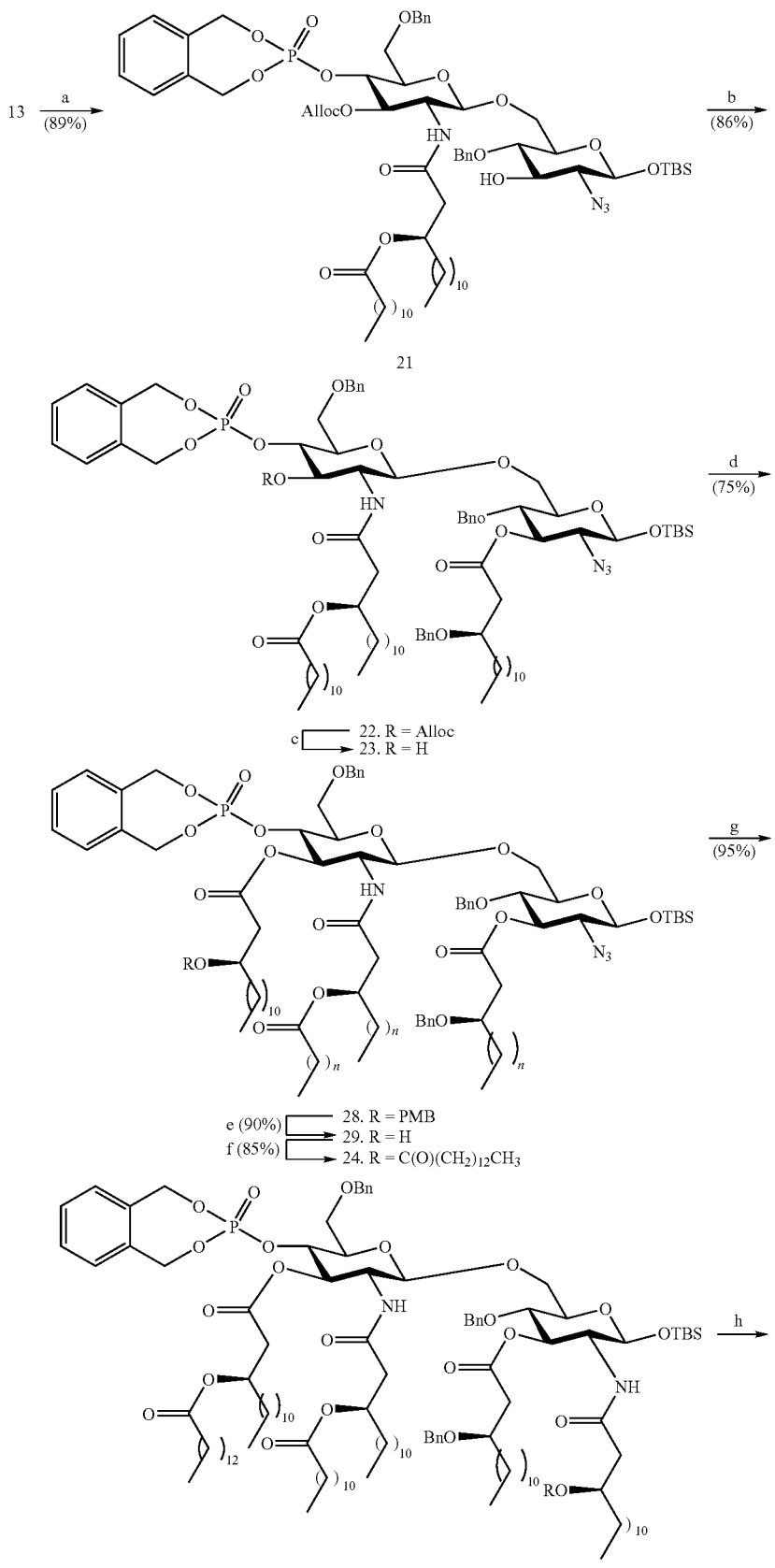

Figure 2:
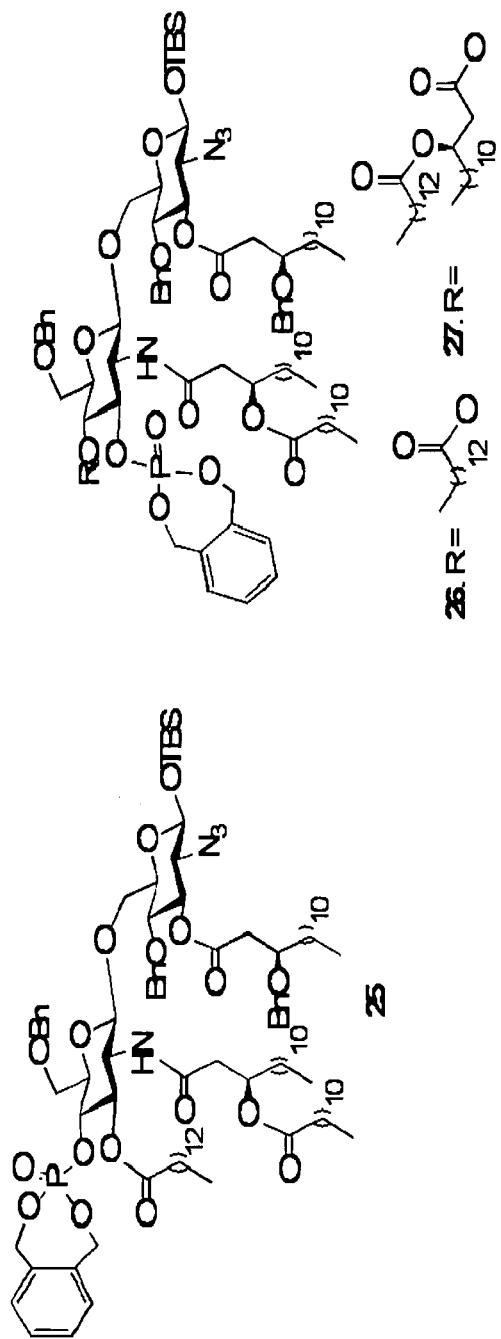
FIG. 2 shows the chemical structures of compounds 25-27.

Having the advanced disaccharide 13 and lipids 14-20 at hand, attention focused on the selective acylation of relevant hydroxyls and amines (Scheme 2). Thus, removal of the Fmoc protecting group of 13 using 1,8-diazabicyclo[5.4.0]undec-7-ene (DBU) in DCM followed by acylation of the resulting amino group with (R)-3-dodecanoyl-tetradecanoic acid (18) using 1,3-dicyclohexylcarbodiimide (DCC) as the activation reagent gave compound 21. Next, the C-3 hydroxyl of 21 was acylated with (R)-3-benzyloxy-tetradecanoic acid (15) using DCC and 4-dimethylaminopyridine (DMAP) (Demchenko et al., *J. Am. Chem. Soc.* 2003, 125, 6103-6112) to give 22 in a yield of 86%. The latter two reactions exploited the finding that an amine can selectively be acylated in the presence of a free hydroxyl using DCC as the activator. The addition of DMAP provides, however, a more reactive reagent and can acylate a less nucleophilic hydroxyl. The removal of the Alloc protecting group of 22 could easily be accomplished by treatment with Pd(PPh$_3$)$_4$ (Tsukamoto et al., *Biosc. Biotech. Biochem.* 1997, 61, 1650-1657); however, the acylation of the resulting hydroxyl of 23 with (R)-tetradecanoyltetradecanoic acid (19) using standard conditions did not, unexpectedly, lead to the formation of 24. Instead compounds 25, 26, and 27 were identified (FIG. 2). The formation of these compounds can be rationalized by migration of the phosphotriester to the C-3' position and elimination of the acyloxy chain of (R)-3-tetradecanoyl-tetradecanoic acid to give tetradecanoic acid and tetradec-2-enoic acid. It is proposed that compound 25 arises from acylation of the starting material with tetradecanoic acid whereas compounds 26 and 27 result from phosphotriester migration followed by acylation with tetradecanoic acid or 19, respectively. To circumvent these side reactions, the (R)-3-tetradecanoyl-tetradecanoyl ester was introduced by a three-step procedure using (R)-3-(p-methoxy)benzyloxy-tetradecanoic acid (17) as the initial acylation reagent. It was reasoned that the (p-methoxy)benzyl (PMB) ether of 17 would be less susceptible to elimination and hence the formation of the elimination product should be suppressed. Furthermore, the higher reactivity of ether protected 17 may also suppress phosphate migration. After installment of the (R)-3-(p-methoxy)benzyloxytetradecanoic ester and selective removal of the PMB ether, the β-hydroxy functionality can be acylated to provide the required compound. Thus, treatment of 23 with 17 in the presence of DCC and DMAP to give 28 followed by removal of the PMB ether using 2,3-dichloro-5,6-dicyano-1,4-benzoquinone (DDQ) in a mixture of DCM and water in the dark, and acylation of the resulting β-hydroxyl of 29 with myristoyl chloride in the presence of pyridine and DMAP afforded 24. Although the three-step procedure to convert 23 into 24 is more laborious than direct acylation with an acyloxyacyl acid, it offers an opportunity to devise a range of compounds that differ in β-hydroxy acylation at the C-3' position. Next, the azido function of 24 was reduced with activated Zn in a mixture of acetic acid and DCM and the amine of the resulting compound was reacted with 15 or 20 in the presence of DCC to give 30 and 31, respectively. Then, attention was focused on the introduction of the anomeric phosphate and removal of the permanent protecting groups. Thus, the anomeric TBS ether of 30 and 31 was removed by treatment with HF in pyridine, conditions that do not affect the acyl and acyloxyacyl esters and the phosphodiester, to give 32 and 33, respectively. These derivatives were phosphorylated using tetrabenzyl diphosphate in the presence of lithium bis(trimethyl)silylamide in THF at −78 C to give (Oikawa et al., *S. Bull. Chem. Soc. Jpn.* 1999, 72, 1857-1867), after purification using Iatro beads, 34 and 35 as only α-anomers. Global deprotection of 34 and 35 by catalytic hydrogenolysis over Pd-black gave the requisite lipid As 1 and 3, respectively.

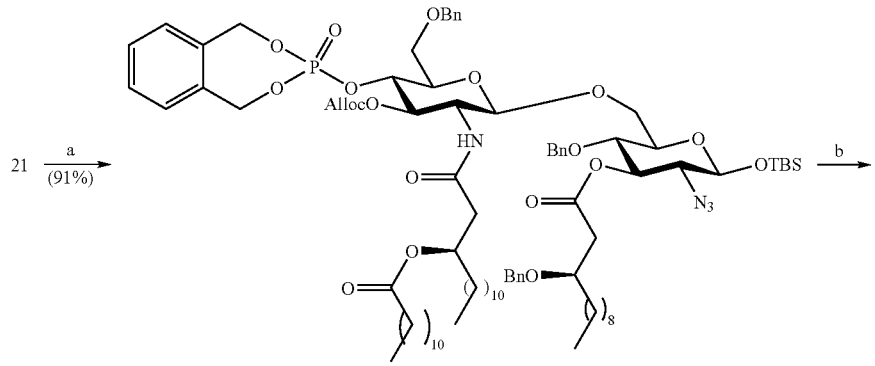

Scheme 3$^a$

-continued

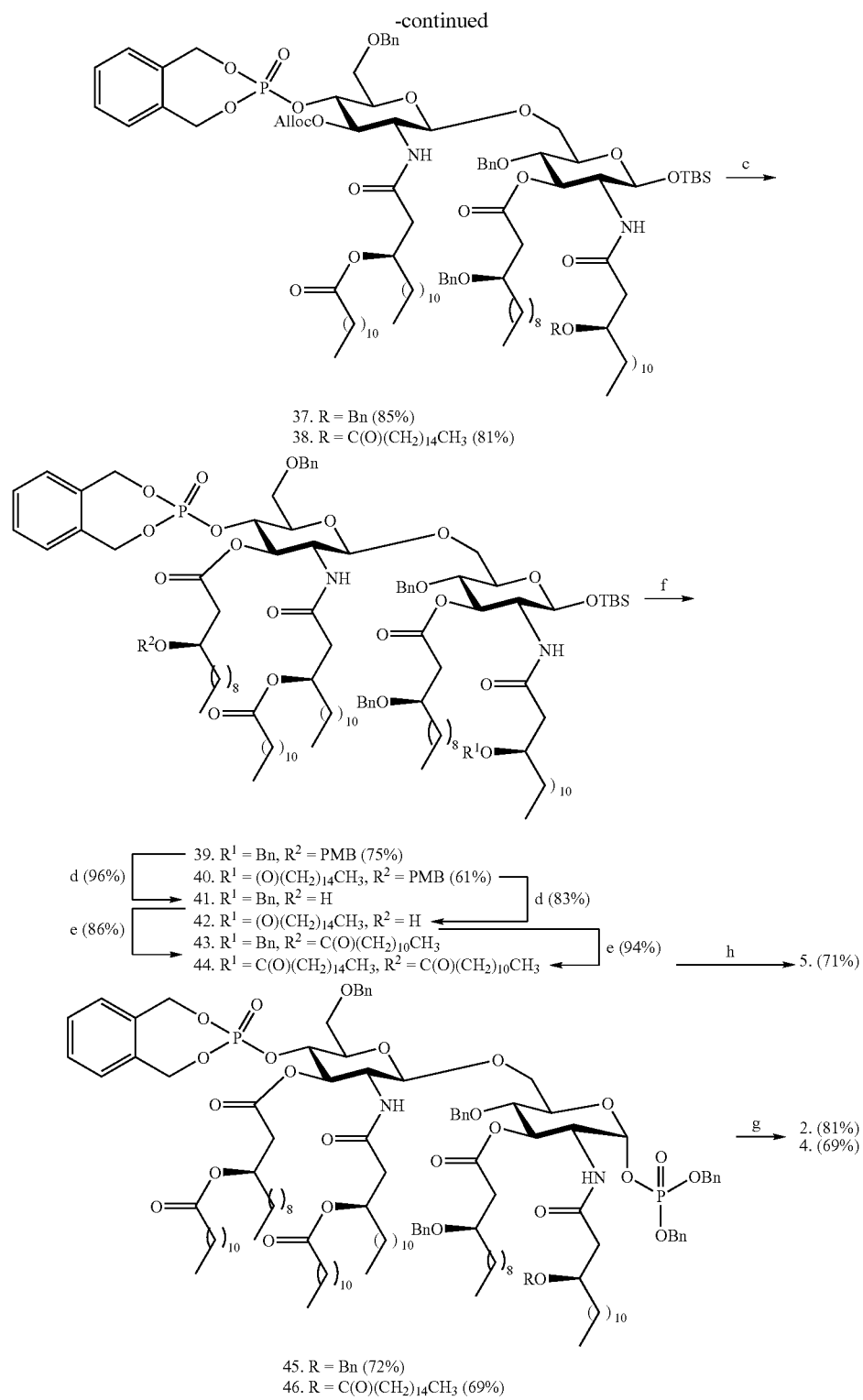

37. R = Bn (85%)
38. R = C(O)(CH$_2$)$_{14}$CH$_3$ (81%)

39. R$^1$ = Bn, R$^2$ = PMB (75%)
d (96%) ⎡ 40. R$^1$ = (O)(CH$_2$)$_{14}$CH$_3$, R$^2$ = PMB (61%) ⎤
        ⎣→ 41. R$^1$ = Bn, R$^2$ = H                          ⎦ d (83%)
e (86%) ⎡ 42. R$^1$ = (O)(CH$_2$)$_{14}$CH$_3$, R$^2$ = H ◄—
        ⎣→ 43. R$^1$ = Bn, R$^2$ = C(O)(CH$_2$)$_{10}$CH$_3$  ⎤ e (94%)  h → 5. (71%)
           44. R$^1$ = C(O)(CH$_2$)$_{14}$CH$_3$, R$^2$ = C(O)(CH$_2$)$_{10}$CH$_3$ ◄— g → 2. (81%)
    4. (69%)

45. R = Bn (72%)
46. R = C(O)(CH$_2$)$_{14}$CH$_3$ (69%)

$^a$ Reagents and conditions: (a) (R)-3-benzyloxy-dodecanoic acid 14, DCC, DMAP, DCM; (b) Zn/HOAc, DCM; then RCOOH, DCC, DCM; (c) Pd(PPh$_3$)$_4$, HCO$_2$H, n-BuNH$_2$, THF; then (R)-3-(p-methoxy)benzyloxy-dodecanoic acid 16, DCC, DMAP, DCM; (d) DDQ, H$_2$O, DMC; (e) lauroyl chloride, pyridine, DMAP, DCM; (f) HF/Pyridine; then tetrabenzyl diphosphate, LiN(TMS)$_2$, THF, -78° C.; (g) H$_2$(50psi), Pd-black, THF; (h) HF/pyridine; then H$_2$ (50psi), Pd-black, THF.

Lipid As 1 and 3 were prepared by first removal of the Alloc protecting group of 22 and acylation of the resulting hydroxyl followed by reduction of the azido moiety and modification of the corresponding amine. To study the orthogonality of the Alloc and azido function, compounds 2, 4, and 5 were prepared by an alternative sequence of reactions involving reduction of the azido function and modification of the C-2 amine before deprotection of Alloc group and acylation of the resulting C-3' hydroxyl (Scheme 3). Thus, the C-3 hydroxyl of 21 was acylated with 14 using DCC and DMAP to give 36 in a yield of 91%. Next, the azido moiety of 36 was reduced with activated Zn in a mixture of acetic acid and DCM without affecting the Alloc group to provide an intermediate amine, which was immediately acylated with (R)-3-benzyloxy-dodecanoic acid (14) or (R)-3-tetradecanoyl-hexadecanoic acid (20), using DCC as the activating system, to give 37 and 38, respectively. Next, Pd(0) mediated removal of the Alloc group of 37 and 38, followed by acylation of the resulting hydroxyl with (R)-3-(p-methoxy)benzyloxy-dodecanoic acid (16) in the presence of DCC/DMAP gave 39 and 40, which after treatment with DDQ to remove the PMB ether were acylated with lauroyl chloride to give fully acylated 43 and 44, respectively in a good overall yield. Finally, cleavage of the anomeric TBS ether of 43 and 44 was performed under standard conditions to give intermediate lactols, which were phosphorylated using tetrabenzyl diphosphate in the presence of lithium bis(trimethyl)silylamide to give 45 and 46. Deprotection of the latter compounds by catalytic hydrogenolysis over Pd-black gave lipid A derivatives 2 and 4. Monophosphoryl derivative 5 could easily be obtained by standard deprotection of the intermediate lactol.

Biological Evaluation of Lipid As and LPS. Based on the results of recent studies (Pasare and Medzhitov, *Seminars Immunol.* 2004, 16, 23-26; Akira et al., *T. Nat. Immunol.* 2001, 2, 675-680) it is clear that LPS-induced cellular activation through TLR4 is complex as many signaling elements are involved. However, it appears that there are two distinct initiation points in the signaling process, one being a specific intracellular adaptor protein called MyD88 and the other an adaptor protein called TRIF which operates independently of MyD88. It is well established that TNF-α secretion is a prototypical measure for activation of the MyD88-dependent pathway, whereas secretion of IFN-β is commonly used as an indicator of TRIF-dependent cellular activation. There are some indications that structurally different lipid As can differentially utilize signal transduction pathways leading to complex patterns of proinflammatory responses. Heterogeneity in lipid A of particular bacterial strains as well as possible contamination with other inflammatory components of the bacterial cell-wall complicates the use of either LPS or lipid A isolated from bacteria to dissect the molecular mechanisms responsible for the biological responses to specific lipid As. To address these issues, we have examined the well-defined compounds 1-5 and *E. coli* LPS for the ability to initiate production of a wide range of cytokines, including TNF-α, INF-β, IL-6, IP-10, RANTES, and IL-1β. It was anticipated that analysis of potencies and efficacies of the mediators would establish whether structural differences in lipid A can modulate inflammatory responses.

Figure 3A:
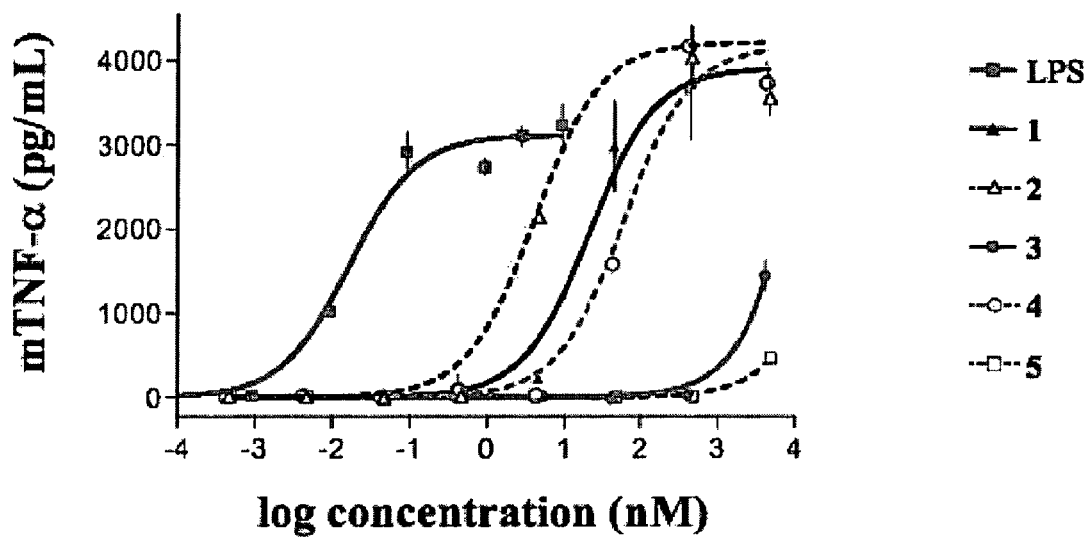
FIG. 3 shows TNF-α and IFN-β production by murine macrophages after stimulation with LPS and lipid A derivatives. Murine RAW γNO(−) cells were incubated for 5.5 hours (h) with increasing concentrations of *E. coli* LPS or lipid A derivatives 1-5 as indicated. TNF-α (A) and IFN-β (B) in cell supernatants were measured using ELISAs.
Figure 3B:
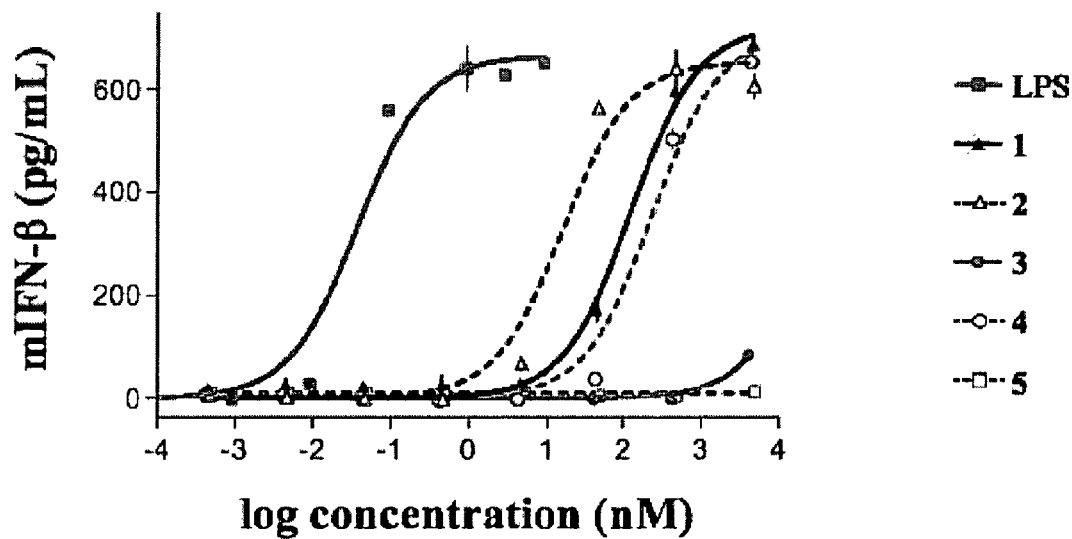
Figure 4A:
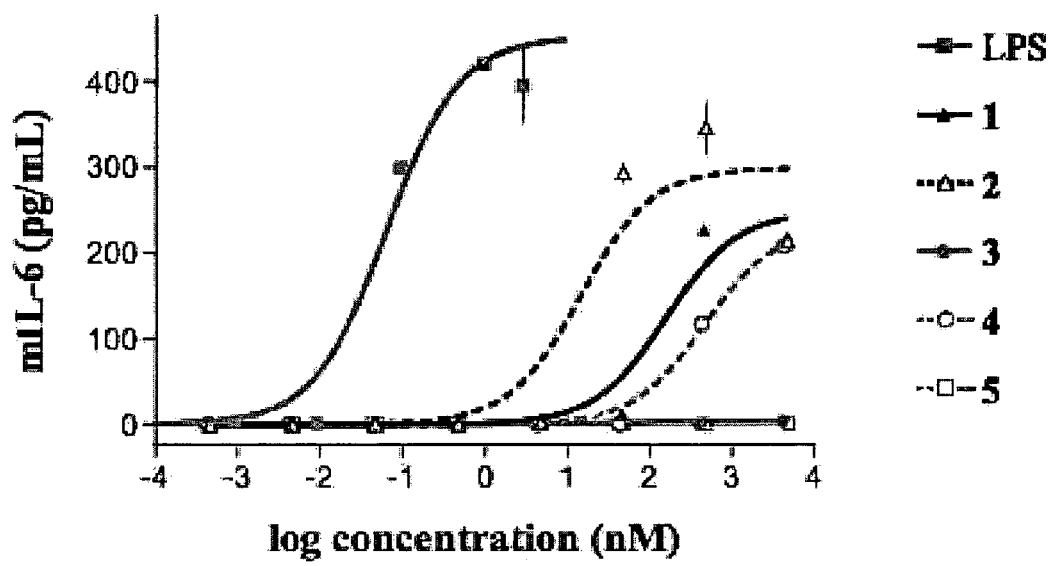
FIG. 4 shows cytokine production by murine macrophages after stimulation with LPS and lipid A derivatives. Murine RAW γNO(−) cells were exposed to increasing concentrations of *E. coli* LPS or lipid A derivatives 1-5 as indicated. Cytokine production was measured in supernatants after 5.5 h incubation for IL-6 (A), IP-10 (B), and RANTES (C) or 24 h for IL-1β (D). The cell lysates were assayed for the presence of pro-IL-1β (E) after 5.5 h incubation.
Figure 4B:
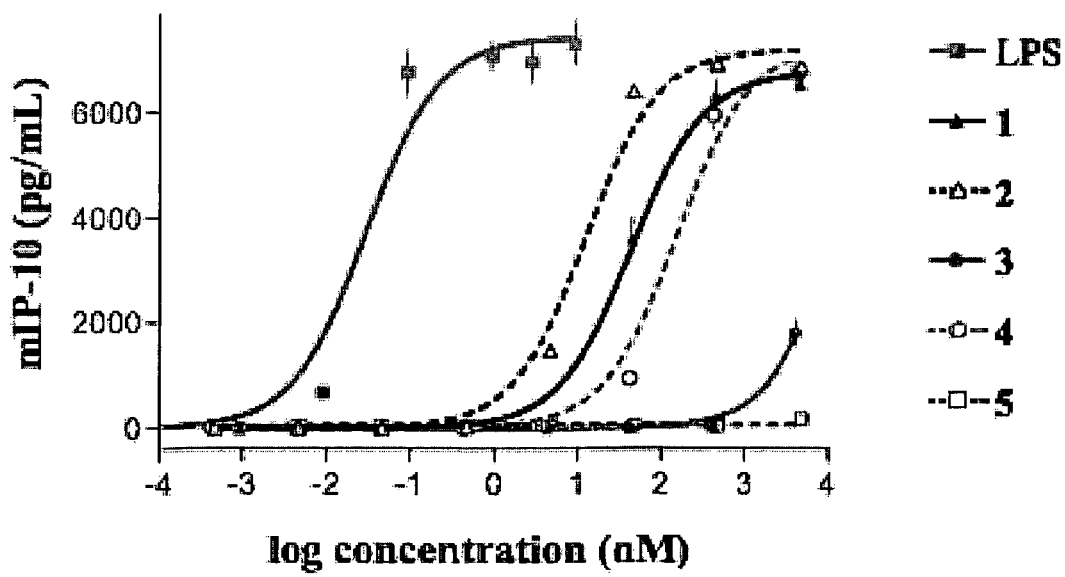
Figure 4C:
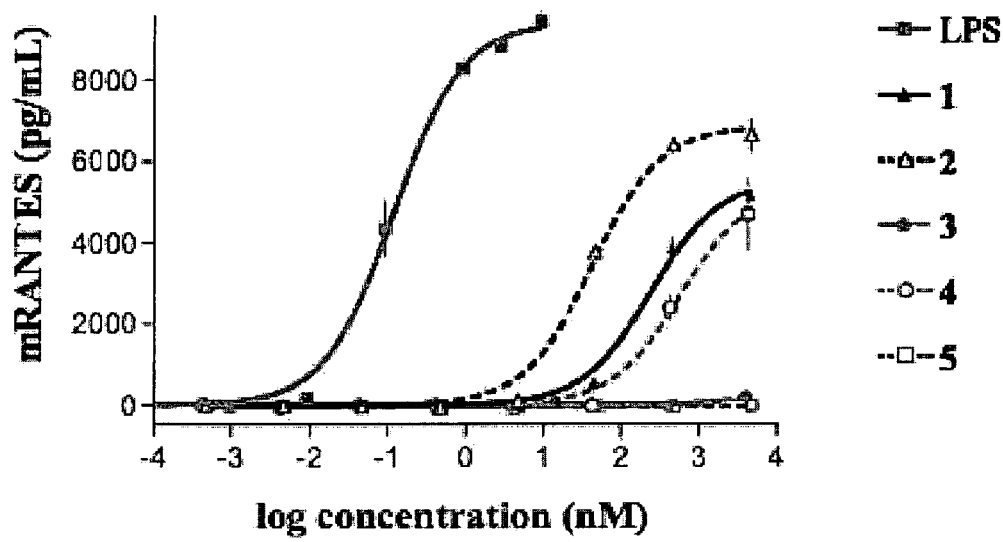
Figure 4D:
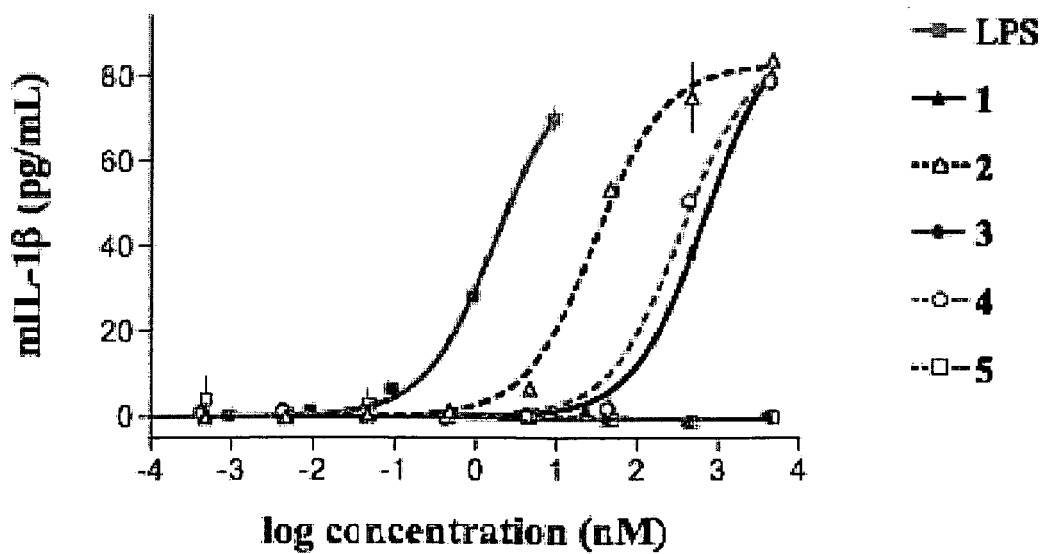
Figure 4E:
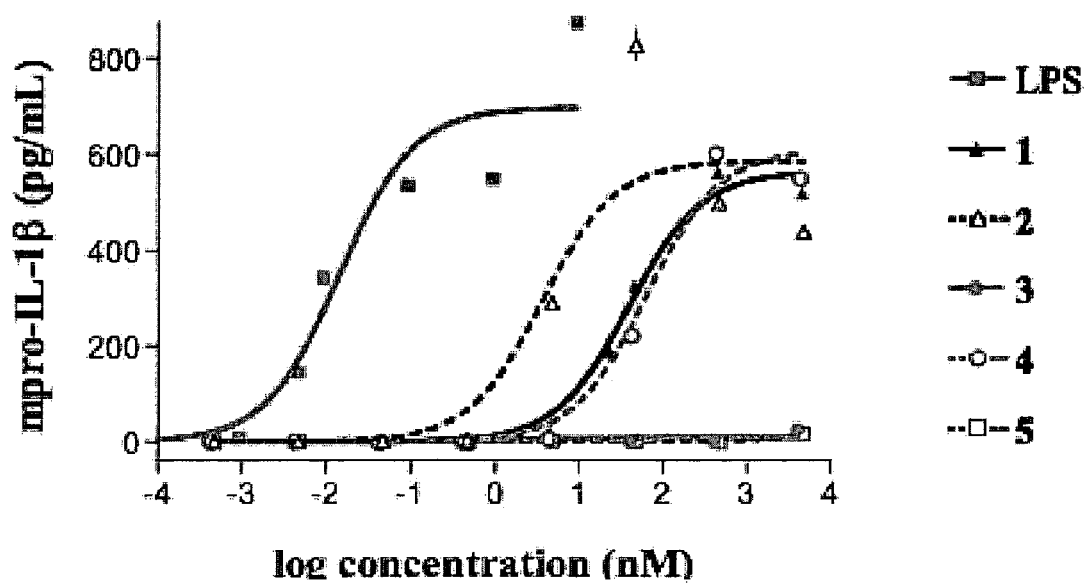

Mouse macrophages (RAW 264.7 γNO(-) cells) were exposed over a wide range of concentrations to compounds 1-5 and *E. coli* 055:B5 LPS. After 5.5 hours, the supernatants were harvested and examined for mouse TNF-α and IFN-β using a commercial and in-house developed capture ELISA assay, respectively. Potencies ($EC_{50}$, concentration producing 50% activity) and efficacies (maximal level of production) were determined by fitting the dose-response curves to a logistic equation using PRISM software. As can be seen in FIG. 3, the lipid As and *E. coli* 055:B5 displayed large differences in potencies. Thus, lipid As 1, 2, and 4 and *E. coli* 055:B5 LPS yielded clear dose response curves. *S. typhimurium* lipid A 3 gave only a partial response at the highest concentration tested, whereas monophosphate 5 was inactive.

Furthermore, the $EC_{50}$ values for *E. coli* 055:B5 LPS were significantly smaller than that of *E. coli* lipid 1 and 2 (Table 1). Probably, the higher potency of LPS is due to its di-KDO moiety, which is attached to the C-6' position of lipid A. In this respect, recent studies (Zughaier et al., *Infect. Immun.* 2004, 72, 371-380) have shown that meningococcal lipid A expressed by a strain defect in KDO biosynthesis has significantly reduced bioactivity compared to KDO containing Meningococcal lipooligosaccharides. It has also been shown that removal of the KDO moieties by mild acidic treatment reduces cellular responses (Demchenko et al., *J. Am. Chem. Soc.* 2003, 125, 6103-6112).

TABLE 1

$EC_{50}$ values* (nM) of *E. coli* LPS and lipid A derivatives 1, 2, and 4.

|  | *E. coli* LPS | Lipid A 1 | Lipid A 2 | Lipid A 4 |
| --- | --- | --- | --- | --- |
| TNF-α | 0.016 | 21 | 4.1 | 60 |
|  | (0.012-0.022) | (16-28) | (2.5-6.7) | (44-81) |
| IFN-β | 0.038 | 124 | 16 | 234 |
|  | (0.025-0.056) | (105-147) | (12-23) | (180-306) |
| IL-6 | 0.063 | 157 | 14 | 462 |
|  | (0.044-0.091) | (91-271) | (6-33) | (383-559) |
| IP-10 | 0.030 | 44 | 12 | 156 |
|  | (0.019-0.046) | (37-52) | (10-16) | (120-204) |
| RANTES | 0.116 | 238 | 43 | 570 |
|  | (0.103-0.131) | (201-281) | (36-51) | (478-681) |
| IL-1β | 1.74[#] | 674 | 30 | 348 |
|  | (1.59-1.91) | (622-728) | (26-35) | (284-428) |
| pro Il-1β | 0.014 | 39 | 3.6 | 63 |
|  | (0.008-0.025) | (32-47) | (1.4-9.4) | (48-84) |
| NF-κB | 0.004 | 38 | 14 | 53 |
|  | (0.003-0.005) | (30-48) | (9-20) | (42-67) |

*Values of $EC_{50}$ are reported as best-fit values and as minimum-maximum range (best-fit value ± std. error).
[#]Plateau not reached; $EC_{50}$ value is best-fit value according to Prism.

Further examination of the data revealed that the hexa-acylated *E. coli* lipid A (1) is significantly more potent than the hepta-acylated *S. typhimurium* lipid A (3). Shortening of lipids, such as in compounds 2 and 4, resulted in higher potencies (smaller $EC_{50}$ values). In the case of the *E. coli* lipid As (1 vs. 2), the differences in $EC_{50}$ values were relatively small, whereas for the *S. typhimurium* lipid As (3 vs. 4) an approximate three orders of magnitude of increase in potencies was observed. Finally, a comparison of the $EC_{50}$ values of TNF-α and IFN-β for each compound indicated that the values of TNF-α are slightly smaller than those of IFN-β (2-6 fold), indicating a somewhat higher potency for TNF-α production. Previously, it was observed that mice exposed to *S. typhimurium* LPS provoked mainly cytokines associated with the TRIF-dependent pathway (Zughaier et al., *Infect. Immun.* 2005, 73, 2940-2950). Interestingly, we have not observed such a bias. It may be possible that such a bias may be due to contaminants or, alternatively, it may be due to lipid A derivatives that have a different acylation pattern.

Having established the $EC_{50}$ values of TNF-α and IFN-β secretion by compounds 1-5 and *E. coli* 055:B5 LPS, attention was focused on IL-6, IP-10, RANTES, and IL-1β responses. Thus, the previously harvested supernatants were analyzed for these cytokines using capture ELISA assays (FIG. 4, Table 1). For IL-6, IP-10, and RANTES, a short incubation time of 5.5 hrs was sufficient for detection. To achieve significant IL-1β secretion, the incubation had to be extended to 24 hrs. However, analyzing cell lysates of the activated cells showed that after 5.5 hrs a significant quantity of IL-1β was present intracellularly. IL-1β is expressed as a pro-protein (pro-IL-1β), which is cleaved by caspase-1 into its active form (IL-1β), which is then secreted. Indeed, analyzing IL-1β of the cell lysates by Western blotting confirmed that it was present as a pro-protein (data not shown). TNF-α is also produced as a pro-protein, which is proteolitically cleaved by tumor necrosis factor-α converting enzyme (TACE) (Skotnicki and Levin, *Annu. Rep. Med. Chem.* 2003, 38, 153-162; Duffy et al., *Thromb. Haemost.* 2003, 89, 622-631). Interestingly, after 5.5 hrs, no TNF-α could be detected in the cell lysates, which indicates that proteolitic processing and secretion is not the rate-limiting step. Furthermore, for each of the synthetic compounds and LPS, $EC_{50}$ values of secreted TNF-α and intracellular pro-IL-1β were very similar. However, $EC_{50}$ values for secreted mature IL-1β were larger by as much as 100-fold.

TACE is constituently expressed in its active form. On the other hand, caspase-1 is present in the cytoplasm as an inactive precursor protein and must be activated by stimulation with LPS or other bacterial components (Yamamoto et al., *Genes Cells* 2004, 9, 1055-1067; Ogura et al., *Cell* 2006, 126, 659-662). Although the mechanism of LPS-mediated activation of caspase-1 is not well understood, it has been shown that it is independent of TLR4 associated adaptor proteins MyD88 and TRIF. Instead, experiments with macrophages obtained from $ACS^{-/-}$ mice have implicated this adaptor protein in LPS-mediated activation of caspase-1. Thus, it appears that activation of caspase-1 is dependent on ACS, whereas the expression of pro-IL-1β and pro-TNF-α are dependent on MyD88. Furthermore, it has been suggested that ACS-promoted caspase-1 activation constitutes the rate-limiting step for IL-1β secretion. On the other hand, our results show that processing of pro-TNF-α by TACE and subsequent secretion are not rate limiting steps. Thus, our results indicate that much higher concentrations of lipid A or LPS are required for caspase-1 activation than for pro-IL-1β expression.

Figure 5:
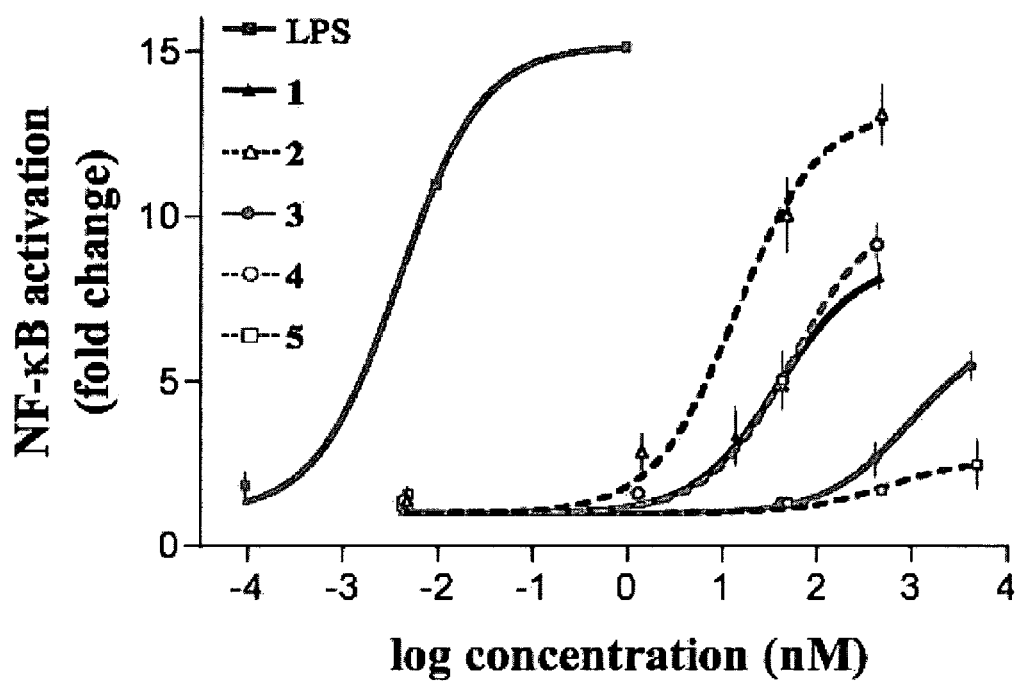
FIG. 5 shows the response of HEK 293T cells expressing murine TLR4, MD2, and CD14 to LPS and lipid A derivatives. Induction of NF-κB activation was determined in triplicate cultures of HEK 293T cells stably transfected with murine TLR4, MD2, and CD14 and transiently transfected with pELAM-Luc, pRL-TK, and pcDNA3 plasmids. Forty-four hours post-transfection, cells were treated with *E. coli* LPS or lipid A derivatives 1-5 at the indicated concentrations or were left untreated (control). Forty-eight hours post-transfection, NF-κB activation was determined by firefly luciferase activity relative to *Renilla* luciferase activity. In the transfection experiment shown, human TNF-α (10 ng/mL) induced 12.1±0.3-fold activation of NF-κB.

To obtain further support that the $EC_{50}$ values of secreted TNF-α protein are not affected by transcriptional, translational, or protein processing processes, dose response curves for the activation of the transcription factor NF-κB were determined for each compound and the results compared with similar data for secretion of TNF-α protein. Thus, compounds 1-5, and *E. coli* LPS were exposed at a range of concentrations to HEK 293T cells stably transfected with human TLR4/MD2/CD14 and transiently transfected with a plasmid containing the reporter gene pELAM-Luc (NF-κB dependent firefly luciferase reporter vector) and a plasmid containing the control gene pRL-TK (Renilla luciferase control reporter vector). As a negative control, wild type HEK 293T cells transiently transfected with plasmids containing the reporter gene pELAM-Luc and control gene pRL-TK were used. After an incubation time of 4 h, the activity was measured using a commercial dual-luciferase assay. As can be seen in FIG. 5 and Table 1, the $EC_{50}$ values for NF-κB activation for each compound are very similar to those of TNF-α protein production, demonstrating that transcription, translation, and protein processing do not impact the dose responses. However, the $EC_{50}$ values for secreted IL-1β protein are at least two orders of a magnitude larger, demonstrating that down stream processes control the dose response of this cytokine. Collectively, our data indicate that a difference in the processing of pro-TNF-α and pro-IL-1β is responsible for the observed differences in $EC_{50}$ values, which represents a novel mechanism for modulating innate immune responses.

Differences in $EC_{50}$ values were observed for the other cytokines. For example, for each compound, the $EC_{50}$ value for RANTES secretion was approximately 10-fold larger than that of TNF-α. Differential responses were also observed for *S. typhimurium* lipid 3, which at the highest concentration tested induced the production of TNF-α, IFN-β, and IP-10 whereas no formation of IL-6, RANTES, and IL-1β could be measured. Examination of the efficacies (maximum responses) of the various cytokines also provided unexpected structure-activity relationships (Table 2). For example, each synthetic compound and *E. coli* 055:B5 LPS induced similar efficacies for the production of IFN-β and IP-10. However, lipid As 1-4 gave lower efficacies for the production of RANTES and IL-6 compared to LPS.

TABLE 2

Cytokine top values* (pg/mL) of dose-response curves of *E. coli* LPS, 1, 2, and 4.

|  | *E. coli* LPS | Lipid A 1 | Lipid A 2 | Lipid A 4 |
| --- | --- | --- | --- | --- |
| TNF-α | 3118 ± 120 | 3924 ± 179 | 4223 ± 329 | 4178 ± 250 |
| IFN-β | 665 ± 38 | 724 ± 25 | 654 ± 37 | 710 ± 44 |
| IL-6 | 451 ± 25 | 249 ± 29 | 299 ± 42 | 233 ± 12 |
| IP-10 | 7439 ± 440 | 6778 ± 214 | 7207 ± 277 | 7320 ± 415 |
| RANTES | 9367 ± 188 | 5531 ± 214 | 6851 ± 216 | 5360 ± 263 |
| IL-1β | 82# ± 2 | 92 ± 2 | 82 ± 2 | 86 ± 4 |
| pro Il-1β | 699 ± 73 | 565 ± 25 | 587 ± 87 | 610 ± 35 |

*Top values are reported as best-fit values ± std. error.
Plateau not reached; top-value is best-fit value according to Prism.

Our results show that the relative quantities of secreted cytokines depend on the nature and concentration of the employed lipid A. This information is important for the development of lipid As as immune modulators. For example, at a relative low dose of LPS or lipid A no IL-1β will be produced. This cytokine is important for the induction of IFN-γ, which in turn is important for biasing an adaptive immune response towards a T helper-1 (Th1) phenotype.

Conclusions

The results of previous studies have shown that the number of acyl chains and phosphates of lipid A are important determinants for potencies of cytokine production. These reports, however, have described the inductions of only one mediator such as TNF-α or IL-6 protein. We have determined, for the first time, the potencies and efficacies of a wide range of (pro)inflammatory mediators induced by a number of well-defined lipid As. This undertaking required the development of a new synthetic approach that allowed for the convenient synthesis of a panel of lipid As. The synthetic approach uses a highly functionalized disaccharide building block that is selectively protected with an Alloc, Fmoc, and anomeric TBDMS group and an azido function, which in a sequential manner can be deprotected or unmasked allowing selective lipid modifications at each position of the disaccharide backbone. The strategy was employed for the preparation of lipid As derived from *E. coli* and *S. typhimurium*. Cellular activation studies with the synthetic compounds and LPS revealed a number of novel structure-activity relationships. For example, it was found that hepta-acylated *S. typhimurium* lipid A gave much lower activities than hexa-acylated *E. coli* lipid A. Furthermore, shortening of lipids, such as in compounds 2 and 4, resulted in higher potencies. In the case of the *E. coli* lipid As (1 vs. 2), the differences in $EC_{50}$ values were relatively small, whereas for the *S. typhimurium* lipid As (3 vs. 4) approximately three orders of magnitude increase in potencies was observed. LPS gave much higher potencies than the synthetic lipid As, which is probably due to its di-KDO moiety. It has been shown, for the first time, that cellular activation with a particular compound can give $EC_{50}$ values for various mediators that differ as much as 100-fold. The differences in responses did not follow a bias towards a MyD88- or TRIF-dependent response. For example, for each compound potencies and efficacies for the induction of TNF-α and IFN-β, which are the prototypical cytokines for the MyD88- or TRIF-dependent pathway, respectively, differed only marginally. On the other hand, large differences were observed between the efficacies of secreted TNF-α and IL-1β, which both depend on the MyD88 pathway. Both cytokines are expressed as pro-proteins, which are processed to the active form by the proteases TACE and caspase-1, respectively. The rate-limiting step for the secretion of IL-1β is the activation of caspase-1, whereas for TNF-α it is the expression of the pro-protein. Surprisingly, our results indicate that LPS-mediated activation of MyD88 resulting in the production of pro-II-1β and pro-TNF-α requires a much lower concentration of LPS or lipid A than ACS-mediated activation of caspase-1. As a result, the $EC_{50}$ values for secreted IL-1β and TNF-α differ significantly. Differences in potencies were also observed for the production of other cytokines. For example, *S. typhimurium* lipid 3 induced the secretion of TNF-α, IFN-1β, and IP-10 at the highest concentration tested, whereas no formation of IL-6, RANTES, and IL-1β could be measured. Further studies are required to uncover the origin of the differences of these responses. Examination of the efficacies (maximum responses) of the various cytokines also provided unexpected structure-activity relationships. For example, each synthetic compound and *E. coli* 055:B5 LPS induced similar efficacies for the production of IFN-β and IP-10. However, lipid As 1-4 gave lower efficacies for the production of RANTES and IL-6 compared to LPS.

Collectively, the results presented in this paper demonstrate that cytokine secretion induced by LPS and lipid A is complex. In particular, the relative quantities of secreted cytokines depend on the nature of the compounds and employed concentration of initiator. This information is important for the development of lipid As as immune modulators. Future examination of the utilization of signaling transduction- and processing pathways of pro-proteins to the active form by different compounds at different concentrations may provide further insight in the underlying mechanism of immune modulation.

Experimental Section

General Synthetic Methods. Column chromatography was performed on silica gel 60 (EM Science, 70-230 mesh). Reactions were monitored by thin-layer chromatography (TLC) on Kieselgel 60 $F_{254}$ (EM Science), and the compounds were detected by examination under UV light and by charring with 10% sulfuric acid in MeOH. Solvents were removed under reduced pressure at <40° C. $CH_2Cl_2$ was distilled from NaH and stored over molecular sieves (3 Å). THF was distilled from sodium directly prior to the application. MeOH was dried by refluxing with magnesium methoxide and then was distilled and stored under argon. Pyridine was dried by refluxing with $CaH_2$ and then was distilled and stored over molecular sieves (3 Å). Molecular sieves (3 and 4 Å), used for reactions, were crushed and activated in vacuo at 390° C. during 8 h in the first instance and then for 2-3 h at 390° C. directly prior to application. Optical rotations were measured with a Jasco model P-1020 polarimeter. $^1H$ NMR and $^{13}C$ NMR spectra were recorded with Varian spectrometers (models Inova500 and Inova600) equipped with Sun workstations. $^1H$ NMR spectra were recorded in $CDCl_3$ and referenced to residual $CHCl_3$ at 7.24 ppm, and $^{13}C$ NMR spectra were referenced to the central peak of $CDCl_3$ at 77.0 ppm. Assignments were made by standard gCOSY and gHSQC. High resolution mass spectra were obtained on a Bruker model Ultraflex MALDI-TOF mass spectrometer. Signals marked with a subscript L symbol belong to the biantennary lipids, whereas signals marked with a subscript L' symbol belong to their side chain. Signals marked with a subscript S symbol belong to the monoantennary lipids.

t-Butyldimethylsilyl 3-O-allyloxycarbonyl-2-azido-4,6-O-benzyldidine-2-deoxy-β-D-glucopyranoside (7): To a cooled (0° C.) solution of compound 6 (3.0 g, 7.37 mmol) and TMEDA (666 μL, 4.42 mmol) in DCM (30 mL) was added dropwise allyl chloroformate (1.00 mL, 8.85 mmol). The reaction mixture was stirred at room temperature for 10 h, and then diluted with DCM (50 mL) and washed with saturated aqueous $NaHCO_3$ (2×100 mL) and brine (2×50 mL). The organic phase was dried ($MgSO_4$) and filtered. Next, the filtrate was concentrated in vacuo. The residue was purified by silica gel column chromatography (hexane/ethyl acetate, 25/1, v/v) to give 7 as a colorless oil (3.20 g, 88%). $R_f$=0.57 (hexane/ethyl acetate, 5/1, v/v). $[α]^{25}_D$=−36.8° (c=1.0, $CHCl_3$). $^1H$ NMR (300 MHz, $CDCl_3$): δ 7.39-7.33 (m, 5H, aromatic), 5.97-5.88 (m, 1H, $OCH_2CH=CH_2$), 5.47 (s, 1H, >CHPh), 5.33 (d, J=17.4 Hz, $OCF_2CH=CH_2$), 5.22 (d, J=17.4 Hz, $OCH_2CH=CH_2$), 4.81 (t, $J_{2,3}=J_{3,4}$=9.9 Hz, H-3), 4.71 (d, 1H, $J_{1,2}$=7.5 Hz, H-1), 4.65 (d, 2H, J=5.4 Hz, $OCH_2CH=CH_2$), 4.28 (d, 1H, $J_{5,6a}$=5.1 Hz, $J_{6a,6b}$=10.5 Hz, H-6a), 3.77 (dd, 1H, $J_{5,6b}=J_{6a,6b}$=10.5 Hz, H-6b), 3.67 (d, 1H, $J_{3,4}=J_{4,5}$=9.0 Hz, H-4), 3.50-3.40 (m, 2H, H-3, H-5), 0.92 (s, 9H, $SiC(CH_3)_3$), 0.16 (s, 3H, $Si(CH_3)_3$), 0.14 (s, 3H, $Si(CH_3)$). $^{13}C$ NMR (75 MHz, $CDCl_3$): δ 154.10 (C=O), 136.72-126.15 (aromatic), 131.13 ($OCH_2CH=CH_2$), 119.03 ($OCH_2CH=CH_2$), 101.51 (>CHPh), 97.69 (C-1), 78.55 (C-4), 75.18 (C-3), 68.90 ($OCH_2CH=CH_2$), 68.41 (C-6), 66.95 (C-5), 66.33 (C-2), 25.48 ($SiC(CH_3)_3$), 17.86 ($SiC(CH_3)_3$), −4.46 ($Si(CH_3)_2$), −5.23 ($Si(CH_3)_2$). HR MS (m/z) calculated for $C_{23}H_{33}N_3O_7Si$ $[M+Na]^+$, 514.1985; found, 514.1907.

t-Butyldimethylsilyl 2-azido-4-O-benzyl-2-deoxy-β-D-glucopyranoside (8). Compound 6 (1.32 g, 3.49 mmol) was dissolved in a solution of $BH_3$ (1 M) in THF (17.5 mL). After stirring at 0° C. for 5 min, dibutylboron triflate (1 M in DCM, 3.49 mL) was added dropwise, and the reaction mixture was stirred at 0° C. for another 1 h. Subsequently, triethylamine (0.5 mL) and methanol (~0.5 mL) were added until the evolution of $H_2$ gas had ceased. The solvents were evaporated in vacuo and the residue was coevaporated with methanol (3×50 mL). The residue was purified by silica gel column chromatography (hexane/ethyl acetate, 8/1, v/v) to give 8 as a colorless oil (1.21 g, 85%). $R_f$=0.40 (hexane/ethyl acetate, 3/1, v/v). $[α]^{25}_D$=+0.9° (c=1.0, $CHCl_3$). $^1H$ NMR (300 MHz, $CDCl_3$): δ 7.32-7.31 (m, 5H, aromatic), 4.81 (d, 1H, $J_2$=11.4 Hz, $CH_{2a}Ph$), 4.70 (d, 1H, $J_2$=11.4 Hz, $CH_{2b}Ph$), 4.55 (d, 1H, $J_{1,2}$=7.5 Hz, H-1), 3.84 (dd, 1H, $J_{5,6a}$=2.4 Hz, $J_{6a,6b}$=12.0 Hz, H-6a), 3.70 (dd, 1H, $J_{5,6b}$=1.5 Hz, $J_{6a,6b}$=12.0 Hz, H-6b), 3.49-3.43 (m, 2H, H-3, H-4), 3.33 (broad, 1H, H-5), 3.22-3.17 (m, 1H, H-2), 0.92 (s, 9H, $SiC(CH_3)_3$), 0.14 (s, 6H, $Si(CH_3)_2$). $^{13}C$ NMR (75 MHz, $CDCl_3$): δ 137.89-128.11 (aromatic), 96.98 (C-1), 77.17 (C-3 or C-4), 75.22 (C-5), 74.88 (C-3 or C-4), 74.75 ($CH_2Ph$), 68.69 (C-2), 61.97 (C-6), 25.56 ($SiC(CH_3)_3$), 17.91 ($SiC(CH_3)_3$), −4.27 ($Si(CH_3)_2$), −5.16 ($Si(CH_3)_2$). HR MS (m/z) calculated for $C_{19}H_{31}N_3O_5Si[M+Na]^+$, 432.1931; found, 432.1988.

t-Butyldimethylsilyl 3-O-allyloxycarbonyl-2-azido-6-O-benzyl-2-deoxy-β-D-glucopyranoside (9): A suspension of compound 7 (3.20 g, 6.52 mmol,) and molecular sieves (4 Å, 500 mg) in THF (50 mL) was stirred at room temperature for 1 h, and then $NaCNBH_3$ (2.46 g, 39.0 mmol) was added. A solution of HCl (2 M in diethyl ether) was added dropwise to this reaction mixture until the mixture became acidic (~5 mL, pH=5). After stirring another 0.5 h, the reaction mixture was quenched with solid $NaHCO_3$, diluted with diethyl ether (100 mL), and washed with saturated aqueous $NaHCO_3$ (2×100 mL) and brine (2×50 mL). The organic phase was dried (MgSO$_4$) and filtered. Next, the filtrate was concentrated in vacuo. The residue was purified by silica gel column chromatography (hexane/ethyl acetate, 7/1, v/v) to give 9 as a colorless oil (3.20 g, 88%). R$_f$=0.42 (hexane/ethyl acetate, 4/1, v/v). [α]$^{25}_D$=−6.2° (c=1.0, CHCl$_3$). $^1$H NMR (300 MHz, CDCl$_3$): δ 7.39-7.34 (m, 5H, aromatic), 6.02-5.89 (m, 1H, OCH$_2$CH=CH$_2$), 5.39 (d, 1H, J=17.4 Hz, OCH$_2$CH=CH$_2$), 5.30 (d, 1H, J=10.5 Hz, OCH$_2$CH=CH$_2$), 4.70-4.58 (m, 5H, H-1, H-3, OCH$_2$CH=CH$_2$, CH$_2$Ph), 3.79-3.70 (m, 3H, H-4, H-6a, H-6b), 3.52-3.46 (m, 1H, H-5), 3.37 (dd, 1H, J$_{1,2}$=8.4 Hz, J$_{2,3}$=9.6 Hz, H-2), 0.94 (s, 9H, SiC(CH$_3$)$_3$), 0.17 (s, 6H, Si(CH$_3$)$_2$). $^{13}$C NMR (75 MHz, CDCl$_3$): δ 154.81 (C=O), 137.59-127.32 (aromatic), 131.07 (OCH$_2$CH=CH$_2$), 118.97 (OCH$_2$CH=CH$_2$), 96.92 (C-1), 78.79 (C-3), 74.25 (C-5), 73.44 (CH$_2$Ph), 69.89, 69.55, 68.84 (C-4, C-6, OCH$_2$CH=CH$_2$), 65.84 (C-2), 25.42 (SiC(CH$_3$)$_3$), 17.75 (SiC(CH$_3$)$_3$), −4.50 (Si(CH$_3$)$_2$), −5.40 (Si(CH$_3$)$_2$). HR MS (m/z) calculated for C$_{23}$H$_{35}$N$_3$O$_7$Si[M+Na]$^+$, 516.2142; found, 516.2197.

t-Butyldimethylsilyl 3-O-allyloxycarbonyl-2-azido-6-O-benzyl-2-deoxy-4-O-(1,5-dihydro-3-oxo-3λ$^5$-3H-2,4,3-benzodioxaphosphepin-3-yl)-β-D-glucopyranoside (10): To a solution of compound 9 (1.30 g, 2.50 mmol) and 1H-tetrazole (3% wt, 10.0 mmol) in DCM (30 mL) was added N,N-diethyl-1,5-dihydro-3H-2,4,3-benzodioxaphosphepin-3-amine (1.20 g, 1.05 mmol). After the reaction mixture was stirred at room temperature for 15 min, it was cooled (−20° C.), stirred for another 10 min and then mCPBA (3.40 g, 50-55% wt, 10.0 mmol) was added. The reaction mixture was stirred at −20° C. for 20 min, and then quenched by the addition of saturated aqueous NaHCO$_3$ (40 mL) and diluted with DCM (30 mL). The organic phase was washed with saturated aqueous NaHCO$_3$ (2×60 mL) and brine (2×40 mL), dried (MgSO$_4$) and filtered. Next, the filtrate was concentrated in vacuo. The residue was purified by silica gel column chromatography (hexane/ethyl acetate, 5/1-3/1, v/v) to give 10 as a pale yellow oil (1.48 g, 89%). R$_f$=0.40 (hexane/ethyl acetate, 1/1, v/v). [α]$^{25}_D$=−10.3° (c=1.0, CHCl$_3$). $^1$H NMR (300 MHz, CDCl$_3$): δ 7.35-7.15 (m, 9H, aromatic), 5.98-5.85 (m, 1H, OCH$_2$CH=CH$_2$), 5.65 (d, 1H, J=1.2 Hz, J=17.4 Hz, OCH$_2$CH=CH$_2$), 5.50 (d, 1H, J=1.2 Hz, J=10.5 Hz, OCH$_2$CH=CH$_2$), 5.18-5.01 (m, 4H, C$_6$H$_4$(CH$_2$O)P), 3.81 (dd, 1H, J$_{2,3}$=10.5 Hz, J$_{3,4}$=9.3 Hz, H-3), 4.64-4.52 (m, 6H, H-1, H-4, OCH$_2$CH=CH$_2$, CH$_2$Ph), 3.82 (d, 1H, J$_{6a,6b}$=9.0 Hz, H-6a), 3.72-3.61 (m, 2H, H-5, H-6b), 3.41 (dd, 1H, J$_{1,2}$=7.4 Hz, J$_{2,3}$=10.5 Hz, H-2), 0.92 (s, 9H, SiC(CH$_3$)$_3$), 0.16 (s, 3H, Si(CH$_3$)), 0.15 (s, 3H, Si(CH$_3$)). $^{13}$C NMR (75 MHz, CDCl$_3$): δ 154.38 (C=O), 138.02-127.56 (aromatic), 131.33 (OCH$_2$CH=CH$_2$), 118.99 (OCH$_2$CH=CH$_2$), 97.13 (C-1), 76.77 (C-3), 74.27 (C-4), 74.08 (C-5), 73.50 (CH$_2$Ph), 69.06 (OCH$_2$CH=CH$_2$), 68.74 (C-6), 68.55 (OC$_6$H$_4$(CH$_2$O)P), 68.50 (OC$_6$H$_4$(CH$_2$O)P), 65.97 (C-2), 25.53 (SiC(CH$_3$)$_3$), 17.92 (SiC(CH$_3$)$_3$), −4:35 (Si(CH$_3$)$_2$), −5.28 (Si(CH$_3$)$_2$). HR MS (m/z) calculated for C$_{31}$H$_{42}$N$_3$O$_{10}$PSi[M+Na]$^+$, 698.2275; found, 698.2315.

t-Butyldimethylsilyl 3-O-allyloxycarbonyl-6-O-benzyl-2-deoxy-4-O-(1,5-dihydro-3-oxo-3λ$^5$-3H-2,4,3-benzodioxaphosphepin-3-yl)-2-(9-fluorenylmethoxycarbonylamino)-β-D-glucopyranoside (11): Acetic acid (300 µL, 5.20 mmol) was added dropwise to a stirred suspension of 10 (1.40 g, 2.08 mmol) and zinc powder (676 mg, 10.4 mmol) in DCM (15 mL). The reaction mixture was stirred at room temperature for 2 h, after which it was diluted with ethyl acetate (50 mL). The solids were removed by filtration and washed with ethyl acetate (2×10 mL). The combined filtrates were washed with saturated aqueous NaHCO$_3$ (2×40 mL) and brine (2×40 mL). The organic phase was dried (MgSO$_4$), filtered, and the filtrate was concentrated in vacuo to afford a crude amine as a pale yellow oil. R$_f$=0.21 (hexane/ethyl acetate, 1/1, v/v). FmocCl (645 mg, 2.50 mmol) was added to a stirred solution of the crude amine and DIPEA (435 µL, 2.50 mmol) in DCM (15 mL) at 0° C. The reaction mixture was stirred at room temperature for 5 h, after which it was diluted with DCM (40 mL) and washed with brine (2×50 mL). The organic phase was dried (MgSO$_4$) and filtered. Next, the filtrate was concentrated in vacuo. The residue was purified by silica gel column chromatography (hexane/ethyl acetate, 4/1-2/1, v/v) to afford 11 as a colorless solid (1.45 g, 80% over two steps). R$_f$=0.54 (hexane/ethyl acetate, 1/1, v/v). [α]$^{25}_D$=−3.9° (c=1.0, CDCl$_3$); $^1$H NMR (500 MHz, CDCl$_3$): δ 7.78-7.20 (m, 17H, aromatic), 5.92-5.82 (m, 1H, OCH$_2$CH=CH$_2$), 5.42 (broad, 1H, H-3), 5.31 (d, 1H, J=17.6 Hz, OCH$_2$CH=CH$_2$), 5.20-5.07 (m, 6H, H-1, OCH$_2$CH=CH$_2$, C$_6$H$_4$(CH$_2$O)P), 4.67-4.56 (m, 5H, H-4, OCH$_2$CH=CH$_2$, CH$_2$Ph), 4.41-4.23 (m, 3H, COOCH$_2$, Fmoc, COOCH2CH, Fmoc), 3.89-3.87 (broad, 1H, H-6a), 3.76-3.74 (broad, 2H, H-5, H-6b), 3.49-3.47 (m, 1H, H-2), 0.88 (s, 4H, SiC(CH$_3$)$_3$), 0.14 (s, 3H, Si(CH$_3$)$_2$), 0.10 (s, 3H, Si(CH$_3$)$_2$). $^{13}$C NMR (75 MHz, CDCl$_3$): δ 155.52 (C=O), 154.80 (C=O), 143.71-119.94 (aromatic), 131.34 (OCH$_2$CH=CH$_2$), 118.85 (OCH$_2$CH=CH$_2$), 95.41 (C-1), 74.77 (C-4), 73.85 (C-5), 73.47 (CH$_2$Ph), 68.94, 68.57, 68.50, 68.42 (C-3, C-6, OCH$_2$CH=CH$_2$, OC$_6$H$_4$(CH$_2$O)P), 68.50 (OC$_6$H$_4$(CH$_2$O)P), 67.12 (CO$_2$CH$_2$CH, Fmoc), 58.69 (C-2), 47.04 (CO$_2$CH$_2$CH, Fmoc), 25.52 (SiC(CH$_3$)$_3$), 17.88 (SiC(CH$_3$)$_3$), −4.26 (Si(CH$_3$)$_2$), −5.38 (Si(CH$_3$)$_2$). HR MS (m/z) calculated for C$_{46}$H$_{54}$NO$_{12}$PSi[M+Na]$^+$, 894.3051; found, 894.3937.

3-O-Allyloxycarbonyl-6-O-benzyl-2-deoxy-4-O-(1,5-dihydro-3-oxo-3λ$^5$-3H-2,4,3-benzodioxaphosphepin-3-yl)-2-(9-fluorenylmethoxycarbonylamino)-D-glucopyranosyl trichloroacetimidate (12): HF/pyridine (1 mL) was added dropwise to a stirred solution of 11 (1.37 g, 1.58 mmol) in THF (10 mL). The reaction mixture was stirred at room temperature for 12 h, after which it was diluted with ethyl acetate (40 mL), and then washed with saturated aqueous NaHCO$_3$ (2×40 mL) and brine (2×40 mL), successively. The organic phase was dried (MgSO$_4$) and filtered. Next, the filtrate was concentrated in vacuo. The residue was purified by silica gel column chromatography (hexane/ethyl acetate, 3/2, v/v) to give a lactol as a pale yellow oil (1.02 g, 98%). HR MS (m/z) calcd for C$_{40}$H$_{40}$NO$_{12}$P[M+Na]$^+$, 780.2186; found, 780.2379. The lactol (1.02 g, 1.35 mmol) thus obtained was dissolved in DCM (20 mL), and trichloroacetonitrile (10 mL) and NaH (5 mg) were added, successively. The reaction mixture was stirred at room temperature for 30 min, after which another portion of NaH (5 mg) was added. After stirring the suspension for another 20 min, the solids were removed by filtration and the filtrate was concentrated in vacuo. The residue was purified by silica gel column chromatography (hexane/ethyl acetate, 1/1, v/v) to give 12 as a colorless solid (1.14 g, 92%).

t-Butyldimethylsilyl 6-O-[3-O-allyloxycarbonyl-6-O-benzyl-2-deoxy-4-O-(1,5-dihydro-3-oxo-3λ$^5$-3H-2,4,3-benzodioxaphosphepin-3-yl)-2-(9-fluorenylmethoxycarbonylamino)-β-D-glucopyranosyl]-2-azido-4-O-benzyl-2-deoxy-β-D-glucopyranoside (13): A suspension of trichloroacetimidate 12 (1.04 g, 1.21 mmol), acceptor 8 (740 mg, 1.82 mmol) and molecular sieves (4 Å, 500 mg) in DCM (20 mL) was stirred at room temperature for 1 h. The mixture was cooled (−60° C.) and then TMSOTf (18 µL, 0.09 mmol) was added. After stirring the reaction mixture for 15 min, it was quenched with solid NaHCO$_3$. The solids were removed by filtration, and the filtrate was washed with saturated aqueous NaHCO$_3$ (2×50 mL) and brine (2×40 mL). The organic phase was dried (MgSO$_4$) and filtered. Next, the filtrate was concentrated in vacuo. The residue was purified by silica gel column chromatography (hexane/ethyl acetate, 2/1, v/v) to give 13 as a colorless solid (1.09 g, 79%). $R_f$=0.37 (DCM/methanol, 50/1, v/v). $[\alpha]^{26}{}_D$=−3.8 (c=1.0, CHCl$_3$). $^1$H NMR (600 MHz, CD$_3$COCD$_3$): δ 7.84-7.20 (m, 22H, aromatic), 6.98 (d, 1H, $J_{NH',2'}$=9.0 Hz, NH'), 5.83 (m, 1H, OCH$_2$CH═CH$_2$), 5.41 (t, 1H, $J_{2',3'}$=9.6 Hz, H-3',), 5.29-5.21 (m, 3H, OCH$_2$CH═CH$_2$, C$_6$H$_4$(CH$_2$O)$_2$P), 5.13-5.03 (m, 3H, H-1', OCH$_2$CH═CH$_2$, C$_6$H$_4$(CH$_2$O)$_2$P), 4.96-4.91 (m, 2H, CH$_{2a}$Ph, C$_6$H$_4$(CH$_2$O)$_2$P), 4.73-4.45 (m, 7H, H-1, H-4', CH$_{2b}$Ph, CH$_2$Ph, OCH$_2$CH═CH$_2$), 4.24-4.13 (m, 4H, H-6, CO$_2$CH$_2$, Fmoc, CO$_2$CH$_2$CH, Fmoc), 3.93-3.79 (m, 4H, H-5', H-6a, H-6'a, H-6'b), 3.69 (m, 1H, H-2'), 3.54 (broad, 3H, H-3, H-4, H-5), 3.19 (dd, 1H, $J_{1,2}$=7.8 Hz, $J_{2,3}$=9.0 Hz, H-2), 0.92 (s, 9H, SiC(CH$_3$)$_3$), 0.17 (s, 6H, Si(CH$_3$)$_2$). $^{13}$C NMR (75 MHz, CD$_3$COCD$_3$): δ 156.39 (C═O), 155.28 (C═O), 144.96-120.56 (aromatic, OCH$_2$CH═CH$_2$), 118.41 (OCH$_2$CH═CH$_2$), 101.14 (C-1'), 97.33 (C-1), 78.54, 77.87, 75.72, 75.25-74.42 (m), 73.83, 70.35, 69.52, 69.04-68.73 (m), 67.91, 67.12, 57.03 (C-2'), 47.64 (CO$_2$CH$_2$, Fmoc), 25.83 (SiC(CH$_3$)$_3$), 18.27 (SiC(CH$_3$)$_3$), −3.85 (Si(CH$_3$)$_2$), −5.21 (Si(CH$_3$)$_2$). HR MS (m/z) calculated for C$_{59}$H$_{69}$N$_4$O$_{16}$PSi[M+Na]$^+$, 1171.4113; found, 1171.4256.

t-Butyldimethylsilyl 6-O-{3-O-allyloxycarbonyl-6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-1-5 tetradecanoylamino]-β-D-glucopyranosyl}-2-azido-4-O-benzyl-2-deoxy-β-D-glucopyranoside (21): DBU (200 μL) was added dropwise to a solution of 13 (730 mg, 0.637 mmol) in DCM (10 mL). The reaction mixture was stirred at room temperature for 1 h, after which it was concentrated in vacuo. The residue was purified by silica gel column chromatography (DCM/methanol, 100/1-100/3, v/v) to afford the free amine as a colorless syrup (567 mg, 96%). $R_f$=0.32 (DCM/methanol, 50/1, v/v). $^1$H NMR (500 MHz, CDCl$_3$): δ 7.39-7.18 (m, 14H, aromatic), 5.96-5.88 (m, 1H, OCH$_2$CH═CH$_2$), 5.38 (d, 1H, J=17.0 Hz, OCH$_2$CH═CH$_2$), 5.25 (d, 1H, J=11.0 Hz, OCH$_2$CH═CH$_2$), 5.21-5.06 (m, 4H, C$_6$H$_4$(CH$_2$O)$_2$P), 4.85 (t, 1H, $J_{2',3'}$=$J_{3',4'}$=9.5 Hz, H-3'), 4.79 (d, 1H, J=11.0 Hz, CH$_{2a}$Ph), 4.67 (d, 1H, J=11.0 Hz, CH$_{2b}$Ph), 4.63-4.55 (m, 5H, H-4', 2×CH$_2$Ph, OCH$_2$CH═CH$_2$), 4.52 (d, 1H, $J_{1,2}$=7.5 Hz, H-1), 4.22 (d, 1H, $J_{1',2'}$=8.0 Hz, H-1'), 4.14 (d, 1H, $J_{6a,6b}$=10.5 Hz, H-6a), 3.87 (d, 1H, $J_{6'a,6'b}$=10.5 Hz, H-6'a), 3.73-3.69 (m, 1H, H-6'b), 3.67-3.65 (m, 1H, H-5'), 3.62-3.59 (m, 1H, H-6b), 3.55-3.52 (m, 1H, H-5), 3.46 (t, 1H, $J_{2,3}$=$J_{3,4}$=9.5 Hz, H-3), 3.32 (t, 1H, $J_{3,4}$=$J_{4,5}$=9.0 Hz, H-4), 3.22 (t, 1H, $J_{1,2}$=$J_{2,3}$=9.0 Hz, H-2), 2.93 (t, 1H, $J_{1',2'}$=8.0, $J_{2',3'}$=10.0 Hz, H-2'), 0.94 (s, 9H, SiC(CH$_3$)$_3$), 0.19 (s, 6H, Si(CH$_3$)$_2$). HR MS (m/z) calcd for C$_{44}$H$_{59}$N$_4$O$_{14}$PSi[M+Na]$^+$, 949.3432; found, 949.4922. DCC (202 mg, 0.979 mmol) was added to a stirred solution of (R)-3-dodecanoyl-tetradecanoic acid 18 (313 mg, 0.734 mmol) in DCM (10 mL). After stirring the reaction mixture for 10 min, the amine (567 mg, 0.612 mmol) in DCM (4 mL) was added, and stirring was continued for another 12 h. The insoluble materials were removed by filtration, and the residue was washed with DCM (2×2 mL). The combined filtrates were concentrated in vacuo and the residue was purified by silica gel column chromatography (hexane/ethyl acetate, 2/1, v/v) to give 21 as a white solid (760 mg, 93%). $R_f$=0.68 (hexane/ethyl acetate, 1/1, v/v). $[\alpha]^{27}{}_D$=−3.0° (c=1.0, CHCl$_3$). $^1$H NMR (600 MHz, CDCl$_3$): δ 7.33-7.14 (m, 14H, aromatic), 5.92 (d, 1H, $J_{NH',2}$=7.8 Hz, NH'), 5.91-5.85 (m, 1H, OCH$_2$CH═CH$_2$), 5.46 (t, 1H, $J_{2',3'}$=$J_{3',4'}$=9.6 Hz, H-3'), 5.34 (d, 1H, J=16.8 Hz, OCH$_2$CH═CH$_2$), 5.21 (d, 1H, J=10.2 Hz, OCH$_2$CH═CH$_2$), 5.09-5.04 (m, 4H, C$_6$H$_4$(CH$_2$O)$_2$P), 4.99 (d, 1H, =8.4 Hz, H-1'), 5.00-4.96 (m, 1H, H-3$_L$), 4.73 (d, 1H, $J_2$=12.0 Hz, CH$_{2a}$Ph), 4.63 (d, 1H, $J_2$=12.0 Hz, CH$_{2b}$Ph), 4.59-4.48 (m, 6H, H-1, H-4', CH$_2$Ph, OCH$_2$CH═CH$_2$), 4.00 (d, 1H, $J_{6'a,6'b}$=10.2 Hz, H-6'a), 3.82 (d, 1H, $J_{6a,6b}$=10.2 Hz, H-6a), 3.73-3.67 (m, 3H, H-5', H-6b, H-6'b), 3.49-3.36 (m, 4H, H-2', H-3, H-4, H-5), 3.18 (t, 1H, $J_{1,2}$=$J_{2,3}$=8.4 Hz, H-2), 2.33 (s, 1H, OH), 2.37 (dd, 1H, $J_{2La,2Lb}$=14.4 Hz, $J_{2La,3L}$=6.0 Hz, H-2$_{La}$), 2.29-2.22 (m, 3H, H-2$_{L'}$, H-2$_{Lb}$), 1.61-1.53 (m, 4H, H-4$_L$, H-3$_L$), 1.23 (broad, 34H, 17×CH$_2$, lipid), 0.90 (s, 9H, SiC(CH$_3$)$_3$), 0.85-0.78 (m, 6H, 2×CH$_3$, lipid), 0.13 (s, 6H, Si(CH$_3$)$_2$). $^{13}$C NMR (75 MHz, CDCl$_3$): δ 173.70 (C═O), 170.00 (C═O), 154.59 (C═O), 138.08-127.57 (aromatic, OCH$_2$CH═CH$_2$), 118.84 (OCH$_2$CH═CH$_2$), 99.30 (C-1'), 96.95 (C-1), 77.65, 77.21, 76.05, 75.04, 74.41, 74.32, 73.78, 71.13, 68.95-67.93 (m), 55.91 (C-2'), −4.02 (Si(CH$_3$)$_2$), −5.26 (Si(CH$_3$)$_2$). HR MS (m/z) calculated for C$_{70}$H$_{107}$N$_4$O$_{17}$PSi[M+Na]$^+$, 1357.7036; found, 1357.8037.

t-Butyldimethylsilyl 6-O-{3-O-allyloxycarbonyl-6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-β-D-glucopyranosyl}-2-azido-4-O-benzyl-3-O—[(R)-3-benzyloxy-tetradecanoyl]-2-deoxy-β-D-glucopyranoside (22): A reaction mixture of (R)-3-benzyloxy-tetradecanoic acid 15 (100 mg, 0.293 mmol) and DCC (93 mg, 0.450 mmol) in DCM (5 mL) was stirred at room temperature for 10 min, and then disaccharide 21 (300 mg, 0.225 mmol) in DCM (3 mL) and DMAP (11 mg, 0.090 mmol) were added. The reaction mixture was stirred at room temperature for 14 h, after which the solids were removed by filtration, and the residue washed with DCM (2×1 mL). The combined filtrates were concentrated in vacuo, and the residue was purified by silica gel column chromatography (hexane/ethyl acetate, 4/1, v/v) to give 22 as a white solid (319 mg, 86%). $R_f$=0.41 (hexane/ethyl acetate, 2/1, v/v). $[\alpha]^{26}{}_D$=−2.8° (c=1.0, CHCl$_3$). $^1$H NMR (500 MHz, CDCl$_3$): δ 7.33-7.15 (m, 19H, aromatic), 5.94-5.85 (m, 2H, NH, OCH$_2$CH═CH$_2$), 5.45 (t, 1H, $J_{2',3'}$=$J_{3',4'}$=9.5 Hz, H-3'), 5.34 (d, 1H, J=17.5 Hz, OCH$_2$CH═CH$_2$), 5.22 (d, 1H, J=10.0 Hz, OCH$_2$CH═CH$_2$), 5.08-4.95 (m, 7H, H-1, H-3, H-3$_L$, C$_6$H$_4$(CH$_2$O)$_2$P), 4.61-4.44 (m, 10H, H-1, H-4', 3×CH$_2$Ph, OCH$_2$CH═CH$_2$), 3.96 (d, 1H, $J_{6'a,6'b}$=10.5 Hz, H-6'a), 3.88-3.85 (m, 1H, H-3$_S$), 3.80 (d, 1H, $J_{6a,6b}$=9.5 Hz, H-6a), 3.72-3.66 (m, 3H, H-5', H-6b, H-6'b), 3.55-3.52 (m, 2H, H-4, H-5), 3.47-3.41 (m, 1H, H-2'), 3.27 (dd, 1H, $4_2$=7.5 Hz, $J_{2,3}$=10.0 Hz, H-2), 2.56 (dd, 1H, $J_{2Sa,2Sb}$=16.0 Hz, $J_{2Sa,3S}$=7.0 Hz, H-2$_{Sa}$), 2.43 (dd, 1H, $J_{2Sa,2Sb}$=16.0 Hz, $J_{2Sb,3S}$=7.0 Hz, H-2$_{Sb}$), 2.35 (dd, 1H, $J_{2La,2Lb}$=15.0 Hz, $J_{2La,3L}$=6.0 Hz, H-20, 2.30-2.20 (m, 3H, H-2$_{L'}$, H-2$_{L'b}$), 1.59-1.52 (m, 6H, H-4$_L$, H-4$_S$, H-3$_L$), 1.23 (broad, 52H, 26×CH$_2$, lipid), 0.90 (s, 9H, SiC(CH$_3$)$_3$), 0.88-0.84 (m, 9H, 3×CH$_3$, lipid), 0.12 (s, 6H, Si(CH$_3$)$_2$). $^{13}$C NMR (75 MHz, CDCl$_3$): δ 173.40 (C═O), 170.55 (C═O), 169.94 (C═O), 154.42 (C═O), 138.46-127.35 (aromatic, OCH$_2$CH═CH$_2$), 118.74 (OCH$_2$CH═CH$_2$), 99.29 (C-1'), 96.96 (C-1), 75.89, 75.62, 74.75, 74.28, 74.02, 73.67, 73.41, 71.34, 70.89, 68.87-67.85 (m), 66.48, −4.18 (Si(CH$_3$)$_2$), −5.38 (Si(CH$_3$)$_2$). HR MS (m/z) calculated for C$_{91}$H$_{139}$N$_4$O$_{19}$PSi[M+Na]$^+$, 1673.9438; found, 1674.1754.

t-Butyldimethylsilyl 6-O-{6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O—[(R)-3-(p-methoxy)benzyloxy-tetradecanoyl]-β-D-glucopyranosyl}-2-azido-4-O-benzyl-3-O-[(R)-3-benzyloxy-tetradecanoyl]-2-deoxy-β-D-glucopyranoside (28): Tetrakis(triphenylphosphine)palladium (29.0 mg, 0.0255 mmol) was added to a solution of 22 (210 mg, 0.127 mmol), n-BuNH$_2$ (25.0 µL, 0.255 mmol), and HCOOH (10.0 µL, 0.255 mmol) in THF (5 mL). After the reaction mixture was stirred at room temperature for 20 min, it was diluted with DCM (20 mL), and washed successively with water (20 mL), saturated aqueous NaHCO$_3$ (2×20 mL), and brine (2×20 mL). The organic phase was dried (MgSO$_4$) and filtered. Next, the filtrate was concentrated in vacuo. The residue was purified by silica gel column chromatography (hexane/ethyl acetate, 4/3, v/v) to give compound 23. A solution of (R)-3-(p-methoxy)benzyloxy-tetradecanoic acid 17 (69 mg, 0.191 mmol) and DCC (52 mg, 0.254 mmol) in DCM (4 mL) was stirred at room temperature for 10 min, and then the intermediate 23 in DCM (1 mL) and DMAP (7 mg, 0.060 mmol) were added. The reaction mixture was stirred for another 10 h, after which the solids were removed by filtration and washed with DCM (2×2 mL). The combined filtrates were concentrated in vacuo. The residue was purified by silica gel column chromatography (hexane/ethyl acetate, 4/1, v/v) to afford 28 as a white solid (182 mg, 75%). R$_f$=0.46 (hexane/ethyl acetate, 2/1, v/v). [α]$^{26}_D$=−2.8° (c=1.0, CHCl$_3$). $^1$H NMR (500 MHz, CDCl$_3$): δ 7.38-6.79 (m, 23H, aromatic), 5.73 (d, 1H, J$_{NH',2'}$=7.5 Hz, NH'), 5.57 (t, 1H, J$_{2',3'}$=J$_{3',4'}$=9.5 Hz, H-3'), 5.07-4.87 (m, 6H, H-1, H-3, C$_6$H$_4$(CH$_2$O)$_2$P), 4.66-4.47 (m, 11H, H-1', H-4', H-3$_L$, 3×CH$_2$Ph, CH$_2$PhOCH$_3$), 3.98 (d, 1H, J$_{6a,6b}$=11.0 Hz, H-6a), 3.91-3.69 (m, 9H, H-5', H-6b, H-6'a, H-6'b, 2×H-3$_S$, CH$_3$OPh), 3.55-3.52 (m, 2H, H-4, 5), 3.47-3.41 (m, 1H, H-2'), 3.38-3.31 (m, 2H, H-2, H-2'), 2.67-2.07 (m, 8H, H-2$_L$, 2×H-2$_S$, H-2$_L$), 1.62-1.59 (m, 8H, H-4$_L$, 2×H-4-s, H-3O, 1.27 (broad, 70H, 35×CH$_2$, lipid), 0.93 (s, 9H, SiC(CH$_3$)$_3$), 0.92-0.87 (m, 12H, 4×CH$_3$, lipid), 0.16 (s, 6H, Si(CH$_3$)$_2$). $^{13}$C NMR (75 MHz, CDCl$_3$): δ 173.65 (C=O), 171.18 (C=O), 170.63 (C=O), 169.87 (C=O), 159.17-113.78 (aromatic), 99.77 (C-1'), 97.06 (C-1), 75.95, 75.71, 75.26, 74.89, 74.43, 74.09, 73.97, 73.75, 73.53, 72.07, 71.48, 71.07, 70.66, 68.90-68.13 (m), 66.54 (C-2), 56.22 (C-2'), 55.17 (CH$_3$OC$_6$H$_S$), −4.08 (Si(CH$_3$)$_2$), −5.31 (Si(CH$_3$)$_2$). HR MS (m/z) calculated for C$_{109}$H$_{169}$N$_4$O$_{20}$PSi[M+Na]$^+$, 1936.1735; found, 1936.2613.

t-Butyldimethylsilyl 6-O-{6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O—[(R)-3-tetradecanoyloxy-tetradecanoyl]-β-D-glucopyranosyl}-2-azido-4-O-benzyl-3-O—[(R)-3-benzyloxy-tetradecanoyl]-2-deoxy-β-D-glucopyranoside (24): DDQ (36 mg, 0.158 mmol) was added to a stirred solution of 15 (200 mg, 0.105 mmol) in a mixture of DCM and H$_2$O (4 mL, 10/1, v/v). The reaction mixture was stirred at room temperature for 1 h, after which it was diluted with DCM. The mixture was washed with brine (20 mL), dried (MgSO$_4$), and concentrated in vacuo. The residue was purified by silica gel column chromatography (hexane/ethyl acetate, 3/1, v/v) to give the alcohol 29 as a colorless syrup (170 mg, 90%). R$_f$=0.50 (hexane/ethyl acetate, 5/3, v/v). HR MS (m/z) calcd for C$_{101}$H$_{161}$N$_4$O$_{19}$Psi [M+Na]$^+$, 1816.1160; found, 1816.3214. Lauroyl chloride (128 µL, 0.475 mmol) was added to a solution of the alcohol 29 (170 mg, 0.095 mmol), pyridine (60 µL, 0.760 mmol), and DMAP (12 mg, 0.095 mmol) in DCM (4 mL). After the reaction mixture was stirred at room temperature for 12 h, it was diluted with DCM and washed with saturated aqueous NaHCO$_3$ (2×20 mL) and brine (2×20 mL). The organic phase was dried (MgSO$_4$) and filtered. Next, the filtrate was concentrated in vacuo. The residue was purified by silica gel column chromatography (hexane/ethyl acetate, 4/1, v/v) to afford 24 as a white solid (162 mg, 85%). R$_f$=0.46 (hexane/ethyl acetate, 5/2, v/v). [α]$^{26}_D$=−2.8° (c=1.0, CHCl$_3$). $^1$H NMR (500 MHz, CDCl$_3$): δ 7.39-7.22 (m, 19H, aromatic), 6.26 (d, 1H, J$_{NH',2'}$=7.5 Hz, NH'), 5.58 (t, 1H, J$_{2',3'}$=J$_{3',4'}$=9.5 Hz, H-3'), 5.32-5.27 (m, 1H, H-3$_L$), 5.16-4.99 (m, 7H, H-1', 3, H-3$_L$, C$_6$H$_4$(CH$_2$O)$_2$P), 4.66-4.49 (m, 8H, H-1', 4', 3×CH$_2$Ph), 4.03 (d, 1H, J$_{6a,6b}$=10.5 Hz, H-6a), 3.93-3.88 (m, 1H, H-3$_S$), 3.82-3.74 (m, 3H, H-5', H-6b, H-6'a), 3.70 (dd, 1H, J$_{5',6'b}$=5.0 Hz, J$_{6'a,6'b}$=10.5 Hz, H-6'b), 3.62-3.55 (m, 2H, H-4, H-5), 3.48 (m, 1H, H-2'), 3.33 (dd, 1H, J$_{1,2}$=8.0 Hz, J$_{2,3}$=10.5 Hz, H-2), 2.70-2.22 (m, 10H, 2×H-2$_S$, 2×H-2$_L$), 1.61-1.51 (m, 10H, 2×H-4$_L$, H-4$_S$, 2×H-3$_L$), 1.26 (broad, 108H, 54×CH$_2$, lipid), 0.95 (s, 9H, SiC(CH$_3$)$_3$), 0.92-0.90 (m, 15H, 5×CH$_3$, lipid), 0.19 (s, 3H, SiCH$_3$), 0.18 (s, 3H, SiCH$_3$). $^{13}$C NMR (75 MHz, CDCl$_3$): δ 173.65 (C=O), 173.60 (C=O), 170.62 (C=O), 170.14 (C=O), 170.10 (C=O), 138.53-127.41 (aromatic), 99.64 (C-1'), 97.05 (C-1), 75.93, 75.70, 75.43, 74.06, 73.73, 73.50, 72.60, 71.46, 70.52, 70.29, 68.82-68.24 (m), 66.54 (C-2), 56.34 (C-2'), −4.12 (Si(CH$_3$)$_2$), −5.32 (Si(CH$_3$)$_2$). HR MS (m/z) calculated for C$_{115}$H$_{187}$N$_4$O$_{20}$PSi[M+Na]$^+$, 2026.3143; found, 2026.6381.

t-Butyldimethylsilyl 6-O-{6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O—[(R)-3-tetradecanoyloxy-tetradecanoyl]-β-D-glucopyranosyl}-4-O-benzyl-3-O—[(R)-3-benzyloxy-tetradecanoyl]-2-[(R)-3-benzyloxy-tetradecanoylamino]-2-deoxy-β-D-glucopyranoside (30): A suspension of 16 (100 mg, 0.05 mmol), zinc (33.0 mg, 0.50 mmol), and acetic acid (18 µL, 0.30 mmol) in DCM (4 mL) was stirred at room temperature for 12 h, after which it was diluted with ethyl acetate (25 mL). The solids were removed by filtration and washed with ethyl acetate (2×3 ml), and the combined filtrates were washed with saturated aqueous NaHCO$_3$ (2×20 mL) and brine (2×20 mL). The organic phase was dried (MgSO$_4$) and filtered. Next, the filtrate was concentrated in vacuo. The residue was purified by silica gel column chromatography (hexane/ethyl acetate, 2.5/1, v/v) to afford the amine as a pale yellow syrup (94 mg, 95%). R$_f$=0.29 (hexane/ethyl acetate, 5/2, v/v); HR MS (m/z) calcd for C$_{115}$H$_{189}$N$_2$O$_{20}$Psi[M+Na]$^+$, 2000.3238; found, 2000.6035. DCC (12 mg, 0.06 mmol) was added to a stirred solution of (R)-3-benzyloxy-tetradecanoic acid 15 (10.0 mg, 0.03 mmol) in DCM (1.5 mL). After stirring the reaction mixture for 10 min, the amine (30.0 mg, 0.015 mmol) in DCM (1 mL) and DMAP (1.0 mg, 0.0075 mmol) were added, and stirring was continued for another 12 h. The insoluble materials were removed by filtration, and the residue was washed with DCM (2×1 mL). The combined filtrates were concentrated in vacuo and the residue was purified by preparative silica gel TLC chromatography (hexane/ethyl acetate, 3.5/1, v/v) to give 30 as a white solid (22.0 mg, 64%). R$_f$=0.54 (hexane/ethyl acetate, 2/1, v/v). [α]$^{26}_D$=−2.6° (c=1.0, CHCl$_3$). $^1$H NMR (500 MHz, CDCl$_3$): δ 7.38-7.19 (m, 24H, aromatic), 6.21 (d, 1H, J$_{NH',2}$=7.0 Hz, NH'), 6.15 (d, 1H, J$_{NH,2}$=9.5 Hz, NH), 5.59 (t, 1H, J$_{2',3'}$=J$_{3',4'}$=9.5 Hz, H-3'), 5.31-5.26 (m, 1H, H-3$_L$), 5.15-4.97 (m, 7H, H-1', H-3, H-3$_L$, C$_6$H$_4$(CH$_2$O)$_2$P), 4.65-4.44 (m, 10H, H-1, H-4', 4×CH$_2$Ph), 4.01 (d, 1H, J$_{6a,6b}$=9.5 Hz, H-6a), 3.90-3.82 (m, 3H, H-2, H-6'a, H-3$_S$), 3.76-3.69 (m, 4H, H-5', H-6b, H-6'b, H-3$_S$), 3.57 (t, 1H, J$_{3,4}$=J$_{4,5}$=9.0 Hz, H-4), 3.53-3.50 (m, 1H, H-5), 3.43-3.38 (m, 1H, H-2'), 2.66-2.22 (m, 12H, 2×H-2$_L$, 2×H-2$_S$, 2×H-2$_L$)1.71-1.45 (m, 12H, 2×H-4$_L$, 2×H-4$_S$, 2×H-3$_L$), 1.26 (broad, 108H, 54×CH$_2$, lipid), 0.91-0.88 (m, 18H, 6×CH$_3$, lipid), 0.86 (s, 9H, SiC(CH$_3$)$_3$). 0.10 (s, 3H, SiCH$_3$), 0.05 (s, 3H, SiCH$_3$). $^{13}$C NMR (75 MHz, CDCl$_3$): δ 178.19 (C=O), 173.68 (C=O), 173.55 (C=O), 171.45 (C=O), 170.87 (C=O), 170.10 (C=O), 138.62-127.42 (aromatic), 99.48 (C-1'), 96.25 (C-1), 76.13, 75.85, 75.44, 74.76, 74.38, 74.10, 72.61, 71.34, 70.62, 70.53, 70.29, 68.94, 68.88-68.22 (m), 56.48 (C-2), 56.04 (C-2'), −3.72 (Si(CH$_3$)$_2$), −5.05 (Si (CH$_3$)$_2$). HR MS (m/z) calculated for C$_{136}$H$_{221}$N$_2$O$_{22}$PSi [M+Na]$^+$, 2316.5641; found, 2316.9641.

t-Butyldimethylsilyl 6-O-{6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O—[(R)-3-tetradecanoyloxy-tetradecanoyl]-β-D-glucopyranosyl}-4-O-benzyl-3-O—[(R)-3-benzyloxy-tetradecanoyl]-2-deoxy-2-[(R)-3-hexadecanoyloxy-tetradecanoylamino]-β-D-glucopyranoside (31): The free amine obtained above (56.0 mg, 0.028 mmol) was acylated in a manner similar to the synthesis of 30 with (R)-3-(hexadecanoyl)oxy-tetradecanoic acid 20 (27 mg, 0.057 mmol) to yield 31 as a white solid (47 mg, 68%), R$_f$=0.48 (hexane/ethyl acetate, 5/2, v/v). [α]$^{25}_D$=−0.87° (c=1.0, CHCl$_3$). $^1$H NMR (500 MHz, CDCl$_3$): δ 7.39-7.21 (m, 19H, aromatic), 6.20 (d, 1H, J$_{NH',2'}$=7.5 Hz, NH'), 5.76 (d, 1H, J$_{NH,2}$=9.0 Hz, NH), 5.58 (t, 1H, J$_{2',3'}$=J$_{3',4'}$=9.5 Hz, H-3'), 5.29-5.26 (m, 1H, H-3$_L$), 5.15-4.97 (m, 8H, H-1', H-3, 2×H-3$_L$, C$_6$H$_4$(CH$_2$O)$_2$P), 4.72 (d, 1H, J$_{1,2}$=8.0 Hz, H-1), 4.64-4.44 (m, 7H, H-4, H-3×CH$_2$Ph), 4.02 (d, 1H, J$_{6a,6b}$=10.5 Hz, H-6a), 3.87-3.81 (m, 3H, H-2, H-6'a, H-3$_S$), 3.74-3.69 (m, 3H, H-5', H-6'b, H-6b), 3.59-3.58 (m, 2H, H-4, H-5), 3.44-3.39 (m, 1H, H-2), 2.64-2.22 (m, 14H, 3×H-2$_L$, H-2$_S$, 3×H-2$_{L'}$), 1.60 (broad, 14H, 3×H-4$_L$, H-4$_S$, 3×H-3$_L$), 1.26 (broad, 132H, 66×CH$_2$, lipid), 0.90-0.87 (m, 30H, 7×CH$_3$, lipid, SiC(CH$_3$)$_3$), 0.12 (s, 3H, SiCH$_3$), 0.10 (s, 3H, SiCH$_3$). $^{13}$C NMR (75 MHz, CDCl$_3$): δ 173.68 (C=O), 173.63 (C=O), 173.57 (C=O), 171.54 (C=O), 170.15 (C=O), 170.10 (C=O), 169.17 (C=O), 138.52-127.46 (aromatic), 99.45 (C-1'), 96.16 (C-1), 76.00, 75.40, 74.92, 74.45, 74.14, 73.50, 72.58, 71.26, 70.84, 70.53, 70.28, 68.89-68.33 (m), 56.40 (C-2 or 2'), 56.35 (C-2 or 2'), −3.83 (Si(CH$_3$)$_2$), −5.13 (Si(CH$_3$)$_2$). HR MS (m/z) calculated for C$_{145}$H$_{245}$N$_2$O$_{23}$PSi[M+Na]$^+$, 2464.7468; found, 2465.0632.

6-O-{6-O-Benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O—[(R)-3-tetradecanoyloxy-tetradecanoyl]-β-D-glucopyranosyl}-4-O-benzyl-3-O—[(R)-3-benzyloxy-tetradecanoyl]-2-[(R)-3-benzyloxy-tetradecanoylamino]-2-deoxy-α-D-glucopyranose (32): HF/pyridine (50 μL) was added dropwise to a stirred solution of 30 (20.0 mg, 0.0087 mmol) in THF (3 mL). The reaction mixture was stirred at room temperature for 5 h, after which it was diluted with ethyl acetate (15 mL), and washed with saturated aqueous NaHCO$_3$ (2×25 mL) and brine (2×20 mL). The organic phase was dried (MgSO$_4$) and filtered. Next, the filtrate was concentrated in vacuo. The residue was purified by silica gel column chromatography (hexane/ethyl acetate, 3/1-4/3, v/v) to give 32 as a white solid (16.0 mg, 84%). R$_f$=0.38 (hexane/ethyl acetate, 1/1, v/v). $^1$H NMR (500 MHz, CDCl$_3$): δ 7.39-7.19 (m, 24H, aromatic), 6.36 (d, 1H, J$_{NH',2'}$=7.0 Hz, NH'), 6.28 (d, 1H, J$_{NH,2}$=9.5 Hz, NH), 5.52 (d, 1H, J$_{1',2'}$=9.0 Hz, H-1'), 5.51 (t, 1H, =J$_{3',4'}$=9.5 Hz, H-3'), 5.41 (t, 1H, J$_{2,3}$=J$_{3,4}$=10.0 Hz, H-3), 5.27-5.25 (m, 1H, H-3$_L$), 5.15-4.96 (m, 6H, H-1, H-3$_L$, C$_6$H$_4$(CH$_2$O)$_2$P), 4.64-4.43 (m, 9H, H-4', 4×CH$_2$Ph), 4.23-4.19 (m, 1H, H-2), 4.13-4.09 (m, 1H, H-5), 3.94-3.82 (m, 4H, H-6a, H-6'a, 2×H-3$_S$), 3.76-3.69 (m, 3H, H-5', H-6'a, H-6b), 3.36-3.33 (m, 2H, H-2', H-4), 2.69-2.27 (m, 12H, 2×H-2$_L$, 2×H-2$_S$, 2×H-2$_{L'}$), 1.58 (broad, 12H, 2×H-4$_L$, 2×H-4$_S$, 2×H-3$_L$), 1.26 (broad, 108H, 54×CH$_2$, lipid), 0.91-0.81 (m, 18H, 6×CH$_3$, lipid). HR MS (m/z) calculated for C$_{130}$H$_{207}$N$_2$O$_{22}$PSi[M+Na]$^+$, 2202.4776; found, 2202.8279.

6-O-{6-O-Benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O—[(R)-3-tetradecanoyloxy-tetradecanoyl]-β-D-glucopyranosyl}-4-O-benzyl-3-O—[(R)-3-benzyloxy-tetradecanoyl]-2-deoxy-2-[(R)-3-hexadecanoyloxy-tetradecanoylamino]-α-D-glucopyranose (33): 31 (39.0 mg, 0.016 mmol) was deprotected in a manner similar to the synthesis of 32 with HF/pyridine (100 mL) in THF (5 mL) to yield 33 as a white solid (33.0 mg, 89%). R$_f$=0.52 (hexane/ethyl acetate, 4/3, v/v). $^1$H NMR (500 MHz, CDCl$_3$): δ 7.40-7.17 (m, 19H, aromatic), 6.41 (d, 1H, J$_{NH',2'}$=6.5 Hz, NH'), 5.95 (d, 1H, J$_{NH,2}$=9.0 Hz, NH), 5.56 (d, 1H, J$_{1',2'}$=8.5 Hz, H-1'), 5.51 (t, 1H, J$_{2',3'}$=J$_{3',4'}$=10.0 Hz, H-3'), 5.39 (t, 1H, J$_{2,3}$=J$_{3,4}$=10.0 Hz, H-3), 5.29-5.26 (m, 1H, H-3$_L$), 5.15-4.95 (m, 7H, H-1, 2×C$_6$H$_4$(CH$_2$O)$_2$P), 4.65-4.42 (m, 7H, H-4', 3×CH$_2$Ph), 4.17-4.08 (m, 2H, H-2, H-5), 3.92 (d, 1H, J$_{6a,6b}$=12.0 Hz, H-6a), 3.91-3.82 (m, 2H, H-6'a, H-3$_S$), 3.76-3.69 (m, 3H, H-5', H-6b, H-6'b), 3.36-3.30 (m, 2H, H-2', H-4), 2.69-2.27 (m, 14H, 3×H-2$_L$, H-2$_S$, 3×H-2$_{L'}$), 1.59 (broad, 14H, 3×H-4$_L$, H-4$_S$×2, 3×H-3$_L$), 1.26 (broad, 132H, 66×CH$_2$, lipid), 0.90-0.88 (m, 21H, 7×CH$_3$, lipid). HR MS (m/z) calculated for C$_{139}$H$_{231}$N$_2$O$_{23}$PSi[M+Na]$^+$, 2350.6603; found, 2350.8623.

Bis(benzyloxy)phosphoryl 6-O-{6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O-[(R)-3-tetradecanoyloxy-tetradecanoyl]-β-D-glucopyranosyl}-4-O-benzyl-3-O—[(R)-3-benzyloxy-tetradecanoyl]-2-[(R)-3-benzyloxy-tetradecanoylamino]-2-deoxy-α-D-glucopyranose (34): To a cooled (−78° C.) solution of 32 (16.0 mg, 0.0073 mmol) and tetrabenzyl diphosphate (16.0 mg, 0.029 mmol) in THF (4 mL) was added dropwise lithium bis(trimethylsilyl)amide in THF (1.0 M, 30 μL, 0.03 mmol). The reaction mixture was stirred for 1 h, and then allowed to warm up to −20° C. After stirring the reaction mixture at −20° C. for 1 h, it was quenched with saturated aqueous NaHCO$_3$ (10 mL), and extracted with ethyl acetate (15 mL). The organic phase was washed with brine (2×15 mL), dried (MgSO$_4$), and concentrated in vacuo. The residue was purified by Iatro beads column chromatography (hexane/ethyl acetate, 5/1-3/1-4/3, v/v) to give 34 as a pale yellow oil (12.0 mg, 67%).

Bis(benzyloxy)phosphoryl 6-O-{6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O-[(R)-3-tetradecanoyloxy-tetradecanoyl]-β-D-glucopyranosyl}-4-O-benzyl-3-O—[(R)-3-benzyloxy-tetradecanoyl]-2-deoxy-2-[(R)-3-hexadecanoyloxy-tetradecanoylamino]-α-D-glucopyranose (35): The phosphorylation of 33 (12 mg, 0.0052 mmol) was performed in a manner similar as for 34 to give 35 as a white solid (9.0 mg, 68%).

6-O-[2-Deoxy-2-[(R)-3-dodecanoyloxy-tetradecanoylamino]-3-O—[(R)-3-tetradecanoyloxy-tetradecanoyl]-β-D-glucopyranosyl]-2-deoxy-3-O—[(R)-3-hydroxy-tetradecanoyl]-2-[(R)-3-hydroxy-tetradecanoylamino]-α-D-glucopyranose 1,4'-bisphosphate (1): A mixture of 34 (12.0 mg, 0.0049 mmol) and Pd black (15.0 mg) in anhydrous THF (5 mL) was shaken under an atmosphere of H$_2$ (50 psi) at room temperature for 30 h, after which it was neutralized with triethylamine (10 μl), and the catalyst removed by filteration and the residue washed with THF (2×1 mL). The combined filtrates were concentrated in vacuo to afford 1 as a colorless film (6.3 mg, 72%). $^1$H NMR (600 MHz, CDCl$_3$): δ 5.19 (broad, 1H, H-1), 4.87-4.83 (m, 4H, H-3, H-3', 2×H-3$_L$), 4.43 (d, 1H, J$_{1',2'}$=8.4 Hz, H-1'), 3.93-3.89 (m, 1H, H-4'), 3.87-3.85 (m, 1H, H-2), 3.74 (broad, 1H, H-5), 3.70 (d, 1H, J$_{6a,6b}$ or J$_{6'a,6'b}$=11.4 Hz, H-6a or 6'a), 3.65 (broad, 1-H, H-3$_S$), 3.57-3.48 (m, 4H, H-6a or 6'a, 6b, 6'b, H-4), 3.21 (t, J$_{3,4}$=J$_{4,5}$=9.6 Hz, H-4), 3.14-3.11 (m, 1H, H-5'), 2.37-1.96 (m, 12H, 2×H-2$_L$, 2×H-2$_S$, 2×H-2$_{L'}$), 1.27 (broad, 12H, 2×H-4$_L$, 2×H-4$_S$, 2×H-3$_L$), 0.94 (broad, 108H, 54×CH$_2$, lipid), 0.56-0.54 (m, 18H, 6×CH$_3$, lipid). HR MS (m/z) (negative) calculated for C$_{94}$H$_{178}$N$_2$O$_{25}$P$_2$, 1797.2194; found, 1796.5488[M−H], 1797.5510[M].

6-O-{2-Deoxy-2-[(R)-3-dodecanoyloxy-tetradecanoylamino]-3-O—[(R)-3-tetradecanoyloxy-tetradecanoyl]-β-D-glucopyranosyl}-2-deoxy-2-[(R)-3-hexadecanoyl-tetradecanoylamino]-3-O—[(R)-3-hydroxy-tetradecanoyl]-α-D-glucopyranose 1,4'-bisphosphate (3): Compound 35 (9.0 mg, 0.0035 mmol) was deprotected in a manner similar to the synthesis of 1 to provide 3 as a colorless film (5.4 mg, 75%). $^1$H NMR (600 MHz, CDCl$_3$): δ 5.11 (broad, 1H, H-1), 4.87-4.82 (m, 5H, H-3, H-3', 3×H-3$_L$), 4.40 (d, 1H, J$_{1',2'}$=8.4 Hz, H-1'), 3.92-3.88 (m, 1H, H-4'), 3.85-2.83 (m, 1H, H-2), 3.77 (broad, 1H, H-5), 3.71-3.62 (m, 3H, H-3$_S$), 3.53-3.43 (m, 3H, H-2'), 3.18 (t, J$_{3,4}$=J$_{4,5}$=9.6 Hz, H-4), 3.10-3.07 (m, 1H, H-5'), 2.34-1.96 (m, 14H, 3×H-2$_L$, H-2$_S$, 3×H-20, 1.23 (broad, 14H, 3×H-4$_L$, H-4$_S$, 3×H-3$_L$), 0.99 (broad, 132H, 66×CH$_2$, lipid), 0.57-0.55 (m, 21H, 7×CH$_3$, lipid). HR MS (m/z) (negative) calculated for C$_{110}$H$_{208}$N$_2$O$_{26}$P$_2$, 2035.4491; found, 2034.4668[M−H], 2035.4692 [M].

t-Butyldimethylsilyl 6-O-{3-O-allyloxycarbonyl-6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-β-D-glucopyranosyl}-2-[(R)-3-dodecanoyloxy-tetradecanoylamino]-2-azido-4-O-benzyl-3-O—[(R)-3-benzyloxy-dodecanoyl]-2-deoxy-β-D-glucopyranoside (36): A solution of (R)-3-benzyloxy-dodecanoic acid 14 (86 mg, 0.281 mmol) and DCC (78 mg, 0.376 mmol) in DCM (5 mL) was stirred at room temperature for 10 min, and then disaccharide 21 (250 mg, 0.188 mmol) in DCM (2 mL) and DMAP (11 mg, 0.094 mmol) were added. The reaction mixture was stirred for another 14 h, after which the solids were removed by filtration, and the residue was washed with DCM (2×1 mL). The combined filtrates were concentrated in vacuo, and the residue was purified by silica gel column chromatography (hexane/ethyl acetate, 4/1 v/v) to give 36 as a white solid (277 mg, 91%). R$_f$=0.41 (hexane/ethyl acetate, 2/1, v/v). [α]$^{26}_D$=−3.0° (c=1.0, CHCl$_3$). $^1$H NMR (600 MHz, CDCl$_3$): δ 7.34-7.15 (m, 19H, aromatic), 6.01 (d, 1H, J$_{NH',2}$=7.2 Hz, NH'), 5.92-6.86 (m, 1H, OCH$_2$CH=CH$_2$), 5.46 (t, 1H, J$_{2',3'}$=J$_{3',4'}$=9.6 Hz, H-3'), 5.34 (d, 1H, J=16.8 Hz, OCH$_2$CH=CH$_2$), 5.22 (d, 1H, J=10.8 Hz, OCH$_2$CH=CH$_2$), 5.08-4.97 (m, 7H, H-1', H-3, H-3$_L$, C$_6$H$_4$(CH$_2$O)$_2$P), 4.61-4.45 (m, 10H, H-1, H-4', 3×CH$_2$Ph, OCH$_2$CH=CH$_2$), 3.97 (d, 1H, J$_{6'a,6'b}$=10.5 Hz, H-6'a), 3.88-3.86 (M, 1H, H-3$_S$), 3.81 (d, 1H, J$_{6a,6b}$=9.5 Hz, H-6a), 3.73-3.68 (m, 3H, H-5', H-6b, H-6'b), 3.56-3.46 (m, 3H, H-2', H-4, H-5), 3.28 (dd, 1H, J$_{1,2}$=7.8 Hz, J$_{2,3}$=10.2 Hz, H-2), 2.56 (dd, 1H, J$_{2Sa,2Sb}$=15.6 Hz, J$_{2Sa,3S}$=7.2 Hz, H-2$_{Sa}$), 2.44 (dd, 1H, J$_{2Sa,2Sb}$=15.6 Hz, J$_{2Sb,S3}$=6.0 Hz, H-2$_{Sb}$), 2.36 (dd, 1H, J$_{2La,2Lb}$=15.0 Hz, J$_{2La,3L}$=6.0 Hz, H-2$_{La}$), 2.30-2.21 (m, 3H, H-2$_{L'}$, H-2$_{L'b}$), 1.57-1.53 (m, 6H, H-4$_L$, H-4$_S$,H-3$_{L'}$), 1.24 (broad, 48H, 24×CH$_2$, lipid), 0.90 (s, 9H, SiC(CH$_3$)$_3$), 0.89-0.85 (m, 9H, 3×CH$_3$, lipid), 0.13 (s, 6H, Si(CH$_3$)$_2$). $^{13}$C NMR (75 MHz, CDCl$_3$): δ 173.54 (C=O), 170.64 (C=O), 170.03 (C=O), 154.49 (C=O), 138.52-127.43 (aromatic, OCH$_2$CH=CH$_2$), 118.84 (OCH$_2$CH=CH$_2$), 99.34 (C-1'), 97.02 (C-1), 76.00, 75.70, 74.33, 74.08, 73.73, 73.48, 71.46, 71.01, 68.95-67.99 (m), 66.55, −4.13 (Si(CH$_3$)$_2$), −5.32 (Si(CH$_3$)$_2$). HR MS (m/z) calculated for C$_{89}$H$_{135}$N$_4$O$_{19}$PSi [M+Na], 1645.9125; found, 1646.2435.

t-Butyldimethylsilyl 6-O-{3-O-allyloxycarbonyl-6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-β-D-glucopyranosyl}-4-O-benzyl-3-O—[(R)-3-benzyloxy-dodecanoyl]-2-deoxy-β-D-glucopyranoside (37) A suspension of 36 (180 mg, 0.111 mmol), zinc (72 mg, 1.11 mmol), and acetic acid (25 μL, 0.444 mmol) in DCM (5 mL) was stirred at room temperature for 12 h, after which it was diluted with ethyl acetate, the solids removed by filtration and the residue washed with ethyl acetate (2×2 mL). The combined filtrates were washed with saturated aqueous NaHCO$_3$ (2×15 mL) and brine (2×15 mL). The organic phase was dried (MgSO$_4$) and filtered. Next, the filtrate was concentrated in vacuo. The residue was purified by silica gel column chromatography (hexane/ethyl acetate, 2.5/1, v/v) to afford the amine as a pale yellow syrup (160 mg, 90%). R$_f$=0.35 (hexane/ethyl acetate, 2/1, v/v); HR MS (m/z) calcd for C$_{89}$H$_{137}$N$_2$O$_{19}$PSi [M+Na]$^+$, 1619.9220; found, 1620.1069. DCC (34 mg, 0.169 mmol) was added to a stirred solution of (R)-3-benzyloxy-tetradecanoic acid 15 (47 mg, 0.141 mmol) in DCM (1.5 mL). After stirring the mixture for 10 min, the amine (150 mg, 0.094 mmol) in DCM (1 mL) was added. The reaction mixture was stirred at room temperature for 10 h, after which the insoluble materials were removed by filtration, and the residue washed with DCM (2×1 mL). The combined filtrates were concentrated in vacuo and the residue was purified by preparative silica gel TLC chromatography (hexane/ethyl acetate, 5/1, v/v) to give 37 as a white solid (153 mg, 85%). R$_f$=0.34 (hexane/ethyl acetate, 3/2, v/v). [α]$^{26}_D$=−2.3° (c=1.0, CHCl$_3$). $^1$H NMR (500 MHz, CDCl$_3$): δ 7.38-7.19 (m, 24H, aromatic), 6.15 (d, 1H, J$_{NH,2}$=9.0 Hz, NH), 5.97-5.89 (m, 2H, NH', OCH$_2$CH=CH$_2$), 5.57 (t, 1H, J$_{2',3'}$=J$_{3',4'}$=9.5 Hz, H-3'), 5.38 (d, 1H, J=17.5 Hz, OCH$_2$CH=CH$_2$), 5.26 (d, 1H, J=10.5 Hz, OCH$_2$CH=CH$_2$), 5.15-5.02 (m, 7H, H-1', H-3, H-3$_L$, C$_6$H$_4$(CH$_2$O)$_2$P), 4.67-4.44 (m, 10H, H-1, H-4', 4×CH$_2$Ph), 4.01 (d, 1H, J$_{6a,6b}$=11.5 Hz, H-6a), 3.90-3.81 (m, 3H, H-2, H-6'a, H-3$_S$), 3.76-3.67 (m, 4H, H-5', H-6$_b$, H-6'$_b$, H-3$_S$), 3.57 (t, 1H, J$_{3,4}$=J$_{4,5}$=9.0 Hz, H-4), 3.53-3.50 (m, 1H, H-5), 3.45-3.40 (m, 1H, H-2'), 2.61-2.25 (m, 8H, H-4, 2×H-2$_S$, H-2$_{L'}$), 1.61-1.44 (m, 8H, H-4$_L$, 2×H-4$_S$, H-3$_{L'}$), 1.27 (broad, 66H, 33×CH$_2$, lipid), 0.91-0.86 (m, 21H, 4×CH$_3$, lipid, SiC(CH$_3$)$_3$), 0.09 (s, 3H, SiCH$_3$), 0.04 (s, 3H, SiCH$_3$). $^{13}$C NMR (75 MHz, CDCl$_3$): δ 173.49 (C=O), 171.43 (C=O), 170.82 (C=O), 170.10 (C=O), 154.45 (C=O), 138.54-127.44 (aromatic, OCH$_2$CH=CH$_2$), 118.79 (OCH$_2$CH=CH$_2$), 98.94 (C-1'), 96.27 (C-1), 76.07, 75.89, 75.77, 75.41, 74.89, 74.63, 74.18, 73.78, 73.66, 71.32, 70.95, 70.56, 68.93-68.24 (m), 56.18 (C-2 or 2'), 55.96 (C-2 or 2'), −3.74 (Si(CH$_3$)$_2$), −5.11 (Si(CH$_3$)$_2$). HR MS (m/z) calculated for C$_{110}$H$_{169}$N$_2$O$_{21}$PSi[M+Na]$^+$, 1936.1622; found, 1936.2714.

t-Butyldimethylsilyl 6-O-{3-O-allyloxycarbonyl-6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-β-D-glucopyranosyl}-4-O-benzyl-3-O—[(R)-3-benzyloxy-dodecanoyl]-2-deoxy-2-[(R)-3-hexadecanoyl-tetradecanoyl]-β-D-glucopyranoside (38) In a manner similar to the synthesis of 37, the free amine (99 mg, 0.062 mmol) synthesized by reduction of 36 was acylated with (R)-3-hexadecanoyl-tetradecanoic acid 20 (45 mg, 0.093 mmol), using DCC (26 mg, 0.124 mmol) as activating agents, to yield 38 as a white solid (103 mg, 81%). R$_f$=0.52 (hexane/ethyl acetate, 2/1, v/v). [α]$^{26}_D$=−5.3° (c=1.0, CHCl$_3$). NMR (600 MHz, CDCl$_3$): δ 7.36-7.17 (m, 19H, aromatic), 5.98 (d, 1H, J$_{NH',2}$=7.2 Hz, NH'), 5.93-5.87 (m, 1H, OCH$_2$CH=CH$_2$), 5.76 (d, 1H, J$_{NH,2}$=9.0 Hz, NH), 5.56 (t, 1H, J$_{2',3'}$=J$_{3',4'}$=9.0 Hz, H-3'), 5.36 (d, 1H, J=17.4 Hz, OCH$_2$CH=CH$_2$), 5.23 (d, 1H, J=10.2 Hz, OCH$_2$CH=CH$_2$), 5.14-4.99 (m, 8H, H-1', 3, 2×H-3$_L$, C$_6$H$_4$(CH$_2$O)$_2$P), 4.70 (d, 1H, J$_{1,2}$=7.8 Hz, H-1), 4.62-4.42 (m, 7H, H-4', 3×CH$_2$Ph), 3.99 (d, 1H, J$_{6a,6b}$=11.4 Hz, H-6a), 3.84-3.78 (m, 3H, H-2, H-6'a, H-3$_S$), 3.74-3.67 (m, 3H, H-5, H-5', H-6'$_b$), 3.58-3.55

(m, 2H, H-4, H-6b), 3.41-3.37 (m, 1H, H-2'), 2.54-2.19 (m, 10H, 2×H-2$_L$, H-2$_S$, 2×H-20, 1.59-1.50 (m, 10H, 2×H-4$_L$, H-4$_S$, 2×H-3$_L$'), 1.23 (broad, 90H, 45×CH$_2$, lipid), 0.88-0.84 (m, 24H, 5×CH$_3$, lipid, SiC(CH$_3$)$_3$), 0.09 (s, 3H, SiCH$_3$), 0.06 (s, 3H, SiCH$_3$). $^{13}$C NMR (75 MHz, CDCl$_3$): δ 173.60 (C=O), 173.43 (C=O), 171.57 (C=O), 170.04 (C=O), 169.14 (C=O), 154.42 (C=O), 138.47-127.43 (aromatic, OCH$_2$CH=CH$_2$), 118.72 (OCH$_2$CH=CH$_2$), 99.09 (C-1'), 96.05 (C-1), 75.96, 75.36, 74.95, 74.80, 74.26, 74.10, 73.77, 73.69, 71.21, 70.91, 70.76, 68.87-67.98 (m), 56.32, 56.03 (C-2'), −3.91 (Si(CH$_3$)$_2$), −5.20 (Si(CH$_3$)$_2$), HR MS (m/z) calculated for C$_{110}$H$_{169}$N$_2$O$_{21}$PSi[M+Na]F, 2084.3450; found, 2084.6633.

t-Butyldimethylsilyl 6-O-{6-O-benzyl-2-deoxy-4-O-(1,5-dihydro-3-oxo-3-3H-2,4,3-benzodioxaphosphepin-3-yl)-2-[(R)-3-dodecanoyloxy-tetradecanoylamino]-3-O-[(R)-3-(p-methoxy)benzyloxy-dodecanoylamino]-β-D-glucopyranosyl}-4-O-benzyl-3-O-[(R)-3-benzyloxy-dodecanoyl]-2-[(R)-3-benzyloxy-tetradecanoyl]-2-deoxy-β-D-glucopyranoside (39): Tetrakis(triphenylphosphine)palladium (6.6 mg, 0.006 mmol) was added to a solution of 37 (55 mg, 0.029 mmol), n-BuNH$_2$ (5.7 µL, 0.058 mmol), and HCOOH (2.2 µL, 0.058 mmol) in THF (5 mL). After stirring the reaction mixture at room temperature for 20 min, it was diluted with DCM (15 mL), and washed with water (10 mL), saturated aqueous NaHCO$_3$ (2×10 mL) and brine (2×10 mL). The organic phase was dried (MgSO$_4$) and filtered. Next, the filtrate was concentrated in vacuo. The residue was purified by silica gel column chromatography (hexane/ethyl acetate, 4/3, v/v) to give the alcohol intermediate. A solution of (R)-3-(p-methoxy)benzyloxy-dodecanoic acid 16 (16.5 mg, 0.049 mmol) and DCC (13.6 mg, 0.066 mmol) in DCM (5 mL) was stirred at room temperature for 10 min, after which the alcohol intermediate in DCM (1 mL) and DMAP (7 mg, 0.060 mmol) were added. The reaction mixture was stirred at room temperature for 5 h, after which the solids were removed by filtration and washed with DCM (2×2 mL). The combined filtrates were concentrated in vacuo and the residue was purified by preparative silica gel TLC (hexane/ethyl acetate, 3/1, v/v) afforded 39 as a white solid (47 mg, 75%). R$_f$=0.29 (hexane/ethyl acetate, 5/2, v/v). [α]$^{26}$$_D$=−4.5° (c=1.0, CHCl$_3$). $^1$H NMR (600 MHz, CDCl$_3$): δ 7.38-6.72 (m, 28H, aromatic), 6.11 (d, 1H, J$_{NH,2}$=9.0 Hz, NH), 5.74 (d, 1H, J$_{NH',2'}$=7.8 Hz, NH'), 5.59 (t, 1H, J$_{2',3'}$=J$_{3',4'}$=9.6 Hz, H-3'), 5.10-5.06 (m, 2H, H-1', H-3), 5.00-4.85 (m, 5H, H-3$_L$, C$_6$H$_4$(CH$_2$O)$_2$P), 4.61 (t, 1H, J$_{3',4'}$=J$_{4',5}$=9.0 Hz, H-4'), 4.57-4.41 (m, 11H, H-1, 4×CH$_2$Ph, CH$_2$PhOCH$_3$), 3.97 (d, 1H, J$_{6a,6b}$=10.8 Hz, H-6a), 3.88-3.81 (m, 4H, H-2, H-6'a, 2×H-3$_S$), 3.71-3.68 (m, 7H, H-5', H-6b, H-6'b, H-3$_S$, CH$_3$OPh), 3.55 (t, 1H, J$_{3,4}$=J$_{4,5}$=9.0 Hz, H-4), 3.47 (broad, 1H, H-5), 3.30-3.26 (m, 1H, H-2'), 2.64-1.69 (m, 10H, H-2$_L$, 3×H-2$_S$, H-2$_{L'}$), 1.67-1.41 (m, 10H, H-4$_L$, 3×H-4-s, H-3$_{L'}$), 1.24 (broad, 80H, 40×CH$_2$, lipid), 0.87-0.81 (m, 24H, 5×CH$_3$, lipid, SiC(CH$_3$)$_3$), 0.06 (s, 3H, SiCH$_3$), 0.01 (s, 3H, SiCH$_3$). HR MS (m/z) calculated for C$_{126}$H$_{195}$N$_2$O$_{22}$PSi[M+Na]$^+$, 2170.3606; found, 2170.4929.

t-Butyldimethylsilyl 6-O-{6-O-benzyl-2-deoxy-4-O-(1,5-dihydro-3-oxo-3λ$^5$-3H-2,4,3-benzodioxaphosphepin-3-yl)-2-[(R)-3-dodecanoyloxy-tetradecanoylamino]-3-O—[(R)-3-(p-methoxy)benzyloxy-dodecanoylamino]-β-D-glucopyranosyl}-4-O-benzyl-3-O-[(R)-3-benzyloxy-dodecanoyl]-2-deoxy-2-[(R)-3-hexadecanoyloxy-tetradecanoylamino]-β-D-glucopyranoside (40): In a manner similar as described for the synthesis of 39, the Alloc group of 38 (72 mg, 0.035 mmol) in THF (6 mL) was removed with tetrakis(triphenylphosphine)palladium (12 mg, 0.011 mmol) in the presence of n-BuNH$_2$ (6.9 µL, 0.07 mmol), HCOOH (2.6 µL, 0.07 mmol). After purification by silica gel column chromatography (hexane/ethyl acetate, 4/3, v/v), the resulting intermediate was acylated with (R)-3-(p-methoxy)benzyloxy-docanoic acid 16 (18 mg, 0.052 mmol) in DCM (5 mL), using DCC (15 mg, 0.07 mmol) and DMAP (2.5 mg, 0.02 mmol) as activating agents. Purification by preparative silica gel TLC (hexane/ethyl acetate, 3/1, v/v) afforded 40 as a white solid (49 mg, 61%). R$_f$=0.30 (hexane/ethyl acetate, 5/2, v/v). [α]$^{25}$$_D$=−6.0° (c 1.0, CHCl$_3$). $^1$H NMR 500 MHz, CDCl$_3$): δ 7.39-6.73 (m, 23H, aromatic), 5.80-5.79 (broad, 2H, NH, NH'), 5.64 (t, 1H, J$_{2',3'}$=J$_{3',4'}$=9.5 Hz, H-3'), 5.16-5.11 (m, 2H, H-1', H-3), 5.06-4.84 (m, 6H, 2×H-3$_L$, C$_6$H$_4$(CH$_2$O)$_2$P), 4.71 (d, 1H, J$_{1,2}$=8.0 Hz, H-1), 4.67-4.44 (m, 9H, H-4', 4×CH$_2$Ph), 4.01 (d, 1H, J$_{6a,6b}$=10.5 Hz, H-6a), 3.88-3.79 (m, 4H, H-2,6'a, 2×H-3$_S$), 3.74-3.69 (6, 3H, H-5', H-6b, H-6'b, CH$_3$OPh), 3.61-3.58 (m, 2H, H-4, H-5), 3.30-3.25 (m, 1H, H-2'), 2.65-2.01 (m, 12H, 2×H-2$_L$, 2×H-2$_S$, 2×1.61-1.50 (m, 12H, 2×H-4$_L$, 2×H-4$_S$, 2×H-30, 1.25 (broad, 102H, 51×CH$_2$, lipid), 0.88-0.84 (m, 27H, 6×CH$_3$, lipid, SiC(CH$_3$)$_3$), 0.08 (s, 3H, SiCH$_3$), 0.06 (s, 3H, SiCH$_3$). $^{13}$C NMR (75 MHz, CDCl$_3$): δ 173.63 (C=O), 171.62 (C=O), 171.14 (C=O), 169.88 (C=O), 169.14 (C=O), 159.20-113.77 (aromatic), 99.61 (C-1'), 96.17 (C-1), 75.98, 75.39, 75.23, 74.91, 74.42, 74.15, 73.92, 73.51, 72.02, 71.26, 71.05, 70.81, 70.63, 68.95, 68.52-68.18 (m), 56.32 (C-2 or 2'), 55.17 (CH$_3$OPh), −3.83 (Si(CH$_3$)$_2$), −5.13 (Si(CH$_3$)$_2$). HR MS (m/z) calculated for C$_{135}$H$_{219}$N$_2$O$_{23}$PSi[M+Na], 2318.5433; found, 2318.7700.

t-Butyldimethylsilyl 6-O-{6-O-benzyl-2-deoxy-4-O-(1,5-dihydro-3-oxo-3λ$^5$-3H-2,4,3-benzodioxaphosphepin-3-yl)-3-O—[(R)-3-dodecanoyloxy-dodecanoyl]-2-[(R)-3-dodecanoyloxy-tetradecanoylamino]-β-D-glucopyranosyl}-4-O-benzyl-3-O—[(R)-3-benzyloxy-dodecanoyl]-2-[(R)-3-benzyloxy-tetradecanoylamino]-2-deoxy-β-D-glucopyranoside (43): DDQ (5 mg, 0.0223 mmol) was added to a stirred solution of 39 (32 mg, 0.0149 mmol) in a mixture of DCM and H$_2$O (3 mL, 10/1, v/v). After stirring the reaction mixture at room temperature for 1 h, it was diluted with DCM (10 mL), and washed with brine (10 mL). The organic phase was dried (MgSO$_4$) and filtered. Next, the filtrate was concentrated in vacuo. The residue was purified by silica gel column chromatography (hexane/ethyl acetate, 3/1, v/v) to give free alcohol 41 as a colorless syrup (29 mg, 96%). R$_f$=0.36 (hexane/ethyl acetate, 2/1, v/v). $^1$H NMR (500 MHz, CDCl$_3$): δ 7.39-7.18 (m, 24H, aromatic), 6.30 (d, 1H, J$_{NH',2'}$=7.5 Hz, NH'), 6.16 (d, 1H, J$_{NH,2}$=9.0 Hz, NH), 5.60 (t, 1H, J$_{2',3'}$=J$_{3',4'}$=10.0 Hz, H-3'), 5.15-4.98 (m, 7H, 1H, H-3, H-3$_L$, C$_6$H$_4$(CH$_2$O)$_2$P), 4.68-4.63 (m, 1H, H-4'), 4.58-4.44 (m, 9H, H-1, 4×CH$_2$Ph), 4.07 (broad, 1H, H-3$_S$), 4.01 (d, 1H, J$_{6a,6b}$=10.0 Hz, H-6a), 3.87-3.82 (On, 3H, H-2, H-6'a, H-3$_S$), 3.73-3.71 (m, 4H, H-5', H-6b, H-6'b, H-3$_S$), 3.59 (t, 1H, J$_{3,4}$=J$_{4,5}$=9.0 Hz, H-4), 3.53-3.50 (m, 1H, H-2', H-5), 2.64-2.23 (m, 10H, H-2$_L$, 3×H-2$_S$, H-2$_{L'}$), 1.69-1.46 (m, 10H, H-4$_L$, 3×H-4$_S$, H-3$_{L'}$), 1.26 (broad, 80H, 40×CH$_2$, lipid), 0.91-0.84 (On, 24H, 5×CH$_3$, lipid, SiC(CH$_3$)$_3$), 0.09 (s, 3H, SiCH$_3$), 0.04 (s, 3H, SiCH$_3$). HR MS (m/z) calcd for C$_{118}$H$_{187}$N$_2$O$_{21}$PSi[M+Na]$^+$, 2050.3031; found, 2050.5063. Lauroyl chloride (50 µl) was added to a solution of alcohol 41 (27 mg, 0.0133 mmol), pyridine (100 µl), and DMAP (1.2 mg, 0.01 mmol) in DCM (2 mL). After the reaction mixture was stirred at room temperature for 12 h, it was diluted with DCM (15 mL) and washed with saturated aqueous NaHCO$_3$ (2×10 mL) and brine (2×10 mL). The organic phase was dried (MgSO$_4$) and filtered. Next, the filtrate was concentrated in vacuo. The residue was purified by preparative silica gel TLC (toluene/ethyl acetate, 5/1, v/v) to afford 43 as a white solid (25 mg, 86%). R$_f$=0.56 (hexane/ethyl acetate, 2/1, v/v).

$[\alpha]^{26}{}_D$=−2.9° (c=1.0, CHCl$_3$). $^1$H NMR (500 MHz, CDCl$_3$): δ 7.38-7.21 (m, 24H, aromatic), 6.19 (d, 1H, J$_{NH',2'}$=7.5 Hz, NH'), 6.17 (d, 1H, J$_{NH,2}$=9.0 Hz, NH), 5.59 (t, 1H, J$_{2',3'}$=J$_{3',4'}$=9.5 Hz, H-3'), 5.30-5.27 (m, 1H, H-3$_L$), 5.15-4.98 (m, 7H, H-1', H-3, C$_6$H$_4$(CH$_2$O)$_2$P), 4.65-4.42 (m, 10H, H-1, H-4', 4×CH$_2$Ph), 4.01 (d, 1H, J$_{6a,6b}$=9.5 Hz, H-6a), 3.91-3.82 (m, 3H, H-2, H-6'a, H-3$_S$), 3.75-3.69 (m, 4H, H-5', H-6b, H-6'b, H-3$_S$), 3.58 (t, 1H, J$_{3,4}$=J$_{4,5}$=9.0 Hz, H-4), 3.53-3.50 (m, 1H, H-5), 3.43-3.38 (m, 1H, H-2'), 2.65-2.22 (m, 12H, 2×H-2$_L$, 2×H-2$_S$, 2×H-20, 1.66-1.52 (m, 12H, 2×H-4$_L$, 2×H-4$_S$, 2×H-3$_L$'), 1.27 (broad, 96H, 48×CH$_2$, lipid), 0.91-0.88 (m, 18H, 6×CH$_3$, lipid), 0.86 (s, 9H, SiC(CH$_3$)$_3$). 0.09 (s, 3H, SiCH$_3$), 0.05 (s, 3H, SiCH$_3$). $^{13}$C NMR (75 MHz, CDCl$_3$): δ 178.18 (C=O), 173.66 (C=O), 173.54 (C=O), 171.45 (C=O), 170.89 (C=O), 170.12 (C=O), 138.64-127.45 (aromatic), 99.52 (C-1'), 96.26 (C-1), 76.15, 75.88, 75.44, 74.78, 74.39, 74.10, 72.65, 71.36, 70.62, 70.54, 70.29, 68.96, 68.89-68.22 (m), 56.50 (C-2), 56.06 (C-2'), −3.77 (Si(CH$_3$)$_2$), −5.09 (Si(CH$_3$)$_2$). HR MS (m/z) calculated for C$_{130}$H$_{209}$N$_2$O$_{22}$PSi[M+Na]$^+$, 2232.4702; found, 2232.8787.

t-Butyldimethylsilyl 6-O-{6-O-benzyl-2-deoxy-4-O-(1,5-dihydro-3-oxo-3λ$^5$-3H-2,4,3-benzodioxaphosphepin-3-yl)-3-O—[(R)-3-dodecanoyloxy-dodecanoyl]-2-[(R)-3-dodecanoyloxy-tetradecanoylamino]-β-D-glucopyranosyl}-4-O-benzyl-3-O—[(R)-3-benzyloxy-dodecanoyl]-2-deoxy-2-[(R)-3-hexadecanoyloxy-tetradecanoylamino]-β-D-glucopyranoside (44): The PMB group of 40 (41 mg, 0.018 mmol) was removed in a manner similar to the synthesis of 41 with DDQ (6.1 mg, 0.158 mmol) in a mixture of DCM and H$_2$O (5 mL, 10/1, v/v). Purification by silica gel column chromatography (hexane/ethyl acetate, 3/1, v/v) gave free alcohol 42 as a colorless syrup (32 mg, 83%). R$_f$=0.39 (hexane/ethyl acetate, 2/1, v/v). $^1$H NMR (600 MHz, CDCl$_3$): δ 7.34-7.15 (m, 24H, aromatic), 6.26 (d, 1H, J$_{NH',2'}$=7.2 Hz, NH), 5.71 (d, 1H, J$_{NH,2}$=9.0 Hz, NH), 5.55 (t, 1H, J$_{2',3'}$=J$_{3',4'}$=9.6 Hz, H-3'), 5.13-4.95 (m, 8H, H-1', H-3, 2×C$_6$H$_4$(CH$_2$O)$_2$P), 4.71 (d, 1H, J$_{1,2}$=7.8 Hz), 4.65-4.59 (m, 1H, H-4'), 4.55-4.10 (m, 6H, 3×CH$_2$Ph), 4.04 (broad, 1H, H-3$_S$), 3.99 (d, 1H, J$_{6a,6b}$=10.2 Hz, H-6a), 3.82-3.76 (m, 3H, H-2, H-6'a, H-3$_S$), 3.73-3.68 (m, 3H, H-5', H-6b, H-6'b), 3.60-3.54 (m, 2H, H-4, H-5), 3.51-3.47 (m, 1H, H-2'), 2.61-2.18 (m, 12H, 2×H-2$_L$, 2×H-2$_S$, 2×H-20, 1.74-1.41 (m, 12H, 2×H-4$_L$, 2×H-4$_S$, 2×H-30, 1.24 (broad, 104H, 52×CH$_2$, lipid), 0.87-0.84 (m, 27H, 6×CH$_3$, lipid, SiC(CH$_3$)$_3$), 0.08 (s, 3H, SiCH$_3$), 0.06 (s, 3H, SiCH$_3$). HR MS (m/z) calcd for C$_{127}$H$_{211}$N$_2$O$_{22}$PSi[M+Na]$^+$, 2198.4858; found, 2198.7722. In a manner similar to the synthesis of 43, alcohol 42 (28 mg, 0.013 mmol) was acylated with lauroyl chloride (50 μL) in the presence of pyridine (100 μL) and DMAP (1.6 mg, 0.013 mmol) in DCM (2 mL). Purification by silica gel column chromatography (toluene/ethyl acetate, 10/1-6/1, v/v) afforded 44 as a pale yellow oil (28.5 mg, 94%). R$_f$=0.52 (hexane/ethyl acetate, 2/1, v/v). $[\alpha]^{26}{}_D$=−1.7° (c=1.0, CHCl$_3$). $^1$H NMR (500 MHz, CDCl$_3$): δ 7.34-7.16 (m, 19H, aromatic), 6.14 (d, 1H, J$_{NH',2'}$=8.0 Hz, NH'), 5.73 (d, 1H, J$_{NH,2}$=9.5 Hz, NH), 5.57 (t, 1H, J$_{2',3'}$=J$_{3',4'}$=9.5 Hz, H-3'), 5.29-5.27 (m, 1H, H-30, 5.15-4.99 (m, 8H, H-1', 3, 2×H-3$_L$, C$_6$H$_4$(CH$_2$O)$_2$P), 4.73 (d, 1H, J$_{1,2}$=7.5 Hz, H-1), 4.65-4.40 (m, 7H, H-4', 3×CH$_2$Ph), 4.02 (d, 1H, J$_{6a,6b}$=10.5 Hz, H-6a), 3.88-3.79 (m, 3H, H-2, H-6'a, H-3$_S$), 3.75-3.69 (m, 3H, H-5', H-6'b, H-6b), 3.62-3.59 (m, 2H, H-4, H-5), 3.46-3.41 (m, 1H, H-2), 2.68-2.23 (m, 14H, 3×H-2$_L$, H-2$_S$, 3×H-2$_L$'), 1.63-1.61 (m, 14H, 3×H-4$_S$, 3×H-3$_L$), 1.27 (broad, 120H, 60×CH$_2$, lipid), 0.91-0.88 (m, 30H, 7×CH$_3$, lipid, SiC(CH$_3$)$_3$), 0.13 (s, 3H, SiCH$_3$), 0.10 (s, 3H, SiCH$_3$). $^{13}$C NMR (75 MHz, CDCl$_3$): δ 173.67 (C=O), 173.62 (C=O), 173.55 (C=O), 171.62 (C=O), 170.13 (C=O), 170.10 (C=O), 169.15 (C=O), 138.52-127.48 (aromatic), 99.57 (C-1'), 96.15 (C-1), 76.00, 75.40, 74.91, 74.45, 74.14, 73.50, 72.56, 71.26, 70.83, 70.54, 70.27, 68.89-68.33 (m), 56.36 (C-2 or 2'), −3.84 (Si(CH$_3$)$_2$), −5.13 (Si(CH$_3$)$_2$). HR MS (m/z) calculated for C$_{139}$H$_{233}$N$_2$O$_{23}$PSi[M+Na]$^+$, 2380.6529; found, 2380.8301.

Bis(benzyloxy)phosphoryl 6-O-{6-O-benzyl-2-deoxy-4-O-(1,5-dihydro-3-oxo-3λ$^5$-3H-2,4,3-benzodioxaphosphepin-3-yl)-3-O—[(R)-3-dodecanoyloxy-dodecanoyl]-2-[(R)-3-dodecanoyloxy-tetradecanoylamino]-β-D-glucopyranosyl}-4-O-benzyl-3-O—[(R)-3-benzyloxy-dodecanoyl]-2-[(R)-3-benzyloxy-tetradecanoylamino]-2-deoxy-α-D-glucopyranose (45): Compound 43 (16 mg, 0.72 μmol) was deprotected in a manner similar to the synthesis of 32 with HF/pyridine (50 μL) in THF (3 mL) to yield the intermediate lactol as a white solid (13 mg, 86%). R$_f$=0.35 (hexane/ethyl acetate, 1/1, v/v). $^1$H NMR (500 MHz, CDCl$_3$): δ 7.40-7.18 (m, 24H, aromatic), 6.37 (d, 1H, J$_{NH',2}$=7.5 Hz, NH'), 6.26 (d, 1H, J$_{NH,2}$=9.5 Hz, NH), 5.55 (d, 1H, =8.0 Hz, H-1'), 5.52 (t, 1H, J$_{2',3'}$=J$_{3',4'}$=9.5 Hz, H-3'), 5.42 (t, 1H, J$_{2,3}$=J$_{3,4}$=10.0 Hz, H-3), 5.28-5.24 (m, 1H, H-3$_L$), 5.15-4.96 (m, 6H, H-1, H-3$_L$, C$_6$H$_4$(CH$_2$O)$_2$P), 4.65-4.43 (m, 9H, H-4', 4×CH$_2$Ph), 4.24-4.19 (m, 1H, H-2), 4.13-4.09 (m, 1H, H-5), 3.94-3.82 (m, 4H, H-6a, H-6'a, 2×H-3$_S$), 3.77-3.68 (m, 3H, H-5', H-6b, H-6'b), 3.37-3.31 (m, 2H, H-2', H-4), 2.69-2.27 (m, 12H, 2×H-2$_L$, 2×H-2$_S$, 2×H-20, 1.59 (broad, 12H, 2×H-4$_L$, 2×H-4$_S$, 2×H-3$_L$'), 1.26 (broad, 80H, 40×CH$_2$, lipid), 0.91-0.88 (m, 18H, 6×CH$_3$, lipid). HR MS (m/z) calculated for C$_{124}$H$_{195}$N$_2$O$_{22}$PSi[M+Na]$^+$, 2118.3837; found, 2118.6284. The anomeric hydroxyl of the resulting lactol (16.0 mg, 0.0073 mmol) was phosphorylated in a manner similar to the synthesis of 34 to afford 45 as a white solid (11.0 mg, 72%).

Bis(benzyloxy)phosphoryl 6-O-{6-O-benzyl-2-deoxy-4-O-(1,5-dihydro-3-oxo-3λ$^5$-3H-2,4,3-benzodioxaphosphepin-3-yl)-3-O—[(R)-3-dodecanoyloxy-dodecanoyl]-2-[(R)-3-dodecanoyloxy-tetradecanoylamino]-β-D-glucopyranosyl}-4-O-benzyl-3-O—[(R)-3-benzyloxy-dodecanoyl]-2-deoxy-2-[(R)-3-hexadecanoyloxy-tetradecanoylamino]-α-D-glucopyranose (46): Compound 44 (24 mg, 0.010 mmol) was deprotected in a manner similar to the synthesis of 32 with HF/pyridine (100 μL) in THF (3 mL) to yield the intermediate lactol as a white solid (22 mg, 97%). R$_f$=0.52 (hexane/ethyl acetate, 1/1, v/v). $^1$H NMR (600 MHz, CDCl$_3$): δ 7.39-7.15 (m, 19H, aromatic), 6.33 (d, 1H, J$_{NH',2}$=7.2 Hz, NH'), 5.89 (d, 1H, J$_{NH,2}$=9.0 Hz, NH), 5.55 (d, 1H, J$_{1',2'}$=8.4 Hz, H-1'), 5.48 (t, 1H, J$_{2',3'}$=J$_{3',4'}$=9.6 Hz, H-3'), 5.36 (t, 1H, J$_{2,3}$=J$_{3,4}$=9.6 Hz, H-3), 5.26-5.22 (m, 1H, H-3$_L$), 5.11-4.88 (m, 7H, H-1, 2×H-3$_L$, C$_6$H$_4$(CH$_2$O)$_2$P), 4.62-4.40 (m, 7H, H-4', 3×CH$_2$Ph), 4.14-4.05 (m, 2H, H-2, H-5), 3.89 (d, 1H, J$_{6a,6b}$=12.6 Hz, H-6a), 3.84-3.79 (m, 2H, H-6'a, H-3$_S$), 3.74-3.67 (m, 3H, H-5', H-6b, H6'b), 3.31-3.28 (m, 2H, H-2', H-4), 2.66-2.23 (m, 14H, 3×H-2$_L$, H-2$_S$, 3×H-2$_L$'), 1.62-1.53 (broad, 14H, 3×H-4$_L$, H-4$_S$×2, 3×H-3$_L$), 1.3 (broad, 120H, 60×CH$_2$, lipid), 0.87-0.85 (m, 21H, 7×CH$_3$, lipid). HR MS (m/z) calculated for C$_{133}$H$_{219}$N$_2$O$_{23}$PSi[M+Na]$^+$, 2266.5664; found, 2266.8252. The anomeric hydroxyl of the resulting lactol (12.0 mg, 0.0053 mmol) was phosphorylated in a manner similar to the synthesis of 34 to afford 46 as a white solid (9.2 mg, 69%).

6-O-{2-Deoxy-3-O—[(R)-3-dodecanoyloxy-dodecanoyl]-2-[(R)-3-dodecanoyloxy-tetradecanoylamino]-β-D-glucopyranosyl}-2-deoxy-3-O—[(R)-3-hydroxy-dodecanoyl]-2-[(R)-3-hydroxy-tetredecanoylamino]-α-D-glucopyranose 1,4'-bisphosphate (2): Compound 45 (8.0 mg, 0.0034 mmol) was deprotected in a manner similar to the synthesis of 1 to provide 2 as a colorless film (4.7 mg, 81%). $^1$H NMR (600 MHz, CDCl$_3$/CD$_3$OD, 1/1, v/v): δ 5.08 (broad, 1H, H-1), 4.79-4.76 (m, 4H, H-3, H-3', 2×H-3$_L$), 4.35 (d, 1H, J$_{1',2'}$=7.8 Hz, H-1'), 3.82 (broad, 1H, H-4'), 3.77-3.75 (m, 1H, H-2), 3.67 (broad, 1H, H-5), 3.61 (d, J$_{6a,6b}$ or J$_{6'a,6'b}$=11.4 Hz, H-6a or 6'a), 3.56 (m, 1H, H-3$_S$), 3.49-3.40 (m, 5H, H-2', H-6a or H-6'a, H-6b, H-6'b, H-3$_S$), 3.12 (t, 1H, J$_{3,4}$=J$_{4,5}$=9.0 Hz, H-4), 3.02 (broad, 1H, H-5'), 2.29-1.84 (m, 12H, 2×H-2$_L$, 2×H-2$_S$, 2×H-2$_{L'}$, 1.18 (broad, 12H, 2×H-4$_L$, 2×H-4$_S$, 2×H-3$_L$), 0.85 (broad, 80H, 40×CH$_2$, lipid), 0.47-0.45 (m, 18H, 6×CH$_3$, lipid). HR MS (m/z) (negative) calculated for C$_{88}$H$_{166}$N$_2$O$_{25}$P$_2$, 1713.1255; found, 1712.0845 [M-H], 1713.0880 [M].

6-O-{2-Deoxy-3-O—[(R)-3-dodecanoyloxy-dodecanoyl]-2-[(R)-3-dodecanoyloxy-tetradecanoylamino]-β-D-glucopyranosyl}-2-deoxy-2-[(R)-3-hexadecanoyloxy-tetradecanoylamino]-3-O—[(R)-3-hydroxy-dodecanoyl]-α-D-glucopyranose 1,4'-bisphosphate (4): Compound 46 (9.2 mg, 0.0041 mmol) was deprotected in a manner similar to the synthesis of 1 to provide 4 as a colorless film (5.5 mg, 69%). $^1$H NMR (500 MHz, CDCl$_3$/CD$_3$OD, 1/1, v/v): δ 5.33 (broad, 1H, H-1), 5.11-5.03 (m, 5H, H-3, H-3', 3×H-3$_L$), 4.61 (d, 1H, J$_{1',2'}$=8.5 Hz, H-1'), 4.16-3.10 (m, 1H, H-4'), 4.09-4.07 (m, 1H, H-2), 4.04 (broad, 1H, H-5), 3.94-3.89 (m, H-6a or H-6'a, H-3$_S$), 3.75-3.67 (m, H-2'), 3.39 (dd, J=8.5 Hz, J=9.5 Hz, H-4), 3.31-3.29 (m, 1H, H-5'), 2.63-2.19 (m, 14H, 3×H-2$_L$, H-2$_S$, 3×H-2$_{L'}$, 1.52 (broad, 14H, 3×H-4$_L$, H-4$_S$, 3×H-3$_L$), 1.18 (broad, 120H, 60×CH$_2$, lipid), 0.81-0.78 (m, 21H, 7×CH$_3$, lipid). HR MS (m/z) (negative) calcd for C$_{104}$H$_{196}$N$_2$O$_{26}$P$_2$, 1951.3552; found, 1950.4846 [M-H], 1951.4910 [M].

6-O-{2-Deoxy-3-O—[(R)-3-dodecanoyloxy-dodecanoyl]-2-[(R)-3-dodecanoyloxy-tetradecanoylamino]-β-D-glucopyranosyl}-2-deoxy-2-[(R)-3-hexadecanoyloxy-tetradecanoylamino]-3-O—[(R)-3-hydroxy-dodecanoyl]-α-D-glucopyranose (5): The resulting lactol in the synthesis of 46 (8.5 mg, 0.0038 mmol) was deprotected in a manner similar to the synthesis of 1 to provide 5 as a colorless film (5.1 mg, 71%). $^1$H NMR (600 MHz, CDCl$_3$/CD$_3$OD, 1/1, v/v): δ 5.01-4.91 (m, 5H, H-3, H-3', 3×H-3$_L$), 4.89 (broad, 1H, H-1), 4.48 (d, 1H, J$_{1',2'}$=8.4 Hz, H-1'), 4.06 (broad, 1H, H-4'), 3.90-3.85 (m, 3H, H-2, H-5, H-6a or H-6'a), 3.75 (broad, H-3$_S$), 3.70 (broad, 1H, H-6a or H-6'a), 3.67-3.62 (m, 2H, H-2', H-6b or H-6'b), 3.58 (broad, 1H, H-6b or 6'b), 3.28-3.20 (m, 2H, H-4, H-5'), 2.61 (m, 1H, H-2$_{Sa}$), 2.53 (m, 1H, H-2$_{Sb}$), 2.40-2.12 (m, 6H, 3×H-2$_L$), 2.11-2.08 (m, 6H, 3×H-2$_c$), 1.45 (broad, 14H, 3×H-4$_L$, H-4$_S$, 3×H-3$_L$), 1.12 (broad, 120H, 60×CH$_2$, lipid), 0.76-0.83 (m, 21H, 7×CH$_3$, lipid). HR MS (m/z) (negative) calculated for C$_{104}$H$_{195}$N$_2$O$_{23}$P, 1871.3888; found, 1870.4127 [M–H], 1871.4128 [M].

Reagents for Biological Experiments. *E. coli* 055:B5 LPS was obtained from List Biologicals. All data presented in this study were generated using the same batch of *E. coli* 055:B5 LPS. Synthetic lipid As were reconstituted in PBS with DMSO (10%) and stored at −80° C.

Cell Maintenance. RAW 264.7 γNO(−) cells, derived from the RAW 264.7 mouse monocyte/macrophage cell line, were obtained from ATCC. The cells were maintained in RPMI 1640 medium (ATCC) with L-glutamine (2 mM), adjusted to contain sodium bicarbonate (1.5 g/L), glucose (4.5 g/L), HEPES (10 mM), and sodium pyruvate (1.0 mM) and supplemented with penicillin (100 u/ml)/streptomycin (100 μg/ml; Mediatech) and fetal bovine serum (FBS, 10%; Hyclone). Human embryonic kidney (HEK) 293T cells were grown in Dulbecco's modified Eagle's medium (ATCC) with L-glutamine (4 mM), glucose (4.5 g/L), and sodium bicarbonate (1.5 g/L) supplemented with penicillin (100 u/mL)/streptomycin (100 μg/mL), Normocin (100 μg/mL), and FBS (10%). Stably transfected HEK 293T cells with murine TLR4, MD2, and CD14 (InvivoGen) were obtained from InvivoGen and grown in the same growth medium as for HEK 293T cells supplemented with the selective agents HygroGold (50 μg/mL; InvivoGen) and blasticidin (10 μg/mL; InvivoGen). All cells were maintained in a humid 5% $CO_2$ atmosphere at 37° C.

Cytokine Induction and ELISAs. RAW 264.7 γNO(−) cells were plated on the day of the exposure assay as 2×10$^5$ cells/well in 96-well tissue culture plates (Nunc). Cells were incubated with different stimuli for 5.5 and 24 hours in replicates of five. Culture supernatants were then collected, pooled, and stored frozen (−80° C.) until assayed for cytokine production. After removal of the supernatant, cells were lysed by adding PBS containing Tween 20 (0.01%) and BSA (1%) in the same volume as that of the supernatant and sonicating for 5 min. The cell lysates were pooled and stored frozen (−80° C.) until assayed for cytokine production.

All cytokine ELISAs were performed in 96-well MaxiSorp plates (Nunc). Cytokine DuoSet ELISA Development Kits (R&D Systems) were used for the cytokine quantification of mouse TNF-α, IL-6, IP-10, RANTES, and IL-1β according to the manufacturer's instructions. The absorbance was measured at 450 nm with wavelength correction set to 540 nm using a microplate reader (BMG Labtech). Concentrations of IFN-β in culture supernatants were determined as follows. ELISA MaxiSorp plates were coated with rabbit polyclonal antibody against mouse IFN-β (PBL Biomedical Laboratories). IFN-β in standards and samples was allowed to bind to the immobilized antibody. Rat anti-mouse IFN-β antibody (USBiological) was then added, producing an antibody-antigen-antibody "sandwich". Next, horseradish peroxidase (HRP) conjugated goat anti-rat IgG (H+L) antibody (Pierce) and a chromogenic substrate for HRP 3,3',5,5'-tetramethylbenzidine (TMB; Pierce) were added. After the reaction was stopped, the absorbance was measured at 450 nm with wavelength correction set to 540 nm. All cytokine values are presented as the means±SD of triplicate measurements, with each experiment being repeated three times.

Transfection and NF-κB Activation Assay. The day before transfection, HEK 293T wild type cells and HEK 293T cells stably transfected with murine TLR4/MD2/CD14 were plated in 96-well tissue culture plates (16,000 cells/well). The next day, cells were transiently transfected using PolyFect Transfection Reagent (Qiagen) with expression plasmids pELAM-Luc (NF-κB-dependent firefly luciferase reporter plasmid, 50 ng/well) (Chow et al., *J. Biol. Chem.* 1999, 274, 10689-10692) and pRL-TK (Renilla luciferase control reporter vector, 1 ng/well; Promega) as an internal control to normalize experimental variations. The empty vector pcDNA3 (Invitrogen) was used as a control and to normalize the DNA concentration for all of the transfection reactions (total DNA 70 ng/well). Forty-four h post-transfection, cells were exposed to the stimuli at the indicated concentrations for 4 h, after which cell extracts were prepared. The luciferase activity was measured using the Dual-Luciferase Reporter Assay System (Promega) according to the manufacturer's instructions and the Fluoroskan Accent FL combination luminometer/fluorometer (Thermo Electron Corporation). Expression of the firefly luciferase reporter gene was normalized for transfection efficiency with expression of *Renilla* luciferase. The data are reported as the means±SD of triplicate treatments. The transfection experiments were repeated at least twice.

Data analysis. Concentration-response data were analyzed using nonlinear least-squares curve fitting in Prism (GraphPad Software, Inc.). These data were fit with the following four parameter logistic equation: $Y=E_{max}/(I+(EC_{50}/X)^{Hill\ slope})$, where Y is the cytokine response, X is logarithm of the concentration of the stimulus, $E_{max}$ is the maximum response, and $EC_{50}$ is the concentration of the stimulus producing 50% stimulation. The Hillslope was set at 1 to be able to compare the $EC_{50}$ values of the different inducers.

General Procedures. 1H NMR and 13C NMR spectra were recorded with Varian spectrometers (models Inova300, Inova500 and Inova600) equipped with Sun workstations. 1H NMR spectra were recorded in CDCl3 and referenced to residual CHCl3 at 7.24 ppm, and 13C NMR spectra were referenced to the central peak of CDCl3 at 77.0 ppm. Assignments were made by standard gCOSY and gHSQC. High resolution mass spectra were obtained on a Bruker model Ultraflex MALDI-TOF mass spectrometer.

Example II

Innate Immune Responses of Synthetic Lipid A Derivatives of Neisseria meningitidis Differences in the pattern and chemical nature of fatty acids of lipid A of Neisseria meningitides lipooligosaccharides (LOS) and Escherichia coli lipopolysaccharides (LPS) may account for differences in inflammatory properties. Furthermore, there are indications that dimeric 3-deoxy-D-manno-oct-2-ulosonic acid (KDO) moieties of LOS and LPS enhance biological activities. Heterogeneity in the structure of lipid A and possible contaminations with other inflammatory components have made it difficult to confirm these observations. To address these problems, a highly convergent approach for the synthesis of a lipid A derivative containing KDO has been developed, which relies on the ability to selectively remove or unmask in a sequential manner an isopropylidene acetal, 9-fluorenylmethoxycarbonyl (Fmoc), allyloxycarbonate (Alloc), azide, and thexyldimethylsilyl (TDS) ether (Zhang et al., 2008 Chemistry—A Eur. J. 14:558-569; Supporting Information for Zhang et al., 2008 Chemistry—A Eur. J. 14:558-569 available online at the Wiley Interscience site on the World Wide Web at wiley-vch.de/contents/jc_2111/2008/f701165_s.pdf). The strategy was employed for the synthesis of N. meningitidis lipid A containing KDO (53). Mouse macrophages were exposed to the synthetic compound and its parent LOS, E. coli lipid A (52), and a hybrid derivative (54) that has the asymmetrical acylation pattern of E. coli lipid A, but the shorter lipids of meningococcal lipid A. The resulting supernatants were examined for tumor necrosis factor alpha (TNF-α) and interferon beta (IFN-β) production. The lipid A derivative containing KDO was much more active than lipid A alone and just slightly less active than its parent LOS, indicating that one KDO moiety is sufficient for full activity of TNF-α and IFN-β induction. The lipid A of N. meningitidis was a significantly more potent inducer of TNF-α and IFN-β than E. coli lipid A, which is due to a number of shorter fatty acids. The compounds did not demonstrate a bias towards a MyD88- or TRIF-dependent response.

This example reports the preparation of a prototypical lipid A derived from N. meningitidis (51) and a similar derivative containing a KDO moiety (53). Proinflammatory properties of these compounds have been determined in a mouse macrophage cell line and the results compared with similar data for lipid A 52, which is derived from E. coli, and compound 54, which has the asymmetrical acylation pattern of E. coli but fatty acids that are similar in length to those of N. meningitidis lipid A. It has been found that the lipid A of N. meningitidis (51) is a more potent inducer of TNF-α and IFN-β than E. coli lipid A (52). The greater potency was attributed to the shorter fatty acids of 51 and not to its symmetrical acylation pattern. Furthermore, the KDO moiety of 53 significantly enhanced the potency of proinflammatory responses.

Results and Discussion

Figure 6:
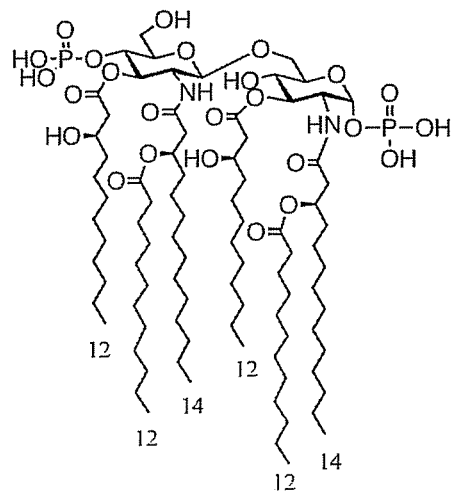
FIG. 6 shows the chemical structure of lipid A derivatives 51, 52 (i.e., 1), 53 and 54 (i.e., 2).
Figure 6:
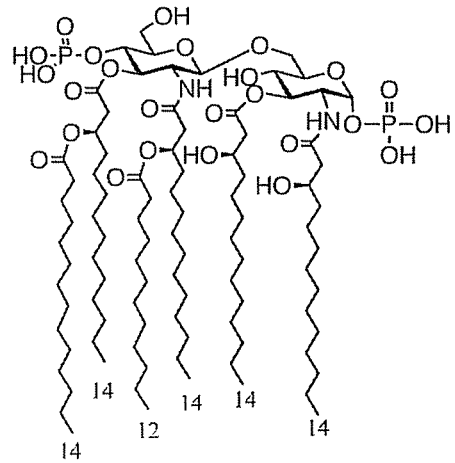
Figure 6:
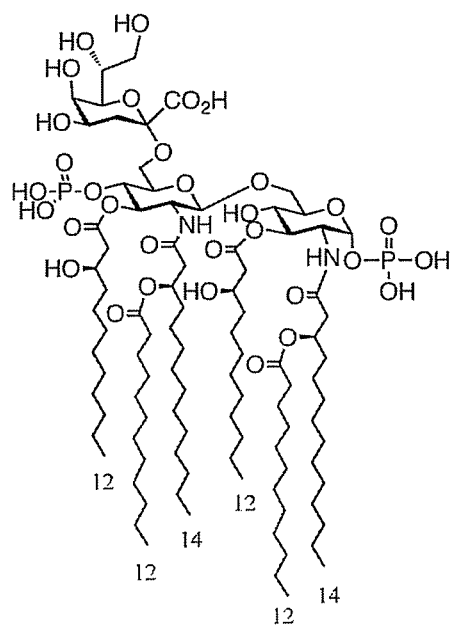
Figure 6:
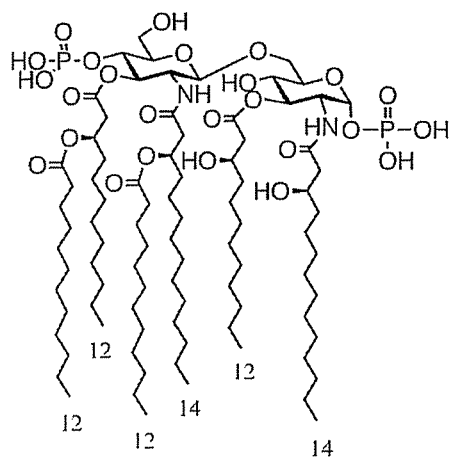

Chemical Synthesis. To determine biological properties of N. meningitidis lipid A and LOS, we have synthesized compounds 51 and 53 (FIG. 6) by a highly convergent approach. Compound 51 is a prototypical lipid A derived from N. meningitidis LOS, and is hexa-substituted in a symmetrical fashion. Compound 53 has a structure similar to 51, except that the C-6' moiety of its lipid A is extended by a KDO moiety. It was envisaged that compound 53 could be prepared from monosaccharides 55 and 56, KDO donor 57, (van der Klein et al., Tetrahedron Lett. 1989, 30, 5477-5480) and fatty acids 58 and 59 (Fukase et al., Tetrahedron 1998, 54, 4033-4050) (Scheme 4). Thus, coupling of 55 with 56 will give orthogonally protected disaccharide 65, which will be subjected to mild acidic conditions to remove the isopropylidene without affecting any of the other protecting groups. The C-6' hydroxyl of the resulting compound can then be regioselectively glycosylated with 57 followed by phosphorylation of the C-4' hydroxyl. Next, the orthogonal protecting groups 9-fluorenylmethoxycarbonyl (Fmoc), allyloxycarbonate (Alloc), and azido will be individually removed, which allows acylation with any lipid at C-2, C-2', and C-3 to give easy access to a panel compounds differing in acylation pattern. At an early stage of the synthesis, the C-3' hydroxyl of 65 was acylated with (R)-3-benzyloxy-dodecanoic acid because it was observed that the C-4'-phosphate triester can migrate during acylation of the C-3' hydroxyl. After completion of the acylations, the anomeric thexyldimethylsilyl (TDS) group can be selectively cleaved and phosphorylation of the resulting lactol followed by global deprotection should provide target compound 53.

Scheme 4.

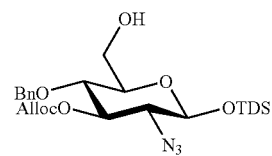

55

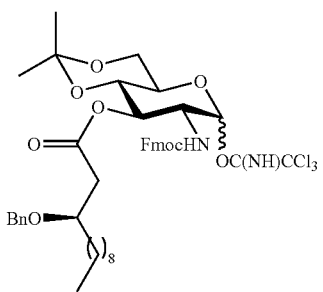

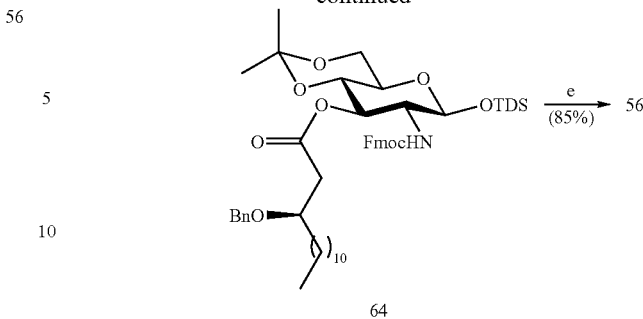

Reagents and conditions: (a) AllocCl, TMEDA, DCM; (b) PhBCl₂, Et₃SiH, MS 4 Å, DCM, -75° C.; (c) 58, DCC, DMAP, DCM; (d) Zn/HOAc, DCM; then FmocCl, DIPEA, DCM; (e) Bu₄NF, AcOH, THF; then CCl₃CN, CsCO₃, DCM.

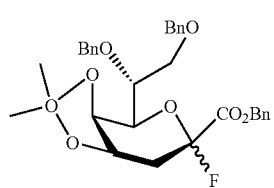

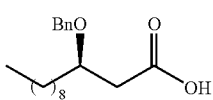

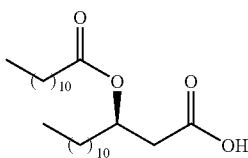

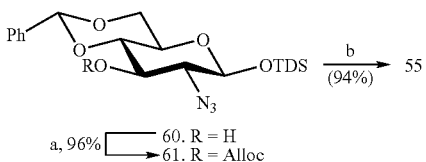

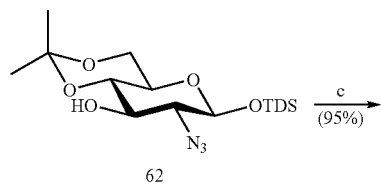

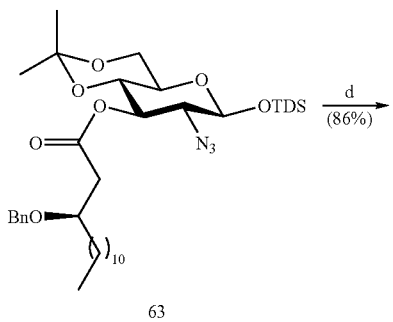

Glycosyl acceptor 55 and donor 56 could be prepared from known derivatives 60 (Eisele et al., *Liebigs Ann.* 1995, 2113-2121) and 62, (Kubasch and Schmidt, *Eur. J. Org. Chem.* 2002, 2710-2726) respectively (Scheme 4). Thus, the C-3 hydroxyl of 60 was protected by an Alloc group by treatment with Alloc chloride in the presence of N,N,N',N'-tetramethylenediamine (TMEDA) (Loewe et al., *J. Org. Chem.* 1994, 59, 7870-7875) in DCM to give 61 in a yield of 96%. Regioselective reductive opening of the benzylidene acetal of 61 proved more difficult than anticipated. Conventional procedures such as treatment with $BH_3 \cdot THF/Bu_2BOTf$ or $BH_3 \cdot THF/TMSOTf$ (Jiang and Chan, *Tetrahedron Lett.* 1998, 39, 355-358) resulted in a loss of the Alloc group. Fortunately, the reaction of 61 with triethyl silane and $PhBCl_2$ in the presence of molecular sieves at -75° C. (Sakagami and Hamana, *Tetrahedron Lett.* 2000, 41, 5547-5551) gave 55 in an excellent yield of 94% as only the C-6 hydroxyl.

The C-3 hydroxyl of 62 was acylated with (R)-3-benzyloxy-dodecanoic acid (58) using 1,3-dicyclohexylcarbodiimide (DCC) and 4-dimethylaminopyridine (DMAP) as the activation reagents to give 63 in an excellent yield of 95%. Next, the azido function of 63 was reduced with zinc in a mixture of acetic acid and DCM. The resulting amine was immediately protected as an Fmoc carbamate by reaction with FmocCl in the presence of diisopropylethylamine (DIPEA) to give fully protected 64. Removal of the anomeric TDS ether of 64 was achieved by treatment with tetrabutylammonium fluoride (TBAF) buffered with acetic acid in THF followed by conversion of the resulting lactol into trichloroacetimidate 56 (α/β~1:1) by reaction with trichloroacetonitrile in the presence of a catalytic amount of NaH (Schmidt and Stumpp, *Liebigs Ann. Chem.* 1983, 1249-1256).

A TMSOTf-mediated glycosylation (Schmidt, *Angew. Chem. Int. Ed.* 1986, 25, 212-235) of 55 with 56 in the presence of molecular sieves (4 Å) in DCM at -40° C. gave disaccharide 65 in a modest yield of 42%. Surprisingly, only the β-anomer of trichloroacetimidate 56 had been consumed while the α-anomer remained intact, even when the temperature or amount of TMSOTf was increased. An attempt to prepare selectively the β-anomer of 56 using $Cs_2CO_3$ as the base resulted unexpectedly in the formation of the α-anomer as the predominant product. Fortunately, the use of trifluoromethanesulfonic acid (TfOH) instead of TMSOTf could drive the glycosylation to completion with consumption of both the α- and β-anomer and provided disaccharide 65 in an excellent yield of 94%. Next, the isopropylidene group of 65 was removed with trifluoroacetic acid (TFA) in wet DCM to yield 66 in an almost quantitative yield.

Scheme 5.
55 + 56 →<sup>a</sup> (94%)
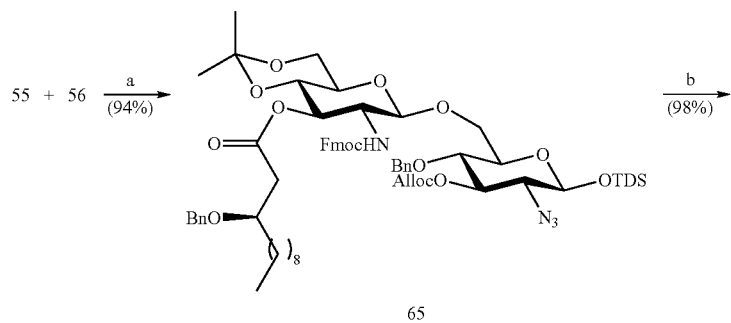
65
→<sup>b</sup> (98%)
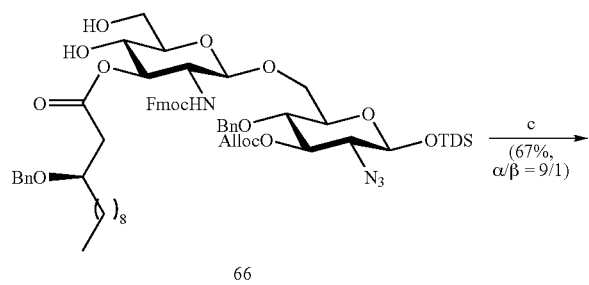
66
→<sup>c</sup> (67%, α/β = 9/1)
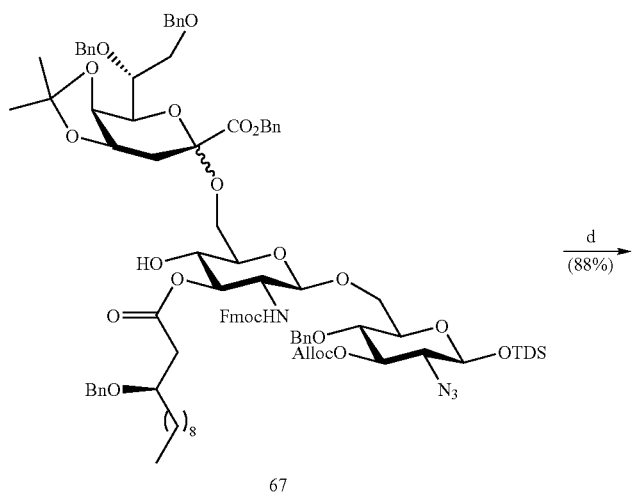
67
→<sup>d</sup> (88%)

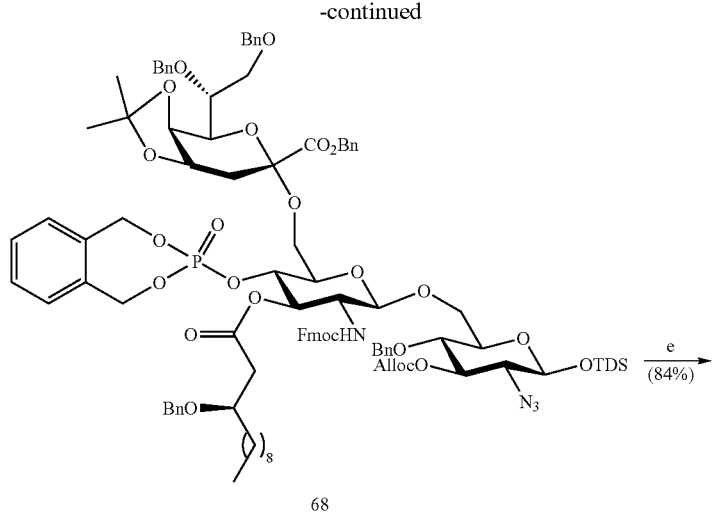
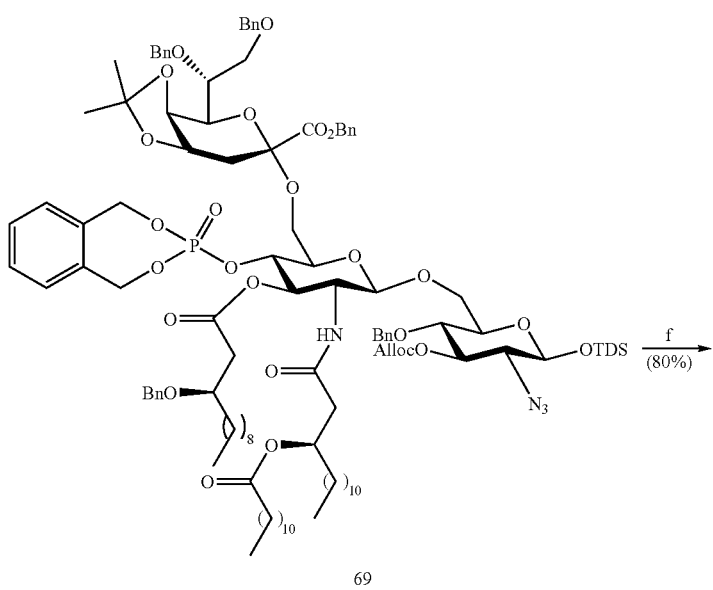
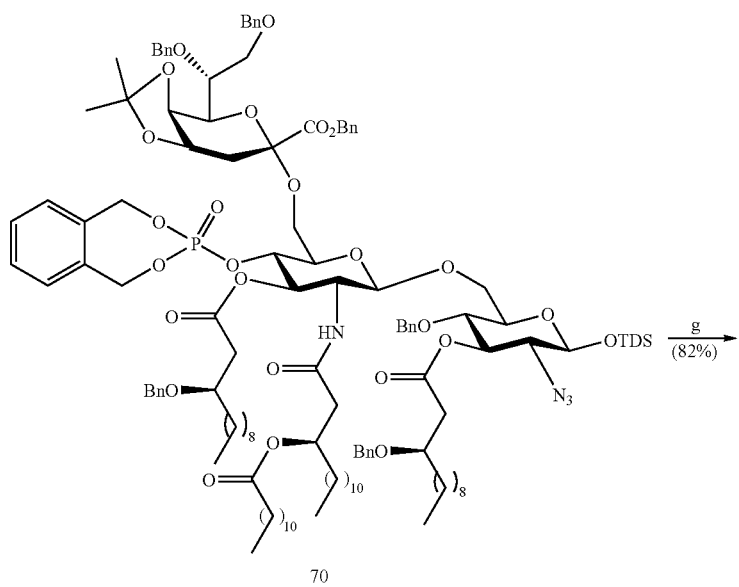

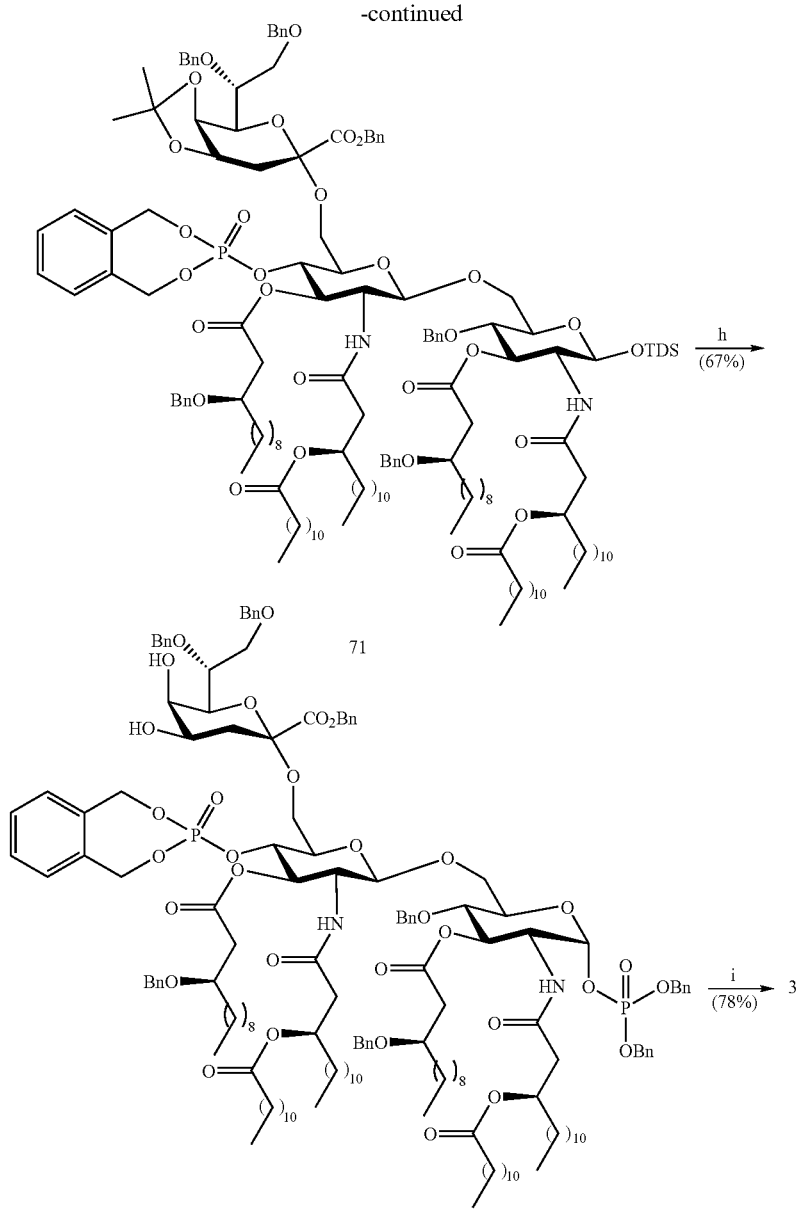

Reagents and conditions: (a) TfOH, DCM, -50° C.; (b) TFA, H₂O, DCM; (c) 57, BF₃·Et₂O, DCM, MS 4 Å, 0° C.; (d) N,N-Diethyl-1,5-dihydro-3H-2,3,4-benzodioxaphosphepin-3-amine, 1H-tetrazole, DCM; then mCPBA, -20° C.; (e) DBU, DCM; then 59, DCC, DCM; (f) Pd(PPh₃)₄, HCO₂H, n-BuNH₂, THF; then 58, DCC, DMAP, DCM; (g) Zn/HOAc, DCM; then 59, DCM, DCM; (h) TFA, H₂O, DCM; then tetrabenzyl diphosphate, LiN(TMS)₂, THF, -78° C.; (i) H₂ (65 psi), Pd-black, THF.

Glycosylation of 66 with KDO donor 57 was carried out with the aid of BF₃·OEt₂ in the presence of MS 4 Å in DCM to afford an inseparable mixture of 67 and its β-anomer (α/β=9/1) in a combined yield of 67% (Scheme 5). The anomeric configuration of the KDO glycosides was established by comparing the difference between the chemical shift values of the C-3 methylene protons (Imoto et al., *Tetrahedron Lett*. 1987, 28, 6277-6280). In this respect, a larger difference between the chemical shift values of C-3 methylene protons is observed for α-anomers of KDO glycosides that reside in a boat conformation, as compared to similar values for the corresponding β-anomers. In the case of KDO glycosides that adopt a chair form, a large chemical shift difference is observed for β-anomers whereas the α-anomer provides a small difference (Unger et al., *Carbohydr. Res*. 1980, 80, 191-195). After careful examination of the NMR spectra of the glycosylation products, it was found that the chemical shift difference of the C-3 methylene protons of the major product was 0.59 ppm while the corresponding difference was 0.12 ppm for the minor product. Furthermore, the KDO glycosides adopted boat conformations due to protection of the C-4,5 diol as an isopropylidene acetal, which was confirmed by the coupling constants of the C-3 methylene protons with H-4 ($J_{H3a,H4}=J_{H3e,H4}=4.8$ Hz). Thus, the data imply that the major product has an α-anomeric configuration. To provide additional evidence of the assigned anomeric configurations, the isopropylidene acetal of glycosylation product 66 was removed by treatment with TFA in DCM. NMR data of the resulting compound showed that the chemical shift difference of the C-3 methylene protons of the major product had decreased to 0.08 ppm while the corresponding difference increased to 0.39 ppm for the minor product. Furthermore, the coupling constants of the C-3 methylene protons with H-4 established that the glycosides adopt a chair conformation. Thus, these data provide convincing evidence that the major product has an α-anomeric configuration.

Phosphilation of 67 with N,N-diethyl-1,5-dihydro-2,3,4-benzodioxaphosphepin-3-amine in the presence of 1H-tetrazole followed by in-situ oxidation with m-chloroperoxybenzoic acid (mCPBA) (Watanabe et al., *Tetrahedron Lett.* 1990, 31, 255-256) gave 68. Fortunately, at this stage of the synthesis the α- and β-anomer could be separated by silica gel column chromatography. Interestingly, the chemical shift difference of the methylene protons of compound 68 and that of its β-anomer were both very small, an observation that may be due to the deshielding effects of the C-3 methylene protons by the aromatic group of the phosphate diester. As a matter of fact, it has been noted that the empirical rule described above does not apply to all subsequent KDO derivatives protected as 4,5-isopropylidene acetals. To provide additional information, the isopropylidene acetal of 68 and its β-anomer were removed. NMR data showed that the chemical shift difference of the C-3 methylene protons was 0.10 while the corresponding difference increased to 0.37 for the α-anomer, an observation that provided an additional piece of evidence to convincingly show that the major product is an α-anomer, because when the isopropylidene acetal was removed, the KDO existed as a chair form. The chair form was demonstrated by the large coupling constant (12.0 Hz) between H-4 and H-3$_{ax}$.

Having the advanced trisaccharide 68 in hand, attention was focused on the selective acylation of relevant hydroxyls and amines. Thus, the Fmoc protecting group of 68 was removed using 1,8-diazabicyclo[5.4.0]undec-7-ene (DBU) in DCM and the resulting amino group acylated with (R)-3-dodecanoyl-tetradecanoic acid (59) using DCC as the activating agent to give compound 69. Removal of the Alloc group of 69 was easily accomplished by treatment with Pd(PPh$_3$)$_4$ in the presence of BuNH$_2$ and HCOOH, (Tsukamoto et al., *Biosc. Biotechnol. Biochem.* 1997, 61, 1650-1657) and subsequent acylation of the resulting hydroxyl with 58 using DCC and DMAP as activating agent afforded 70. Next, reduction of the azido function of 70 with zinc in a mixture of acetic acid and DCM followed by acylation of the resulting amine with 59 using standard conditions furnished fully acylated 71.

Next, the isopropylidene acetal and anomeric TDS of 71 were removed by treatment with TFA/H$_2$O (3/2, v/v) in DCM and the anomeric hydroxyl of the resulting compound was regioselectively phosphorylated using tetrabenzyl diphosphate in the presence of lithium bis(trimethyl)silylamide in THF at −78° C. (Oikawa et al., *Bull. Chem. Soc. Jpn.* 1999, 72, 1857-1867) to give anomeric phosphate 72 as only the α-anomer. Finally, global deprotection of 72 could easily be accomplished by catalytic hydrogenolysis over Pd-black to give target product 53.

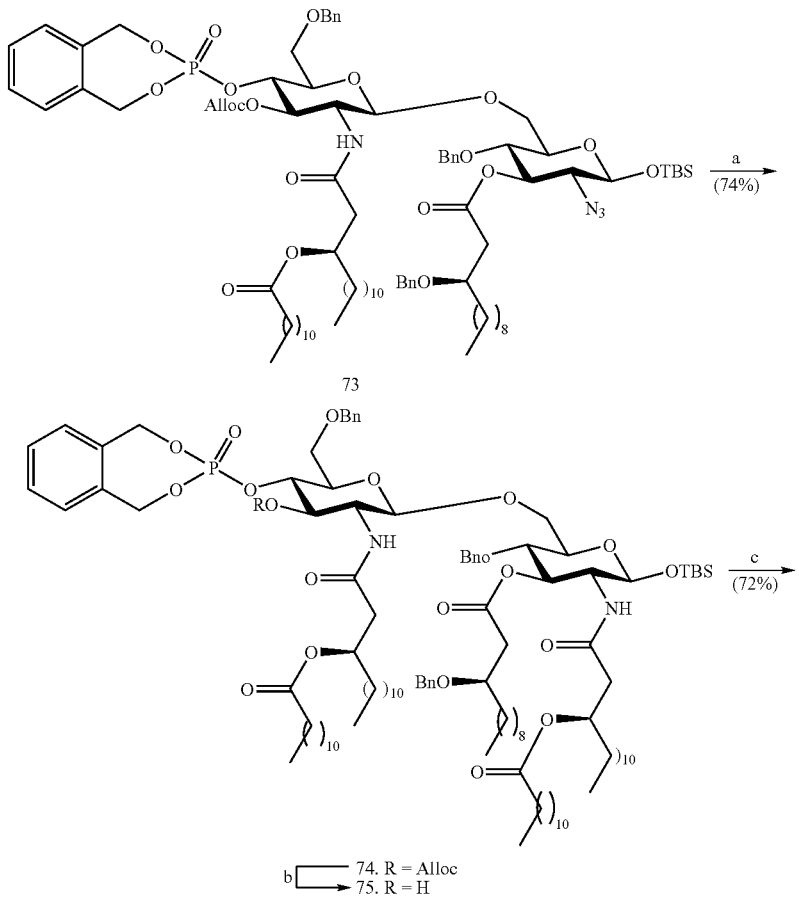

Scheme 6.

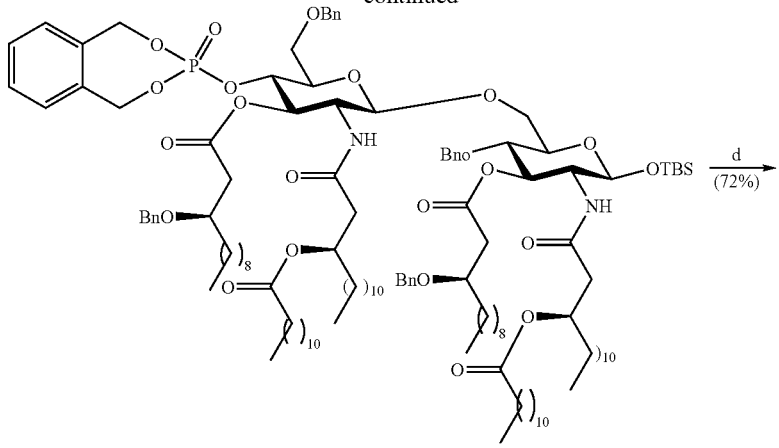

76

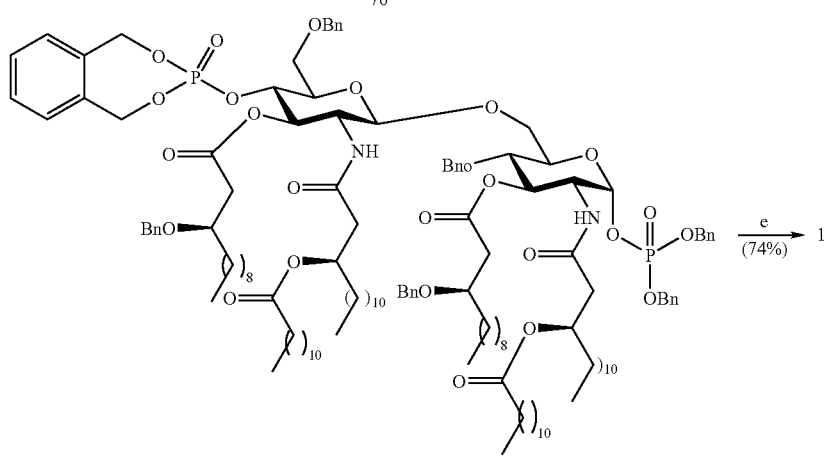

77

Reagents and conditions: (a) Zn/HOAc, DCM; then 59, DCC, DCM; (b) Pd(PPh₃)₄, HCO₂H, n-BuNH₂, THF; (c) 58, DCC, DMAP, DCM; (d) HF/pyridine; then tetrabenzyl diphosphate, LiN(TMS)₂, THF, -78° C.; (e) H₂(65psi), Pd-black, THF.

Lipid A derivative 51 could easily be prepared by starting from previously reported (Zhang et al., *J. Am. Chem. Soc.* 2007, 129, 5200-5216—Example I) compound 73 (Scheme 6). Thus, the azido function of 73 was reduced with activated Zn in a mixture of acetic acid and DCM and the amine of the resulting compound was reacted with (R)-2-dodecanoyloxy-tetradecanoic acid (59) in the presence of DCC to give 74. The removal of the Alloc protecting group of 74 could easily be accomplished by treatment with Pd(PPh₃)₄ and the hydroxyl group of the resulting compound 75 was acylated with (R)-2-benzyloxy-tetradecanoic acid (58) using DCC and DMAP as activating agents to afford fully acylated 76. The anomeric tert-butyldimethylsilyl (TBS) ether of 76 was removed by treatment with HF in pyridine and the resulting anomeric hydroxyl phosphorylated using tetrabenzyl diphosphate in the presence of lithium bis(trimethyl)silylamide in THF at −78° C. (Oikawa et al., *Bull. Chem. Soc. Jpn.* 1999, 72, 1857-1867) to give 77. Global deprotection of 77 by catalytic hydrogenolysis gave the requisite lipid A 51.

Scheme 7.

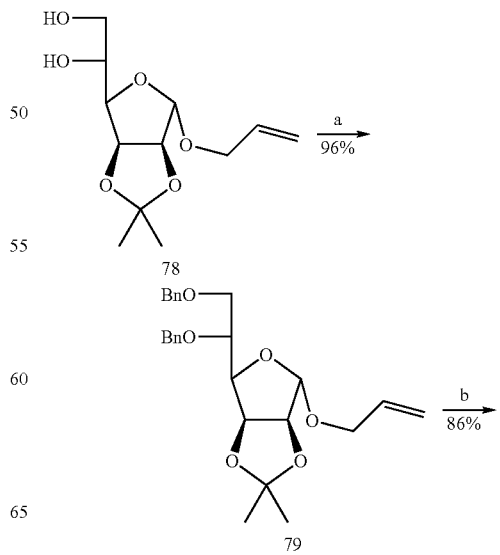

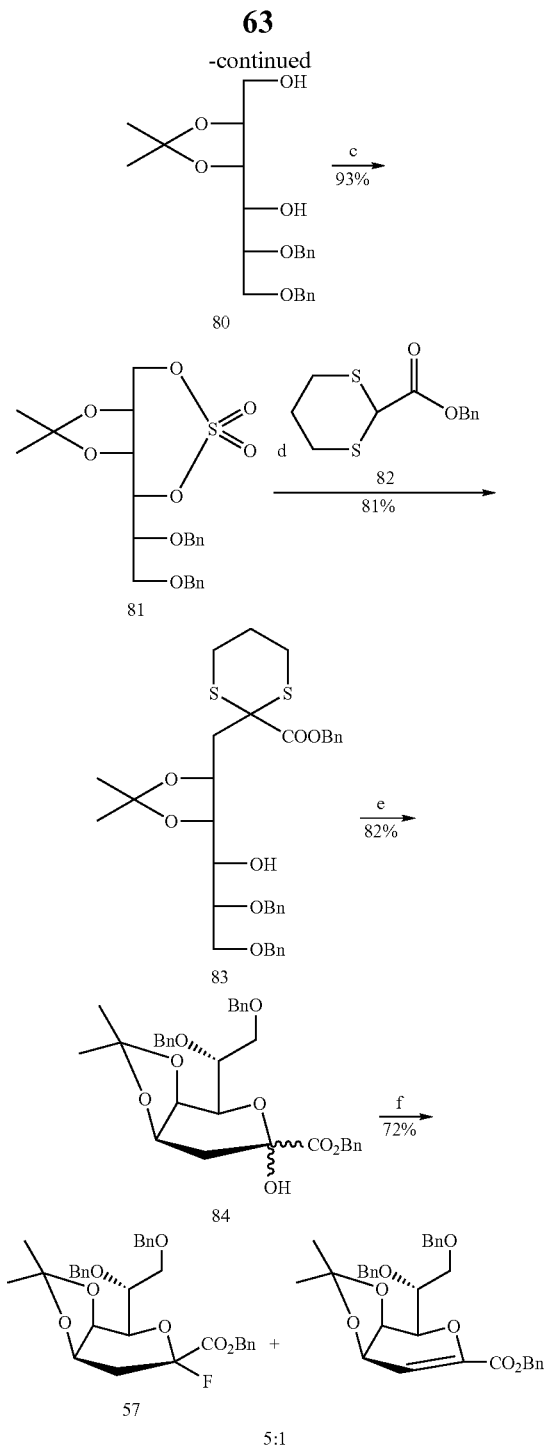

Synthesis of the KDO donor. Reagents and conditions: (a) BnBr, NaH, DMF; (b) 1: Pd/C, CH$_3$OH, reflux; 2: I$_2$, pyridine, H$_2$O, THF; 3: NaBH$_4$, EtOH; (c) 1: SOCl$_2$, Et$_3$N, DCM, -15° C; 2: NaIO$_4$, RuCl$_3$, H$_2$O, CH$_3$CN, DCM; (d) BuLi, HMPA, THF, -40° C; then H$_2$SO$_4$, H$_2$O, THF, 50° C.; (e) NBS, NaHCO$_3$, H$_2$O, acetone; (f) DAST, MS 4 Å, DCM, -60° C → rt.

Biological Evaluation. Based on the results of recent studies (Akira et al., *Nat. Immunol.* 2001, 2, 675-680; Pasare and Medzhitov, *Semin. Immunol.* 2004, 16, 23-26) it is clear that LPS-induced cellular activation through TLR4 is complex as many signaling elements are involved. However, it appears that there are two distinct initiation points in the signaling process, one being a specific intracellular adaptor protein called MyD88 and the other an adaptor protein called TRIF, which operates independently of MyD88. It is well established that TNF-α secretion is a prototypical measure for activation of the MyD88-dependent pathway, whereas secretion of IFN-β is commonly used as an indicator of TRIF-dependent cellular activation.

There are some indications that structurally different lipid As can differentially utilize signal transduction pathways leading to complex patterns of proinflammatory responses. For example, it has been suggested that meningococcal LOS is a potent inducer of MyD88- and TRIF-dependent cytokines, whereas at the same pmole concentrations *E. coli* LPS induced comparable levels of MyD88 derived cytokines but significantly less TRIF-associated cytokines (Zughaier et al., *Inject. Immun.* 2005, 73, 2940-2950; Zughaier et al., *Infect. Immun.* 2004, 72, 371-380). In addition, there are indications that the KDO moieties of meningococcal LOS are required for optimal biological properties (Zughaier et al., *Vaccine* 2006, 24, 1291-1297).

To address these issues, we have examined the well-defined compounds 51-54 and *E. coli* LPS for the ability to initiate production of TNF-α and IFN-β. Compounds 51 and 52 (Zhang et al., *J. Am. Chem. Soc.* 2007, 129, 5200-5216—Example I) are prototypical lipid As derived from *N. meningitidis* LOS and *E. coli* LPS, respectively. Both compounds are hexa-acylated but differ in the nature and substitution pattern of fatty acids. Compound 53 has a structure similar to 51, except that the C-6' moiety of its lipid A is extended by a KDO moiety. Compound 54 (Zhang et al., *J. Am. Chem. Soc.* 2007, 129, 5200-5216—Example I) is a hybrid derivative that has the asymmetrical acylation pattern of *E. coli* lipid A but the shorter lipids of meningococcal lipid.

Mouse macrophages (RAW 264.7 γNO(-) cells) were exposed over a wide range of concentrations to compounds 51-54 and meningococcal LOS. After 5.5 hours, the supernatants were harvested and examined for mouse TNF-α and IFN-β using a commercial and in-house developed capture ELISA, respectively. Potencies (EC$_{50}$, concentration producing 50% activity) and efficacies (maximal level of production) were determined by fitting the dose-response curves to a logistic equation using PRISM software.

Figure 7A:
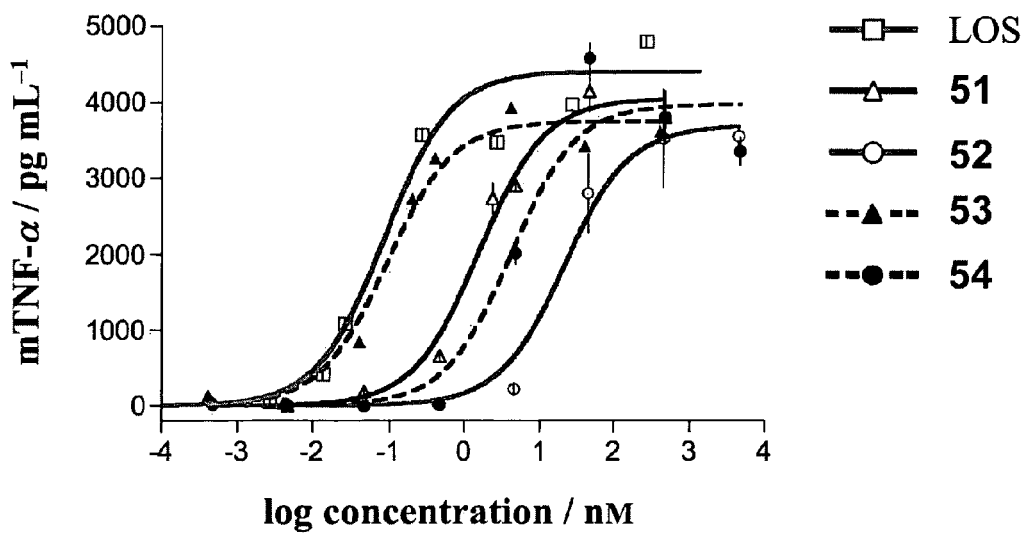
FIG. 7 shows TNF-α and IFN-β production by murine macrophages after stimulation with LOS and lipid A derivatives. Murine RAW γNO(−) cells were incubated for 5.5 h with increasing concentrations of N meningitidis LOS or lipid A derivatives 51-54 as indicated. TNF-α (a) and IFN-β (b) in cell supernatants were measured using ELISAs.
Figure 7B:
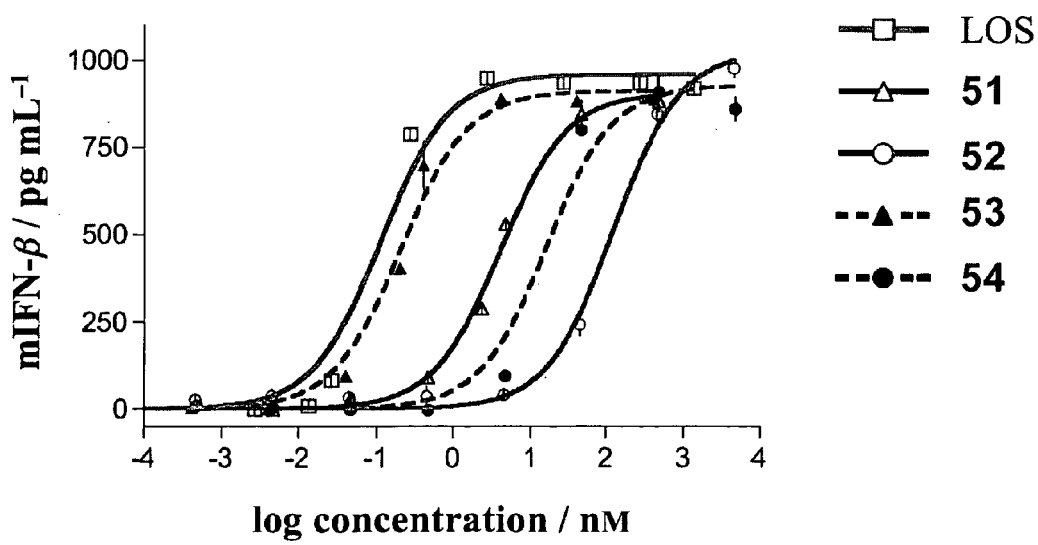

As can be seen in FIG. 7, synthetic *N. meningitidis* lipid A (51) is a significantly more potent inducer of TNF-α and IFN-β than *E. coli* lipid A (52). Furthermore, the difference in EC$_{50}$ values of the hybrid derivative 54 and *N. meningitidis* lipid A (51) is very small (Table 3). Thus, the data suggest that the shorter fatty acids of *N. meningitidis* lipid A are primarily responsible for its greater biological activity.

TABLE 3

EC$_{50}$ values[a] (nM) of *N. meningitidis* LOS and lipid A derivatives 51-54.

| | TNF-α | IFN-β |
|---|---|---|
| *N. meningitidis* LOS | 0.085 (0.058-0.13) | 0.11 (0.085-0.15) |
| lipid A 51 | 1.5 (1.3-1.9) | 4.0 (3.6-4.5) |
| lipid A 52 | 21 (16-28) | 124 (105-147) |
| lipid A 53 | 0.092 (0.074-0.12) | 0.20 (0.17-0.49) |
| lipid A 54 | 4.1 (2.5-6.7) | 16 (12-23) |

[a]Values of EC$_{50}$ are reported as best-fit values and as minimum-maximum range (best-fit value ± std. error).

The EC$_{50}$ values of the KDO containing derivative 53 and meningococcal LOS are very similar whereas these values are significantly smaller than those of lipid A 51. These results demonstrate the importance of the core region of LOS for biological activity and that one KDO moiety is sufficient for full activity of TNF-α and IFN-β induction by LOS.

Finally, a comparison of the $EC_{50}$ values of TNF-α and IFN-β for each compound indicated that the values for TNF-α are slightly smaller than those of IFN-β (2-6 fold), indicating a somewhat higher potency for TNF-α production. No significant differences were observed between efficacies of secreted TNF-α and IFN-β. Thus, it appears that for the compounds tested there is no clear bias towards a MyD88- or TRIF-dependent response. It may be possible that previously observed bias may be due to contaminants or, alternatively, due to minor lipid A components having unique acylation substitutions or patterns.

Conclusion

A convergent approach for the synthesis of a lipid A derivative containing KDO has been developed, which allows for the convenient synthesis of a panel of analogues differing in fatty acid acylation patterns and degree of phosphorylation. The new synthetic approach relies on the ability to selectively remove or unmask in a sequential manner an isopropylidene acetal, a Fmoc carbamate, an Alloc carbonate, azide, and TDS ether. The strategy was employed for the synthesis of *N. meningitidis* lipid A containing KDO (53). The compound was tested for cytokine production along with the synthetic *N. meningitidis* lipid A (51), its parent LOS, *E. coli* lipid A (52), and a hybrid derivative (54) that has the asymmetrical acylation pattern of *E. coli* lipid A but the shorter lipids of meningococcal lipid A. Examination of potencies and efficacies of TNF-α and IFN-β production showed that the lipid A derivative containing KDO was much more active than lipid A alone and just slightly less active than its parent LOS, indicating that one KDO moiety is sufficient for full activity of TNF-α and IFN-β production. It still needs to be established whether the increase in activity is due to specific interactions with relevant cell surface receptors or due to alterations in pharmacokinetic properties. It has also been found that the lipid A of *N. meningitidis* is a significantly more potent inducer of TNF-α and IFN-α than *E. coli* lipid A, which is attributed to a number of shorter fatty acids. For each compound, the values for TNF-α were only slightly smaller than those for IFN-β whereas no significant differences were observed between the efficacies. Thus, the compounds tested do not demonstrate a clear bias towards a MyD88- or TRIF-dependent response.

Experimental Section

General synthetic methods. Column chromatography was performed on silica gel 60 (EM Science, 70-230 mesh). Reactions were monitored by thin-layer chromatography (TLC) on Kieselgel 60 F254 (EM Science), and compounds were detected by examination under UV light and by charring with 10% sulfuric acid in MeOH. Solvents were removed under reduced pressure at <40"C. $CH_2Cl_2$ was distilled from NaH and stored over molecular sieves (3 Å). Tetrahydrofuran (THF) was distilled from sodium directly prior to application. MeOH was dried by refluxing with magnesium methoxide and then was distilled and stored under argon. Pyridine was dried by heating under refluxing over $CaH_2$ and then distilled and stored over molecular sieves (3 Å). Molecular sieves (3 and 4 Å) used for reactions, were crushed and activated in vacuo at 390° C. during 8 h and then for 2-3 h at 390° C. directly prior to application. Optical rotations were measured using a Jasco model P-1020 polarimeter. $^1$H NMR and $^{13}$C NMR spectra were recorded on Varian spectrometers (models Inova500 and Inova600) equipped with Sun workstations. $^1$H NMR spectra were recorded in $CDCl_3$ and referenced to residual $CHCl_3$ at 7.24 ppm, and $^{13}$C NMR spectra were referenced to the central peak of $CDCl_3$ at 77.0 ppm. Assignments were made by standard gCOSY and gHSQC. High resolution mass spectra were obtained on a Bruker model Ultraflex MALDI-TOF mass spectrometer. Signals marked with a subscript L belong to the biantennary lipids, whereas signals marked with a subscript L' belong to their side chain. Signals marked with a subscript S symbol belong to the monoantennary lipids.

Dimethylthexylsilyl 3-O-allyloxycarbonyl-2-azido-4,6-O-benzylidene-2-deoxy-(R)-D-glucopyranoside (71): To a cooled (0° C.) solution of compound 70 (1.25 g, 2.87 mmol) and N,N,N',N'-tetramethylethylenediamine (TMEDA) (281 µL, 1.87 mmol) in DCM (10 mL) was added dropwise allyl chloroformate (366 µL, 3.44 mmol). The reaction mixture was stirred at room temperature for 3 h, and then diluted with DCM (20 mL) and washed with saturated aqueous $NaHCO_3$ (2×20 mL) and brine (2×20 mL). The organic phase was dried ($MgSO_4$), filtered, and the filtrate was concentrated in vacuo. The residue was purified by silica gel column chromatography (hexane/ethyl acetate, 30/1, v/v) to give 71 as a colorless oil (1.43 g, 96%). $R_f$=0.60 (hexane/ethyl acetate, 5/1, v/v); $[\alpha]^{25}_D$=−34.9° (c=1.0, $CHCl_3$). $^1$H NMR (500 MHz, $CDCl_3$): δ 7.42-7.32 (m, 5H, aromatic), 5.98-5.86 (m, 1H, $OCH_2CH=CH_2$), 5.47 (s, 1H, >CHPh), 5.33 (d, 1H, J=17.0 Hz, $OCH_2CH=CHH$), 5.22 (d, 1H, J=11.0 Hz, $OCH_2CH=CH/1$), 4.87 (t, 1H, $J_{2,3}=J_{3,4}$=10.0 Hz, H-3), 4.69 (d, 1H, $J_{1,2}$=7.5 Hz, H-1), 4.64 (d, 2H, J=6.0 Hz, $OCH_2CH=CH_2$), 4.28 (dd, 1H, $J_{5,6a}$=5.0 Hz, $J_{6a,6b}$=10.0 Hz, H-6a), 3.76 (dd, 1H, $J_{5,6b}=J_{6a,6b}$=10.5 Hz, H-6b), 3.67 (d, 1H, $J_{3,4}=J_{4,5}$=9.0 Hz, H-4), 3.48-3.40 (m, 2H, H-2, H-5), 1.68-1.63 [m, 1H, $CH(CH_3)_2$], 0.89-0.87 [m, 12H, $SiC(CH_3)_2CH(CH_3)_2$], 0.19 (s, 3H, $SiCH_3$), 0.18 (s, 3H, $SiCH_3$). $^{13}$C NMR (75 MHz, $CDCl_3$): δ 154.15 (C=O), 136.75-126.17 (m, aromatic, $OCH_2CH=CH_2$), 119.07 ($OCH_2CH=CH_2$), 101.54 (>CHPh), 97.56 (C-1), 78.57 (C-4), 75.35 (C-3), 68.93 ($OCH_2CH=CH_2$), 68.57 (C-6), 67.12 (C-2), 66.32 (C-5), 33.82 [$SiC(CH_3)_2CH(CH_3)_2$], 24.78 [$SiC(CH_3)_2CH(CH_3)_2$], 19.88, 19.76, 18.46, 18.36 [$SiC(CH_3)_2CH(CH_3)_2$], −2.21 ($SiCH_3$), −3.24 ($SiCH_3$). HR MS (m/z) calculated for $C_{25}H_{37}N_3O_7Si$ [M+Na]$^+$, 542.2298; found, 542.2475.

Dimethylthexylsilyl 3-O-allyloxycarbonyl-2-azido-4-O-benzyl-2-deoxy-(R)-D-glucopyranoside (55): A suspension of 61 (1.20 g, 2.31 mmol) and molecular sieve (4 Å, 300 mg) in DCM (20 mL) was stirred at room temperature for 1 h. The mixture was cooled (−75° C.) and then triethylsilane (0.55 mL, 3.47 mmol) and $PhBCl_2$ (0.52 mL, 3.93 mmol) were added dropwise. After stirring the reaction mixture for 1 h, it was quenched by addition of $Et_3N$ (1 mL) and methanol (1 mL). The reaction mixture was warmed up to room temperature and then diluted with ethyl acetate (40 mL). The molecular sieve was removed by filtration, and the filtrate was washed with saturated aqueous $NaHCO_3$ (30 mL). The organic phase was dried ($MgSO_4$), filtered, and the filtrate was concentrated in vacuo. The residue was purified by silica gel column chromatography (hexane/ethyl acetate, 10/1, v/v) to give 55 as a colorless oil (1.13 g, 94%). $R_f$=0.35 (hexane/ethyl acetate, 5/1, v/v); $[\alpha]^{25}_D$=−17.1° (c=1.0, $CHCl_3$); $^1$H NMR (300 MHz, $CDCl_3$): δ 7.28-7.22 (m, 5H, aromatic), 5.99-5.85 (m, 1H, $OCH_2CH=CH_2$), 5.37 (dd, 1H, J=1.2 Hz, J=15.6 Hz, $OCH_2CH=CHH$), 5.27 (dd, 1H, J=1.2 Hz, J=11.0 Hz, $OCH_2CH=CHH$), 4.80 (dd, 1H, $J_{2,3}$=10.5 Hz, $J_{3,4}$=9.3 Hz, H-3), 4.70-2.59 (m, 5H, H-1, $CH_2Ph$, $OCH_2CH=CH_2$), 3.84 (dd, 1H, $J_{5,6a}$=2.4 Hz, $J_{6a,6b}$=11.7 Hz, H-6a), 3.71 (dd, 1H, $J_{5,6b}$=4.2 Hz, $J_{6a,6b}$=11.7 Hz, H-6b), 3.65 (t, 1H, $J_{3,4}=J_{4,5}$=9.6 Hz, H-4), 3.42-3.37 (m, 1H, H-5), 3.34 (dd, 1H, $J_{1,2}$=7.2 Hz, $J_{2,3}$=10.5 Hz, H-2), 1.71-1.62 [m, 1H, $CH(CH_3)_2$], 0.90-0.88 [m, 12H, $SiC(CH_3)_2CH(CH_3)_2$], 0.20 (s, 3H, $SiCH_3$), 0.17 (s, 3H, $SiCH_3$). $^{13}$C NMR (75 MHz, $CDCl_3$): δ 154.24 (C=O), 137.26-127.89 (m, aromatic), 131.17 ($OCH_2CH=CH_2$), 119.13 ($OCH_2CH=CH_2$), 96.81

(C-1), 78.52 (C-3), 75.29 (C-4), 74.99 (C-5), 74.66 (OCH$_2$CH=CH$_2$), 68.82 (CH$_2$Ph), 66.49 (C-2), 61.49 (C-6), 33.73 [SiC(CH$_3$)$_2$CH(CH$_3$)$_2$], 24.69 [SiC(CH$_3$)$_2$CH(CH$_3$)$_2$], 19.79, 19.71, 18.35, 18.28 [SiC(CH$_3$)$_2$CH(CH$_3$)$_2$], −2.22 (SiCH$_3$), −3.32 (SiCH$_3$). HR MS (m/z) calculated for C$_{25}$H$_{39}$N$_3$O$_7$Si[M+Na]$^+$, 544.2455; found, 544.2548.

Dimethylthexylsilyl 2-azido-3-O—[(R)-3-benzyloxy-dodecanoyl]-2-deoxy-4,6-O-isopropylidene-(R)-D-glucopyranoside (63): A reaction mixture of (R)-3-benzyloxy-dodecanoic acid 58 (970 mg, 3.17 mmol) and DCC (949 mg, 4.60 mmol) in DCM (10 mL) was stirred at room temperature for 10 min, and then compound 62 (1.15 g, 2.88 mmol) and DMAP (35 mg, 0.29 mmol) were added. The reaction mixture was stirred at room temperature for 10 h, after which the solids were removed by filtration, and the residue washed with DCM (2×1 mL). The combined filtrates were concentrated in vacuo, and the residue was purified by silicon gel column chromatography (eluent: hexane/ethyl acetate, 15/1, v/v) to yield 63 as a syrup (1.82 g, 94%). R$_f$=0.55 (hexane/ethyl acetate, 8/1, v/v); [α]$^{25}_D$=−10.0° (c=1.0, CHCl$_3$); $^1$H NMR (300 MHz, CDCl$_3$): δ 7.34-7.26 (m, 5H, aromatic), 4.91 (t, 1H, J$_{2,3}$=J$_{3,4}$=9.6 Hz, H-3), 4.62 (d, 1H, J$_{1,2}$=7.5 Hz, H-1), 4.60 (d, 1H, J=11.4 Hz, CHHPh), 4.48 (d, 1H, J=11.4 Hz, CHHPh), 3.89-3.83 (m, 2H, H-6a, H-3$_S$), 3.74 (t, 1H, J$_{5,6b}$=J$_{6a,6b}$=10.5 Hz, H-6b), 3.64 (t, 1H, J$_{3,4}$=J$_{4,5}$=9.6 Hz, H-4), 3.34-3.23 (m, 2H, H-2, H-5), 2.71 (dd, 1H, J$_{2Sa,2Sb}$=15.0 Hz, J$_{2Sa,3S}$=6.3 Hz, H-2$_{Sa}$), 2.51 (dd, 1H, J$_{2Sa,2Sb}$=15.0 Hz, J$_{2Sb,3S}$=6.0 Hz, H-2$_{Sb}$), 1.69-1.47 [m, 3H, H-4$_S$, CH(CH$_3$)], 1.38 (s, 3H, CH$_3$ of isopropylidene), 1.28 (s, 3H, CH$_3$ of isopropylidene), 1.24 [bs, 14H, H-(5$_S$-11$_S$)], 0.89-0.84 [m, 15H, H-12$_S$, SiC(CH$_3$)$_2$CH(CH$_3$)$_2$], 0.19 (s, 3H, SiCH$_3$), 0.18 (s, 3H, SiCH$_3$). $^{13}$C NMR (75 MHz, CDCl$_3$): δ 170.56 (C=O), 138.50-127.50 (m, aromatic), 99.67 [C(CH$_3$)$_2$ of isopropylidene], 97.43 (C-1), 75.70 (C-3$_S$), 71.63 (C-4), 71.46, 71.41 (C-3, CH$_2$Ph), 67.46, 67.37 (C-2, C-5), 61.93 (C-6), 39.77 (C-2$_S$), 34.50-14.07 [m, SiC(CH$_3$)$_2$CH(CH$_3$)$_2$, CH$_3$ of isopropylidene, C-(4$_S$-12$_S$)], −2.25 (SiCH$_3$), −3.32 (SiCH$_3$). HR MS (m/z) calculated for C$_{36}$H$_{61}$H$_3$O$_7$Si[M+Na]$^+$, 698.4176; found, 698.3518.

Dimethylthexylsilyl 3-O—[(R)-3-benzyloxy-dodecanoyl]-2-deoxy-2-(9-fluorenylmethoxycarbonyl)-4,6-O-isopropylidene-(R)-D-glucopyranoside (64): A suspension of compound 63 (1.82 g, 2.70 mmol) and zinc (<10 micron, 1.75 g, 27.0 mmol) in a mixture of acetic acid (300 μL) and DCM (15 mL) was stirred at room temperature for 5 h, after which it was diluted with ethyl acetate (40 mL). The solids were removed by filtration, and the residue was washed with ethyl acetate (2×3 mL). The combined filtrates were washed with saturated aqueous NaHCO$_3$ (2×30 mL) and brine (2×20 mL). The organic phase was dried (MgSO$_4$), filtered, and the filtrate was concentrated in vacuo to afford the crude amine as a pale yellow oil. The resulting amine was dissolved in DCM (15 mL), and then FmocCl (767 mg, 2.97 mmol) and DIPEA (517 μL, 2.97 mmol) were added. The reaction mixture was stirred at room temperature for 2 h, after which it was diluted with DCM (20 mL) and washed with brine (2×30 mL). The organic phase was dried (MgSO$_4$) and concentrated in vacuo. The residue was purified by silica gel column chromatography (eluent: hexane/ethyl acetate, 10/1, v/v) to yield 64 as a colorless syrup (2.02 g, 86%, two steps). R$_f$=0.55 (hexane/ethyl acetate, 5/1, v/v); [α]$^{25}_D$=−2.8° (c=1.0, CHCl$_3$); $^1$H NMR (300 MHz, CDCl$_3$): δ 7.73-7.25 (m, 13H, aromatic), 5.35 (d, 1H, J$_{NH,2}$=9.0 Hz, NH), 5.27 (t, 1H, J$_{2,3}$=J$_{3,4}$=9.6 Hz, H-3), 4.81 (d, 1H, J$_{1,2}$=7.2 Hz, H-1), 4.55 (d, 1H, J=11.1 Hz, CHHPh), 4.43 (d, 1H, J=11.1 Hz, CHHPh), 4.27-4.13 (m, 3H, OCH$_2$CH of Fmoc), 3.89-3.69 (m, 5H, H-2, H-4, H-6a, H-6b, H-3$_S$), 3.47 (bs, 1H, H-5), 2.70 (dd, 1H, J$_{2Sa,2Sb}$=14.7 Hz, J$_{2Sa,3S}$=5.1 Hz, H-2$_{Sa}$), 2.46 (dd, 1H, J$_{2Sa,2Sb}$=14.7 Hz, J$_{2Sb,3S}$=6.0 Hz, H-2$_{Sb}$), 1.59-1.50 (m, 3H, H-4$_S$, CH(CH$_3$)), 1.43 (s, 3H, CH$_3$ of isopropylidene), 1.34 (s, 3H, CH$_3$ of isopropylidene), 1.23-1.16 [bs, 14H, H-(5$_S$-11$_S$)], 1.16-0.84 [m, 15H, H-12$_S$, SiC(CH$_3$)$_2$CH(CH$_3$)$_2$], 0.13 (s, 3H, SiCH$_3$), 0.10 (s, 3H, SiCH$_3$). $^{13}$C NMR (75 MHz, CDCl$_3$): δ 171.78 (C=O), 155.82 (C=O), 143.79-119.83 (m, aromatic), 99.45 [C(CH$_3$)$_2$ of isopropylidene], 96.93 (C-1), 75.66 (C-3$_S$), 72.08 (C-3), 71.83 (C-4), 71.15 (CH$_2$Ph), 67.07 (C-5, OCH$_2$ of Fmoc), 62.00 (C-6), 58.55 (C-2), 46.92 (OCH$_2$CH of Fmoc), 39.76 (C-2$_S$), 34.41-14.04 [m, SiC(CH$_3$)$_2$CH(CH$_3$)$_2$, CH$_3$ of isopropylidene, C-(4$_S$-12$_S$)], −2.00 (SiCH$_3$), −3.42 (SiCH$_3$). HR MS (m/z) calculated for C$_{51}$H$_{73}$NO$_9$Si[M+Na]$^+$, 894.4952; found, 894.4984.

Dimethylthexylsilyl 3-O—[(R)-3-benzyloxy-dodecanoyl]-2-deoxy-2-(9-fluorenylmethoxycarbonyl)-4,6-O-isopropylidene-(R)-D-glucopyranosyl-(16)-3-O-allyloxycarbonyl-2-azido-4-O-benzyl-2-deoxy-(R)-D-glucopyranoside (65): A mixture of Bu$_4$NF (1 M in THF, 5 mL) and acetic acid (800 μL) was added dropwise to a stirred solution of 64 (1.30 g, 1.49 mmol) in THF (15 mL). After stirring at room temperature for 36 h, the reaction mixture was diluted with DCM (20 mL), and then washed with saturated aqueous NaHCO$_3$ (2×25 mL) and brine (2×25 mL). The organic phase was dried (MgSO$_4$), filtered, and the filtrate was concentrated in vacuo. The residue was purified by silica gel column chromatography (eluent: hexane/ethyl acetate, 5/2, v/v) to afford a lactol as a pale yellow oil (978 mg, 90%). The resulting lactol (810 mg, 1.11 mmol) was dissolved in a mixture of trichloroacetonitrile (2.0 mL) and DCM (6 mL), and then Cs$_2$CO$_3$ (181 mg, 0.55 mmol) was added. The reaction mixture was stirred at room temperature for 1 h, after which it was diluted with DCM (20 mL), and then washed with saturated aqueous NaHCO$_3$ (2×25 mL) and brine (2×25 mL). The organic phase was dried (Na$_2$SO$_4$), filtered, and the filtrate was concentrated in vacuo. The residue was purified by silica gel column chromatography (eluent: hexane/ethyl acetate, 2/1, v/v) to yield 56 as a pale yellow foam (880 mg, 91%). A suspension of trichloroacetimidate 56 (880 mg, 1.01 mmol), acceptor 55 (480 mg, 0.92 mmol) and molecular sieves (4 Å, 500 mg) in DCM (10 mL) was stirred at room temperature for 1 h. The mixture was cooled (−50° C.) and then TfOH (4.4 μL, 0.05 mmol) was added. After stirring the reaction mixture for 30 min, it was allowed to warm up to −10° C. in 30 min and then quenched with solid NaHCO$_3$ (50 mg) and diluted with DCM (20 mL). The solution was washed with saturated aqueous NaHCO$_3$ (2×25 mL) and brine (2×25 mL). The organic phase was dried (MgSO$_4$), filtered, and the filtrate was concentrated in vacuo. The residue was purified by silica gel column chromatography (eluent: hexane/ethyl acetate, 7/1-4/1, v/v) to yield disaccharide 65 as a colorless solid (1.07 g, 94%). R$_f$=0.50 (hexane/ethyl acetate, 4/1, v/v); [α]$^{24}_D$=−9.6° (c=1.0, CHCl$_3$); NMR (600 MHz, CDCl$_3$): δ 7.82-7.19 (m, 18H, aromatic), 6.76 (d, 1H, J$_{NH',2}$=9.6 Hz, NH'), 5.88-5.83 (m, 1H, OCH$_2$CH=CH$_2$), 5.29 (d, J=16.8 Hz, OCH$_2$CH=CHH), 5.23 (t, 1H, J$_{2,3}$=J$_{3,4}$=9.6 Hz, H-3'), 5.16 (d, J=10.2 Hz, OCH$_2$CH=CHR), 4.88 (d, 1H, J$_{1',2'}$=8.4 Hz, H-1'), 4.80-4.69 (m, 2H, H-1, H-3), 4.69 (d, 1H, J=10.8 Hz, CHHPh), 4.60-4.52 (m, 4H, CH$_2$Ph, OCH$_2$CH=CH$_2$), 4.39 (d, 1H, J=11.4 Hz, CHHPh), 4.24-4.21 (m, 1H, OCHH of Fmoc), 4.12 (d, 1H, J$_{6a,6b}$=10.8 Hz, H-6a), 4.08-4.01 (m, 2H, OCHHCH of Fmoc), 3.89-3.84 (m, 2H, H-6'a, H-6b), 3.82-3.79 (m, 2H, H-4', H-6'b), 3.78-3.72 (m, 3H, H-2', H-4, H-3$_S$), 3.67-3.65 (m, 1H, H-5), 3.40-3.33 (m, 2H, H-2, H-5'), 2.57 (dd, 1H, J$_{2Sa,2Sb}$=15.6 Hz, J$_{2Sa,3S}$=6.0 Hz, H-2$_{Sa}$), 2.33 (dd, 1H, J$_{2Sa,2Sb}$=15.0 Hz, J$_{2Sb,3S}$=6.0 Hz, H-2$_{Sb}$), 1.71-1.66 [m 1H, CH(CH$_3$)$_2$], 1.46-1.39 (m, 2H, H-4$_S$), 1.39-1.11 [m, 20H, CH₃ of isopropylidene, H-($5_S$-$11_S$)], 0.91-0.83 [m, 15H, H-$12_S$, SiC(CH₃)₂CH(CH₃)₂], 0.24 (s, 3H, SiCH₃), 0.23 (s, 3H, SiCH₃). $^{13}$C NMR (75 MHz, CDCl₃): δ 171.30 (C=O), 156.58 (C=O), 154.91 (C=O), 144.85-118.58 (m, OCH₂CH=CH₂, aromatic), 102.42 (C-1'), 99.91 [C(CH₃)₂ of isopropylidene], 97.08 (C-1), 75.66 (C-$3_S$), 79.23 (C-3), 76.67, 75.97 (C-4, 3s), 75.05 (CH₂Ph), 74.51 (C-5), 72.96 (C-3'), 73.46 (C-4'), 71.29 (CH₂Ph), 68.93 (OCH₂CH=CH₂), 68.51 (C-6), 67.86, 67.25 (C-2,5'), 67.08 (OCH₂ of Fmoc), 62.40 (C-6'), 57.27 (C-2'), 47.58 (OCH₂CH of Fmoc), 40.00 (C-$2_S$), 34.88-14.14 [m, SiC(CH₃)₂CH (CH₃)₂, CH₃ of isopropylidene, C-($4_S$-$12_S$)], -1.81 (SiCH₃), -3.26 (SiCH₃). HR MS (m/z) calculated for C₆₈H₉₂N₄O₁₅Si [M+Na]⁺, 1255.6221; found, 1255.6168.

Dimethylthexylsilyl 3-O—[(R)-3-benzyloxy-dodecanoyl]-2-deoxy-2-(9-fluorenylmethoxycarbonyl)-(R)-D-glucopyranosyl-(1→6)-3-O-allyloxycarbonyl-2-azido-4-O-benzyl-2-deoxy-(R)-D-glucopyranoside (66): TFA/H₂O (3/2, v/v, 250 µL) was added dropwise to a stirred solution of 65 (960 mg, 0.78 mmol) in DCM (15 mL). The reaction mixture was stirred at room temperature for 30 min, after which it was diluted with ethyl acetate (15 mL) and then washed with saturated aqueous NaHCO₃ (2×15 mL) and brine (2×15 mL). The organic phase was dried (MgSO₄), filtered, and the filtrate was concentrated in vacuo. The residue was purified by silica gel column chromatography (eluent: hexane/ethyl acetate, 2/1, v/v) to afford 66 as a pale yellow oil (882 mg, 98%). $R_f$=0.35 (hexane/ethyl acetate, 1/1, v/v); $[α]^{24}_D$=-1.0, CHCl₃); $^1$H NMR (300 MHz, CD₃COCD₃): δ 7.84-7.18 (m, 18H, aromatic), 6.64 (d, 1H, $J_{NH',2}$=9.3 Hz, NH'), 5.92-5.79 (m, 1H, OCH₂CH=CH₂), 5.29 (dd, J=1.5 Hz, J=14.4 Hz, OCH₂CH=CHH), 5.22-5.14 (m, 2H, H-3', OCH₂CH=CHH), 4.85-4.79 (m, 3H, H-1, H-1', H-3), 4.74 (d, 1H, J=11.4 Hz, CHHPh), 4.59-4.52 (m, 4H, CH₂Ph, OCH₂CH=CH₂), 4.42 (d, 1H, J=11.7 Hz, CHHPh), 4.21-4.10 (m, 4H, H-6a, OCH₂CH of Fmoc), 3.93-3.84 (m, 2H, H-6b, H-6'a), 3.81-3.62 (m, 6H, H-2', H-4, H-4', H-5', H-6'b, H-$3_S$), 3.45-3.39 (m, 2H, H-2, H-5), 2.62 (dd, 1H, $J_{2Sa,2Sb}$=15.6 Hz, $J_{2Sa,3S}$=6.3 Hz, H-$2_{Sa}$), 2.41 (dd, 1H, $J_{2Sa,2Sb}$=15.6 Hz, $J_{2Sb,3S}$=5.4 Hz, H-$2_{Sb}$), 1.73-1.64 [m 1H, CH(CH₃)₂], 1.44-1.39 (m, 2H, H-$4_S$), 1.28-1.09 [m, 14H, H-($5_S$-$11_S$)], 0.96-0.83 [m, 15H, H-$12_S$, SiC(CH₃)₂CH (CH₃)₂], 0.23 (s, 3H, SiCH₃), 0.22 (s, 3H, SiCH₃). $^{13}$C NMR (75 MHz, CD₃COCD₃): δ 171.80 (C=O), 156.48 (C=O), 154.86 (C=O), 144.81-120.51 (m, OCH₂CH=CH₂, aromatic), 118.51 (OCH₂CH=CH₂), 102.01 (C-1'), 97.02 (C-1), 79.21 (C-3), 71.11 (C-5), 76.72, 76.56, 76.07 (C-3', 4, 3s), 74.93 (CH₂Ph), 74.66 (C-5'), 71.37 (CH₂Ph), 69.66 (C-4'), 68.86 (OCH₂CH=CH₂), 68.46 (C-6), 67.20 (C-2), 67.02 (OCH₂ of Fmoc), 62.40 (C-6'), 56.79 (C-2'), 47.59 (OCH₂CH of Fmoc), 39.98 (C-$2_S$), 34.83-14.09 [m, SiC(CH₃)₂CH(CH₃)₂, C-($4_S$-$12_S$)], -1.83 (SiCH₃), -3.34 (SiCH₃). HR MS (m/z) calculated for C₆₅H₈₈N₄O₁₅Si[M+Na]⁺, 1215.5913; found, 1215.6797.

Dimethylthexylsilyl benzyl (7,8-di-O-benzyl-3-deoxy-4,5-O-isopropylidene-α/β-D-manno-oct-2-ulopyranosyl)onate-(2→6)-3-O—[(R)-3-benzyloxy-dodecanoyl]-2-deoxy-2-(9-fluorenylmethoxycarbonyl)-(R)-D-glucopyranosyl-(1→6)-3-O-allyloxycarbonyl-2-azido-4-O-benzyl-2-deoxy-(R)-D-glucopyranoside (67): A suspension of 66 (610 mg, 0.51 mmol), 57 (495 mg, 0.91 mmol) and molecular sieves (4 Å, 400 mg) in DCM (8 mL) was stirred at room temperature for 1 h. The mixture was cooled (0° C.) and then BF₃·Et₂O (77 µL, 0.61 mmol) was added dropwise. After stirring the reaction mixture for 1 h, it was quenched with solid NaHCO₃ (100 mg) and then diluted with DCM (20 mL). The solids were removed by filtration, and the filtrate was washed with saturated aqueous NaHCO₃ (2×25 mL) and brine (2×25 mL). The organic phase was dried (MgSO₄), filtered, and the filtrate was concentrated in vacuo. The residue was purified by silica gel column chromatography (eluent: hexane/ethyl acetate, 6/1→4/1, v/v) to afford 67 as an amorphous solid (590 mg, 67%). $R_f$=0.45 (hexane/ethyl acetate, 3/1, v/v); $[α]^{24}_D$=-4.9° (c=1.0, CHCl₃); $^1$H NMR of a-anomer (600 MHz, CD₃COCD₃): δ 7.84-7.18 (m, 33H, aromatic), 6.62 (d, 1H, =9.0 Hz, NH'), 5.89-5.82 (m, 1H, OCH₂CH=CH₂), 5.30-23 (m, 2H, CO₂CHHPh, OCH₂CH=CHH), 5.20-5.12 (m, 3H, H-3', CO₂CHHPh, OCH₂CH=CHH), 4.84-4.49 (m, 12H, H-1, H-1', H-3, 7×CHH₂Ph, OCH₂CH=CH₂), 4.43-4.39 (m, 3H, H-4'', H-5'', CHHPh), 4.23-4.18 (m, 1H, OCHH of Fmoc), 4.17-4.10 (m, 3H, H-6a, OCHHCH of Fmoc), 4.00-3.91 (m, 3H, H-6'', H-7'', H-8a''), 3.84 (dd, 1H, $J_{5',6a}$=5.4 Hz, $J_{6a',6b'}$=10.8 Hz, H-6a'), 3.78-3.77 (m, 2H, H-$3_S$, H-8b''), 3.73-3.70 (m, 3H, H-4, H-5, H-6b), 3.67-3.65 (m, 2H, H-2', H-6b''), 3.48 (bs, 2H, H-4', H-5'), 3.81 (dd, 1H, $J_{1,2}$=8.4 Hz, $J_{2,3}$=9.6 Hz, H-2), 2.62-2.54 (m, 2H, H-$3_a$'', H-$2_{Sa}$), 2.39 (dd, 1H, $J_{2Sa,2Sb}$=15.6 Hz, $J_{2Sb,3S}$=5.4 Hz, H-$2_{Sb}$), 1.97 (dd, 1H, $J_{3a'',3b''}$=15.0 Hz, $J_{3b'',4''}$=2.4 Hz, H-3b''), 1.68-1.62 [m 1H, CH(CH₃)₂], 1.43-1.39 (m, 2H, H-$4_S$), 1.31 (s, 3H, CH₃ of isopropylidene), 1.27 (s, 3H, CH₃ of isopropylidene), 1.16-1.08 [m, 14H, H-($5_S$-$11_S$)], 0.88-0.83 [m, 15H, H-$12_S$, $_{SiC(CH_3)}$₂CH(CH₃)₂], 0.22 (s, 3H, SiCH₃), 0.21 (s, 3H, SiCH₃). $^{13}$C NMR (75 MHz, CD₃COCD₃): δ 171.76 (C=O), 168.49 (C=O), 156.46 (C=O), 154.85 (C=O), 144.81-120.48 (m, OCH₂CH=CH₂, aromatic), 118.59 (OCH₂CH=CH₂), 109.11 (C-2''), 102.02 (C-1'), 98.34 [C(CH₃)₂ of isopropylidene], 97.00 (C-1), 79.20 (C-3), 77.87 (C-7''), 76.99 (C-4), 76.48 (C-3'), 76.07 (C-$3_S$), 75.29 (C-5'), 74.99 (CH₂Ph), 74.85 (C-5), 73.54 (CH₂Ph), 73.47 (CH₂Ph), 72.32 (C-4''), 71.74 (C-6), 71.41 (C-8'', CH₂Ph), 70.71 (C-5''), 70.21 (C-6''), 69.72 (C-4'), 68.90 (OCH₂CH=CH₂), 68.73 (C-6), 67.11 (C-2, CO₂CH₂Ph), 67.00 (OCH₂ of Fmoc), 63.30 (C-6'), 56.74 (C-2'), 47.64 (OCH₂CH of Fmoc), 39.96 (C-$2_S$), 34.79-14.08 [m, 3'', SiC(CH₃)₂CH(CH₃)₂, CH₃ of isopropylidene, C-($4_S$-$12_S$)], -1.72 (SiCH₃), -3.29 (SiCH₃). HR MS (m/z) calculated for C₉₉H₁₂₆N₄O₂₀Si[M+Na]⁺, 1745.8218; found, 1745.9780.

Dimethylthexylsilyl benzyl (7,8-di-O-benzyl-3-deoxy-4,5-O-isopropylidene-α-D-manno-oct-2-ulopyranosyl)onate-(2→6)-3-O—[(R)-3-benzyloxy-dodecanoyl]-2-deoxy-4-O-(1,5-dihydro-3-oxo-3λ⁵-3H-2,4,3-benzodioxaphosphepin-3-yl)-2-(9-fluorenylmethoxycarbonyl)-(R)-D-glucopyranosyl-(1→6)-3-O-allyloxycarbonyl-2-azido-4-O-benzyl-2-deoxy-(R)-D-glucopyranoside (68): 1H-tetrazole (3% wt, 10.0 mmol) in DCM (2.5 mL) was added to a solution of compound 67 (480 mg, 0.28 mmol) and N,N-diethyl-1,5-dihydro-3H-2,4,3-benzodioxaphosphepin-3-amine (133 mg, 0.56 mmol) in DCM (8 mL). After the reaction mixture was stirred at room temperature for 40 min, it was cooled (-20° C.), stirred for another 10 min and then 3-chloroperoxybenzoic acid (mCPBA) (500 mg, 50-55% wt, 1.12 mmol) was added. The reaction mixture was stirred at -20° C. for 20 min, and then quenched by the addition of saturated aqueous NaHCO₃ (20 mL) and diluted with DCM (20 mL). The solution was washed with saturated aqueous NaHCO₃ (2×30 mL) and brine (2×20 mL). The organic phase was dried (MgSO₄), filtered, and the filtrate was concentrated in vacuo. The residue was purified by silica gel column chromatography (eluent: hexane/ethyl acetate, 4/1, v/v) to give 68 as an amorphous solid (470 mg, 88%). $R_f$=0.45 (hexane/ethyl acetate, 3/1, v/v); $[α]^{24}_D$=+6.0° (c=1.0, CHCl₃); $^1$H NMR (600 MHz, CD₃COCD₃): δ 7.85-7.20 (m, 35H, aromatic), 6.84-6.74 (m, 3H, aromatic×2, NH'), 6.62 (d, 1H, $J_{NH',2}$=9.0 Hz, NH'), 5.91-5.85 (m, 1H, OCH$_2$CH=CH$_2$), 5.46 (t, 1H, J$_{2',3'}$=J$_{3',4'}$=9.6 Hz, H-3'), 5.32-5.23 (m, 3H, CO$_2$CH$_2$Ph, OCH$_2$CH=CHH), 5.18 (dd, 1H, J=1.2 Hz, J=10.8 Hz, OCH$_2$CH=CHH), 5.08-4.89 (m, 5H, H-1', H-3, 3×OCHHPh), 4.85-4.79 (m, 3H, H-1, 2×CHHPh), 4.71-4.63 (m, 4H, H-4', H-4'', 2×CHHPh), 4.61-4.56 (m, 6H, 4×CHHPh, OCH$_2$CH=CH$_2$), 4.46-4.43 (m, 2H, H-5'', CHHPh), 4.20-4.16 (m, 3H, OCH$_2$CH of Fmoc), 4.10-4.07 (m, 2H, H-6a, H-6''), 4.02-4.01 (m, 2H, H-7'', H-8''), 3.93 (dd, 1H, J$_{5',6a'}$=4.8 Hz, J$_{6a,6b}$=11.4 Hz, H-6a'), 3.85 (dd, 1H, J$_{7'',8a''}$=4.8 Hz, J=10.8 Hz, H-8a''), 3.81-3.77 (m, 4H, H-5, H-6a, H-6b', H-3$_S$), 3.67-3.60 (m, 3H, H-2', H-4, H-5'), 3.35 (dd, 1H, J$_{1,2}$=7.8 Hz, J$_{2,3}$=10.2 Hz, H-2), 2.70 (dd, 1H, J$_{2Sa,2Sb}$=16.8 Hz, J$_{2Sbm3S}$=6.6 Hz, H-2$_{Sb}$), 2.53 (dd, 1H, J$_{2Sa,2Sb}$=16.8 Hz, J$_{2Sb,3S}$=4.8 Hz, H-2$_{Sb}$), 2.26 (dd, 1H, J$_{3a'',3b''}$=14.4 Hz, J$_{3a'',4''}$=7.2 Hz, H-3a''), 2.12 (dd, 1H, J$_{3a'',3b''}$=14.4 Hz, J$_{3b'',4''}$=4.8 Hz, H-3b''), 168-1.63 (m 1H, CH(CH$_3$)$_2$), 1.47-1.43 (m, 2H, H-4$_S$), 1.37 (s, 3H, CH$_3$ of isopropylidene), 1.31 (s, 3H, CH$_3$ of isopropylidene), 1.16-1.08 [m, 14H, H-(5$_S$-11$_S$)], 0.89-0.83 [m, 15H, H-12$_S$, SiC(CH$_3$)$_2$CH(CH$_3$)$_2$], 0.24 (s, 3H, SiCH$_3$), 0.23 (s, 3H, SiCH$_3$). $^{13}$C NMR (75 MHz, CD$_3$COCD$_3$): δ 171.78 (C=O), 168.35 (C=O), 156.47 (C=O), 155.03 (C=O), 144.93-120.62 (m, OCH$_2$CH=CH$_2$, aromatic), 118.71 (OCH$_2$CH=CH$_2$), 109.06 (C-2''), 102.03 (C-1'), 99.13 [C(CH$_3$)$_2$ of isopropylidene], 97.02 (C-1), 79.25 (C-3), 78.01 (C-7''), 77.49 (C-4), 75.91 (C-5 or 3$_S$), 74.96, 74.90 (C-5 or 3$_S$, CH$_2$Ph), 74.68 (C-4'), 73.97 (C-3'), 73.76 (CH$_2$Ph), 73.42 (C-5', CH$_2$Ph), 71.80 (C-5''), 71.65 (CH$_2$Ph), 70.56 (C-4''), 70.35 (C-8''), 69.54 (C-6), 69.19 (C-6''), 69.03 (OCH$_2$CH=CH$_2$), 68.82 [2×(OCH$_2$)$_2$Ph], 67.43 (CO$_2$CH$_2$Ph), 67.34 (C-2), 67.25 (OCH$_2$ of Fmoc), 62.91 (C-6'), 57.32 (C-2'), 47.77 (OCH$_2$CH of Fmoc), 39.78 (C-2$_S$), 34.88-14.20 [m, 3'', SiC(CH$_3$)$_2$CH(CH$_3$)$_2$, CH$_3$ of isopropylidene, C-(4$_S$-12$_S$)], −1.61 (SiCH$_3$), −3.18 (SiCH$_3$). HR MS (m/z) calculated for C$_{105}$H$_{129}$N$_4$O$_{25}$Si[M+Na]$^+$, 1927.8350; found, 1927.8330.

Dimethylthexylsilyl benzyl (7,8-di-O-benzyl-3-deoxy-4,5-O-isopropylidene-α-D-manno-oct-2-ulopyranosyl)onate-(2→6)-3-O—[(R)-3-benzyloxy-dodecanoyl]-2-deoxy-4-0-(1,5-dihydro-3-oxo-3λ$^5$-3H-2,4,3-benzodioxaphosphepin-3-yl)-2-[(R)-3-dodecanoyloxy-tetradecanoyl]-(R)-D-glucopyranosyl-(1→6)-3-O-allyloxycarbonyl-2-azido-4-O-benzyl-2-deoxy-(R)-D-glucopyranoside (69): DBU (100μL) was added dropwise to a stirred solution of 68 (300 mg, 0.16 mmol) in DCM (5 mL). The reaction mixture was stirred at room temperature for 30 min, and then concentrated in vacuo. The residue was purified by silica gel column chromatography (eluent: hexane/ethyl acetate, 5/2, v/v) to yield an amine intermediate as a pale yellow oil (250 mg, 94%). R$_f$=0.25 (hexane/ethyl acetate, 5/2, v/v). A reaction mixture of 59 (95 mg, 0.22 mmol) and DCC (62 mg, 0.30 mmol) in DCM (3 mL) was stirred at room temperature for 10 min, and then the above obtained amine (250 mg, 0.15 mmol) was added, and stirring was continued for another 12 h. The insoluble materials were removed by filtration, and the residue was washed with DCM (2×0.5 mL). The combine filtrates were concentrated in vacuo, and the residue was purified by silica gel column chromatography (eluent: hexane/ethyl acetate, 5/1, v/v) to yield 69 as an amorphous solid (280 mg, 89%). R$_f$=0.55 (hexane/ethyl acetate, 5/2, v/v); [α]$_D^{25}$=+7.1° (c=1.0, CHCl$_3$); $^1$H NMR (600 MHz, CDCl$_3$): δ 7.36-7.07 (m, 27H, aromatic), 6.69 (d, 1H, J=7.2 Hz, aromatic), 6.51 (d, 1H, J=7.2 Hz, aromatic), 5.90-5.84 (m, 1H, OCH$_2$CH=CH$_2$), 5.62 (d, 1H, J$_{NH',2}$=7.2 Hz, NH'), 5.53 (t, 1H, J$_{2',3'}$=J$_{3',4'}$=9.6 Hz, H-3'), 5.20 (d, 1H, J=17.4 Hz, OCH$_2$CH=CHH), 5.23-5.16 (m, 3H, CO$_2$CH$_2$Ph, OCH$_2$CH=CHH), 5.03-5.16 (m, 3H, H-1', H-3$_L$, CHHPh), 4.89-4.81 (m, 2H, H-3, CHHPh), 4.75-4.71 (m, 2H, H-3, CHHPh), 4.68-4.64 (m, 4H, H-4', CHHPh×3), 4.61-4.57 (m, 4H, H-1, H-4'', OCH$_2$CH=CH$_2$), 4.57-4.47 (m, 6H, 6×CHHPh), 4.38 (bs, 1H, H-5''), 4.04 (bs, 1H, H-7''), 3.99 (d, 1H, J=10.2 Hz, H-6''), 3.89-3.84 (m, 2H, H-8a'', H-3$_S$), 3.80-3.74 (m, 3H, H-6a, H-6a', H-8a''), 3.63 (d, 1H, J$_{6a',6b'}$=10.8 Hz, H-6b'), 3.59-3.54 (m, 2H, H-5, H-6b), 3.80 (dd, 1H, J=4.8 Hz, J=9.6 Hz, H-5'), 3.33 (t, 1H, J$_{3,4}$=J$_{4,5}$=9.0 Hz, H-4), 3.26 (dd, 1H, J$_{1,2}$=7.8 Hz, J$_{2,3}$=10.2 Hz, H-2), 3.11 (dd, 1H, J=7.8 Hz, H-2'), 2.69-2.63 (m, 2H, H-2$_S$), 2.32-2.20 (m, 3H, H-2$_L$), 2.18 (dd, 1H, J$_{3a'',3b''}$=14.4 Hz, J$_{3a'',4''}$=6.6 Hz, H-3a''), 2.10 (dd, 1H, J$_{3a'',3b''}$=14.4 Hz, J$_{3b'',4''}$=5.4 Hz, H-3b''), 2.05 (dd, J$_{2La,2Lb}$=15.0 Hz, J$_{2Lb,3L}$=5.4 Hz, H-2$_{Lb}$), 1.66-1.46 [m, 7H, H-4$_S$, H-4$_L$, H-3$_L$', CH(CH$_3$)$_2$], 1.38 [s, 3H, CH$_3$ of isopropylidene], 1.31 [s, 3H, CH$_3$ of isopropylidene], 1.22 [bs, 48H, H-(5$_S$-11$_S$), H-(5$_L$-13$_L$), H-(4$_L$-11$_L$)], 0.86-0.84 [m, 21H, H-12$_S$, H-14$_L$, H-12$_L$', SiC(CH$_3$)$_2$CH(CH$_3$)$_2$], 0.16 [s, 6H, Si(CH$_3$)$_2$]. $^{13}$C NMR (75 MHz, CD$_3$COCD$_3$): S173.59 (C=O), 171.06 (C=O), 169.98 (C=O), 167.78 (C=O), 154.35 (C=O), 138.84-127.46 (m, OCH$_2$CH=CH$_2$, aromatic), 119.17 (OCH$_2$CH=CH$_2$), 108.66 (C-2''), 99.89 (C-1'), 98.58 [C(CH$_3$)$_2$ of isopropylidene], 96.48 (C-1), 78.60 (C-3), 77.00 (C-7''), 76.87 (C-4), 75.54 (C-3$_S$), 74.46 (CH$_2$Ph), 74.12 (C-4'), 73.84 (C-5), 73.35 (CH$_2$Ph), 73.19 (CH$_2$Ph), 72.56 (C-5'), 71.72 (C-3'), 71.16 (CH$_2$Ph), 70.83 (C-5''), 70.74 (C-3$_L$), 69.79 (C-4'', 8''), 68.83 (C-6, OCH$_2$CH=CH$_2$), 68.44 (C-6'', CH$_2$Ph), 68.71 (CH$_2$Ph), 66.97 (CO$_2$CH$_2$Ph), 66.62 (C-2), 61.81 (C-6'), 56.76 (C-2'), 41.62 (C-20, 38.91 (C-2s), 34.47-14.09 [m, 3'', SiC(CH$_3$)$_2$CH(CH$_3$)$_2$, CH$_3$ of isopropylidene, C-(4$_S$-12$_S$), C-(4$_L$-14$_L$), C-(2$_L$-120], −1.86 (SiCH$_3$), −3.41 (SiCH$_3$). 1-1R MS (m/z) calculated for C$_{105}$H$_{129}$N$_4$O$_{25}$Si[M+Na]$^+$, 2114.1273; found, 2114.2964.

Dimethylthexylsilyl benzyl (7,8-di-O-benzyl-3-deoxy-4,5-O-isopropylidene-α-D-manno-oct-2-ulopyranosyl)onate-(2→6)-3-O—[(R)-3-benzyloxy-dodecanoyl]-2-deoxy-4-0-(1,5-dihydro-3-oxo-3λ$^5$-3H-2,4,3-benzodioxaphosphepin-3-yl)-2-[(R)-3-dodecanoyloxy-tetradecanoyl]-(R)-D-glucopyranosyl-(1→6)-2-azido-4-O-benzyl-3-O-[(R)-3-benzyloxy-dodecanoyl]-2-deoxy-(R)-D-glucopyranoside (70): Tetrakis(triphenylphosphine)palladium (32.5 mg, 0.028 mmol) was added to a solution of 69 (295 mg, 0.141 mmol), n-BuNH$_2$ (28 μL, 0.28 mmol), and HCOOH (11 μL, 0.28 mmol) in THF (5 mL). After stirring the reaction mixture at room temperature for 20 min, it was diluted with DCM (20 mL), and washed successively with water (20 mL), saturated aqueous NaHCO$_3$ (2×20 mL) and brine (2×20 mL). The organic phase was dried (MgSO$_4$), filtered, and the filtrate was concentrated in vacuo. The residue was purified by silica gel column chromatography (hexane/ethyl acetate, 4/1, v/v) to give an alcohol intermediate as a colorless syrup (268 mg, 95%). R$_f$=0.45 (eluent: hexane/ethyl acetate, 3/1, v/v); $^1$H NMR (500 MHz, CDCl$_3$): δ 7.43-7.14 (m, 27H, aromatic), 6.75 (d, 1H, J=7.5 Hz, aromatic), 6.65 (d, 1H, J=7.0 Hz, aromatic), 5.68 (d, 1H, J$_{NH',2}$=8.0 Hz, NH'), 5.53 (t, 1H, J$_{2',3'}$=10.0 Hz, H-3'), 5.23 (d, 1H, J=12.5 Hz, CO$_2$CHHPh), 5.18 (d, 1H, J=12.5, CO$_2$CHHPh), 5.10-4.92 (m, 4H, H-1', H-3$_L$, 2×CHHPh), 4.85-4.50 (m, 13H, H-1, H-4', H-4'', 10×CHHPh), 4.41 (bs, 1H, H-5''), 4.10-4.08 (m, 1H, H-7''), 4.02 (d, 1H, J=9.5 Hz, H-6''), 3.95-3.89 (m, 3H, H-6a', H-8a'', H-3$_S$), 3.83-3.79 (m, 2H, H-6a, H-8b''), 3.73 (d, 1H, J$_{6a,6b}$=10.5 Hz, H-6b), 3.67 (dd, 1H, J$_{5',6b}$=5.5 Hz, J$_{a',b}$=11.0 Hz, H-6b'), 3.48-3.42 (m, 3H, H-3, H-5, H-5'), 3.33-3.24 (m, 2H, H-2', H-4), 3.15 (dd, 1H, J$_{1,2}$=8.0 Hz, J$_{2,3}$=10.0 Hz, H-2), 2.76-2.67 (m, 4H, H-3a'', H-2$_{La}$, H-20, 2.15-2.08 (2H, H-3b'', H-2$_{Lb}$), 1.68-1.53 [m, 7H, H-4$_S$, H-4$_L$, H-3$_L$', CH(CH$_3$)$_2$], 1.42 (s, 3H, CH$_3$ of isopropylidene), 1.36 (s, 3H, CH₃ of isopropylidene), 1.28 [bs, 48H, H-(5$_S$-11$_S$), H-(5$_L$-13$_L$), H-(4$_L$-11$_L$)], 0.91-0.90 [m, 21H, H-12$_S$, H-14$_L$, H-12$_L'$, SiC(CH₃)₂CH(CH₃)₂], 0.20 [s, 6H, Si(CH₃)₂]. HR MS (m/z) calculated for C₁₁₂H₁₆₃N₄O₂₄Si[M+Na]⁺, 2030.1062; found, 2030.4662. A solution of (R)-3-benzyloxy-dodecanoic acid 58 (72 mg, 0.234 mmol) and DCC (72 mg, 0.351 mmol) in DCM (5 mL) was stirred at room temperature for 10 min, and then the above obtained intermediate (235 mg, 0.117 mmol) and DMAP (7 mg, 0.06 mmol) were added. The reaction mixture was stirred for another 10 h, after which the solids were removed by filtration and washed with DCM (2×2 mL). The combined filtrates were concentrated in vacuo. The residue was purified by silica gel column chromatography (eluent: hexane/ethyl acetate, 5/1-4/1, v/v) to afford 70 as a white solid (228 mg, 84%). R$_f$=0.60 (hexane/ethyl acetate, 3/1, v/v); [α]$^{25}_D$+7.9° (c=1.0, CHCl₃); ¹H NMR (500 MHz, CDCl₃): δ 7.42-7.12 (m, 32H, aromatic), 6.74 (d, 1H, J=7.5 Hz, aromatic), 6.56 (d, 1H, J=7.0 Hz, aromatic), 5.65 (d, 1H, J$_{NH',2}$=7.5 Hz, NH'), 5.58 (t, 1H, J$_{2',3'}$=9.5 Hz, H-3'), 5.25 (s, 2H, CO₂CH₂Ph), 5.16 (t, 1H, J$_{2,3}$=J$_{3,4}$=9.5 Hz, H-3), 5.10-00 (m, 2H, H-3$_L$, CHHPh), 4.98 (d, 1H, J$_{1',2'}$=8.5 Hz, H-1'), 4.92 (dd, 1H, J=11.0 Hz, J=14.0 Hz, CHHPh), 4.81-4.47 (m, 15H, H-1, H-4', H-4", 12×CHHPh), 4.44 (bs, 1H, H-5"), 4.12-4.10 (m, 1H, H-7"), 4.05 (d, 1H, J=9.5 Hz, H-6"), 3.96-3.89 (m, 3H, H-8a", 2×H-3$_S$), 3.85-3.79 (m, 3H, H-6a, H-6a', H-8b"), 3.68 (d, 1H, J$_{6a',6b'}$=11.0 Hz, H-6b'), 3.64-3.57 (m, 2H, H-5, H-6b), 3.41 (dd, 1H, J=3.0 Hz, J=10.0 Hz, H-5'), 3.33 (t, 1H, J$_{3,4}$=J$_{4,5}$=9.0 Hz, H-4), 3.22 (dd, 1H, J$_{1,2}$=8.0 Hz, J$_{2,3}$=10.5 Hz, H-2), 3.18 (dd, 1H, J=7.5 Hz, H-2'), 2.76-2.68 (m, 2H, H-2$_S$), 2.63 (dd, 1H, J$_{2Sa,2Sb}$=16.0 Hz, J$_{2Sa,3S}$=7.0 Hz, H-2$_{Sa}$), 2.50 (dd, 1H, J$_{2Sa,2Sb}$=16.0 Hz, J$_{2Sb,3S}$=6.0 Hz, H-2$_{Sb}$), 2.38-2.26 (m, 3H, H-2$_L$), 2.22 (dd, 1H, J$_{3a",3b"}$=14.0 Hz, J$_{3a",4"}$=7.5 Hz, H-3a"), 2.16 (dd, 1H, J$_{3a",3b"}$=14.0 Hz, J$_{3b",4"}$=5.5 Hz, H-3b"), 2.11 (dd, J$_{2La,2Lb}$=14.5 Hz, J$_{2Lb,3L}$=5.0 Hz, H-2$_{Lb}$), 1.69-1.54 [m, 9H, 2×H-4$_S$, H-4$_L$, H-3$_L$, CH(CH₃)₂], 1.44 (s, 3H, CH₃ of isopropylidene), 1.37 (s, 3H, CH₃ of isopropylidene), 1.22 [bs, 62H, 2×H-(5$_S$-11$_S$), H-(5$_L$-130, H-(4$_L$-110], 0.92-0.90 [m, 24H, 2×H-12$_S$, H-14$_L$, H-12$_L'$, SiC(CH₃)₂CH(CH₃)₂], 0.22 [s, 6H, Si(CH₃)₂]. ¹³C NMR (75 MHz, CDCl₃): δ 173.56 (C=O), 171.09 (C=O), 170.58 (C=O), 169.92 (C=O), 167.77 (C=O), 138.84-127.43 (m, aromatic), 108.66 (C-2"), 99.90 (C-1'), 98.60 (C(CH₃)₂ of isopropylidene), 96.40 (C-1), 77.43-76.58 (C-3, 7"), 76.58 (C-4), 75.75 (C-3$_S$), 75.51 (C-3$_S$), 74.17 (C-5), 73.94 (C-4'), 73.87 (CH₂Ph), 73.36 (CH₂Ph), 73.19 (CH₂Ph), 72.52 (C-5'), 71.74 (C-3'), 71.47 (CH₂Ph), 71.15 (CH₂Ph), 70.83 (C-5"), 70.75 (C-3$_L$), 69.80 (C-4", 8"), 68.95 (C-6), 68.40 (C-6", CH₂Ph), 68.09 (CH₂Ph), 66.97 (CO₂CH₂Ph), 66.90 (C-2), 61.79 (C-6'), 56.70 (C-2'), 41.64 (C-2$_L$), 39.72 (C-2$_S$), 38.92 (C-2$_S$), 34.48-14.09 [m, 3", SiC(CH₃)₂CH(CH₃)₂, CH₃ of isopropylidene, 2×C-(4$_S$-12$_S$), C-(4$_L$-14$_L$), C-(2$_L$)], −1.84 (SiCH₃), −3.42 (SiCH₃). HR MS (m/z) calculated for C₁₃₁H₁₉₁N₄O₂₆Si[M+Na]⁺, 2318.3151; found, 2318.5374.

Dimethylthexylsilyl benzyl (7,8-di-O-benzyl-3-deoxy-4,5-O-isopropylidene-α-D-manno-oct-2-ulopyranosyl)onate-(2→6)-3-O—[(R)-3-benzyloxy-dodecanoyl]-2-deoxy-4-O-(1,5-dihydro-3-oxo-3λ⁵-3H-2,4,3-benzodioxaphosphepin-3-yl)-2-[(R)-3-dodecanoyloxy-tetradecanoyl]-β-D-glucopyranosyl-(1→6)-4-O-benzyl-3-O—[(R)-3-benzyloxy-dodecanoyl]-2-deoxy-2-[(R)-3-dodecanoyloxy-tetradecanoyl]-(R)-D-glucopyranoside (71): A suspension of compound 70 (120 mg, 52 μmol) and zinc (<10 micron, 210 mg, 3.2 mmol) in a mixture of acetic acid (100 μL) and DCM (5 mL) was stirred at room temperature for 1 h, after which it was diluted with ethyl acetate (20 mL). The solids were removed by filtration, and the residue was washed with ethyl acetate (2×3 mL). The combined filtrates were washed with saturated aqueous NaHCO₃ (2×20 mL) and brine (2×20 mL). The organic phase was dried (MgSO₄), filtered, and the filtrate was concentrated in vacuo. The residue was purified by silica gel column chromatography (hexane/ethyl acetate, 4/1, v/v) to afford the amine as a pale yellow syrup (108 mg, 92%). R$_f$=0.45 (hexane/ethyl acetate, 5/2, v/v). A solution of (R)-3-dodecanoyloxy-dodecanoic acid 59 (43 mg, 100 μmol) and DCC (31 mg, 150 μmol) in DCM (5 mL) was stirred at room temperature for 10 min, and then the above obtained intermediate (120 mg, 53 μmol) was added. The reaction mixture was stirred for another 10 h, after which the solids were removed by filtration and washed with DCM (2×1 mL). The combined filtrates were concentrated in vacuo. The residue was purified by silica gel column chromatography (eluent: hexane/ethyl acetate, 5/1-4/1, v/v) to afford 71 as an amorphous solid (126 mg, 89%). R$_f$=0.65 (hexane/ethyl acetate, 5/2, v/v); [α]$^{25}_D$=+4.3° (c=1.0, CHCl₃); ¹H NMR (600 MHz, CDCl₃): δ 7.47-7.17 (m, 32H, aromatic), 6.76 (d, 1H, J=7.8 Hz, aromatic), 6.66 (d, 1H, J=6.0 Hz, aromatic), 5.71-5.69 (m, 2H, NH, NH'), 5.64 (t, 1H, J$_{2',3'}$=J$_{3,4}$=9.6 Hz, H-3'), 5.30 (d, 1H, J=13.2 Hz, CO₂CHHPh), 5.25 (d, 1H, J=13.2 Hz, CO₂CHHPh), 5.16 (t, 1H, J$_{2,3}$=J$_{3,4}$=9.5 Hz, H-3), 5.15 (t, 1H, J$_{2,3}$=J$_{3,4}$=9.6 Hz, H-3), 5.13-5.05 (m, 3H, 2×H-3$_L$, CHHPh), 5.04 (d, 1H, =8.4 Hz, H-1'), 4.97 (dd, 1H, J=11.4 Hz, J=13.8 Hz, CHHPh), 4.87-4.75 (m, 4H, 4×CHHPh), 4.73-4.69 (m, 1H, H-4'), 4.68 (d, 1H, J$_{1,2}$=7.8 Hz, H-1), 4.65-4.46 (m, 10H, H-4", H-5", 8×CHHPh), 4.15-4.13 (m, 1H, H-7"), 4.06 (d, 1H, J=9.6 Hz, H-6"), 3.99-3.93 (m, 3H, H-2, H-8a", H-3$_S$), 3.89-3.84 (m, 4H, H-6a, H-6a', H-8b", H-3$_S$), 3.66 (d, 1H, J$_{6a',6b'}$=10.8 Hz, H-6b'), 3.62-3.56 (m, 2H, H-5, H-6b), 3.49 (dd, 1H, J=4.2 Hz, J=10.2 Hz, H-5'), 3.38 (t, 1H, J$_{3,4}$=J$_{4,5}$=9.0 Hz, H-4), 3.19 (dd, 1H, 1=7.8 Hz, H-2'), 2.77 (dd, 1H, J$_{2Sa,2Sb}$=16.2 Hz, J$_{2Sa,3S}$=7.2 Hz, H-2$_{Sa}$), 2.72 (dd, 1H, J$_{2Sa,2Sb}$=16.2 Hz, J$_{2Sb,3S}$=4.8 Hz, H-2$_{Sb}$), 2.61 (dd, 1H, J$_{2Sa,2Sb}$=16.2 Hz, J$_{2Sa,3S}$=7.2 Hz, H-2$_{Sa}$), 2.49 (dd, 1H, J$_{2Sa,2Sb}$=16.2 Hz, J$_{2Sb,3S}$=5.4 Hz, H-2$_{Sb}$), 2.43-2.24 (m, 8H, H-3a", 2×H-2$_{La}$, H-2$_{Lb}$, 2×H-2$_L'$), 2.19 (dd, 1H, J$_{3a",3b"}$=15.0 Hz, J$_{3b",4"}$=5.4 Hz, H-3b"), 2.16 (dd, 1H, J$_{2La,2Lb}$=15.0 Hz, J$_{2Lb,3L}$=6.0 Hz, H-2$_{Lb}$), 1.68-1.58 [m, 15H, 2×H-4$_S$, 2×H-4$_L$, 2×H-3$_L'$, CH(CH₃)₂], 1.46 (s, 3H, CH₃ of isopropylidene), 1.39 (s, 3H, CH₃ of isopropylidene), 1.22 [bs, 96H, 2×H-(5$_S$-11$_S$), 2×H-(5$_L$-13$_L$), 2×H-(4$_L$-11$_L'$)], 0.96-0.87 [m, 30H, 2×H-12$_S$, 2×H-14$_L$, 2×H-12$_L'$, SiC(CH₃)₂CH(CH₃)₂], 0.21 (s, 3H, SiCH₃), 0.20 (s, 3H, SiCH₃). ¹³C NMR (75 MHz, CDCl₃): δ 173.60 (C=O), 173.54 (C=O), 171.62 (C=O), 171.06 (C=O), 169.95 (C=O), 169.05 (C=O), 168.04 (C=O), 139.00-127.43 (m, aromatic), 108.69 (C-2"), 99.60 (C-1'), 98.43 [C(CH₃)₂ of isopropylidene], 85.85 (C-1), 77.26 (C-7"), 76.90 (C-4), 75.50-75.41 (3C, C-3, C-3$_S$×2), 74.22-74.08 (4C, C-4', 5, CH₂Ph×2), 73.37 (CH₂Ph), 72.52 (C-5'), 71.75 (C-3'), 71.27 (CH₂Ph), 71.21 (CH₂Ph), 70.98 (C-5"), 70.71 (C-3$_{L×2}$), 70.20 (C-8"), 69.88 (C-4"), 68.85 (C-6), 68.62 (C-6"), 68.41 (CH₂Ph), 68.13 (CH₂Ph), 66.98 (CO₂CH₂Ph), 61.90 (C-6'), 56.74 (C-2'), 56.20 (C-2), 41.56 (C-20, 41.47 (C-2$_L$), 39.60 (C-2s), 38.96 (C-2s), 34.47-14.09 [m, 3", SiC(CH₃)₂CH(CH₃)₂, CH₃ of isopropylidene, 2×C-(4$_S$-12$_S$), 2×C-(4$_L$-14$_L$), 2×C-(2$_L'$-12u)], −1.56 (SiCH₃), −3.31 (SiCH₃). HR MS (m/z) calculated for C₁₅₇H₂₄₁N₂O₂₉Si[M+Na]⁺, 2700.6850; found, 2700.6572.

Bis(benzyloxy)phosphoryl benzyl (7,8-di-O-benzyl-3-deoxy-α-D-manno-oct-2-ulopyranosyl)onate-(2→6)-3-O—[(R)-3-benzyloxy-dodecanoyl]-2-deoxy-4-O-(1,5-dihydro-3-oxo-3λ⁵-3H-2,4,3-benzodioxaphosphepin-3-yl)-2-[(R)-3-dodecanoyloxy-tetradecanoyl]-(R)-D-glucopyranosyl-(1→6)-4-O-benzyl-3-O—[(R)-3-benzyloxy-dodecanoyl]-2-deoxy-2-[(R)-3-dodecanoyloxy-tetradecanoyl]-α-D- glucopyranose (72): TFA/H$_2$O (3/2, v/v, 100 μL) was added dropwise to a stirred solution of 71 (30 mg, 11 μmol) in DCM (2 mL). The reaction mixture was stirred at room temperature for 6 h, after which it was diluted with ethyl acetate (10 mL) and then washed with saturated aqueous NaHCO$_3$ (2×10 mL) and brine (2×10 mL). The organic phase was dried (MgSO$_4$), filtered, and the filtrate was concentrated in vacuo. The residue was purified by preparative silica gel TLC (eluent: hexane/ethyl acetate, 3/1, v/v) to afford the lactol as a pale yellow syrup (25 mg, 89%). R$_f$=0.25 (hexane/acetone, 1/1, v/v); $^1$H NMR (600 MHz, CDCl$_3$): δ 7.42-7.19 (m, 32H, aromatic), 6.82 (d, 1H, J=7.8 Hz, aromatic), 6.64 (d, 1H, J=6.0 Hz, aromatic), 5.91 (d, 1H, J$_{2,NH}$=9.6 Hz, NH), 5.81 (d, 1H, J$_{2',NH'}$=7.8 Hz, NH'), 5.44 (t, 1H, J$_{2',3'}$=9.6 Hz, H-3'), 5.38 (d, 1H, J$_{1',2'}$=7.8 Hz, H-1'), 5.32 (dd, 1H, J=9.6 Hz, J=10.2 Hz, H-3), 5.19 (d, 1H, J=12.6 Hz, CO$_2$CHHPh), 5.14 (d, 1H, J=12.6 Hz, CO$_2$CHHPh), 5.11-5.07 (m, 2H, H-1, H-3$_L$), 5.01-4.88 (m, 3H, H-3$_L$, 2×CHHPh), 4.83 (dd, 1H, J=12.2 Hz, J=13.8 Hz, CHHPh), 4.74-4.67 (m, 3H, 3×CHHPh), 4.64-4.59 (m, 1H, H-4'), 4.58-4.41 (m, 10H, 7×CHHPh), 4.35-4.31 (m, 2H, H-4", CHHPh), 4.12-3.94 (m, 5H, H-2, H-5, H-5", H-6", H-7"), 3.86-3.72 (m, 7H, H-6a, H-6a', H-6b', H-8a", H-8b", 2×H-3$_S$), 3.66 (d, 1H, J$_{5',6b'}$=7.2 Hz, J$_{6a',6b'}$=12.0 Hz, H-6b'), 3.46 (bs, 1H, H-5'), 3.24 (t, 1H, J$_{3,4}$=J$_{4,5}$=9.6 Hz, H-4), 3.02 (dd, 1H, J=7.8 Hz, H-2'), 2.68 (dd, 1H, J$_{2Sa,2Sb}$=16.2 Hz, J$_{2Sa,3S}$=4.8 Hz, H-2$_{Sa}$), 2.61 (dd, 1H, J$_{2Sa,2Sb}$=16.2 Hz, J$_{2Sb,3S}$=6.6 Hz, H-2$_{Sb}$), 2.55 (dd, 1H, J$_{2Sa,2Sb}$=15.6 Hz, J$_{2Sa,3S}$=7.8 Hz, H-2$_{Sa}$), 2.41 (dd, 1H, J$_{2Sa,2Sb}$=16.2 Hz, J$_{2Sb,3S}$=4.8 Hz, H-2$_{Sb}$), 2.34-2.22 (m, 7H, 2×H-2$_{La}$, H-2L$_b$, H-2$_L$×4), 2.18 (dd, 1H, J$_{3a'',3b''}$=12.6 Hz, J$_{3a'',4''}$=4.6 Hz, H-3a"), 2.11 (dd, J$_{2La,2Lb}$=15.6 Hz, J$_{2Lb,3L}$=6.0 Hz, H-2$_{Lb}$), 1.96 (t, 1H, J$_{3a'',3b''}$=J$_{3b'',4''}$=12.6 Hz, H-3b"), 1.61-1.48 (m, 14H, 2×H-4$_S$, 2×H-4$_L$, 2×3$_u$), 1.22 [bs, 96H, 2×H-(5$_S$-11$_S$), 2×H-(5$_L$-13$_L$), 2×H-(4$_L'$-11$_L'$)], 0.96-0.87 (m, 18H, 2×H-12$_S$, 2×H-14$_L$, 2×H-12$_L'$). HR MS (m/z) calculated for C$_{146}$H$_{219}$N$_2$O$_{29}$Si[M+Na]$^+$, 2518.5359; found, 2518.2606. To a cooled (−78° C.) solution of the lactol intermediate (23 mg, 9.2 μmol) and tetrabenzyl diphosphate (10 mg, 18.4 μmol) in THF (2 mL) was added dropwise lithium bis(trimethylsilyl)amide in THF (1.0 M, 15 μL, 15 μmol). The reaction mixture was stirred for 1 h, and then allowed to warm up to −20° C. After stirring the reaction mixture for 1 h at −20° C., it was quenched with saturated aqueous NaHCO$_3$ (10 mL), and diluted with ethyl acetate (15 mL). The organic phase was washed with brine (2×15 mL), dried (MgSO$_4$), filtered, and the filtrate was concentrated in vacuo. The residue was purified by Iatro beads column chromatography (hexane/ethyl acetate, 3/1→2/1→1/1→3/4, v/v) to give 72 as a colorless syrup (19 mg, 75%). R$_f$=0.50 (hexane/acetone, 1/1, v/v); $^1$H NMR (500 MHz, CDCl$_3$): δ 7.40-7.14 (m, 42H, aromatic), 6.82 (d, 1H, J=8.0 Hz, aromatic), 6.69 (d, 1H, J=7.5 Hz, aromatic), 6.41 (d, 1H, J$_{2',NH'}$=8.5 Hz, NH'), 6.04 (d, 1H, J$_{2,NH}$=8.5 Hz, NH), 5.65 (bs, 1H, H-1), 5.35 (t, 1H, J$_{2',3}$=J$_{3',4'}$=9.5 Hz, H-3'), 5.24-4.73 (m, 12H, H-1', H-3, 5×CHHPh), 4.61-4.36 (m, 11H, H-4', 5×CHHPh), 4.38 (d, 1H, J=11.5 Hz, CHHPh), 4.27-4.23 (m, 1H, H-4",), 4.19-4.14 (m, 1H, H-2), 4.09-3.96 (m, 4H, H-5, H-5", H-6", H-7"), 3.91-3.74 (m, 8H, H-6a, H-6a', H-6b, H-6b', H-8a", H-8b", 2×H-3$_S$), 3.53-3.44 (m, 3H, H-2', H-4, H-5'), 2.70 (dd, 1H, J$_{2Sa,2Sb}$=16.5 Hz, J$_{2Sa,3S}$=7.0 Hz, H-2$_{Sa}$), 2.65 (dd, 1H, J$_{2Sa,2Sb}$=16.5 Hz, J$_{2Sb,3S}$=5.0 Hz, H-2$_{Sb}$), 2.56 (dd, 1H, J$_{2Sa,2Sb}$=16.0 Hz, J$_{2Sa,3S}$=7.5 Hz, H-2$_{Sa}$), 2.48 (dd, 1H, J$_{2Sa,2Sb}$=16.0 Hz, J$_{2Sb,3S}$=5.0 Hz, H-2$_{Sb}$), 2.31-2.18 (m, 7H, 2×H-2$_{La}$, H-2$_{Lb}$, 2×H-20, 2.12 (dd, 1H, J$_{3a'',3b''}$=11.0 Hz, J$_{3a'',4''}$=5.0 Hz, H-3a"), 2.09 (dd, J$_{2La,2Lb}$=16.5 Hz, J$_{2Lb,3L}$=6.0 Hz, H-2$_{Lb}$), 2.04 (t, 1H, J$_{3a'',3b''}$=J$_{3b'',4''}$=12.5 Hz, H-3b"), 1.61-1.49 (m, 14H, 2×H-4$_S$, 2×H-4$_L$, 2×3$_u$), 1.26 [bs, 96H, 2×H-(5$_S$-11$_S$), 2×H-(5$_L$-13$_L$), 2×H-(4$_L$-11$_L$)], 0.90-0.88 (m, 18H, 2×H-12s, 2×H-14$_L$, 2×H-12$_{L'}$). HR MS (m/z) calculated for C$_{160}$H$_{232}$N$_2$O$_{32}$Si[M+Na]$^+$, 2778.5961; found, 2778.9185.

(3-Deoxy-α-D-manno-oct-2-ulopyranosyl)onate-(2→6)-3-O—[(R)-3-hydroxy-dodecanoyl]-2-deoxy-2-[(R)-3-dodecanoyloxy-tetradecanoyl]-(R)-D-glucopyranosyl-(1→6)-3-O—[(R)-3-hydroxy-dodecanoyl]-2-deoxy-2-[(R)-3-dodecanoyloxy-tetradecanoyl]-α-D-glucopyranose 1,4'-biphosphate (53): A mixture of 72 (9 mg, 3.3 μmol) and Pd black (15.0 mg) in anhydrous THF (3 mL) was shaken under an atmosphere of H$_2$ (65 psi) at room temperature for 30 h, after which it was neutralized with triethylamine (10 μL), and the catalyst was removed by filteration and the residue washed with THF (2×1 mL). The combined filtrates were concentrated in vacuo to afford 3 as a colorless film (5.0 mg, 78%). $^1$H NMR (600 MHz, CDCl$_3$): δ 5.24 (bs, 1H, H-1), 4.91-4.83 (m, 4H, H-3, H-3', 2×H$_L$), 3.86 (m, 1H, H-2), 3.82-3.45 (m, 11H, H-5, H-5', H-5", H-6a, H-6b, H-6'a, H-6'b, H-6", H-7", H-8"a, H-8"b), 3.80 (m, 2H, H-4', H-4"), 3.76 (m, 1H, H-3$_S$), 3.72 (m, 1H, H-3$_S$), 3.60 (m, 1H, H-2'), 3.29 (m, 1H, H-4), 2.23-2.07 (m, 8H, 2×H-2$_S$, 2×H-2$_L$), 2.04-1.98 (m, 4H, 2×H-2$_L$), 1.76 (dd, 1H, J$_{3a'',3b''}$=15.0 Hz, J$_{3a'',4''}$=5.4 Hz, H-3a"), 1.61 (t, 1H, J$_{3a'',3b''}$=J$_{3b'',4''}$=15.0 Hz, H-3b"), 1.41-1.19 (m, 14H, 2×H-4$_S$, 2×H-4$_L$, 2×H-3$_L$), 1.12 [bs, 96H, 2×H-(5$_S$-11$_S$), 2×H-(5$_L$-13$_L$), 2×H-(4$_L$-11$_L$)], 0.91-0.88 (m, 18H, 2×H-12s, 2×H-14$_L$, 2×H-12$_{L'}$). HR MS (m/z) (negative) calculated for C$_{160}$H$_{232}$N$_2$O$_{32}$Si, 1933.1838; found, 1932.6287[M], 1954.5441 [M+Na—H], 1976.4611 [M+2Na-2H].

Allyl 5,6-di-O-benzyl-2,3-di-O-isopropylidene-α-D-mannofuranoside (79): NaH (1.27 g, 53.0 mmol) was added portionwise to a stirred solution of 78 (2.50 g, 10.6 mmol) in dry DMF (20 mL). After stirring the reaction mixture for 30 min, it was cooled (0° C.) and then BnBr (5.0 mL, 42.4 mmol) was added. The reaction mixture was stirred at room temperature for 10 h, after which it was quenched by addition of methanol (5 mL), diluted with ethyl acetate (50 mL), and washed with brine (2×30 mL). The organic phase was dried (MgSO$_4$), filtered, and the filtrate was concentrated in vacuo. The residue was purified by silica gel column chromatography (eluent: hexane/ethyl acetate, 10/1, v/v) to afford 79 as a colorless oil (4.29 g, 92%). R$_f$=0.65 (hexane/ethyl acetate, 6/1, v/v); $^1$H NMR (300 MHz, CDCl$_3$): ™7.39-7.20 (m, 10H, aromatic), 5.86 (m, 1H, OCH$_2$CH═CH$_2$), 5.23 (dd, 1H, J=17.4 Hz, J=1.5 Hz, OCH$_2$CH═CHH), 5.15 (dd, 1H, J=17.4 Hz, 10.2 Hz, OCH$_2$CH═CHH), 5.00 (s, 1H, H-1'), 4.84 (dd, 1H, J=3.3 Hz, J=5.7 Hz, H-3), 4.80 (d, 1H, J=11.1 Hz, CHHPh), 4.69 (d, 1H, J=11.1 Hz, CHHPh), 4.65-4.54 (m, 3H, H-2, 2×CHHPh), 4.11-4.05 (m, 2H, H-4, OCHHCH═CH$_2$), 4.00-3.81 (m, 3H, H-4, H-6a, OCHHCH═CH$_2$), 3.65 (dd, 1H, J$_{5,6b}$=5.4 Hz, J$_{6a,6b}$=16.5 Hz, H-6b), 1.44 (s, 3H, CH$_3$), 1.36 (s, 3H, CH$_3$); HR MS (m/z) calculated for C$_{26}$H$_{32}$O$_6$[M+Na]$^+$, 463.2091; found, 463.2118.

5,6-di-O-Benzyl-2,3-di-O-isopropylidene-D-mannitol (80): A suspension of 79 (3.20 g, 7.27 mmol) and Pd/C (50 mg) in methanol (70 mL) was refluxed for 16 h, after which the catalyst was removed by filtration, and the filtrate was concentrated in vacuo to afford the isomerization product as a pale yellow. The obtained intermediate was dissolved in a mixture of THF (50 mL), pyridine (2 mL) and H$_2$O (10 mL) at 0° C., and then H$_2$ (2.77 g, 10.9 mmol) was added portion wise. After stirring the reaction mixture for 30 min, it was diluted with ethyl acetate (100 mL), washed with aqueous NaS$_2$O$_3$ (2×50 mL, 15%), saturated aqueous NaHCO$_3$ (2×50 mL) and brine (2×50 mL), successively. The organic phase was dried (MgSO$_4$) and filtered. Next, the filtrate was concentrated in vacuo. The residue was purified by silica gel column chromatography (eluent: hexane/ethyl acetate, 4/1-3/1, v/v) to afford a lactol as a colorless oil (2.18 g, 75%). R$_f$=0.65 (hexane/ethyl acetate, 2/1, v/v); HR MS (m/z) calculated for C$_{23}$H$_{28}$O$_6$[M+Na]$^+$, 423.1778; found, 423.2083. The above obtained lactol (2.00 g, 5.00 mmol) was dissolved in ethanol (30 mL), and then NaBH$_4$ (285 mg, 7.50 mmol) was added portionwise. After stirring the reaction mixture for 10 h, it was cooled (0° C.), quenched with acetic acid (15 mL), and diluted with ethyl acetate (80 mL). The solution was washed with saturated aqueous NaHCO$_3$ (2×50 mL) and brine (2×40 mL). The organic phase was dried (MgSO$_4$), filtered, and the filtrate was concentrated in vacuo. The residue was purified by silica gel column chromatography (eluent: hexane/ethyl acetate, 5/2-3/2, v/v) to afford 80 as an amorphous solid (1.89 g, 94%). R$_f$=0.45 (hexane/ethyl acetate, 3/2, v/v); NMR (300 MHz, CDCl$_3$): ™7.39-7.22 (m, 10H, aromatic), 4.73 (d, 1H, J=11.7 Hz, CHHPh), 4.58-4.54 (m, 3H, CHI/Ph), 4.45 (dd, 1H, J=1.5 Hz, J=6.9 Hz, H-3), 4.22 (m, 1H, H-2), 3.86-3.71 (m, 5H, 2×H-1, H-4, H-5, H-6b); 3.63 (dd, 1H, J=3.9 Hz, J=8.1 Hz, H-6a), 1.56 (s, 3H, CH$_3$), 1.38 (s, 3H, CH$_3$). HR MS (m/z) calculated for C$_{23}$H$_{30}$O$_6$[M+Na]$^+$, 425.1935; found, 425.1886.

5,6-di-O-Benzyl-2,3-di-O-isopropylidene-1,4-di-O-sulfate-D-mannitol (81): To a cooled (−15° C.) solution of 80 (1.44 g, 3.53 mmol) and Et$_3$N (2.0 mL, 14.2 mmol) in DCM (20 mL) was added dropwise thionyl chloride (387 μl, 5.30 mmol). After stirring the reaction mixture for 30 min, it was diluted with DCM (30 mL), and then washed with saturated aqueous NaHCO$_3$ (2×40 mL) and brine (2×40 mL). The organic phase was allowed to pass through a pad of silica gel, which was then eluted with ethyl acetate (50 mL). The combined eluents were concentrated in vacuo to afford the crude cyclic sulfite as a slightly colored oil. The above obtained crude product was dissolved in a mixture of DCM (10 mL) and acetonitrile (10 mL), and then RuCl$_3$.H$_2$O (14.7 mg, 71 NaIO$_4$ (1.13 g, 5.30 mmol) and H$_2$O (15 mL) were added, successively. After stirring the reaction mixture for 20 min, it was diluted with ethyl acetate (40 mL), and then washed with saturated aqueous NaHCO$_3$ (2×40 mL) and brine (2×40 mL). The organic phase was dried (MgSO$_4$), filtered, and the filtrate was concentrated in vacuo. The residue was purified by silica gel column chromatography (eluent: hexane/ethyl acetate, 10/1, v/v) to afford 81 as an amorphous solid (1.89 g, 94%). R$_f$=0.45 (hexane/ethyl acetate, 4/1, v/v); $^1$H NMR (300 MHz, CDCl$_3$): ™7.40-7.22 (m, 10H, aromatic), 4.99 (d, J$_{4,5}$=9.0 Hz, H-4), 4.77-4.72 (m, 2H, H-3, CHHPh), 4.66 (d, 1H, J=12.0 Hz, CHHPh), 4.59 (d, 1H, J=11.4 Hz, CHHPh), 4.53 (d, 1H, J=12.0 Hz, CHHPh), 4.43-4.26 (m, 3H, 2×H-1, H-2); 3.95 (ddd, 1H, J=1.8 Hz, J=3.9 Hz, J=9.0 Hz, H-5), 3.82 (dd, 1H, J$_{5,6a}$=1.8 Hz, J$_{6a,6b}$=10.5 Hz, H-6a), 3.82 (dd, 1H, J$_{5,6b}$=3.9 Hz, J$_{6a,6b}$=10.5 Hz, H-6b), 1.54 (s, 3H, CH$_3$), 1.48 (s, 3H, CH$_3$). HR MS (m/z) calculated for C$_{23}$H$_{28}$O$_8$S[M+Na]$^+$, 487.1397; found, 487.1464.

Benzyl 2-deoxy-4,5-di-O-isopropylidene-7,8-di-O-benzyl-D-glycero-D-galacto-octulosonate 1,3-propylene dithioacetal (83): To a cooled solution (−45° C.) of 82 (330 mg, 1.3 mmol) in a mixture of THF (2 mL) and HMPA (0.8 mL) was added BuLi (2.5 M in hexane, 0.56 mL, 1.4 mmol). The reaction mixture was stirred for 2 h, after which a solution of 81 (470 mg, 1.0 mmol) in THF (1 mL) was added dropwise. The stirring continued at room temperature for another 2 h till TLC analysis showed compound 81 nearly completely disappeared. Then, the reaction mixture was first neutralized with sulfuric acid (1 M in THF, 1 mL) followed by the addition of H$_2$O (15 μL), after which another portion of sulfuric acid (1 m in THF, 1 mL) was added till pH 3. After heating the mixture (50° C.) for 1 h, it was cooled (25° C.), diluted with ethyl acetate (30 mL), and then washed with saturated aqueous NaHCO$_3$ (2×40 mL) and brine (2×30 mL). The organic phase was dried (MgSO$_4$), filtered, and the filtrate was concentrated in vacuo. The residue was purified by silica gel column chromatography (eluent: toluene/ethyl acetate, 30/1, v/v) to afford 83 as a colorless oil (510 mg, 78%). R$_f$=0.55 (hexane/ethyl acetate, 3/1, v/v); $^1$H NMR (300 MHz, CDCl$_3$): ™7.40-7.21 (m, 15H, aromatic), 5.24 (d, 1H, J=12.6 Hz, CO$_2$CHHPh), 5.14 (d, 1H, J=12.6 Hz, CO$_2$CHHPh), 4.74 (d, 1H, J=11.4 Hz, CHHPh), 4.63-4.53 (m, 4H, H-4, 2×CHHPh), 4.39 (dd, 1H, J=1.2 Hz, J=6.9 Hz, H-5), 3.85 (dd, 1H, J=3.0 Hz, J=10.5 Hz, H-8a), 3.75-3.67 (m, 2H, H-6, H-8b), 3.60-3.54 (m, 1H, H-7), 3.25 (ddd, 1H, J=2.7 Hz, J=14.6 Hz, CH$_{2axi}$ of SCH$_2$), 3.06 (ddd, 1H, J=2.4 Hz, J=14.6 Hz, CH'$_{2axi}$ of SCH'$_2$), 2.75-2.60 (m, 3H, H-3a, CH$_{2equo}$ of SCH$_2$, CH'$_{2equo}$ of SCH'$_2$), 2.43 (dd, 1H, J$_{3a,3b}$=15.0 Hz, J$_{3b,4}$=3.0 Hz, H-3b), 2.09-2.03 (m, 1H,) 1.92-1.78 (m, 1H), 1.39 (s, 3H, CH$_3$ of isopropylidene), 1.29 (s, 3H, CH$_3$ of isopropylidene). HR MS (m/z) calculated for C$_{32}$H$_{42}$O$_7$S$_2$[M+Na]$^+$, 661.2264; found, 661.2397.

Benzyl 3-deoxy-4,5-di-O-isopropylidene-7,8-di-O-benzyl-<,(R)-D-manno-2-octulopyranosonate (84): To a stirred suspension of 83 (1.06 g, 1.66 mmol) and NaHCO$_3$ (1 g, 11.9 mmol) in a mixture of CH$_3$COCH$_3$ (20 mL) and H$_2$O (1 mL) was added NBS (1.77 g, 9.96 mmol) at 0° C. After stirring the reaction mixture for 10 min, it was quenched with aqueous Na$_2$S$_2$O$_3$ (15%, 100 mL), diluted with ethyl acetate (50 mL), and then washed with saturated aqueous NaHCO$_3$ (2×40 mL) and brine (2×40 mL). The organic phase was dried (MgSO$_4$), filtered, and the filtrate was concentrated in vacuo. The residue was purified by silica gel column chromatography (eluent: hexane/ethyl acetate, 6/1-4/1, v/v) to afford 84 as a colorless oil (1.89 g, 94%). R$_f$=0.35 (hexane/ethyl acetate, 4/1, v/v). HR MS (m/z) calculated for C$_{32}$H$_{36}$O$_8$ [M+Na]$^+$, 571.2302; found, 571.3219.

Benzyl 3-deoxy-4,5-di-O-isopropylidene-7,8-di-O-benzyl-α,(R)-D-manno-2-octulopyranosyl fluoride (57): A suspension of 84 (700 mg, 1.28 mmol) and molecular sieves (4 Å, 100 mg) in DCM (6 mL) was stirred at room temperature for 1 h. The mixture was cooled (−60° C.) and then DAST (220 μL, 1.66 mmol) was added dropwise. After stirring the reaction mixture at room temperature for 30 min, it was cooled (−30° C.) and then quenched by stirring with acetic acid (150 μL) for 2 min. Then, the solids were removed by filtration, and the filtrate was washed with saturated aqueous NaHCO$_3$ (2×40 mL) and brine (2×40 mL). The organic phase was dried (MgSO$_4$), filtered, and the filtrate was concentrated in vacuo. The residue was purified by silica gel column chromatography (eluent: hexane/ethyl acetate, 6/1, v/v) to afford a mixture (631 mg) of 57 (75%) and its elimination product (15%). R$_f$=0.60 (hexane/ethyl acetate, 5/1, v/v). HR MS (m/z) calculated for C$_{32}$H$_{35}$FO$_7$ [M+Na]$^+$, 573.2259; found, 573.2516. See scheme 7.

t-Butyldimethylsilyl 3-O-allyloxycarbonyl-6-O-benzyl-2-deoxy-4-O-(1,5-dihydro-3-oxo-3[$^5$-3H-2,4,3-benzodioxaphosphepin-3-yl)-2-[(R)-3-dodecanoyloxy-tetradecanoylamino]-(R)-D-glucopyranosyl-(1→6)-4-O-benzyl-2-[(R)-3-benzyloxy-dodecanoylamino]-3-O—[(R)-3-dodecanoyloxy-dodecanoyl]-2-deoxy-(R)-D-glucopyranoside (74): A suspension of 73 (180 mg, 0.111 mmol), zinc (<10 micron, 72 mg, 1.11 mmol), and acetic acid (25 μL, 0.444 mmol) in DCM (5 mL) was stirred at room temperature for 12 h, after which it was diluted with ethyl acetate (20 mL), the solids removed by filtration and the residue washed with ethyl acetate (2×2 mL). The combined filtrates were washed with saturated aqueous NaHCO₃ (2×15 mL) and brine (2×15 mL). The organic phase was dried (MgSO₄), filtered, and the filtrate was concentrated in vacuo. The residue was purified by silica gel column chromatography (eluent: hexane/ethyl acetate, 5/2, v/v) to afford an amine as a pale yellow syrup (160 mg, 90%). $R_f$=0.35 (hexane/ethyl acetate, 2/1, v/v); HR MS (m/z) calculated for $C_{89}H_{137}N_2O_{19}PSi[M+Na]^+$, 1619.9220; found, 1620.1069. A reaction mixture of (R)-3-dodecanoyl-tetradecanoic acid 59 (31 mg, 73 μmmol) and DCC (20 mg, 98 μmol) in DCM (2 mL) was stirred at room temperature for 10 min, and then the above obtained amine (78 mg, 49 μmol) was added. The reaction mixture was stirred at room temperature for 10 h, after which the insoluble materials were removed by filtration, and the residue was washed with DCM (2×1 mL). The combined filtrates were concentrated in vacuo and the residue was purified by preparative silica gel TLC (eluent: hexane/ethyl acetate, 5/1, v/v) to give 74 as an amorphous solid (82 mg, 84%). $R_f$=0.51 (hexane/ethyl acetate, 2/1, v/v). $[\alpha]^{26}_D$=−3.0° (c=1.0, CHCl₃). ¹H NMR (500 MHz, CDCl₃): ™7.37-7.18 (m, 19H, aromatic), 5.85 (d, 1H, $J_{NH',2'}$=7.5 Hz, NH'), 5.86-5.79 (m, 1H, OCH₂CH=CH₂), 5.65 (d, 1H, $J_{NH,2}$=9.0 Hz, NH), 5.45 (t, 1H, $J_{2',3'}$=$J_{3',4'}$=10.0 Hz, H-3'), 5.28 (d, 1H, J=16.0 Hz, OCH₂CH=CHH), 5.16 (d, 1H, J=11.0 Hz, OCH₂CH=CHH), 5.04-4.92 (m, 8H, H-1', H-3, 2×H-3$_L$, o-C₆H₄(CH₂O)₂P), 4.63 (d, 1H, $J_{1,2}$=7.5 Hz, H-1), 4.55-4.35 (m, 9H, H-4', 3×CH₂Ph, OCH₂CH=CH₂), 3.92 (d, 1H, $J_{6a,6b}$=10.5 Hz, H-6a), 3.78-3.71 (m, 3H, H-2, H-6'a, H-3$_S$), 3.67-3.62 (m, 3H, H-5, H-6b, H-6'b), 3.50-3.48 (m, 2H, H-4, H-5'), 3.39-3.32 (m, 1H, H-2'), 2.48-2.13 (m, 10H, 2×H-2$_L$, H-2$_S$, 2×H-2$_L$'), 1.63-1.42 (m, 10H, 2×H-4$_L$, H-4$_S$, 2×H-3$_L$'), 1.26 [bs, 82H, H-(5$_S$-11$_S$), 2×H-(5$_L$-13$_L$), 2×H-(4$_{L'}$-11$_{L'}$)], 0.90-0.86 [m, 24H, 2×H-12$_S$, 2×H-14$_L$, 2×H-12u SiC(CH₃)₃], 0.11 (s, 3H, SiCH₃), 0.09 (s, 3H, SiCH₃). ¹³C NMR (75 MHz, CDCl₃): ™ 173.66 (C=O), 173.51 (C=O), 170.10 (C=O), 169.19 (C=O), 154.47 (C=O), 138.51-127.48 (aromatic, OCH₂CH=CH₂), 118.78 (OCH₂CH=CH₂), 99.13 (C-1'), 96.11 (C-1), 76.02-74.85 (m, C-3, C-3', C-4, C-4', C-3$_S$), 74.31, 74.17, 73.47 (C-5, C-5', CH₂Ph), 71.26 (CH₂Ph), 70.99 (C-3$_L$), 70.72 (C-3$_L$), 68.93-68.01 (m, C-6, C-6', OCH₂CH=CH₂, 2×CH₂Ph), 56.37 (C-2), 56.11 (C-2'), 41.69 (C-2$_L$), 39.52 (C-2$_S$), 34.51-14.10 [m, SiC(CH₃)₃, C-(4$_S$-12$_S$), 2×C-(4$_L$-14$_L$), 2×C-(4-120], −3.86 (SiCH₃), −5.15 (SiCH₃). HR MS (m/z) for calculated for $C$-15$H_{185}N_2O_{22}PSi[M+Na]^+$, 2028.2824; found, 2028.2843.

t-Butyldimethylsilyl 6-O-benzyl-3-O—[(R)-3-benzyloxy-dodecanoyl]-2-deoxy-4-O-(1,5-dihydro-3-oxo-3λ⁵-3H-2,4,3-benzodioxaphosphepin-3-yl)-2-[(R)-3-dodecanoyloxy-tetradecanoylamino]-(R)-D-glucopyranosyl-(1→6)-4-O-benzyl-2-[(R)-3-benzyloxy-dodecanoylamino]-3-O—[(R)-3-dodecanoyloxy-dodecanoyl]-2-deoxy-(R)-D-glucopyranoside (76): Tetrakis(triphenylphosphine)palladium (6.9 mg, 6 μmol) was added to a solution of 74 (62 mg, 31 μmol), n-BuNH₂ (6.1 μL, 62 μmol), and HCOOH (2.3 μL, 62 μmol) in THF (5 mL). After stirring the reaction mixture at room temperature for 20 min, it was diluted with DCM (10 mL), and washed with water (20 mL), saturated aqueous NaHCO₃ (2×20 mL) and brine (2×20 mL), successively. The organic phase was dried (MgSO₄), filtered, and the filtrate was concentrated in vacuo. The residue was purified by silica gel column chromatography (eluent: hexane/ethyl acetate, 4/3, v/v) to give 75 as a colorless syrup. A solution of (R)-3-benzyloxy-dodecanoic acid 58 (14 mg, 47 μmol) and DCC (13 mg, 62 μmol) in DCM (2 mL) was stirred at room temperature for 10 min, and then the above obtained intermediate 75 and DMAP (1.8 mg, 15 μmol) were added. The reaction mixture was stirred for another 10 h, after which the solids were removed by filtration and washed with DCM (2×1 mL). The combined filtrates were concentrated in vacuo. The residue was purified by silica gel column chromatography (eluent: hexane/ethyl acetate, 4/1, v/v) to afford 76 as an amorphous white solid (49 mg, 72%, 2 steps). $R_f$=0.45 (hexane/ethyl acetate, 2/1, v/v). ¹H NMR (600 MHz, CDCl₃): ™7.37-7.10 (m, 24H, aromatic), 5.69 (d, 1H, $J_{NH,2}$=8.4 Hz, NH), 5.63 (d, 1H, $J_{NH',2'}$=7.8 Hz, NH'), 5.59 (t, 1H, $J_{2',3'}$=$J_{3',4'}$=9.6 Hz, H-3'), 5.10 (t, 1H, $J_{2,3}$=$J_{3,4}$=9.6 Hz, H-3), 5.07 (1H, $J_{1',2'}$=8.4 Hz, H-1'), 5.04-4.85 (m, 6H, 2×H-3$_L$, o-C₆H₄(CH₂O)₂P), 4.69 (t, 1H, $J_{1,2}$=7.8 Hz, H-1), 4.63-4.41 (m, 9H, H-4', 4×CH₂Ph,), 3.97 (d, 1H, $J_{6a,6b}$=10.8 Hz, H-6a), 3.88-3.78 (m, 4H, H-2, H-5, 2×H-3$_S$), 3.72-3.67 (m, 3H, H-5', H-6b, H-6'a), 3.58-3.54 (m, 2H, H-4, H-6'b), 3.29-3.25 (m, 1H, H-2'), 2.66-2.01 (m, 12H, 2×H-2$_L$, 2×H-2$_S$, 2×H-2$_L$'), 1.58-1.54 (m, 12H, 2×H-4$_L$, 2×H-4$_S$, 2×H-3$_L$'), 1.24 [bs, 96H, 2×H-(5$_S$-11$_S$), 2×H-(5$_L$-13$_L$), 2×H-(4$_L$-11$_L$)], 0.87-0.84 [m, 27H, 2×H-12$_S$, 2×H-14$_L$, 2×H-12$_L$, SiC(CH₃)₃], 0.09 (s, 3H, SiCH₃), 0.07 (s, 3H, SiCH₃). ¹³C NMR (75 MHz, CDCl₃): ™173.64 (C=O), 171.63 (C=O), 171.40 (C=O), 169.89 (C=O), 168.15 (C=O), 138.63-127.48 (aromatic), 99.45 (C-1'), 96.16 (C-1), 75.89 (C-4), 75.57 (C-3$_S$), 75.38 (C-3$_S$), 74.92 (C-4'), 74.38 (C-3), 74.19 (CH₂Ph), 73.79 (C-6'), 73.50 (CH₂Ph), 71.99 (C-3'), 71.33 (CH₂Ph), 71.28 (CH₂Ph), 70.80 (C-3$_S$), 70.54 (C-3$_S$), 68.93-68.18 (m, C-5, C-5', C-6, 2×CH₂Ph), 56.26 (C-2'), 56.31 (C-2), 41.68 (C-2$_L$), 41.42 (C-2$_L$), 39.51 (C-2$_S$), 38.92 (C-2$_S$), 34.50-14.10 [m, SiC(CH₃)₃, 2×C-(4$_S$-12$_S$), 2×C-(4$_L$-14$_L$), 2×C-(2$_L$-120], −3.81 (SiCH₃), −5.10 (SiCH₃). HR MS (m/z) calculated for $C_{130}H_{209}N_2O_{22}PSi[M+Na]^+$, 2232.4702; found, 2232.5168.

Bis(benzyloxy)phosphoryl 6-O-benzyl-3-O—[(R)-3-benzyloxy-dodecanoyl]-2-deoxy-4-O-(1,5-dihydro-3-oxo-3λ⁵-3H-2,4,3-benzodioxaphosphepin-3-yl)-2-[(R)-3-dodecanoyloxy-tetradecanoylamino]-(R)-D-glucopyranosyl-(1→6)-4-O-benzyl-2-[(R)-3-benzyloxy-dodecanoylamino]-3-O—[(R)-3-dodecanoyloxy-dodecanoyl]-2-deoxy-α-D-glucopyranose (77): HF/pyridine (40 μL) was added dropwise to a stirred solution of 76 (31 mg, 14 μmol) in THF (2 mL). The reaction mixture was stirred at room temperature for 5 h, after which it was diluted with ethyl acetate (15 mL), and washed with saturated aqueous (2×20 mL) and brine (2×20 mL). The organic phase was dried (MgSO₄), filtered, and the filtrate was concentrated in vacuo. The residue was purified by silica gel column chromatography (eluent: hexane/ethyl acetate, 3/1-4/3, v/v) to give a lactol intermediate as an amorphous solid (25.8 mg, 88%). $R_f$=0.39 (hexane/ethyl acetate, 1/1, v/v); ¹H NMR (600 MHz, CDCl₃): ™7.38-6.81 (m, 24H, aromatic), 5.90 (d, 1H, $J_{NH,2}$=9.0 Hz, NH), 5.83 (d, 1H, $J_{NH',2'}$=7.2 Hz, NH'), 5.53 (t, 1H, $J_{2',3'}$=$J_{3',4'}$=9.6 Hz, H-3'), 5.48 (d, 1H, $J_{1',2'}$=8.4 Hz, H-1'), 5.34 (t, 1H, $J_{2,3}$=$J_{3,4}$=9.6 Hz, H-3), 5.12-5.10 (m, 2H, H—I, H-3$_L$), 5.03-4.84 (m, 5H, H-3$_L$, o-C₆H₄(CH₂O)₂P), 4.63-4.37 (m, 9H, H-4', 4×CH₂Ph), 4.14-4.11 (m, 1H, H-2), 4.05-4.02 (m, 1H, H-5), 3.88-3.80 (m, 4H, H-6a, H-6'a, 2×H-3$_S$), 3.80-3.68 (m, 3H, H-5', H-6b, H-6'b), 3.29 (t, 1H, $J_{3,4}$=$J_{4,5}$=9.6 Hz, H-4), 3.17-3.13 (m, 1H, H-2'), 2.71-2.12 (m, 12H, 2×H-2$_L$, 2×H-2$_S$, 2×H-2c), 1.62-1.51 (broad, 12H, 2×H-4$_L$, 2×H-4$_S$, 2×H-3$_L$'), 1.23 [bs, 96H, 2×H-(5$_L$-11$_S$), 2×H-(5$_L$-13$_L$)], 2×0.87-0.85 (m, 18H, 2×H-12$_S$, 2×H-14$_L$, 2×H-12$_L$'). HR MS (m/z) calcd for $C_{124}H_{195}N_2O_{22}PSi[M+Na]^+$, 2118.3837; found, 2118.5320. To a cooled (−78° C.) solution of the above obtained lactol (14 mg, 6.7 μmol) and tetrabenzyl diphosphate (18 mg, 34 μmol) in anhydrous THF (2 mL) was added dropwise lithium bis(trimethylsilyl)amide in THF (1.0 M, 20 μL, 20 μmol). The reaction mixture was stirred for 1 h, and then allowed to warm up to −20° C. After stirring the reaction mixture for 1 h, it was quenched with saturated aqueous NaHCO$_3$ (10 mL), and extracted with ethyl acetate (15 mL). The organic phase was washed with brine (2×15 mL), dried (MgSO$_4$), filtered, and the filtrate was concentrated in vacuo. The residue was purified by Iatro beads column chromatography (hexane/ethyl acetate, 5/1→3/1→1/1, v/v) to give 77 as a colorless syrup (13 mg, 81%).

3-O—[(R)-3-Hydroxy-dodecanoyl]-2-deoxy-2-[(R)-3-dodecanoyloxy-tetradecanoylamino]-(R)-D-glucopyranosyl-(1→6)-2-[(R)-3-hydroxy-dodecanoylamino]-3-O—[(R)-3-dodecanoyloxy-dodecanoyl]-2-deoxy-α-D-glucopyranoside 1,4'-bisphosphate (51): A reaction mixture of 77 (10 mg, 4.2 μmol) and Pd black (15 mg) in anhydrous THF (5 mL) was shaken under an atmosphere of H$_2$ (60 psi) at room temperature for 30 h, after which it was neutralized with triethylamine (10 μL), and the catalyst was removed by filtration and the residue was washed with THF (2×1 mL). The combined filtrates were concentrated in vacuo to afford 51 as a colorless film (5.4 mg, 74%). $^1$H NMR (500 MHz, CDCl$_3$): ™5.13 (bs, 1H, H-1), 4.84 (bs, 4H, H-3, H-3', 2×H-3$_L$), 3.93 (m, 1H, H-2), 3.68 (m, 1H, H-3$_S$), 3.66 (m, 1H, H-3$_S$), 3.51 (m, H-2'), 3.17 (m, H, H-4), 2.33-1.95 (m, 12H, 2×H-2$_L$, 2×H-2$_S$, 2×H-2c), 1.24 (bs, 12H, 2×H-4$_L$, 2×H-4$_S$, 2×H-3$_L$), 0.91 [bs, 96H, 2×H-(5$_S$-11$_S$), 2×H-(5$_L$-13$_L$), 2×H-(4$_L$-11$_L$)], 0.54-0.52 (m, 18H, 2×H-12$_S$, 2×H-14$_L$, 2×H-12$_{L'}$). HR MS (m/z) (negative) for C$_{88}$H$_{166}$N$_2$O$_{25}$P$_2$, 1713.1255; found, 1712.2797 [M–H], 1713.2834 [M].

Cell maintenance. RAW 264.7 γNO(–) cells, derived from the RAW 264.7 mouse monocyte/macrophage cell line, were obtained from ATCC. The cells were maintained in RPMI 1640 medium (ATCC) with L-glutamine (2 mM), adjusted to contain sodium bicarbonate (1.5 g L$^{-1}$), glucose (4.5 g L$^{-1}$), HEPES (10 mM), and sodium pyruvate (1.0 mM) and supplemented with penicillin (100 u mL$^{-1}$)/streptomycin (100 μg mL$^{-1}$; Mediatech) and fetal bovine serum (FBS, 10%; Hyclone). Cells were maintained in a humid 5% CO$_2$ atmosphere at 37° C.

Cytokine induction and ELISAs. RAW 264.7 γNO(–) cells were plated on the day of the exposure assay as 2×10$^5$ cells/well in 96-well tissue culture plates (Nunc). Cells were incubated with different stimuli for 5.5 h in replicates of five. Culture supernatants were then collected, pooled, and stored frozen (–80° C.) until assayed for cytokine production.

Cytokine ELISAs were performed in 96-well MaxiSorp plates (Nunc). A DuoSet ELISA Development Kit (R&D Systems) was used for the quantification of mouse TNF-α according to the manufacturer's instructions. The absorbance was measured at 450 nm with wavelength correction set to 540 nm using a microplate reader (BMG Labtech). Concentrations of IFN-β in culture supernatants were determined as follows. ELISA MaxiSorp plates were coated with rabbit polyclonal antibody against mouse IFN-β (PBL Biomedical Laboratories). IFN-β in standards and samples was allowed to bind to the immobilized antibody. Rat anti-mouse IFN-β antibody (USBiological) was then added, producing an antibody-antigen-antibody "sandwich". Next, horseradish peroxidase (HRP) conjugated goat anti-rat IgG (H+L) antibody (Pierce) and a chromogenic substrate for HRP 3,3',5,5'-tetramethylbenzidine (TMB; Pierce) were added. After the reaction was stopped, the absorbance was measured at 450 nm with wavelength correction set to 540 nm. All cytokine values are presented as the means±SD of triplicate measurements, with each experiment being repeated three times.

Data analysis. Concentration-response data were analyzed using nonlinear least-squares curve fitting in Prism (GraphPad Software, Inc.). These data were fit with the following four parameter logistic equation: $Y = E_{max}/(1+(EC_{50}/X)^{Hill\ slope})$, where Y is the cytokine response, X is logarithm of the concentration of the stimulus, $E_{max}$ is the maximum response, and $EC_{50}$ is the concentration of the stimulus producing 50% stimulation. The Hillslope was set at 1 to be able to compare the $EC_{50}$ values of the different inducers.

General procedures. Column chromatography was performed on silica gel 60 (EM Science, 70-230 mesh). Reactions were monitored by thin-layer chromatography (TLC) on Kieselgel 60 F254 (EM Science), and compounds were detected by examination under UV light and by charring with 10% sulfuric acid in MeOH. Solvents were removed under reduced pressure at <40° C. CH$_2$Cl$_2$ was distilled from NaH and stored over molecular sieves (3 Å). Tetrahydrofuran (THF) was distilled from sodium directly prior to application. MeOH was dried by refluxing with magnesium methoxide and then was distilled and stored under argon. Pyridine was dried by heating under refluxing over CaH$_2$ and then distilled and stored over molecular sieves (3 Å). Molecular sieves (3 and 4 Å) used for reactions, were crushed and activated in vacuo at 390° C. during 8 h and then for 2-311 at 390° C. directly prior to application.

$^1$H NMR and $^{13}$C NMR spectra were recorded with Varian spectrometers (models Inova300, Inova500 and Inova600) equipped with Sun workstations. $^1$H NMR spectra were recorded in CDCl$_3$ and referenced to residual CHCl$_3$ at 7.24 ppm, and $^{13}$C NMR spectra were referenced to the central peak of CDCl$_3$ at 77.0 ppm. Assignments were made by standard gCOSY and gHSQC. High resolution mass spectra were obtained on a Bruker model Ultraflex MALDI-TOF mass spectrometer.

Example III

Synthetic Tetra-Acylated Lipid As Derived from *Porphyromonas gingivalis* are Antagonists of Human TLR4

Tetra-acylated lipid As derived from *Porphyromonas gingivalis* LPS have been synthesized using a key disaccharide intermediate functionalized with levulinate (Lev), allyloxycarbonate (Alloc) and anomeric dimethylthexylsilyl (TDS) as orthogonal protecting groups and 9-fluorenylmethoxycarbamate (Fmoc) and azido as amino protecting groups (Zhang et al., 2008 Org. Biomol. Chem. 6:3371-3381; Electronica Supplementary Information for Zhang et al., 2008 Org. Biomol. Chem. 6:3371-3381 available at the RSC Publishing site on the World Wide Web at rsc.org/suppdata/OB/b8/b809090d/b809090d.pdf). Furthermore, an efficient cross metathesis has been employed for the preparation of the unusual branched R-(3)-hydroxy-13-methyltetradecanic acid and (R)-3-hexadecanoyloxy-15-methyl-hexadecanoic acid of *P. gingivalis* lipid A. Biological studies have shown that the synthetic lipid As can not activate human and mouse TLR2 and TLR4 to produce cytokines. However, it has been found that the compounds are potent antagonist of cytokine secretion by human monocytic cells induced by enteric LPS.

We describe a highly convergent chemical synthesis of tetra-acylated lipid As 103 and 104 employing levulinate (Lev) and allyloxycarbonate (Alloc) as hydroxyl protecting groups, dimethylthexylsilyl (TDS) as an anomeric protecting group and 9-fluorenylmethoxycarbamate (Fmoc) and azido as amino protecting groups to manipulate each of the important functionalities in a selective manner. Furthermore, an efficient cross metathesis is employed for the preparation of the branched R-(3)-hydroxy-13-methyltetradecanic acid and (R)-3-hexadecanoyloxy-15-methyl-hexadecanoic acid.

Biological evaluations demonstrate that compound 103 is a potent antagonist of cytokines secretion induces by enteric LPS.

Result and Discussion

Figure 9:
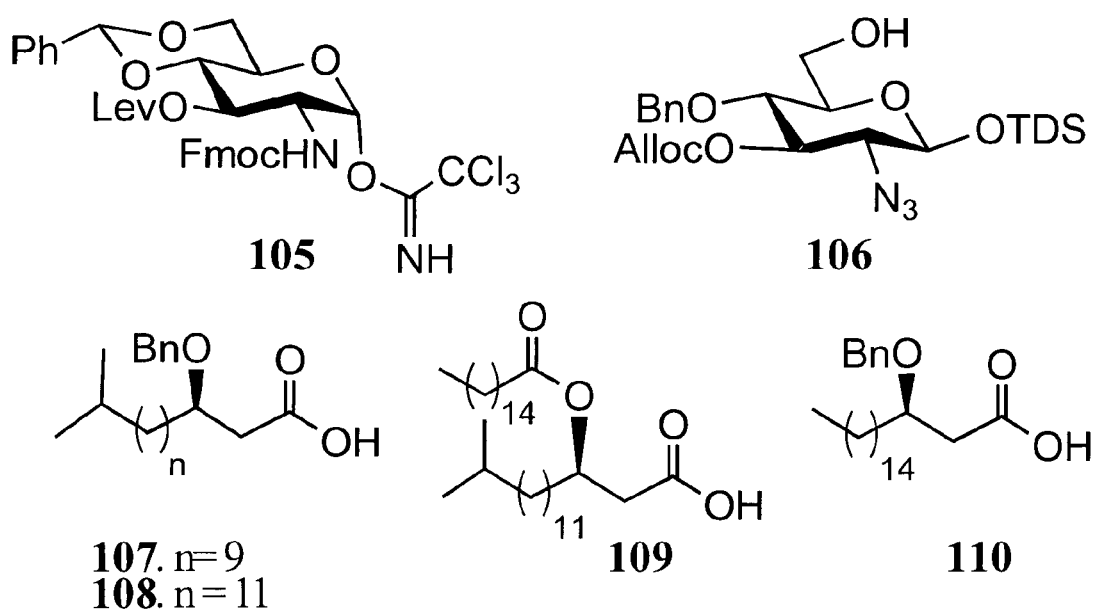
FIG. 9 shows building blocks for the synthesis of *P. gingivalis* lipid A.

Chemical synthesis. It was envisaged that lipid As derived from *P. gingivalis* can easily be obtained from monosaccharide building blocks 105 and 106 and fatty acids 107-110 (FIG. 9). Optically pure 3-hydroxy fatty acids such as 107-109, having a terminal isopropyl group, are important constituents and synthetic intermediates of a wide range of biologically interesting natural compounds, including flavolipin (Kawai et al., *Eur. J. Biochem.*, 1988, 171, 73-80), N-4909 (a stimulator of apolipoprotein E secretion) (Hiramoto et al., *J. Antibiot.*, 1996, 49, 949-952), liposidomycin-B (Ubukata et al., *J. Org. Chem.*, 1992, 57, 6392-6403) and several lipid A derivatives (Darveau et al., *Infect. Immun.*, 2004, 72, 5041-5051). While several chemical and enzymatic approaches have been developed for the preparation of such compounds (Katoh et al., *Tetrahedron: Asymmetry*, 1994, 5, 1935-1944; Shiozaki et al., *Tetrahedron Lett.*, 1996, 37, 3875-3876; Shioiri et al., *Tetrahedron*, 1998, 54, 15701-15710; Shiozaki et al., *Tetrahedron*, 1998, 54, 11861-11876; Yanai and Hiramoto, *J. Antibiot.*, 1999, 52, 150-159), these methods suffer from time-consuming procedures that give low overall yields and may involve harsh and difficult to handle reaction conditions. We envisaged that a cross metathesis (Chatterjee et al., *J. Am. Chem. Soc.*, 2003, 125, 11360-11370) of a fatty acid terminating in an alkene with 2-methyl-propene or 4-methyl-1-pentene followed by reduction of the double bond of the resulting compound would give easy entry into isopropyl terminating fatty acids. Employing this synthetic strategy, methyl R-(3)-hydroxy-13-methyltetradecanic acid (114) and methyl R-(3)-hydroxy-15-methyl hexadecanic acid (115), which are key intermediates for the chemical synthesis of lipid As derived from *P. gingivalis*, would be readily available by a cross metatheses of 111 with 2-methyl-propene or 4-methyl-1-pentene followed by asymmetric hydrogenation of the 3-keto function of the resulting product using the asymmetric catalyst RuCl$_2$-[(R)-BINAP] and hydrogenation of the alkene (Scheme 8). It was, however, observed that 2-methyl-propene is rather difficult to handle because it is a gas at room temperature and therefore 2-methyl-2-butene was employed, which should provide the same compound (Chatterjee et al., *Org. Lett.*, 2002, 4, 1939-1942). Thus, compound 111, which could be easily prepared by a known two-step synthetic procedure (Zhang et al., *Chem.-Eur.* 1, 2008, 14, 558-569—Example II), was reacted with 2-methyl-2-butene and 4-methyl-1-pentene in the presence of Grubbs $2^{nd}$ generation catalyst (Chatterjee et al., *J. Am. Chem. Soc.*, 2003, 125, 11360-11370) to afford 112 and 113, respectively. The ketone of the cross metathesis products 112 and 113 was enantioselectively reduced by catalytic hydrogenation in the presence of (R)—RuCl$_2$(BINAP) to give optically pure 114 and 115 having R-configuration (Keegan et al., *Tetrahedron: Asymmetry*, 1996, 7, 3559-3564). The optical purity of the compounds was established by NMR spectroscopic analysis (Nakahata et al., *Bull. Chem. Soc. Jpn.*, 1982, 55, 2186-2189) employing the shift reagent Eu(hfmc)$_3$ in CDCl$_3$ (e.e. >99%). It should be mentioned that the (S)-isomers can be easily prepared using (S)—RuCl$_2$(BINAP)$_2$ as the catalyst. Next, the methyl ester of compounds 114 and 115 were hydrolyzed under standard conditions and the resulting acids were converted into dicyclohexaneamine salts, which were recrystallized from CH$_3$CN. The carboxylates were protected as 2-(4-bromophenyl)-2-oxoethyl esters to give key intermediates 116 and 118 (Keegan et al., *Tetrahedron: Asymmetry*, 1996, 7, 3559-3564). The ester protecting group can easily be removed by treatment with zinc in acetic acid without affecting ether or ester groups, and therefore the 3-hydroxyl of 116 and 118 can be protected as a benzyl ether or modified with an acyl group, both of which are important intermediates for the synthesis of the target lipids. Thus, 116 and 118 were treated with benzaldehyde in the presence of TMSOTf and (TMS)$_2$O in THF followed by addition of the reducing agent Et$_3$SiH (Fukase et al., *Tetrahedron*, 1998, 54, 4033-4050) to give benzylated derivatives 117 and 119, respectively. The 2-(4-bromophenyl)-2-oxoethyl esters 117 and 119 were removed by treatment with zinc in acetic acid to give lipids 107 and 108, respectively. Fatty acid 109 was easily obtained by acylation of the hydroxyl of 118 with hexadecanoyl chloride in the presence of pyridine and DMAP to yield 120, which was deprotected using the standard produce.

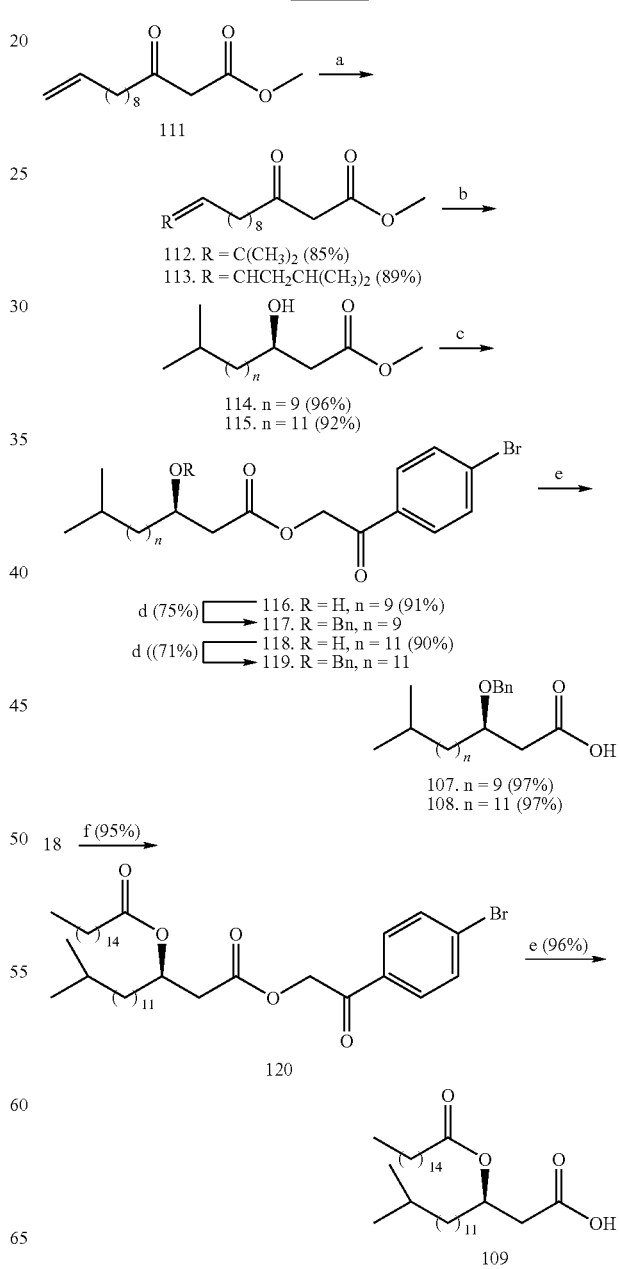

-continued

Reagents and conditions: a) 2-methyl-2-butene or 4-methyl-1-pentene, Grubbs 2nd generation catalyst; b) RuCl$_2$[(R)-BINAP], H$_2$ (65 psi), 2M HCl, CH$_3$OH, 40° C., then H$_2$ (1 atm), Pd/C, CH$_3$OH; c) LiOH•H$_2$O, THF/H$_2$O, then dicyclohexaneamine, CH$_3$CN, then 2,4′-dibromoacetophenone, Et$_3$N, EtOAc; d) benzaldehyde, (TMS)$_2$O, TMSOTf, THF, Et$_3$SiH; e) Zn/HOAc, 60° C.; f) hexadecanoyl chloride, pyridine, DMAP, DCM.

Target compounds 103 and 104 differ in the pattern of O-acylation and compound 103 has an R-(3)-hydroxy-hexadecanoic acid at C-3 of the proximal saccharide moiety whereas compound 104 has a (R)-3-hydroxy-15-methyl-hexadecanoic acid at C-3 of the distal saccharide. To synthesize these structurally similar compounds, we have developed a convergent approach that employs the advanced disaccharide intermediate 124 (Scheme 9), which is protected with Lev, Fmoc, Alloc, azido and anomeric TDS as a set of orthogonal protecting groups and thus disaccharide 124 can selectively be modified with any lipid at C-2, C-3, C-2′ and C-3′. Therefore the strategy provides easy access to a wide range of lipid As for SAR studies. Furthermore, it has been found that 4′-phosphate of lipid As tends to migrate to the 3′-hydroxyl (Zhang et al., *J. Am. Chem. Soc.*, 2007, 129, 5200-5216—Example I), and therefore the phosphate was introduced after installing the fatty acid at the 3′-hydroxyl. The distal 4,6-diol of 124 was protected as a benzylidene acetal, which at a late stage of the synthesis can be regioselectively opened to give a C-4′ hydroxyl which can then be phosphorylated Another attractive feature of the approach is that glycosyl donor 105 and acceptor 106 can be synthesized from the common intermediate 21, which can be easily prepared from glucosamine (Scheme 9) (Zhang et al., *Chem.-Eur. J.*, 2008, 14, 558-569—Example II).

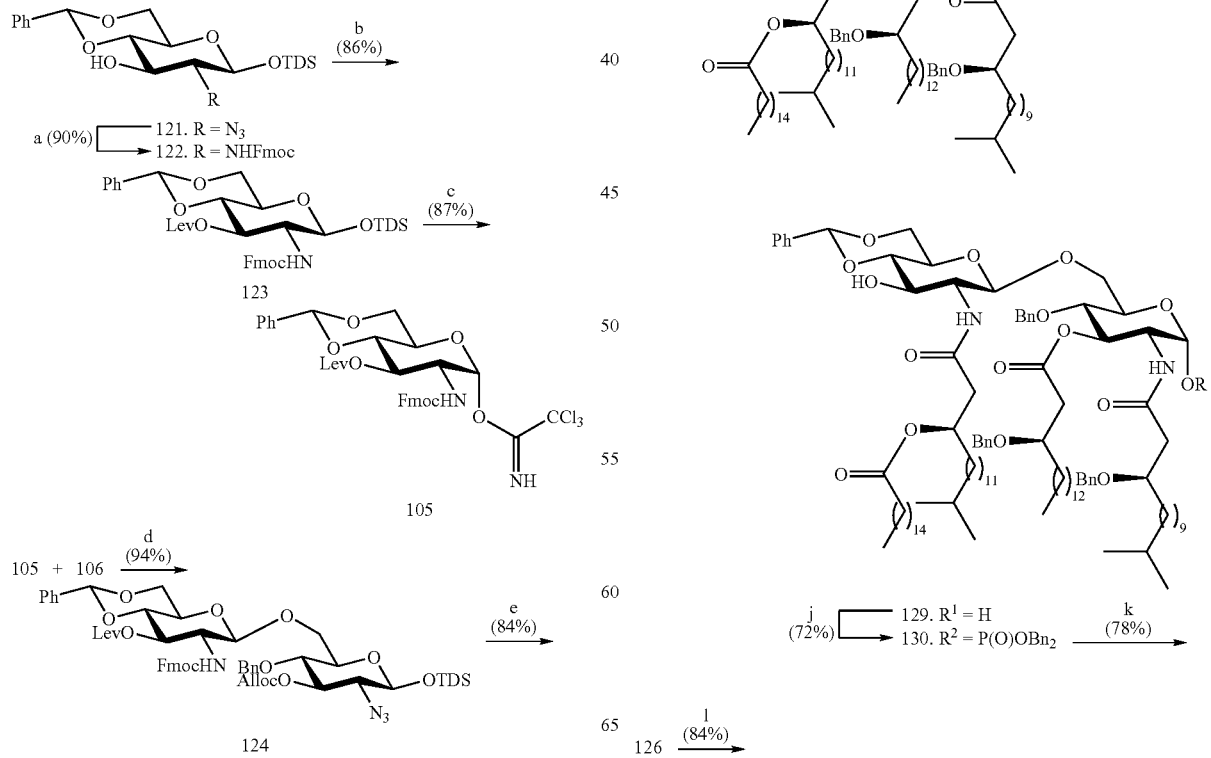

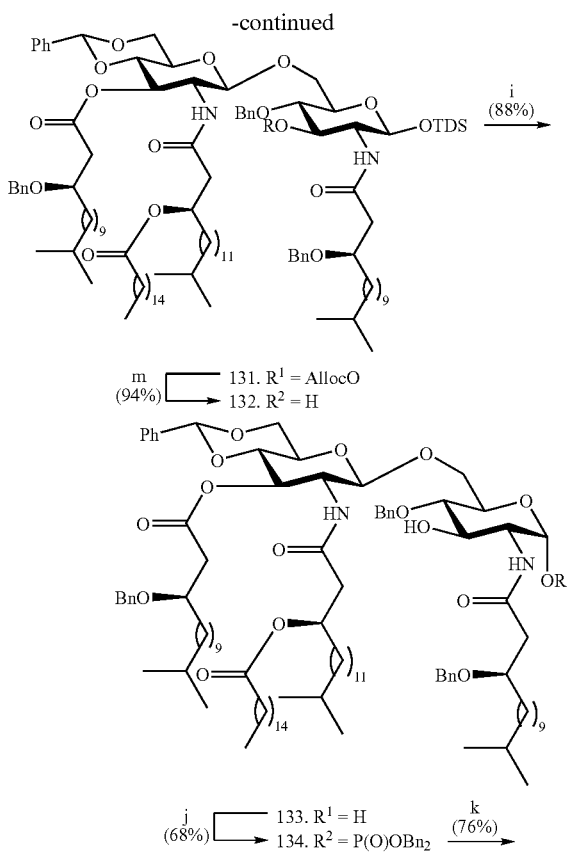

131. $R^1$ = AllocO
m (94%)
132. $R^2$ = H

133. $R^1$ = H
j (68%)
134. $R^2$ = P(O)OBn$_2$
k (76%)

Reagents and conditions: a) Zn/HOAc, DCM then FmocCl, DIPEA, DCM;
b) levulinic acid, DCC, DMAP, DCM; c) Bu$_4$NF/HOAc, THF, then CNCCl$_3$, NaH, THF; d) TfOH, DCM, -50° C.; e) DBU, DCM, then (R)-3-hexadecanoyloxy-15-methyl-hexadecanoic acid 109, DCC, DCM; f) Zn/HOAc, DCM, then (R)-3-benzyloxy-15-methyl-hexadecanoic acid 108, DCC, DCM; g) Pd(PPh$_3$)$_4$, HCO$_2$H, n-BuNH$_2$, THF; then (R)-3-benzyloxy-hexadecanoic acid 110, DCC, DMAP, DCM; h) H$_2$NNH$_2$, HOAc, DCM/CH$_3$OH; i) Bu$_4$NF/HOAc, THF; j) tetrazenzyl diphosphate, LiN(TMS)$_2$, THF, -78° C.; k) H$_2$ (50 psi), Pd black, THF; l) H$_2$NNH$_2$, HOAc, DCM/CH$_3$OH, then (R)-3-benzyloxy-13-methyl-tetradecanoic acid 107, DCC, DMAP, DCM; m) Pd(PPh$_3$)$_4$, HCO$_2$H, n-BuNH$_2$, THF.

Thus, glycosyl acceptor 106 was synthesized from 121 according to the reported procedure (Zhang et al., Chem.-Eur. J., 2008, 14, 558-569—Example II). For the synthesis of glycosyl donor 105, the azido moiety of 121 could be easily converted to Fmoc carbamate by reduction with zinc in acetic acid followed by reaction of the resulting amine with FmocCl in the presence of DIPEA to give 122 in a yield of 86%. The hydroxyl of compound 122 was protected as a Lev ester using levulinic acid, DCC and DMAP to afford 123. Removal of the anomeric TDS of 123 was easily accomplished by treatment with Bu$_4$NF in the presence of acetic acid to give a lactol, which was immediately reacted with trichloroacetonitrile in the presence of NaH to afford trichloroacetimidate 105 (Schmidt and Stumpp, Liebigs Ann. Chem., 1983, 1249-1256). A trifluoromethanesulfonic acid (TfOH)-mediated glycosylation of 105 with 106 proceeded in a stereoselective manner to give disaccharide 124 in an excellent yield of 94% (Scheme 9) (Zhang et al., Chem.-Eur. J., 2008, 14, 558-569— Example II).

Having the advanced disaccharide 124 and lipids 107-110 at hand, attention focused on the selective acylation of relevant hydroxyls and amines. Thus, removal of the Fmoc protecting group of 124 using 1,8-diazobicyclo[5.4.0]undec-7-ene (DBU) in DCM followed by acylation of the resulting amino group with lipid 109 using dicyclohexylcarbodiimide (DCC) as the activation reagent gave compound 125 (Scheme 9). Next, the azido moiety of 125 was reduced by treatment with zinc and acetic acid in DCM, and the amine of the resulting compound acylated with 107 in the presence of DCC to afford 126 as the common intermediate for the synthesis of target molecules 103 and 104. For the synthesis of 103, the Alloc protecting group of 126 was removed by reaction with Pd(PPh$_3$)$_4$ in the presence of HCOOH and n-BuNH$_2$ (Tsukamoto et al., Biosc. Biotechnol. Biochem., 1997, 61, 1650-1657), and the resulting hydroxyl acylated with (R)-3-benzyloxy-hexadecanoic acid 110 using DCC and DMAP as the activation reagent to give 127. Next, removal of the Lev group of 127 was easily accomplished by treatment with hydrazine acetate to give 128, which treated with Bu$_4$NF in the presence of acetic acid to give the desired product 129 in a yield of 72% and a small amount of a side product arising from elimination of the 3-acyloxyl group. The anomeric center of resulting 129 was phosphorylated using tetrabenzyl diphosphate in the presence of lithium bis(trimethypsilylmide in THF at -78° C. to give 130 as only the α-anomer (Oikawa et al., Bull. Chem. Soc. Jpn., 1999, 72, 1857-1867). Global deprotection of 130 by catalytic hydrogenolysis over Pd-black gave requisite lipid A 103.

The synthesis of 104 could easily be accomplished in a similar manner to the synthesis of 103, however, in this case the Lev protecting group of the common intermediate 126 was removed to give an alcohol, which was acylated with lipid 7 using standard conditions to afford 131. Next, subsequent Alloc (→132) and anomeric TDS protecting group removal gave 133. As expected no elimination was observed in this reaction, due to the poor leaving group ability of the C-3 hydroxyl. Standard anomeric phosphorylation of 133 and deprotection of the resulting compound 134 gave target lipid A 104.

Biological evaluation of lipid As and LPS. Based on the results of recent studies (Akira et al., Nat. Immunol., 2001, 2, 675-680; Pasare and Medzhitov, Semin. Immunol., 2004, 16, 23-26), it is clear that enteric LPS induces cellular activation through TLR4 and it appears that there are two distinct initiation points in the signaling process, one being a specific intracellular adaptor protein called MyD88 and the other an adaptor protein called TRIF, which operates independently of MyD88. It is well established that TNF-α secretion is a prototypical measure for activation of the MyD88-dependent pathway, whereas secretion of IFN-β and IP-10 are commonly used as an indicator of TRIF-dependent cellular activation.

The carbohydrate backbone, degree of phosphorylation and fatty acid acylation patterns differ considerably among lipid As of various bacterial species and there is evidence to support that these structural variations account for significant differences in inflammatory responses (Dixon and Darveau, J. Dent. Res., 2005, 84, 584-595). Several studies have also indicated that LPS from various bacterial species such as P. gingivalis, Leptospira interrogans, Legionella pneumophila, Bacteroides fragilis NCTC-9343 and Pseudomonas aeruginosa PAC-611 can induce cellular activation in a TLR2-dependent manner (Werts et al., Nat. Immunol., 2001, 2, 346-352; Girard et al., J. Cell Sci., 2003, 116, 293-302; Erridge et al., J. Med. Microbiol., 2004, 53, 735-740; QueGewirth et al., J. Biol. Chem., 2004, 279, 25420-25429). However, it may be possible that these cellular responses are derived from contamination by lipoproteins.

Figure 10:
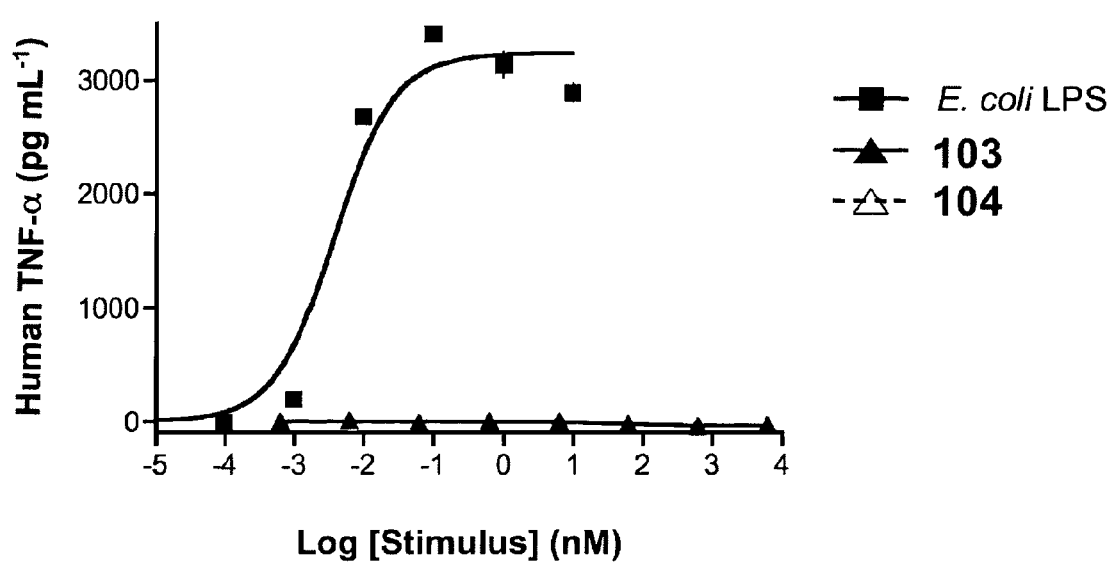
FIG. 10 shows concentration-response curves of *E. coli* LPS and synthetic compounds 103 and 104 in human monocytic cells. MM6 cells were incubated for 5.5 h at 37° C. with increasing concentrations of *E. coli* LPS and synthetic compounds 103 and 104 as indicated. TNF-α protein in cell supernatants was measured using ELISA. (103 and 104 show background values and therefore overlap in the figure). Treatment with *E. coli* LPS, 103 and 104 did not affect cell viability, as judged by cellular exclusion of trypan blue.

We have chemically synthesized the tetra-acylated lipid As 103 and 104 (FIG. 8) to study whether LPS derived from P. gingivalis can induce cellular activation in a TLR2- or TLR4-dependent manner. Furthermore, there are indications that LPS of *P. gingivalis* can antagonize cytokine production induced by enteric LPS and therefore these properties have also been studied. Thus, a human monocytic cell line (Mono Mac 6 cells) was exposed over a wide range of concentrations to compounds 103 and 104 and *E. coli* 055:B5 LPS. After 5.5 hours, the supernatants were harvested and examined for human TNF-α using a commercial capture ELISA. Potencies ($EC_{50}$, concentration producing 50% activity) and efficacies (maximal level of production) were determined by fitting the dose-response curves to a logistic equation using PRISM software. As can be seen in FIG. 10, LPS is a potent inducer of TNF-α whereas the synthetic compounds 103 and 104 did not exhibit any activity. A similar experiment using mouse macrophages (RAW 264.7 γNO(–) cells) did not lead to secretion of cytokines (e.a. TNF-a, IL-6, IP-10, IFN-β and IL-1β) when exposed to compounds 103 and 104 (data not shown).

Synthesis and secretion of the TNF-α protein depends on a complex process involving activation of transcription factors, up-regulation of the genes responsible for production of the cytokine, transcription of the message, and then translation of the mRNA and processing of a protein (Jongeneel, *Immunobiology*, 1995, 193, 210-216; Mijatovic et al., *Eur. J. Biochem.*, 2000, 267, 6004-6011; Crawford et al., *J. Biol. Chem.*, 1997, 272, 21120-21127). This process is tightly controlled and therefore it may be possible that a compound can activate NF-kB or induce expression of TNF-α mRNA without causing production or secretion of the TNF-α protein (Wolfert et al., *J. Biol. Chem.*, 2002, 277, 39179-39186).

Figure 11A:
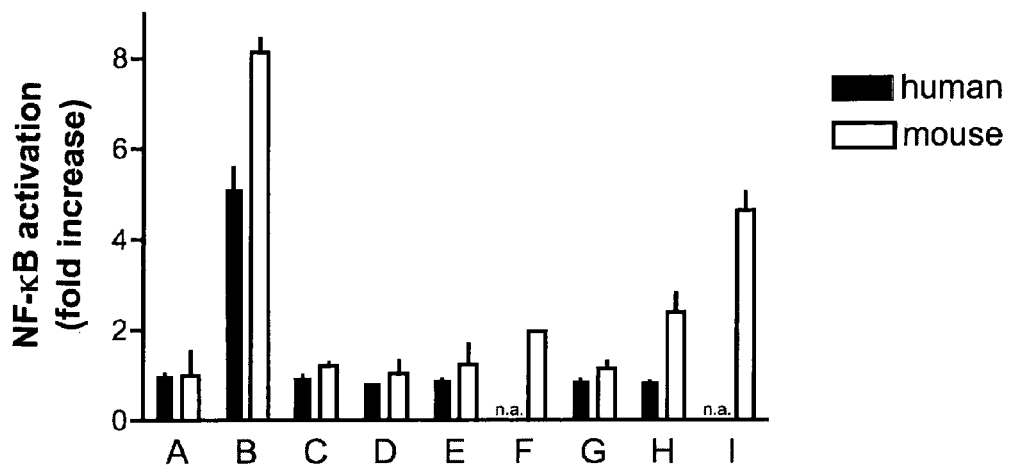
FIG. 11 shows the response of HEK 293T cells expressing human or murine TLRs to 103 and 104. Induction of NF-κB activation was determined in triplicate cultures of HEK 293T cells stably transfected with human or mouse (a) TLR4/MD2/CD14 and (b) TLR2 and transiently transfected with pELAM-Luc and pRL-TK plasmids. Forty-four h post-transfection, cells were treated with (B) *E. coli* LPS (10 ng mL$^{-1}$), (C) Pam$_3$CysSK$_4$ (1 μg mL$^{-1}$), (D, E and F) 103 (0.1, 1 and 10 μg mL$^{-1}$, respectively), (G, H and I) 104 (0.1, 1 and 10 μg mL$^{-1}$, respectively) or (A) were left untreated (control). Forty-eight h post-transfection, NF-κB activation was determined by firefly luciferase activity relative to *Renilla* luciferase activity. n.a. indicates not analyzed.
Figure 11B:
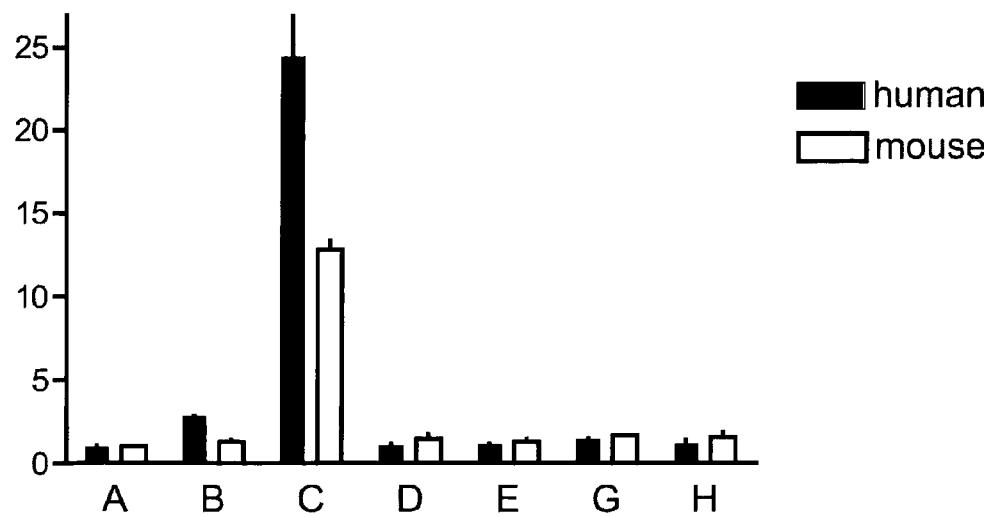

To examine the ability of the synthetic compounds to induce activation of NF-kB, HEK 293T cells were employed that were stably transfected with various immune receptors and transiently transfected with a plasmid containing the reporter gene pELAM-Luc (NF-κB-dependent firefly luciferase reporter vector) and a plasmid containing the control gene pRL-TK (*Renilla* luciferase control reporter vector) (FIG. 11). No activation of NF-kB was observed when cells transfected with human TLR4/MD2/CD14 and human or mouse TLR2 were exposed to compounds 103 and 104. As expected, LPS, which is a prototypical activator for TLR4, could activate cells transfected with TLR4/MD2/CD14, and $Pam_3CysSK_4$, which is a well-established agonist of TLR2, was able to activate the TLR2-containing cells. However, at high concentrations, compound 104 could induce NF-kB activation in cells transfected with mouse TLR4/MD2/CD14. These results clearly demonstrate that compounds 103 and 104 do not induce cellular activation in a TLR2-dependent manner. Although compound 104 is a weak activator of mouse TLR4, it could not induce the secretion of cytokines.

Figure 12:
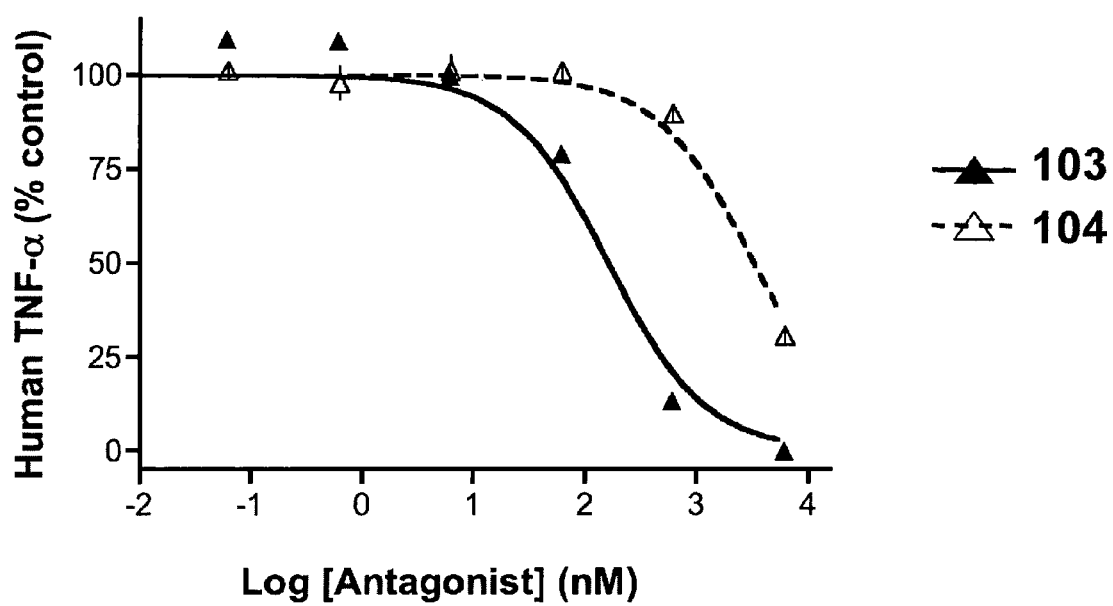
FIG. 12 shows antagonism of *E. coli* LPS by synthetic compounds 103 and 104 in human monocytic cells. TNF-α concentrations were measured after preincubation of MM6 cells with increasing concentrations of 103 or 104 as indicated for 1 h at 37° C., followed by 5.5 h of incubation with *E. coli* LPS (1 ng mL$^{-1}$). Results are expressed as percentage of cytokine concentration of control cells, which are incubated only with *E. coli* LPS.

Compounds that lack proinflammatory properties may still interact with relevant receptors (TLR4/MD2/CD14), and thereby inhibit TNF-α production induced by *E. coli* LPS. Thus, the human monocytic cells and mouse macrophages (MM6 and RAW cells) were exposed to a combination of *E. coli* LPS (10 ng/mL) and a wide range of concentrations of lipid As 103 and 104 and, after an incubation time of 5.5 h, the supernatant was examined for human or mouse TNF-a. Only marginal inhibition was observed in the mouse cell line. However, both compounds were able to antagonize TNF production by the human cell line (FIG. 12) and it was found that compound 103 was a significantly more potent antagonist than 104 ($IC_{50}$ concentration producing 50% inhibition for 103 and 104 were 160 nM and 3.2 μM, respectively).

It has been reported that *P. gingivalis* LPS can initiate innate immune responses in a TLR2— and/or TLR4-dependent manner (Darveau et al., *Infect. Immun.*, 2004, 72, 5041-5051). The heterogeneity of LPS and lipid A preparations has limited, however, the identification of specific compounds that are responsible for this unusual mode of activation. It has already been reported that penta-acylated and tri-acylated lipid As 101 and 102 can only activate human and mouse cells in a TLR4-dependent manner (Sawada et al., *Clin. Exp. Immunol.*, 2007, 148, 529-536). Furthermore, we have found no evidence that the tetra-acetylated compounds 103 and 104 can active human or mouse TLR2. It may be possible that a yet to be identified *P. gingivalis* lipid A may exhibit TLR2-dependent activity, however, it is more likely that lipoprotein contaminants are responsible for the observed activity.

An exciting observation reported here is that the tetra-acylated lipid A 103 is a potent antagonist of TNF-α production induced by enteric LPS. The acylation pattern of 103 is important for optimal activity because compound 104 exhibits a significantly reduced activity. Antagonists of cell surface receptors that recognize enteric LPS have the potential for being used as therapeutic interventions for patients with Gram-negative septicemia. Success in this area has been limited and most efforts have been directed towards the synthesis of analogs of lipid A of *R. sphaeroides* (Christ et al., *J. Am. Chem. Soc.*, 1994, 116, 3637-3638; Christ et al., *Science*, 1995, 268, 80-83). These compounds are bis-phosphorylated and contain unsaturated and keto containing fatty acids, which complicates the chemical synthesis. Furthermore, the C-4' phosphate is prone to migration, which results in loss of activity. An attractive feature of compounds 103 and 104 is that they are mono-phosphorylated and can be prepared by a highly convergent synthetic approach. Furthermore, it is to be expected that analog synthesis will provide more potent compounds that have simpler structures.

Experimental
chemical synthesis

General synthetic methods. Column chromatography was performed on silica gel 60 (EM Science, 70-230 mesh). Reactions were monitored by thin-layer chromatography (TLC) on Kieselgel 60 F254 (EM Science) and compounds were detected by examination under UV light and by charring with 10% sulfuric acid in MeOH. Solvents were removed under reduced pressure at <40° C. $CH_2Cl_2$ was distilled from NaH and stored over molecular sieves (3 Å). Tetrahydrofuran (THF) was distilled from sodium directly prior to the application. MeOH was dried by refluxing with magnesium methoxide and then was distilled and stored under argon. Pyridine was dried by refluxing with $CaH_2$ and then was distilled and stored over molecular sieves (3 Å). Molecular sieves (3 and 4 Å) used for reactions, were crushed and activated in vacuo at 390° C. during 8 h and then for 2-3 h at 390° C. directly prior to application. Optical rotations were measured with a Jasco model P-1020 polarimeter. $^1H$ NMR and $^{13}C$ NMR spectra were recorded with Varian spectrometers (models Inova500 and Inova600) equipped with Sun workstations. $^1H$ NMR spectra were recorded in $CDCl_3$ and referenced to residual $CHCl_3$ at 7.24 ppm and $^{13}C$ NMR spectra were referenced to the central peak of $CDCl_3$ at 77.0 ppm. Assignments were made by standard gCOSY and gHSQC. High resolution mass spectra were obtained on a Bruker model Ultraflex MALDI-TOF mass spectrometer. Signals marked with a subscript L symbol belong to the biantennary lipids, whereas signals marked with a subscript L'. symbol belong to their side chain. Signals marked with a subscript S symbol belong to the monoantennary lipids.

Dimethylthexylsilyl 6-O—[4,6-O-benzylidene-2-deoxy-2-(9-fluorenylmethoxycarbonyl amino)-3-O-levulinoyl-β-D-glucopyranosyl]-3-O-allyloxycarbonyl-2-azido-4-O-benzyl-2-deoxy-β-D-glucopyranoside (124). A suspension of trichloroacetimidate 105 (600 mg, 0.82 mmol), acceptor 106

(407 mg, 78 mmol) and molecular sieves (4 Å, 500 mg) in DCM (10 mL) was stirred at room temperature for 1 h. The mixture was cooled (−50° C.) and then trifluoromethanesulfonic acid (TfOH) (10 µL, 0.078 mmol) was added. After stirring the reaction mixture for 15 min, it was allowed to warm up to −20° C. in 1 h, after which it was quenched with solid $NaHCO_3$. The solids were removed by filtration and the filtrate was washed with saturated aqueous $NaHCO_3$ (2×50 mL) and brine (2×40 mL). The organic phase was dried ($MgSO_4$) and filtered. Next, the filtrate was concentrated in vacuo. The residue was purified by silica gel column chromatography (eluent: hexane/ethyl acetate, 3/1, v/v) to give 124 as an amporphous solid (840 mg, 94%). $R_f$=0.40 (hexane/ethyl acetate, 2/1, v/v); $[\alpha]^{26}_D$=−15.5° (c=1.0, $CHCl_3$); $^1H$ NMR (300 MHz, $CD_3COCD_3$): δ 7.84-7.22 (m, 18H, aromatic), 6.79 (d, 1H, =9.3 Hz, NH'), 5.87 (m, 1H, $OCH_2CH=CH_2$), 5.65 (s, 1H, >CHPh), 5.37 (t, 1H, $J_{2',3'}=J_{3',4'}$=9.9 Hz, H-3'), 5.30 (d, 1H, J=18.3 Hz, $OCH_2CH=CHH$), 5.17 (d, 1H, J=10.5 Hz, $OCH_2CH=CHH$), 4.94 (d, 1H, $J_{1,2}$=8.7 Hz, H-1), 4.86-4.80 (m, 2H, H-1, H-3), 4.71 (d, 1H, J=10.8 Hz, CHHPh), 4.59-4.55 (m, 3H, $OCH_2CH=CH_2$, CHHPh), 4.32-4.29 (m, 2H, H-6'a, $CO_2CHH$ of Fmoc), 4.17-4.08 (m, 3H, H-6a, $CO_2CHHCH$ of Fmoc), 3.92-3.67 (m, 6H, H-2', H-4, H-4', H-5, H-6b, H-6'b), 3.56 (m, 1H, H-5'), 3.41 (dd, 1H, $J_{1,2}$=7.5 Hz, $J_{2,3}$=10.2 Hz, H-2), 2.61 (t, 2H, J=6.6 Hz, $CH_2$ of Lev), 2.47 (t, 2H, J=6.6 Hz, $CH_2$ of Lev), 1.95 (s, 3H, $CH_3$ of Lev), 1.70 (m, 1H, CH of TDS), 0.91 [bs, 12H, $SiC(CH_3)_2CH(CH_3)_2$], 0.26 (s, 3H, $SiCH_3$), 0.25 (s, 3H, $SiCH_3$). $^{13}C$ NMR (75 MHz, $CD_3OCD_3$): δ 172.47 (C=O), 156.64 (C=O), 154.94 (C=O), 144.94-120.54 (aromatic), 132.67 ($OCH_2CH=CH_2$), 118.63 ($OCH_2CH=CH_2$), 102.42 (C-1'), 101.58 (>CHPh), 97.12 (C-1), 79.49 (C-4'), 79.24 (C-3), 76.68 (C-4), 75.09 ($CH_2Ph$), 74.50 (C-5), 72.64 (C-3'), 68.96-68.92 (m, C-6', $OCH_2CH=CH_2$), 68.57 (C-6), 67.28 (C-2), 67.08 ($CH_2$ of Fmoc), 66.92 (C-5'), 57.26 (C-2'), 47.64 (CH of Fmoc), 38.04 ($CH_2$ of Lev), 34.49 (CH of TDS), 29.33 (C-13 of Lev), 28.44 ($CH_2$ of Lev), −1.77 ($SiCH_3$), −3.22 ($SiCH_3$). HR MS (m/z) calculated for $C_{58}H_{70}N_4O_{15}Si$ [M+Na]$^+$, 1113.4499; found, 1113.6394.

Dimethylthexylsilyl 6-O-14,6-O-benzylidene-2-deoxy-2-[(R)-3-hexadecanoyloxy-15-methyl-hexadecanoylamino]-3-O-levulinoyl-β-D-glucopyranosyl]-3-O-allyloxycarbonyl-2-azido-4-O-benzyl-2-deoxy-β-D-glucopyranoside (125). 1,8-Diazabicyclo[5.4.0]undec-7-ene (DBU) (60 µl) was added dropwise to a solution of 124 (620 mg, 0.569 mmol) in DCM (8 mL). The reaction mixture was stirred at room temperature for 4 h, after which it was concentrated in vacuo. The residue was purified by silica gel column chromatography (DCM/methanol, 100/1→100/3, v/v) to afford an amine as a colorless syrup (454 mg, 92%). $R_f$=0.30 (hexane/ethyl acetate, 1/1, v/v); HR MS (m/z) calcd for $C_{43}H_{60}N_4O_{13}Si$ [M+Na]$^+$, 891.3818; found, 891.2115. DCC (188 mg, 0.913 mmol) was added to a stirred solution of (R)-3-hexadecanoyl-15-methylhexadecanoic acid 109 (345 mg, 0.659 mmol) in DCM (5 mL). After stirring the reaction mixture for 10 min, the resulting amine (440 mg, 0.507 mmol) in DCM (2 mL) was added and the stirring was continued for another 12 h. The insoluble materials were removed by filtration and the residue was washed with DCM (2×2 mL). The combined filtrates were concentrated in vacuo and the residue was purified by silica gel column chromatography (eluent: hexane/ethyl acetate, 2/1, v/v) to give 125 as an amorphous solid (634 mg, 91%). $R_f$=0.65 (hexane/ethyl acetate, 2/1, v/v); $[\alpha]^{25}_D$=−15.2° (c=1.0, $CHCl_3$); $^1H$ NMR (300 MHz, $CDCl_3$): δ 7.23-7.03 (m, 10H, aromatic), 5.81 (d, 1H, $J_{NH',2}$=8.4 Hz, NH'), 5.69 (m, 1H, $OCH_2CH=CH_2$), 5.27 (s, 1H, >CHPh), 5.19 (t, 1H, $J_{2',3'}=J_{3',4'}$=9.6 Hz, H-3'), 5.14 (d, 1H, J=17.1 Hz, $OCH_2CH=CHH$), 5.04 (d, 1H, J=10.2 Hz, $OCH_2CH=CHH$), 4.83 (m, 1H, H-3$_L$), 4.72 (d, 1H, $J_{1',2}$=8.4 Hz, H-1'), 4.54 (t, 1H, $J_{2,3}=J_{3,4}$=9.9 Hz, H-3), 4.42-4.37 (m, 5H, H-1, $CH_2Ph$, $OCH_2CH=CH_2$), 4.08 (dd, 1H, =4.8 Hz, $J_{6'a,6'b}$=10.2 Hz, H-6'a), 3.74 (d, 1H, $J_{6a,6b}$=10.5 Hz, H-6a), 3.63-3.36 (m, 5H, H-2', H-4, H-4', H-6b, H-6'b), 3.33-3.26 (m, 2H, H-5, H-5'), 3.11 (dd, 1H, =7.5 Hz, $J_{2,3}$=9.9 Hz, H-2), 2.59-2.30 (m, 4H, $CH_2$ of Lev), 2.17 (dd, 1H, $J_{2La,2Lb}$=14.4 Hz, $J_{2La,3L}$=6.0 Hz, H-2$_{La}$), 2.29-2.22 (m, 3H, H-2$_L'$, H-2$_{Lb}$), 1.91 (s, 3H, $CH_3$ of Lev), 1.51-1.28 (m, 5H, H-4$_L$, H-3$_{L'}$, CH of TDS), 1.04 (broad, 44H, 22×$CH_2$ of lipid), 0.70-0.64 (m, 21H, 4×$CH_3$ of thexyl, 3×$CH_3$ of lipid), 0.00 [s, 6H, $Si(CH_3)_2$]. $^{13}C$ NMR (75 MHz, $CDCl_3$): δ 206.45 (C=O), 173.75 (C=O), 172.17 (C=O), 170.05 (C=O), 154.32 (CO),=137.51-126.19 (aromatic), 131.26 ($OCH_2CH=CH_2$), 119.21 ($OCH_2CH=CH_2$), 101.42 (>CHPh), 100.91 (C-1'), 96.92 (C-1), 78.84 (C-4'), 78.58 (C-3), 76.02 (C-4), 74.63 ($CH_2Ph$), 74.35 (C-5), 71.42 (C-3'), 70.75 (C-3$_L$), 68.90 ($OCH_2CH=CH_2$), 68.63 (C-6'), 68.06 (C-6), 66.46 (C-2), 66.19 (C-5'), 55.80 (C-2'), −1.86 ($SiCH_3$), −3.56 ($SiCH_3$). HR MS (m/z) calculated for $C_{76}H_{122}N_4O_{16}Si$ [M+Na]$^+$, 1397.8517; found, 1397.7814.

Dimethylthexylsilyl 6-O-{4,6-O-benzylidene-2-deoxy-2-[(R)-3-hexadecanoyloxy-15-methyl-hexadecanoylamino]-3-O-levulinoyl-β-D-glucopyranosyl}-3-O-allyloxycarbonyl-4-O-benzyl-2-[(R)-3-benzyloxy-15-methyl-hexadecanoylamino]-2-deoxy-β-D-glucopyranoside (126). A suspension of 125 (256 mg, 0.186 mmol), zinc (<10 micron, 121 mg, 1.86 mmol) and acetic acid (100 µl.) in DCM (5 mL) was stirred at room temperature for 2 h, after which it was diluted with ethyl acetate (30 mL). The solids were removed by filtration and washed with ethyl acetate (2×4 mL) and the combined filtrates were washed with saturated aqueous $NaHCO_3$ (2×20 mL) and brine (2×20 mL). The organic phase was dried ($MgSO_4$) and filtered. Next, the filtrate was concentrated in vacuo. The residue was purified by silica gel column chromatography (eluent: DCM/methanol, 50/1, v/v) to afford an amine as a pale yellow syrup (188 mg, 75%). $R_f$=0.30 (hexane/ethyl acetate, 1/1, v/v); HR MS (m/z) calcd for $C_{76}H_{124}N_2O_{16}Si$ [M+Na]$^+$, 1371.8612; found, 1371.9028. DCC (51 mg, 0.246 mmol) was added to a stirred solution of (R)-3-benzyloxy-15-methyl-hexadecanoic acid 108 (69 mg, 0.185 mmol) in DCM (3 mL). After stirring the reaction mixture for 10 min, the amine (166 mg, 0.123 mmol) in DCM (1 mL) was added and the stirring was continued for another 12 h. The insoluble materials were removed by filtration and the residue was washed with DCM (2×1 mL). The combined filtrates were concentrated in vacuo and the residue was purified by silica gel column chromatography (eluent: hexane/ethyl acetate, 6/1, v/v) to give 126 as an amorphous solid (184 mg, 88%). $R_f$=0.55 (hexane/ethyl acetate, 4/1, v/v); $[\alpha]^{25}_D$-9.5° (c=1.0, $CHCl_3$); $^1H$ NMR (300 MHz, $CDCl_3$): δ 7.36-7.18 (m, 15H, aromatic), 6.28 (d, 1H, $J_{NH,2}$=8.7 Hz, NH), 5.90 (d, 1H, $J_{NH',2}$=8.4 Hz, NH'), 5.77 (m, 1H, $OCH_2CH=CH_2$), 5.40 (s, 1H, >CHPh), 5.34 (t, 1H, $J_{2',3'}=J_{3',4'}$=9.6 Hz, H-3'), 5.23 (d, 1H, J=17.1 Hz, $OCH_2CH=CHH$), 5.13 (d, 1H, J=9.9 Hz, $OCH_2CH=CHH$), 4.99-4.86 (m, 3H, H-1', H-3, H-3$_L$), 4.56-4.37 (m, 7H, H-1, 4×CHHPh, $OCH_2CH=CH_2$), 4.25 (dd, 1H, $J_{5',6'a}$=5.1 Hz, $J_{6'a,6'b}$=10.8 Hz, H-6'a), 3.88 (d, 1H, $J_{6a,6b}$=11.4 Hz, H-6a), 3.75-3.51 (m, 7H, H-2, H-2', H-4, H-4', H-6b, H-6'b, H-3$_S$), 3.46-3.38 (m, 2H, H-5, H-5'), 2.73-2.41 (m, 4H, $CH_2$ of Lev), 2.40-2.18 (m, 6H, H-2$_S$, H-2$_L$, H-2$_L$), 2.05 (s, 3H, $CH_3$ of Lev), 1.53-1.39 (m, 7H, H-4$_S$, H-4$_L$, CH of TDS), 1.17-1.07 (m, 64H, 32×$CH_2$ of lipid), 0.79-0.73 (m, 27H, 4×$CH_3$ of TDS, 5×$CH_3$ of lipid), 0.06 (s, 3H, $SiCH_3$), 0.00 (s, 3H, $SiCH_3$). $^{13}C$ NMR (75 MHz, $CDCl_3$): δ 206.47 (C=O), 173.75 (C=O), 172.12 (C=O), 170.82 (C=O), 170.03 (C=O), 154.85 (C=O), 138.22-126.22 (aromatic), 131.40 (OCH$_2$CH=CH$_2$), 118.94 (OCH$_2$CH=CH$_2$), 101.41 (>CHPh), 100.92 (C-1), 95.85 (C-1), 78.90 (C-4'), 78.75 (C-3), 76.37 (C-4), 76.05 (C-3$_S$), 74.46 (CH$_2$Ph), 74.27 (C-5), 71.42 (C-3'), 70.80 (C-3$_L$, CH$_2$Ph), 68.63-68.54 (C-6, C-6', OCH$_2$CH=CH$_2$), 66.20 (C-5'), 56.04 (C-2, C-2'), −1.52 (SiCH$_3$), −3.28 (SiCH$_3$). HR MS (m/z) calculated for C$_{100}$H$_{162}$N$_2$O$_{18}$Si [M+Na], 1730.1484; found, 1730.1412.

Dimethylthexylsilyl 6-O-{4,6-O-benzylidene-2-deoxy-2-[(R)-3-hexadecanoyloxy-5-methyl-hexadecanoylamino]-3-O-levulinoyl-β-D-glucopyranosyl}-4-O-benzyl-3-O—[(R)-3-benzyloxy-hexadecanoyl]-2-[(R)-3-benzyloxy-15-methyl-hexadecanoylamino]-2-deoxy-β-D-glucopyranoside (127). Tetrakis(triphenylphosphine)palladium (11 mg, 0.01 mmol) was added to a solution of 126 (80 mg, 0.047 mmol), n-BuNH$_2$ (9.4 μL, 0.094 mmol) and HCOOH (3.5 μL, 0.094 mmol) in THF (2 mL). After stirring the reaction mixture at room temperature for 30 min, it was diluted with DCM (15 mL) and washed with water (10 mL), saturated aqueous NaHCO$_3$ (2×10 mL) and brine (2×10 mL). The organic phase was dried (MgSO$_4$) and filtered. Next, the filtrate was concentrated in vacuo. The residue was purified by preparative silica gel TLC chromatography (eluent: hexane/ethyl acetate, 3/2, v/v) to give an alcohol as a pale yellow syrup (72 mg, 95%). R$_f$=0.55 (hexane/ethyl acetate, 3/2, v/v); $^1$H NMR (500 MHz, CDCl$_3$): δ 7.43-7.24 (m, 15H, aromatic), 6.37 (d, 1H, J$_{NH,2}$=6.0 Hz, NH), 5.90 (d, 1H, J$_{NH',2'}$=8.5 Hz, NH'), 5.46 (s, 1H, >CHPh), 5.37 (t, 1H, J$_{2',3'}$=J$_{3',4'}$=9.5 Hz, H-3'), 5.03 (m, H-3$_L$), 4.90 (d, 1H, J=11.0 Hz, CHHPh), 4.87 (d, 1H, =8.0 Hz, H-1'), 4.63 (d, 1H, J=11.0 Hz, CHHPh), 4.58 (d, 1H, J$_{1,2}$=8.0 Hz, H-1), 4.55 (d, 1H, J=12.0 Hz, CHHPh), 4.49 (d, 1H, J=12.0 Hz, CHHPh), 4.28 (dd, 1H, J$_{5',6'a}$=5.0 Hz, J=11.0 Hz, H-6'a), 3.98 (d, 1H, J$_{6a,6b}$=10.0 Hz, H-6a), 3.80-3.67 (m, 5H, H-2', H-3, H-6b, H-6'b, H-3$_S$), 3.63 (t, 1H, J$_{3',4'}$=9.5 Hz, H-4'), 3.50-3.36 (m, 4H, H-2, H-4, H-5, H-5'), 2.78-2.48 (m, 4H, CH$_2$ of Lev), 2.43-2.23 (m, 6H, H-2$_S$, H-2$_L$, H-20, 2.11 (s, 3H, CH$_3$ of Lev), 1.67-1.45 (m, 7H, H-4$_S$, H-3$_L$', H-4$_L$, CH of TDS), 1.23-1.12 (m, 64H, 32×CH$_2$ of lipid), 0.87-0.80 (m, 27H, 4×CH$_3$ of TDS, 5×CH$_3$ of lipid), 0.14 (s, 3H, SiCH$_3$), 0.09 (s, 3H, SiCH$_3$). HR MS (m/z) calculated for C$_{96}$H$_{158}$N$_2$O$_{16}$Si [M+Na], 1646.1273; found, 1646.1384. A solution of (R)-3-benzyloxy-hexadecanoic acid 110 (15 mg, 0.042 mmol) and DCC (11.5 mg, 0.056 mmol) in DCM (2 mL) was stirred at room temperature for 10 min, after which the alcohol intermediate (45 mg, 0.028 mmol) and DMAP (1 mg, 8 μmol) were added. The reaction mixture was stirred at room temperature for 10 h, after which the solids were removed by filtration and washed with DCM (2×1 mL). The combined filtrates were concentrated in vacuo and the residue was purified by preparative silica gel TLC chromatography (eluent: hexane/ethyl acetate, 5/2, v/v) to afford 127 as an amorphous white solid (52 mg, 95%). R$_f$=0.45 (hexane/ethyl acetate, 5/2, v/v); [α]$^{26}_D$=−8.8° (c=1.0, CHCl$_3$); $^1$H NMR (300 MHz, CDCl$_3$): δ 7.37-7.14 (m, 20H, aromatic), 6.12 (d, 1H, J$_{NH,2}$=9.3 Hz, NH), 5.88 (d, 1H, J$_{NH',2'}$=8.1 Hz, NH'), 5.39 (s, 1H, >CHPh), 5.34 (t, 1H, J$_{2',3'}$=J$_{3',4'}$=9.9 Hz, H-3'), 5.34 (t, 1H, J$_{2,3}$=J$_{3,4}$=9.9 Hz, H-3), 5.00 (m, 1H, H-3$_L$), 4.85 (d, 1H, =8.1 Hz, H-1'), 4.52-4.35 (m, 7H, H-1, 6×CHHPh), 4.25 (dd, 1H, =4.5 Hz, J$_{5',6'a}$=4.5 Hz, J$_{6'a,6'b}$=10.5 Hz, H-6'a), 3.87 (d, 1H, J$_{6a,6b}$=10.5 Hz, H-6a), 3.81-3.46 (m, 8H, H-2, H-2', H-4, H-4', H-6'b, H-6'b, 2×H-3$_S$), 3.46-3.36 (m, 2H, H-5, H-5'), 2.76-2.61 (m, 2H, CH$_2$ of Lev), 2.52-2.44 (m, 3H, CH$_2$ of Lev, H-2$_S$), 2.35-2.15 (m, 7H, 3×H-2$_S$, H-2$_L$, H-20, 2.06 (s, 3H, CH$_3$ of Lev), 1.54-1.37 (m, 9H, 2×H-4$_S$, H-3$_L$', H-4$_L$, CH of TDS), 1.23-1.06 (m, 86H, 43×CH$_2$ of lipid), 0.83-0.73 (m, 30H, 4×CH$_3$ of TDS, 6×CH$_3$ of lipid), 0.07 (s, 3H, SiCH$_3$), 0.00 (s, 3H, SiCH$_3$). $^{13}$C NMR (75 MHz, CDCl$_3$): δ 206.43 (C=O), 173.70 (C=O), 172.12 (C=O), 171.38 (C=O), 170.73 (C=O), 169.96 (C=O), 138.59-126.19 (aromatic), 101.36 (>CHPh), 100.88 (C-1), 96.08 (C-1), 78.86 (C-4'), 75.91 (C-4), 75.76 (C-3$_S$), 75.43 (C-3$_S$), 74.58 (C-3), 74.40 (C-5), 74.08 (CH$_2$Ph), 71.43 (C-3'), 71.33 (CH$_2$Ph), 70.77 (C-3$_L$), 70.54 (CH$_2$Ph), 68.15 (C-6, C-6'), 66.15 (C-5'), 55.91 (C-2'), 55.80 (C-2), −1.50 (SiCH$_3$), −3.24 (SiCH$_3$).CHR MS (m/z) calculated for C$_{119}$H$_{194}$N$_2$O$_{18}$Si [M+Na]$^+$, 1990.3988; found, 1990.3204.

6-O-{4,6-O-Benzylidene-2-deoxy-2-[(R)-3-hexadecanoyloxy-15-methyl-hexadecanoyl amino]-β-D-glucopyranosyl}-4-O-benzyl-3-O—[(R)-3-benzyloxy-hexadecanoyl]-2-[(R)-3-benzyloxy-15-methyl-hexadecanoylamino]-2-deoxy-α-D-glucopyranose (129). A reaction mixture of 127 (25 mg, 0.013 mmol) and hydrazine acetate (1.3 mg, 0.014 mmol) in a mixture of DCM (2 mL) and methanol (0.2 mL) was stirred at room temperature 611, after which it was concentrated in vacuo. The residue was purified by preparative silica gel TLC (eluent: hexane/ethyl acetate, 5/2, v/v) to afford 128 as a pale yellow syrup (23 mg, 96%). R$_f$=0.40 (hexane/ethyl acetate, 5/2, v/v); $^1$H NMR (300 MHz, CDCl$_3$): δ 7.30-7.12 (m, 20H, aromatic), 6.15 (d, 1H, J$_{NH,2}$=9.3 Hz, NH), 5.87 (d, 1H, J$_{NH',2'}$=5.7 Hz, NH'), 5.47 (s, 1H, >CHPh), 5.08 (t, 1H, J$_{2,3}$=J$_{3,4}$=9.9 Hz, H-3), 5.05 (m, 1H, H-3$_L$), 4.73 (d, 1H, J$_{1',2'}$=8.1 Hz, H-1'), 4.53-4.36 (m, 7H, H-1, 6×CHHPh), 4.23 (dd, 1H, J$_{5',6'a}$=5.2 Hz, J$_{6'a,6'b}$=10.2 Hz, H-6'a), 4.16 (t, 1H, J$_{2',3'}$=J$_{3',4'}$=9.6 Hz, H-3'), 3.92 (d, 1H, J$_{6a,6b}$=10.2 Hz, H-6a), 3.83-3.76 (m, 2H, H-2, H-3$_S$), 3.70-3.58 (m, 3H, H-5', H-6b, H-3$_S$), 3.52-3.73 (m, 4H, H-4, H-4', H-5, H-6'b), 3.26 (m, 1H, H-2'), 2.50 (dd, 1H, J$_{2Sa,2Sb}$=15.9 Hz, J$_{2Sa,3S}$=6.9 Hz, H-2$_{Sa}$), 2.38-2.18 (m, 7H, 3×H-2$_S$, H-2$_L$, H-2$_{L'}$), 1.54-1.38 (m, 9H, 2×H-4$_S$, H-3$_{L'}$, H-4$_L$, CH of TDS), 1.26-1.09 (m, 86H, 43×CH$_2$ of lipid), 0.81-0.73 (m, 30H, 4×CH$_3$ of thexyl, 6×CH$_3$ of lipid), 0.06 (s, 3H, SiCH$_3$), 0.00 (s, 3H, SiCH$_3$). MS (m/z) calcd for C$_{114}$H$_{188}$N$_2$O$_{16}$Si [M+Na]$^+$, 1892.3620; found, 1892.4476. Acetic acid (100 μL) was added to a solution of Bu$_4$NF (1 N in THF, 1 mL) and then 128 (35 mg, 0.019 mmol) was added. The reaction mixture was stirred at room temperature for 10 h, after which it was diluted with ethyl acetate (10 mL) and washed with saturated aqueous NaHCO$_3$ (2×10 mL) and brine (2×10 mL). The organic phase was dried (MgSO$_4$) and filtered. Next, the filtrate was concentrated in vacuo. The residue was purified by preparative silica gel TLC chromatography (eluent: DCM/acetone, 6/1, v/v) to afford 129 as a pale yellow syrup (21 mg, 65%). R$_f$=0.40 (DCM/acetone, 6/1, v/v); $^1$H NMR (500 MHz, CDCl$_3$): δ 7.51-7.19 (m, 20H, aromatic), 6.31 (d, 1H, J$_{NH,2}$=9.5 Hz, NH), 6.19 (d, 1H, J$_{NH',2'}$=5.5 Hz, NIT), 5.55 (s, 1H, >CHPh), 5.43 (t, 1H, J$_{2,3}$=J$_{3,4}$=9.5 Hz, H-3), 5.15-5.09 (m, 2H, H-1, H-1'), 5.01 (m, 1H, H-3$_L$), 4.63-4.45 (m, 6H, 6×CHHPh), 4.36 (m, 1H, H-6'a), 4.22 (m, 1H, H-2), 4.14 (m, 1H, H-3'), 4.02 (d, 1H, J$_{6a,6b}$=11.5 Hz, H-6a), 3.85-3.76 (m, 3H, H-6'b, 2×H-3$_S$), 3.67-3.47 (m, 3H, H-4', H-5', H-6b), 3.41 (m, 1H, H-4), 3.30 (m, 1H, H-2'), 2.61-2.24 (m, 8H, 2×H-2$_S$, H-2$_L$, H-2$_L$), 1.66-1.49 (m, 8H, 2×H-4$_S$, H-4$_L$), 1.26-1.17 (m, 86H, 43×CH$_2$ of lipid), 0.91-0.87 (m, 18H, 6×CH$_3$ of lipid). MS (m/z) calculated for C$_{106}$H$_{170}$N$_2$O$_{16}$ [M+Na]$^+$ 1750.2443; found, 1750.2439.

6-O-{2-Deoxy-2-[(R)-3-hexadecanoyloxy-15-methyl-hexadecanoylamino]-β-D-glucopyranosyl}-3-O—[(R)-3-hydroxy-hexadecanoyl]-2-deoxy-2-[(R)-3-hydroxy-15-methyl-hexadecanoylamino]-α-D-glucopyranose 1-phosphate (103). To a cooled (−78° C.) solution of 129 (10 mg, 0.0058 mmol) and tetrabenzyl diphosphate (12 mg, 0.022 mmol) in THF (1.5 mL) was added dropwise lithium bis(trimethylsilyl)amide in THF (1.0 M, 15 pt, 0.015 mmol). The reaction mixture was stirred for 1 h and then allowed to warm up to −20° C. After the reaction mixture was stirred at −20° C. for 1 h, it was quenched with saturated aqueous NaHCO$_3$ (10 mL) and extracted with ethyl acetate (10 mL). The organic phase was washed with brine (2×10 mL), dried (Na$_2$SO$_4$) and concentrated in vacuo. The residue was purified by Iatro beads column chromatography (hexane/ethyl acetate, 5/1→3/1→4/3, v/v) to give 130 as a pale yellow oil (8.3 mg, 72%). R$_f$=0.55 (hexane/ethyl acetate, 3/2, v/v); $^1$H NMR (500 MHz, CDCl$_3$): δ 7.44-7.18 (m, 30H, aromatic), 6.30 (d, 1H, J$_{NH,2}$=9.0 Hz, NH), 5.63 (bs, 1H, H-1), 5.55 (s, 1H, >CHPh), 5.31 (t, 1H, J$_{2,3}$=J$_{3,4}$=10.0 Hz, H-3), 5.23 (m, 1H, H-3$_L$), 5.13-4.91 (m, 5H, H-1, 4×CHHPh), 4.62 (d, 1H, J=11.0 Hz, CHHPh), 4.52-4.45 (m, 4H, 4×CHHPh), 4.39 (d, 1H, J=12.0 Hz, CHHPh), 4.34-4.26 (m, 2H, H-2, H-6'a), 4.14 (m, 1H, H-5), 3.95-3.91 (m, 2H, H-3', H-6a), 3.84-3.74 (m, 3H, H-6b, H-6'b, H-3$_S$), 3.70 (m, 1H, H-3$_S$), 3.61 (m, 1H, H-2'), 3.55 (t, 1H, J$_{3',4'}$=J$_{4',5}$=9.5 Hz, H-4'), 3.46 (t, 1H, J$_{3,4}$=J$_{4,5}$=9.5 Hz, H-4), 3.36 (m, 1H, H-5'), 2.57 (dd, 1H, J$_{2Sa,2Sb}$=16.0 Hz, J$_{2Sa,3S}$=8.0 Hz, H-2$_{Sa}$), 2.51-2.40 (m, 3H, H-2$_S$, H-2$_L$), 2.26-2.18 (m, 4H, H-2$_S$, H-2$_L$), 1.63-1.50 (m, 8H, 2×H-4$_S$, H-3$_L$, H-4$_L$), 1.32-1.17 (m, 86H, 43×CH$_2$ of lipid), 0.90-0.87 (m, 18H, 6×CH$_3$ of lipid). MS (m/z) calculated for C$_{120}$H$_{183}$N$_2$O$_{19}$P [M+Na], 2010.3045; found, 2010.2429. A mixture of 130 (10.5 mg, 0.0053 mmol) and Pd black (15.0 mg) in anhydrous THF (5 mL) was shaken under an atmosphere of H$_2$ (50 psi) at room temperature for 26 h, after which it was neutralized with triethylamine (10 µL). The catalyst was removed by filtration and the residue washed with THF (2×1 mL). The combined filtrates were concentrated in vacuo to afford 103 as a colorless film (6.0 mg, 78%). $^1$H NMR (500 MHz, CDCl$_3$/CD$_3$OD, 1/1, v/v): δ 5.28 (broad, 1H, H-1), 4.96-4.82 (m, 3H, H-1', H-3, H-3$_L$). HR MS (m/z) (negative) calculated for C$_{78}$H$_{149}$N$_2$O$_{19}$P, 1449.0492; found, 1449.7284.

Dimethylthexylsilyl 6-O-{4,6-O-benzylidene-3-O—[(R)-3-benzyloxy-13-methyl-tetradecanoylamino]-2-deoxy-2-[(R)-3-hexadecanoyloxy-15-methyl-hexadecanoylamino]-β-D-glucopyranosyl}-3-O-allyloxycarbonyl-4-O-benzyl-2-[(R)-3-benzyloxy-15-methyl-hexa decanoylamino]-2-deoxy-β-D-glucopyranoside (131). A reaction mixture of 126 (80 mg, 0.047 mmol) and hydrazine acetate (4.7 mg, 0.052 mmol) in a mixture of DCM (3 mL) and methanol (0.3 mL) was stirred at room temperature 6 h, after which it was concentrated in vacuo. The residue was purified by silica gel column chromatography (eluent: hexane/ethyl acetate, 3/1, v/v) to afford an alcohol as a pale yellow syrup (69 mg, 92%). R$_f$=0.40 (hexane/ethyl acetate, 5/2, v/v); $^1$H NMR (300 MHz, CDCl$_3$): δ 7.46-7.17 (m, 15H, aromatic), 6.35 (d, 1H, J$_{NH,2}$=9.0 Hz, NH), 5.99 (d, 1H, J$_{NH',2'}$=5.7 Hz, NH'), 5.77 (m, 1H, OCH$_2$CH=CH$_2$), 5.46 (s, 1H, >CHPh), 5.23 (d, 1H, J=17.1 Hz, OCH$_2$CH=CHH), 5.14 (d, 1H, J=10.2 Hz, OCH$_2$CH=CHH), 5.02 (m, 1H, H-3$_L$), 4.94 (dd, 1H, J=8.7 Hz, J=10.5 Hz, H-3), 4.75 (d, 1H, J$_{1',2'}$=8.1 Hz, H-1'), 4.58-4.37 (m, 7H, H-1, 4×CHHPh, OCH$_2$CH=CH$_2$), 4.23 (dd, 1H, J$_{5',6'a}$=4.5 Hz, J$_{6'a,6'b}$=10.5 Hz, H-6'a), 4.13 (m, 1H, H-3), 3.88 (d, 1H, J$_{6a,6b}$=10.5 Hz, H-6a), 3.76-3.31 (m, 8H, H-2, H-4, H-4', H-5, H-5', H-6b, H-6'b, H-3$_S$), 3.27 (m, 1H, H-2'), 2.33-2.17 (m, 6H, H-2$_S$, H-2$_L$, H-20, 1.55-1.37 (m, 7H, H-4$_S$, H-3$_L$', H-4$_L$, CH of TDS), 1.17-1.07 (m, 64H, 32×CH$_2$ of lipid), 0.82-0.73 (m, 27H, 4×CH$_3$ of TDS, 5×CH$_3$ of lipid), 0.06 (s, 3H, SiCH$_3$), 0.00 (s, 3H, SiCH$_3$). HR MS (m/z) calculated for C$_{95}$H$_{156}$N$_2$O$_{16}$Si [M+Na]$^+$, 1632.1116; found, 1631.8767. A solution' of (R)-3-benzyloxy-13-methyl-tetradecanoic acid 107 (21 mg, 0.061 mmol) and DCC (17 mg, 0.081 mmol) in DCM (2 mL) was stirred at room temperature for 10 min, after which the alcohol intermediate (65 mg, 0.040 mmol) and DMAP (1 mg, 8 µmol) were added. The reaction mixture was stirred at room temperature for 12 h, after which the solids were removed by filtration and washed with DCM (2×1 mL). The combined filtrates were concentrated in vacuo and the residue was purified by preparative silica gel TLC chromatography (eluent: hexane/ethyl acetate, 4/1, v/v) to afford 131 as an amorphous solid (71 mg, 91%). R$_f$=0.50 (hexane/ethyl acetate, 3/1, v/v); [α]$^{24}_D$=−11.1° (c=1.0, CHCl$_3$); $^1$H NMR (600 MHz, CDCl$_3$): δ 7.37-7.21 (m, 20H, aromatic), 6.35 (d, 1H, J$_{NH,2}$=9.0 Hz, NH), 5.84 (m, 1H, OCH$_2$CH=CH$_2$), 5.79 (d, 1H, J$_{NH',2'}$=9.0 Hz, NH'), 5.41 (s, 1H, >CHPh), 5.41 (t, 1H, J$_{2',3'}$=J$_{3',4'}$=9.6 Hz, H-3'), 5.29 (d, 1H, J=17.4 Hz, OCH$_2$CH=CHH), 5.19 (d, 1H, J=10.2 Hz, OCH$_2$CH=CHH), 5.00-4.96 (m, 2H, H-3, H-3$_L$), 4.87 (d, 1H, J$_{1',2'}$=7.8 Hz, H-1'), 4.61-4.37 (m, 9H, H-1, 6×CHHPh, OCH$_2$CH=CH$_2$), 4.29 (dd, 1H, J$_{5',6'a}$=5.4 Hz, J$_{6'a,6'b}$=10.8 Hz, H-6'a), 3.94 (d, 1H, J$_{6a,6b}$=10.2 Hz, H-6a), 3.81-3.78 (m, 3H, H-2, H-6b, H-3$_S$), 3.74-3.67 (m, 3H, H-2', H-6'b, H-3$_S$), 3.64-3.58 (m, 2H, H-4, H-4'), 3.50-3.45 (m, 2H, H-5, H-5'), 2.64-2.12 (m, 8H, H-2$_S$, H-2$_L$), 1.59-1.46 (m, 9H, H-4$_S$, H-3$_L$', H-4$_L$, CH of TDS), 1.23-1.13 (m, 80H, 40×CH$_2$ of lipid), 0.86-0.79 (m, 33H, 4×CH$_3$ of TDS, 7×CH$_3$ of lipid), 0.13 (s, 3H, SiCH$_3$), 0.06 (s, 3H, SiCH$_3$). $^{13}$C NMR (75 MHz, CDCl$_3$): δ 173.80 (C=O), 171.06 (C=O), 170.82 (C=O), 169.65 (C=O), 154.86 (C=O), 138.41-126.14 (aromatic), 131.40 (OCH$_2$CH=CH$_2$), 118.94 (OCH$_2$CH=CH$_2$), 101.41 (>CHPh), 100.93 (C-1'), 95.86 (C-1), 78.93 (C-4'), 78.75 (C-3), 76.31 (C-4), 76.05 (C-3$_S$), 75.65 (C-3$_S$), 74.45 (CH$_2$Ph), 74.21 (C-5), 71.24 (C-3'), 71.16 (CH$_2$Ph), 70.80 (CH$_2$Ph), 70.74 (C-3$_L$), 68.63 (C-6, OCH$_2$CH=CH$_2$), 68.28 (C-6'), 66.27 (C-5'), 56.03 (C-2), 55.73 (C-2'), −1.52 (SiCH$_3$), −3.27 (SiCH$_3$). HR MS (m/z) calculated for C$_{117}$H$_{190}$N$_2$O$_{18}$Si [M+Na]$^+$, 1962.3675; found, 1962.3035.

6-O-{4,6-O-Benzylidene-3-19-[(R)-3-benzyloxy-13-methyl-tetradecanoylamino]-2-deoxy-2-[(R)-3-hexadecanoyloxy-15-methyl-hexadecanoylamino]-β-D-glucopyranosyl)-4-O-benzyl-2-[(R)-3-benzyloxy-15-methyl-hexadecanoylamino]-2-deoxy-β-D-glucopyranose (133). Tetrakis(triphenylphosphine)palladium (6.3 mg, 0.0054 mmol) was added to a stirred solution of 131 (35 mg, 0.018 mmol), n-BuNH$_2$ (3.6 µL, 0.036 mmol) and HCOOH (1.4 µL, 0.036 mmol) in THF (2 mL). After stirring the reaction mixture at room temperature for 1 h, it was diluted with DCM (10 mL) and washed with water (10 mL), saturated aqueous NaHCO$_3$ (2×10 mL) and brine (2×10 mL). The organic phase was dried (MgSO$_4$) and filtered. Next, the filtrate was concentrated in vacuo. The residue was purified by preparative silica gel TLC chromatography (eluent: hexane/ethyl acetate, 5/2, v/v) to give 132 as a pale yellow syrup (31 mg, 94%). R$_f$=0.50 (hexane/ethyl acetate, 3/2, v/v); $^1$H NMR (300 MHz, CDCl$_3$): δ 7.29-7.13 (m, 20H, aromatic), 6.29 (d, 1H, J$_{NH,2}$=5.7 Hz, NH), 5.69 (d, 1H, J$_{NH',2'}$=8.7 Hz, NH'), 5.31 (s, 1H, >CHPh), 5.28 (t, 1H, J$_{2',3'}$=J$_{3',4'}$=8.7 Hz, H-3'), 4.89 (m, 1H, H-3$_L$), 4.80 (d, 1H, J=11.7 Hz, CHHPh), 4.70 (d, 1H, J$_{1',2'}$=8.4 Hz, H-1'), 4.53-4.26 (m, 6H, H-1, 5×CHHPh), 4.18 (dd, 1H, J$_{5',6'a}$=4.5 Hz, J$_{6'a,6'b}$=10.5 Hz, H-6'a), 3.89 (d, 1H, J$_{6a,6b}$=10.8 Hz, H-6a), 3.78-3.58 (m, 5H, H-2', H-6b, H-6'b, 2×H-3$_S$), 3.53 (t, 1H, J=8.4 Hz, J=9.6 Hz, H-4), 3.44-3.25 (m, 4H, H-2, H-4, H-5, H-5'), 2.54 (dd, 1H, J$_{2Sa,2Sb}$=15.0 Hz, J$_{2Sa,3s}$=6.0 Hz, H-2$_{Sa}$), 2.33-2.17 (m, 6H, H-2$_S$, H-2$_L$, H-20, 2.6 (dd, 1H, J$_{2La,2Lb}$=15.0 Hz, J$_{2La,3L}$=5.7 Hz, H-2$_{La}$), 1.49-1.36 (m, 9H, H-4$_S$, H-4$_L$', H-4$_L$, CH of TDS), 1.14-1.06 (m, 80H, 40×CH$_2$ of lipid), 0.76-0.71 (m, 33H, 4×CH$_3$ of TDS, 7×CH$_3$ of lipid), 0.05 (s, 3H, SiCH$_3$), 0.00 (s, 3H, SiCH$_3$). HR MS (m/z) calculated for C-13H$_{186}$N$_2$O$_{16}$Si [M+Na]$^+$, 1878.3464; found, 1878.3721. Acetic acid (100 µL) was added to a solution of Bu$_4$NF (1 N in THF, 1 mL) and then 132

(26 mg, 0.014 mmol) was added. The reaction mixture was stirred at room temperature for 20 h, after which it was diluted with ethyl acetate (10 mL) and washed with saturated aqueous NaHCO$_3$ (2×10 mL) and brine (2×10 mL). The organic phase was dried (MgSO$_4$) and filtered. Next, the filtrate was concentrated in vacuo. The residue was purified by preparative silica gel TLC chromatography (eluent: hexane/ethyl acetate, 1/1, v/v) to afford 133 as a pale yellow syrup (21 mg, 88%). $R_f$=0.40 (hexane/ethyl acetate, 1/1, v/v); $^1$H NMR (300 MHz, CDCl$_3$): δ 7.40-7.25 (m, 20H, aromatic), 6.67 (d, 1H, $J_{NH,2}$=7.8 Hz, NH), 5.91 (d, 1H, $J_{NH',2'}$=8.1 Hz, NH'), 5.45-5.39 (m, 2H, H-3', >CHPH), 5.24 (d, 1H, $J_{1',2'}$=8.4 Hz, H-1'), 5.08 (d, 1H, $J_{1,2}$=2.7 Hz, H-1), 4.96 (m, 1H, H-3$_L$), 4.92 (d, 1H, J=11.7 Hz, CHHPh), 4.64-4.32 (m, 6H, H-6'a, 5×CHHPh), 4.05-3.51 (m, 10H, H-2', H-3, H-4', H-5, H-5', H-6a, H-6b, H-6'b, 2×H-3$_S$), 3.53 (dd, 1H, J=8.4 Hz, J=9.6 Hz, H-4), 3.44-3.25 (m, 4H, H-2, H-4, H-5, H-5'), 2.63 (dd, 1H, $J_{2Sa,2Sb}$=16.4 Hz, $J_{2Sa,3S}$=6.0 Hz, H-2$_{Sa}$), 2.53-2.17 (m, 7H, H-2s, H-2$_L$, H-20, 1.64-1.47 (m, 8H, H-4$_S$, H-4$_{L'}$, H-4$_L$), 1.25-1.15 (m, 80H, 40×CH$_2$ of lipid), 0.87-0.85 (m, 21H, 7×CH$_3$ of lipid). HR MS (m/z) calculated for C$_{105}$H$_{168}$N$_2$O$_{16}$Si [M+Na]$^+$, 1736.2286; found, 1736.3901.

6-O-{2-Deoxy-2-[(R)-3-hexadecanoyloxy-15-methyl-hexadecanoylamino]-3-O-[(R)-3-hydroxy-13-methyl-tetradecanoylamino]-β-D-glucopyranosyl}-2-deoxy-2-[(R)-3-hydroxy-15-methyl-hexadecanoylamino]-α-D-glucopyranose 1-phosphate (104). Compound 133 (15 mg, 0.0088 mmol) was phosphorylated in a manner similar to the synthesis of 129 to afford 134 as a pale yellow syrup (11.8 mg, 68%). $R_f$=0.60 (hexane/ethyl acetate, 3/2, v/v); $^1$H NMR (500 MHz, CDCl$_3$): δ 7.39-7.26 (m, 30H, aromatic), 6.65 (d, 1H, $J_{NH',2'}$=8.0 Hz, NH'), 6.50 (d, 1H, $J_{NH,2}$=8.5 Hz, NH), 5.65 (bs, 1H, H-1), 5.42 (s, 1H, >CHPh), 5.35 (t, 1H, $J_{2',3'}$=$J_{3',4'}$=10.0 Hz, H-3'), 5.10-4.99 (m, 5H, H-3$_L$, 4×CHHPh), 4.92 (d, 1H, $J_{1,2}$=9.0 Hz, H-1), 4.81 (d, 1H, J=10.5 Hz, CHHPh), 4.61 (d, 1H, J=10.5 Hz, CHHPh), 4.52-4.42 (m, 4H, 4×CHHPh), 4.32 (m, 1H, H-6'a), 4.13 (m, 1H, H-2), 3.95-3.74 (m, 6H, H-2', H-6a, H-6b, H-6'b, 2×H-3$_S$), 3.66-3.60 (m, 2H, H-3, H-4'), 3.43 (m, 1H, H-5'), 3.36 (m, 1H, H-5), 2.69 (dd, 1H, $J_{2Sa,2Sb}$=14.5 Hz, $J_{2Sa,3S}$=6.0 Hz, H-2$_{Sa}$), (m, 7H, H-2$_S$, H-2$_L$, H-2$_L$), 1.59-1.50 (m, 8H, H-4$_S$, H-4$_{L'}$, H-4$_L$), 1.27-1.17 (m, 80H, 40×CH$_2$ of lipid), 0.89-0.87 (m, 21H, 7×CH$_3$ of lipid). HR MS (m/z) calculated for C$_{119}$H$_{181}$N$_2$O$_{19}$P [M+Na]$^+$, 1996.2888; found, 1996.0125. Compound 134 (9.6 mg, 0.0049 mmol) was deprotected in a manner similar to the synthesis of 103 to provide 104 as a colorless film (5.3 mg, 76%). $^1$H NMR (500 MHz, CDCl$_3$/CD$_3$OD, 1/1, v/v): δ 5.18 (broad, 1H, H-1), 4.80-4.64 (m, 2H, H-3', H-3$_L$), 4.56 (broad, 1H, H-1'). HR MS (m/z) (negative) calculated for C$_{77}$H$_{147}$N$_2$O$_{19}$P, 1435.0336; found, 1435.5624.

Methyl 13-methyl-3-oxo-12-teradecenoate (112). Grubbs 2$^{nd}$ generation catalyst (27.2 mg, 0.032 mmol) was added to a stirred solution of compound III (1.0 g, 4.17 mmol) in 2-methyl-2-butene (20 mL) under an atmosphere of nitrogen. After stirring the reaction mixture at room temperature for 24 h, it was concentrated in vacuo to 0.5 mL and subjected to purification by silica gel column chromatography (eluent: hexane/ethyl acetate, 30/1, v/v) to afford 112 as a colorless oil (949 mg, 85%). $R_f$=0.50 (hexane/ethyl acetate, 10/1, v/v); $^1$H NMR (300 MHz, CDCl$_3$): δ 5.08 (t, 1H, $J_{11,12}$=6.9 Hz, H-12), 3.71 (s, 3H, OCH$_3$), 3.42 (s, 2H, H-2), 2.50 (t, 2H, $J_{4,5}$=7.5 Hz, H-4), 1.91 (m, 2H, H-11), 1.66 (s, 3H, H-14), 1.57-1.54 (m, 5H, H-5, H-14), 1.25 [bs, 101-1, H-(6-10)]. HR MS (m/z) calculated for C$_{16}$H$_{28}$O$_3$ [M+Na]$^+$, 291.1931; found, 291.1965.

Methyl 15-methyl-3-oxo-12-hexadecenoate (113). Grubbs 2$^{nd}$ generation catalyst (13.6 mg, 0.016 mmol) was added to a stirred solution of compound III (125 mg, 0.52 mmol) in 4-methyl-1-pentene (2 mL) under an atmosphere of nitrogen. After stirring the reaction mixture at room temperature for 16 h, it was concentrated in vacuo to 0.5 mL and subjected to purification by silica gel column chromatography (eluent: hexane/ethyl acetate, 30/1, v/v) to afford 113 as a colorless oil (137 mg, 89%). $R_f$=0.50 (hexane/ethyl acetate, 10/1, v/v); $^1$H NMR (300 MHz, CDCl$_3$): δ 5.32-5.29 (m, 2H, H-12, H-13), 3.66 (s, 3H, OCH$_3$), 3.38 (s, 2H, H-2), 2.46 (t, 2H, $J_{4,5}$=7.2 Hz, H-4), 1.92 (m, 2H, H-14), 1.79 (m, 2H, H-11), 1.55-1.47 (m, 4H, H-5, H-15), 1.22 [bs, 10H, H-(6-10)], 0.80 (d, 6H, $J_{15,16}$=6.9 Hz, H-16). HR MS (m/z) calculated for C$_{18}$H$_{32}$O$_3$ [M+Na], 319.2238; found, 319.2607.

Methyl (R)-3-hydroxy-13-methyl-tetradecanoate (114). A solution of 112 (800 mg, 2.99 mmol) in methanol (15 mL) was degassed with nitrogen for 10 min, after which 2 M HCl (0.2 mL) and RuCl$_2$-[(R)-BINAP] (20 mg) were added under an atmosphere of nitrogen. The reaction mixture was shaken under an atmosphere of H$_2$ (65 psi) at 45° C. for 12 h, after which it was quenched with Et$_3$N (100 μL). The solids were filtered off and the filtrate was concentrated in vacuo. The residue was purified by silica gel column chromatography (eluent: hexane/ethyl acetate, 6/1, v/v) to afford an alcohol as a colorless oil. The resulting intermediate was shaken with Pd/C (10 mg) in methanol (15 mL) under an atmosphere of H$_2$ (1 atm) for 12 h, after which the catalyst was filtered off and the filtrate was concentrated in vacuo. The residue was purified by silica gel column chromatography (eluent: hexane/ethyl acetate, 6/1, v/v) to afford 114 as a colorless oil (780 mg, 96%, two steps). $R_f$=0.45 (hexane/ethyl acetate, 4/1, v/v); [α]$^{25}_D$=−7.2° (c=1.0, CHCl$_3$); $^1$H NMR (300 MHz, CDCl$_3$): δ 3.98 (m, 1H, H-3), 3.69 (s, 3H, OCH$_3$), 2.50 (dd, 1H, $J_{2a,2b}$=13.5 Hz, $J_{2a,3}$=3.6 Hz, H-2a), 2.38 (dd, 1H, $J_{2a,2b}$=13.5 Hz, $J_{2b,3}$=8.7 Hz, H-2b), 1.53-1.36 (m, 3H, H-4, H-13), 1.23-1.09 [m, 16H, H-(5-12)], 0.84 (d, 6H, $J_{13,14}$=6.9 Hz, H-14); $^{13}$C NMR (75 MHz, CDCl$_3$): δ 173.51 (C=O), 68.03 (C-3), 51.71 (CH$_3$O), 41.08 (C-2), 39.03 (C-12), 36.52 (C-4), 22.64 (C-14). HR MS (m/z) calculated for C$_{16}$H$_{32}$O$_3$ [M+Na]$^+$, 295.2244; found, 295.2194.

Methyl (R)-3-hydroxy-15-methyl-hexadecanoate (115). In a manner similar to the synthesis of compound 114, compound 113 (100 mg, 0.338 mmol) was reduced by a two step procedure to afford 115 as a colorless oil (93 mg, 92%, two steps). $R_f$=0.50 (hexane/ethyl acetate, 4/1, v/v); [α]$^{25}_D$=−6.0° (c=1.0, CHCl$_3$); $^1$H NMR (300 MHz, CDCl$_3$): δ 3.95 (m, 1H, H-3), 3.66 (s, 3H, OCH$_3$), 2.47 (dd, 1H, $J_{2a,2b}$=16.2 Hz, $J_{2a,3}$=3.3 Hz, H-2a), 2.36 (dd, 1H, $J_{2a,2b}$=16.2 Hz, $J_{2b,3}$=9.0 Hz, H-2b), 1.53-1.32 (m, 3H, H-4, H-15), 1.21-1.03 [m, 20H, H-(5-14)], 0.81 (d, 6H, $J_{15,16}$=6.3 Hz, H-16); $^{13}$C NMR (75 MHz, CDCl$_3$): δ 173.47 (C=O), 67.97 (C-3), 51.67 (CH$_3$O), 41.08 (C-2), 39.02 (C-12), 36.51 (C-4), 22.62 (C-14). HR MS (m/z) calculated for C$_{18}$H$_{36}$O$_3$ [M+Na], 323.2557; found, 323.1925.

2-(4-Bromophenyl)-2-oxoethyl-(R)-3-hydroxy-13-methyl-tetradecanoate (116). LiOH.H$_2$O (101 mg, 4.4 mmol) in H$_2$O (10 mL) was added to a stirred solution of 114 (600 mg, 2.2 mmol) in THF (150 mL). After stirring the reaction mixture at room temperature for 10 h, the THF was removed in vacuo. The aqueous residue was neutralized with 1N HCl (4.4 mL) and extracted with ethyl acetate (20 mL). The organic phase was dried (Na$_2$SO$_4$) and filtered. The filtrate was concentrated in vacuo to afford an acid intermediate. Next, this intermediate was refluxed with dicyclohexaneamine (0.52 mL, 2.64 mmol) in CH$_3$CN (80 mL) for 2 h. After the reaction mixture cooled down to room temperature, the precipitated solid was collected by filtration to give a salt as a white solid. This product was dissolved in EtOAc (25 mL) and then Et$_3$N (0.37 mL, 2.64 mmol) and 2,4'-dibromoacetophenone (672 mg, 2.42 mmol) were added. After stirring the reaction mixture at room temperature for 12 h, it was diluted with DCM (50 mL) and washed with brine (2×30 mL). The organic phase was dried (MgSO$_4$) and filtered. Next, the filtrate was concentrated in vacuo. The residue was purified by silica gel column chromatography (eluent: DCM) to afford 116 as an amorphous solid (910 mg, 91%, three steps). R$_f$=0.35 (DCM); [α]$^{25}_D$=−0.8° (c=1.0, CHCl$_3$); NMR (300 MHz, CDCl$_3$): δ 7.76 (d, 2H, J=8.7 Hz, aromatic), 7.63 (d, 2H, J=8.7 Hz, aromatic), 5.41 (d, 1H, J=16.5 Hz, CH'$_{2a}$), 5.29 (d, 1H, J=16.5 Hz, CH'$_{2b}$), 4.10 (m, 1H, H-3), 2.67 (dd, 1H, J$_{2a,2b}$=15.0 Hz, J$_{2a,3}$=2.4 Hz, H-2a), 2.54 (dd, 1H, J$_{2a,2b}$=15.0 Hz, J$_{2b,3}$=9.0 Hz, H-2b), 1.60-1.45 (m, 3H, H-4, H-13), 1.24-1.12 [m, 16H, H-(5-12)], 0.84 (d, 6H, J$_{13,14}$=6.6 Hz, H-14). $^{13}$C NMR (75 MHz, CDCl$_3$): δ 191.63 (C=O), 171.95 (C=O), 132.54-129.29 (m, aromatic), 68.45 (C-3), 65.78 (C-2'), 41.99 (C-2), 39.04 (C-12), 36.56 (C-4), 22.65 (C-14). HR MS (m/z) calculated for C$_{23}$H$_{35}$BrO$_4$ [M+Na]$^+$, 477.1611; found, 477.1241.

2-(4-Bromophenyl)-2-oxoethyl (R)-3-hydroxy-15-methyl-hexadecanoate (118). In a manner similar to the synthesis of 116, compound 115 (960 mg, 3.2 mmol) was hydrolyzed with LiOH.H$_2$O (202 mg, 4.8 mmol), recrystallized by refluxing with DCHA (0.76 mL, 3.84 mmol) and protected by reacting with 2,4'-dibromoacetophenone (979 mg, 3.52 mmol) to afford 118 as an amorphous solid (1.39 g, 90%). R$_f$=0.35 (DCM); [α]$^{25}_D$=−1.2° (c=1.0, CHCl$_3$); NMR (300 MHz, CDCl$_3$): δ 7.74 (d, 2H, J=8.4 Hz, aromatic), 7.60 (d, 2H, J=8.4 Hz, aromatic), 5.39 (d, 1H, J=16.5 Hz, CH'$_{2a}$), 5.29 (d, 1H, J=16.5 Hz, CH'$_{2b}$), 4.08 (m, 1H, H-3), 2.65 (dd, 1H, J$_{2a,2b}$=15.0 Hz, J$_{2a,3}$=3.0 Hz, H-2a), 2.54 (dd, 1H, J$_{2a,2b}$=15.0 Hz, J$_{2b,3}$=9.0 Hz, H-2b), 1.58-1.46 (m, 3H, H-4, H-15), 1.24-1.13 [m, 20H, H-(5-14)], 0.83 (d, 6H, J$_{15,16}$=6.6 Hz, H-14). $^{13}$C NMR (75 MHz, CDCl$_3$): δ 191.60 (C=O), 171.86 (C=O), 132.49-129.24 (m, aromatic), 68.38 (C-3), 65.74 (C-2'), 41.96 (C-2), 39.00 (C-14), 36.54 (C-4), 22.61 (C-16). HR MS (m/z) calculated for C$_{25}$H$_{39}$BrO$_4$ [M+Na]$^+$, 505.1924; found, 505.1160.

2-(4-Bromophenyl)-2-oxoethyl (R)-3-benzyloxy-13-methyl-tetradecanoate (117). To a cooled (0° C.) solution of 116 (405 mg, 0.89 mmol), benzaldehyde (0.27 mL, 2.67 mmol) aired TMS$_2$O (1.13 mL, 5.34 mmol) in dry THF (20 mL) was added dropwise TMSOTf (77 μL, 0.445 mmol). After stirring the reaction mixture for 15 min, Et$_3$SiH (0.50 mL, 3.12 mmol) was added dropwise. The stirring continued at room temperature for another 4 h, after which the reaction mixture was neutralized with Et$_3$N (60 μL), diluted with ethyl acetate (40 mL) and washed with brine (2×25 mL). The organic phase was dried (MgSO$_4$) and filtered. Next, the filtrate was concentrated in vacuo. The residue was purified by silica gel column chromatography (eluent: hexane/ethyl acetate, 25/1, v/v) to afford 117 as an amorphous solid (363 mg, 75%). R$_f$=0.55 (hexane/ethyl acetate, 6/1, v/v); [α]$^{25}_D$=−6.2° (c=1.0, CHCl$_3$); $^1$H NMR (300 MHz, CDCl$_3$): δ 7.77-7.23 (m, 9H, aromatic), 5.27 (d, 1H, J=16.5 Hz, CH'$_{2a}$), 5.21 (d, 1H, J=16.5 Hz, CH'$_{2b}$), 4.58 (d, 1H, J=11.4 Hz, CHH Ph), 4.53 (d, 1H, J=11.4 Hz, CHHPh), 3.93 (m, 1H, H-3), 2.77 (dd, 1H, J$_{2a,2b}$=15.0 Hz, J$_{2a,3}$=7.2 Hz, H-2a), 2.64 (dd, 1H, J$_{2a,2b}$=15.0 Hz, J$_{2b,3}$=5.4 Hz, H-2b), 1.66-1.24 (m, 3H, H-4, H-13), 1.24-1.11 [m, 16H, H-(5-12)], 0.84 (d, 6H, J$_{13,14}$=6.9 Hz, H-14); $^{13}$C NMR (75 MHz, CDCl$_3$): δ 191.36 (C=O), 171.19 (C=O), 138.56-127.56 (m, aromatic), 75.85 (C-3), 71.54 (CH$_2$Ph), 65.76 (C-2'), 39.54 (C-2), 39.00 (C-12), 34.36 (C-4), 22.62 (C-14). HR MS (m/z) calculated for C$_{30}$H$_{41}$BrO$_4$ [M+Na]$^+$, 567.2080; found, 567.2116.

2-(4-Bromophenyl)-2-oxoethyl (R)-3-benzyloxy-15-methyl-hexadecanoate (119). In a manner similar to the synthesis of 117, the hydroxyl of compound 118 (627 mg, 1.30 mmol) was benzylated to afford 119 as an amorphous solid (528 mg, 71%). R$_f$=0.60 (hexane/ethyl acetate, 6/1, v/v); [α]$^{24.4}_D$=−6.7° (c=1.0, CHCl$_3$); $^1$H NMR (300 MHz, CDCl$_3$): δ 7.76-7.24 (m, 10H, aromatic), 5.27 (d, 1H, J=16.5 Hz, CH'$_{2a}$), 5.21 (d, 1H, J=16.5 Hz, CH'$_{2b}$), 4.58 (d, 1H, J=11.4 Hz, CHHPh), 4.52 (d, 1H, J=11.4 Hz, CHHPh), 3.92 (m, 1H, H-3), 2.77 (dd, 1H, J$_{2a,2b}$=15.3 Hz, J$_{2a,3}$=7.2 Hz, H-2a), 2.64 (dd, 1H, J$_{2a,2b}$=15.3 Hz, J$_{2b,3}$=5.4 Hz, H-2b), 1.66-1.36 (m, 3H, H-4, H-13), 1.24-1.12 [m, 20H, H-(5-14)], 0.84 (d, 6H, J$_{15,16}$=6.9 Hz, H-16). $^{13}$C NMR (75 MHz, CDCl$_3$): δ 191.22 (C=O), 171.15 (C=O), 138.58-127.53 (m, aromatic), 75.95 (C-3), 71.56 (CH$_2$Ph), 65.79 (C-2'), 39.51 (C-2), 39.06 (C-14), 34.39 (C-4), 22.65 (C-16). HR MS (m/z) calculated for C$_{32}$H$_{45}$BrO$_4$ [M+Na]$^+$, 595.2393; found, 595.2437.

(R)-3-Benzyloxy-13-methyl-tetradecanoic acid (107). Zinc dust (<10 micron, 382 mg, 5.87 mmol) was added portionwise to a solution of 117 (320 mg, 0.587 mmol) in acetic acid (15 mL). The reaction mixture was stirred at 60° C. for 2 h and then diluted with DCM (20 mL). The solids were filtered off through a pad of Celite and the residue was washed with DCM (3×5 mL). The combined filtrates were concentrated in vacuo and the residue was purified by silica gel column chromatography (eluent: DCM/methanol, 100/1, v/v) to afford 107 as an amorphous solid (198 mg, 97%). R$_f$=0.40 (toluene/ethyl acetate, 3/1, v/v); [α]$^{25}_D$=−2.3° (c=1.0, CHCl$_3$); $^1$H NMR (300 MHz, CDCl$_3$): δ 7.35-7.25 (m, 5H, aromatic), 4.55 (s, 2H, CH$_2$Ph), 3.86 (m, 1H, H-3), 2.62 (dd, 1H, J$_{2a,2b}$=15.6 Hz, J$_{2a,3}$=6.9 Hz, H-2a), 2.53 (dd, 1H, J$_{2a,2b}$=15.6 Hz, J$_{2b,3}$=5.1 Hz, H-2b), 1.66-1.45 (m, 3H, H-4, H-13), 1.38-1.10 [m, 16H, H-(5-12)], 0.85 (d, 6H, J$_{15,16}$=6.9 Hz, H-14); $^{13}$C NMR (75 MHz, CDCl$_3$): δ 176.76 (C=O), 138.04-127.73 (aromatic), 75.70 (C-3), 71.53 (CH$_2$Ph), 39.42 (C-2), 39.03 (C-12), 34.09 (C-4), 22.66 (C-14); HR MS (m/z) calculated for C$_{22}$H$_{36}$O$_3$ [M Na]$^+$, 371.2557; found, 371.1906.

(R)-3-Benzyloxy-15-methyl-hexadecanoic acid (108). In a manner similar to the synthesis of 107, compound 119 (350 mg, 0.611 mmol) was treated with zinc (<10 micron, 397 mg, 6.11 mmol) to afford 108 as an amorphous solid (207 mg, 97%). R$_f$=0.45 (toluene/ethyl acetate, 3/1, v/v); [α]$^{25}_D$=−2.5° (c=1.0, CHCl$_3$); $^1$H NMR (300 MHz, CDCl$_3$): δ 7.34-7.26 (m, 5H, aromatic), 4.57 (s, 2H, CH$_2$Ph), 3.87 (m, 1H, H-3), 2.64 (dd, 1H, J$_{2a,2b}$=15.6 Hz, J$_{2a,3}$=6.9 Hz, H-2a), 2.55 (dd, 1H, J$_{2a,2b}$=15.6 Hz, J$_{2b,3}$=5.1 Hz, H-2b), 1.68-1.38 (m, 3H, H-4, H-15), 1.26-1.14 [m, 20H, H-(5-14)], 0.86 (d, 6H, J$_{15,16}$=6.9 Hz, H-16); $^{13}$C NMR (75 MHz, CDCl$_3$): δ 176.95 (C=O), 138.08-127.71 (aromatic), 75.71 (C-3), 71.53 (CH$_2$Ph), 39.47 (C-2), 39.05 (C-12), 34.12 (C-4), 22.65 (C-14). HR MS (m/z) calculated for C$_{24}$H$_{40}$O$_3$ [M+Na]$^+$, 399.2870; found, 399.2552.

2-(4-Bromophenyl)-2-oxoethyl-(R)-3-hexadecanoyloxy-15-methyl-hexadecanoate (120). Palmitoyl chloride (0.41 mL, 1.34 mmol) was added dropwise to a stirred solution of 118 (540 mg, 1.12 mmol), pyridine (0.22 mL, 2.68 mmol) and DMAP (13 mg, 0.11 mmol) in DCM (10 mL). After stirring the reaction mixture at room temperature for 10 h, it was diluted with DCM (20 mL) and then washed with saturated aqueous NaHCO$_3$ (2×20 mL) and brine (2×20 mL). The organic phase was dried (MgSO$_4$) and filtered. Next, the filtrate was concentrated in vacuo. The residue was purified by silica gel column chromatography (eluent: toluene) to afford 120 as an amorphous solid (767 mg, 95%). $R_f$=0.70 (DCM); $[\alpha]^{25}_D$=−0.1° (c=1.0, CHCl$_3$); $^1$H NMR (300 MHz, CDCl$_3$): δ 7.73 (d, 2H, J=8.4 Hz, aromatic), 7.59 (d, 2H, J=8.4 Hz, aromatic), 5.29-5.24 (m, 3H, H-3, OCH$_2$COPhBr), 2.70 (m, 2H, H-2), 2.28 (t, 2H, $J_{2',3'}$=7.5 Hz, H-2'), 1.64-1.42 (m, 5H, H-4, H-15, H-3'), 1.23-1.11 [m, 44H, H-(5-14), H-(4'-15')], 0.84-0.82 (m, 9H, H-16, H-16'); $^{13}$C NMR (75 MHz, CDCl$_3$): δ 190.78 (C=O), 173.20 (C=O), 169.80 (C=O), 132.83-129.06 (m, aromatic), 70.08 (C-3), 65.84 (OCH$_2$COPhBr). HR MS (m/z) calculated for $C_{41}H_{69}BrO_5$ [M+Na]$^+$, 743.4221; found, 745.4365.

(R)-3-Hexadecanoyloxy-15-methyl-hexadecanoic acid (109). In a manner similar to the synthesis of 107, compound 120 (500 mg, 0.666 mmol) was treated with zinc (<10 micron, 430 mg, 6.66 mmol) to afford 109 as an amorphous solid (335 mg, 96%). $R_f$=0.35 (toluene/ethyl acetate, 4/1, v/v); $[0]^{25}_D$=−0.6° (c=1.0, CHCl$_3$); $^1$H NMR (300 MHz, CDCl$_3$): δ 5.19 (m, 1H, H-3), 2.58 (m, 2H, H-2), 2.25 (t, 2H, J=7.5 Hz, H-2'), 1.60-1.43 (m, 5H, H-4, H-15, H-3'), 1.23-1.14 [m, 44H, H-(5-14), H-(4'-15')], 0.85-0.83 (m, 9H, H-16, H-16'); $^{13}$C NMR (75 MHz, CDCl$_3$): δ 176.24 (C=O), 173.27 (C=O), 69.95 (C-3). HR MS (m/z) calculated for $C_{33}H_{64}O_4$ [M Na]$^+$, 547.4697; found, 547.5009.

Dimethylthexylsilyl 4,6-O-benzylidene-2-deoxy-2-(9-fluorenylmethoxycarbonylamino)-β-D-glucopyranoside (122). A suspension of compound 121 (1.02 g, 2.34 mmol) and zinc (<10 micron, 1.52 g, 23.4 mmol) in a mixture of acetic acid (250 µL) and DCM (12 mL) was stirred at room temperature for 4 h, after which it was diluted with ethyl acetate (40 mL). The solids were removed by filtration and the residue was washed with ethyl acetate (2×4 mL). The combined filtrates were washed with saturated aqueous NaHCO$_3$ (2×30 mL) and brine (2×25 mL). The organic phase was dried (MgSO$_4$) and filtered. The filtrate was concentrated in vacuo to afford an amine as a pale yellow oil. The resulting amine was dissolved in DCM (12 mL) and then FmocCl (664 mg, 2.57 mmol) and DIPEA (447 µL, 2.57 mmol) were added. The reaction mixture was stirred at room temperature for 3 h, after which it was diluted with DCM (20 mL) and washed with brine (2×30 mL). The organic phase was dried (MgSO$_4$) and filtered. Next, the filtrate was concentrated in vacuo. The residue was purified by silica gel column chromatography (eluent: hexane/ethyl acetate, 3/1, v/v) to yield 122 as an amorphous solid (1.38 g, 90%, two steps). $R_f$=0.55 (hexane/ethyl acetate, 3/2, v/v); $[\alpha]^{25}_D$=−13.9° (c=1.0, CHCl$_3$); $^1$H NMR (300 MHz, CD$_3$COCD$_3$): δ 7.86-7.23 (m, 13H, aromatic), 6.64 (d, 1H, $J_{NH,2}$=9.0 Hz, NH), 5.61 (s, 1H, >CHPh), 4.92 (d, 1H, $J_{1,2}$=7.8 Hz, H-1), 4-32-4.19 (m, 4H, H-6a, OCH$_2$CH of Fmoc), 3.88 (m, 1H, H-3), 3.78 (t, 1H, $J_{5,6b}$=$J_{6a,6b}$=9.9 Hz, H-6b), 3.56 (t, 1H, $J_{3,4}$=$J_{4,5}$=9.3 Hz, H-4), 3.54 (m, 1H, H-2), 3.44 (m, 1H, H-5), 1.61 (m, 1H, CH of TDS), 0.86-0.84 [m, 12H, SiC(CH$_3$)$_2$CH(CH$_3$)$_2$], 0.15 (s, 3H, SiCH$_3$), 0.14 (s, 3H, SiCH$_3$). $^{13}$C NMR (75 MHz, CDCl$_3$): δ 156.96 (C=O), 144.99-120.57 (m, aromatic), 101.93 (>CHPh), 97.80 (C-1), 82.77 (C-4), 71.75 (C-3), 69.09 (C-6), 67.11 (C-5), 66.86 (OCH$_2$ of Fmoc), 61.28 (C-2), 47.84 (OCH$_2$CH of Fmoc), 34.59 (CH of TDS), −1.83 (SiCH$_3$), −3.23 (SiCH$_3$). HR MS (m/z) calculated for $C_{36}H_{45}NO_7Si$ [M+Na]$^+$, 654.2857; found, 654.2962.

Dimethylthexylsilyl 4,6-O-benzylidene-2-deoxy-2-(9-fluorenylmethoxycarbonylamino)-3-O-levulinoyl-β-D-glucopyranoside (123). A solution of levulinic acid (234 mg, 2.02 mmol) and 1,3-dicyclohexylcarbodiimide (DCC) (499 mg, 2.42 mmol) in DCM (8 mL) was stirred at room temperature for 10 min, after which compound 122 (1.16 g, 1.84 mmol) and DMAP (12 mg, 0.1 mmol) were added and the stirring was continued for another 10 h. The insoluble materials were removed by filtration and the residue was washed with DCM (2×1 mL). The combined filtrates were concentrated in vacuo and the residue was purified by silica gel column chromatography (eluent: DCM/CH$_3$OH, 60/1, v/v) to give 123 as an amorphous solid (1.16 g, 86%). $R_f$=0.55 (hexane/ethyl acetate, 2/1, v/v); $[\alpha]^{25}_D$=−14.6° (c=1.0, CHCl$_3$); $^1$H NMR (300 MHz, CD$_3$COCD$_3$): δ 7.86-7.29 (m, 13H, aromatic), 6.62 (d, 1H, $J_{NH,2}$=9.6 Hz, NH), 5.63 (s, 1H, >CHPh), 5.31 (t, 1H, $J_{2,3}$=$J_{3,4}$=9.9 Hz, H-3), 5.09 (d, 1H, $J_{1,2}$=7.8 Hz, H-1), 4.32-4.19 (m, 4H, H-6a, OCH$_2$CH of Fmoc), 3.83 (t, 1H, $J_{5,6b}$=$J_{6a,6b}$=9.9 Hz, H-6b), 3.78 (t, 1H, $J_{3,4}$, $J_{4,5}$=9.3 Hz, H-4), 3.68 (m, 1H, H-2), 3.54 (m, 1H, H-5), 2.64 (t, 2H, J=6.9 Hz, CH$_2$ of Lev), 2.49 (t, 2H, J=6.9 Hz, CH$_2$ of Lev), 2.01 (s, 3H, CH$_3$ of Lev), 1.62 (m, 1H, CH of TDS), 0.86-0.84 (m, 12H, SiC(CH$_3$)$_2$CH(CH$_3$)$_2$), 0.17 (s, 6H, Si(CH$_3$)$_2$). $^{13}$C NMR (75 MHz, CDCl$_3$): 172.49 (C=O), 156.73 (C=O), 145.07-120.64 (m, aromatic), 101.67 (>CHPh), 97.55 (C-1), 79.80 (C-4), 72.64 (C-3), 69.03 (C-6), 67.11 (C-5, OCH$_2$ of Fmoc), 59.33 (C-2), 47.83 (OCH$_2$CH of Fmoc), 38.13 (CH$_2$ of Lev), 34.66 (CH of TDS), −1.85 (SiCH$_3$), −3.25 (SiCH$_3$). HR MS (m/z) calculated for $C_{41}H_{51}NO_9Si$[M+Na]$^+$, 752.3225; found 752.2672.

4,6-O-Benzylidene-2-deoxy-2-(9-fluorenylmethoxycarbonylamino)-3-O-levulinoyl-D-glucopyranosyl trichloroacetimidate (105). A mixture of Bu$_4$NF (1 M in THF, 5 mL) and acetic acid (500 µl) was added dropwise to a stirred solution of 123 (800 mg, 1.10 mmol) in THF (15 mL). After stirring the reaction mixture at room temperature for 24 h, it was diluted with DCM (20 mL) and then washed with saturated aqueous NaHCO$_3$ (2×30 mL) and brine (2×30 mL). The organic phase was dried (MgSO$_4$) and filtered. Next, the filtrate was concentrated in vacuo. The residue was purified by silica gel column chromatography (eluent: DCM/CH$_3$OH, 30/1, v/v) to afford a lactol as a pale yellow solid (606 mg, 94%). $R_f$=0.60 (hexane/ethyl acetate, 3/5, v/v). $^1$H NMR (300 MHz, CDCl$_3$): δ 7.88-7.31 (m, 13H, aromatic), 6.62 (d, 1H, $J_{NH,2}$=9.6 Hz, NH), 5.64 (s, 1H, >CHPh), 5.39 (t, 1H, $J_{2,3}$=$J_{3,4}$=9.9 Hz, H-3), 5.09 (bs, 1H, H-1), 4.43-4.17 (m, 4H, H-6a, OCH$_2$CH of Fmoc), 4.13-3.97 (m, 2H, H-2, H-5), 3.81 (t, 1H, $J_{5,6b}$=$J_{6a,6b}$=9.9 Hz, H-6b), 3.80 (t, 1H, $J_{3,4}$=$J_{4,5}$=9.6 Hz, H-4), 2.65 (t, 2H, J=6.6 Hz, CH$_2$ of Lev), 2.50 (t, 2H, J=6.6 Hz, CH$_2$ of Lev), 2.00 (s, 3H, CH$_3$ of Lev). HR MS (m/z) calculated for $C_{33}H_{33}NO_9$[M+Na]$^+$, 610.2048; found, 610.2293. The resulting lactol (606 mg, 1.03 mmol) was dissolved in a mixture of trichloroacetonitrile (2.0 mL) and DCM (10 mL) and then Cs$_2$CO$_3$ (163 mg, 0.50 mmol) was added. The reaction mixture was stirred at room temperature for 1 h, after which it was diluted with DCM (20 mL) and then washed with saturated aqueous NaHCO$_3$ (2×30 mL) and brine (2×30 mL). The organic phase was dried (Na$_2$SO$_4$) and filtered. Next, the filtrate was concentrated in vacuo. The residue was purified by silica gel column chromatography (eluent: hexane/ethyl acetate, 4/3, v/v) to yield 105 as a pale yellow solid (700 mg, 93%). $R_f$=0.45 (hexane/ethyl acetate, 3/2, v/v).

Biological Experiments

Cell maintenance. Mono Mac 6 (MM6) cells, provided by Dr. H. W. L. Ziegler-Heitbrock (Institute for Inhalationbiology, Munich, Germany), were cultured in RPMI 1640 medium with L-glutamine (BioWhittaker) supplemented with penicillin (100 u mL$^{-1}$)/streptomycin (100 µg mL$^{-1}$; Mediatech, OPI supplement (1%; Sigma; containing oxaloacetate, pyruvate and bovine insulin) and fetal calf serum (FCS; 10%; HyClone). New batches of frozen cell stock were grown up every 2 months and growth morphology evaluated. Before each experiment, MM6 cells were incubated with calcitriol (10 ng mL$^{-1}$; Sigma) for 2 days to differentiate into macrophage like cells. RAW 264.7 γNO(−) cells, derived from the RAW 264.7 mouse monocyte/macrophage cell line, were obtained from ATCC. The cells were maintained in RPMI 1640 medium (ATCC) with L-glutamine (2 mM), adjusted to contain sodium bicarbonate (1.5 g L$^{-1}$), glucose (4.5 g L$^{-1}$), HEPES (10 mM) and sodium pyruvate (1.0 mM) and supplemented with penicillin (100 u mL$^{-1}$)/streptomycin (100 µg mL$^{-1}$) and FBS (10%). Human embryonic kidney (HEK) 293T cells were grown in Dulbecco's modified Eagle's medium (ATCC) with L-glutamine (4 mM), glucose (4.5 g L$^{-1}$) and sodium bicarbonate (1.5 g L$^{-1}$) supplemented with penicillin (100 u mL$^{-1}$)/streptomycin (100 µg mL$^{-1}$), Normocin (100 µg mL$^{-1}$; InvivoGen) and FBS (10%). Stably transfected HEK 293T cells with human and murine TLR4/MD2/CD14 and human and murine TLR2 were obtained from InvivoGen and grown in the same growth medium as for HEK 293T cells supplemented with the appropriate selective agents HygroGold (50 µg mL$^{-1}$; InvivoGen) and blasticidin (10 µg mL$^{-1}$; InvivoGen). All cells were maintained in a humid 5% $CO_2$ atmosphere at 37° C.

Reagents for biological experiments. E. coli 055:B5 LPS was obtained from List Biologicals and Pam$_3$CysSK$_4$ was obtained from Calbiochem. All data presented in this study were generated using the same batch of E. coli 055:B5 LPS. Synthetic compounds 103 and 104 were reconstituted in PBS with dry THF (10%) and stored at −80° C.

Cytokine induction and ELISAs. On the day of the exposure assay differentiated MM6 cells were harvested by centrifugation and suspended (10$^6$ cells mL$^{-1}$) in tissue culture tubes and RAW 264.7 γNO(−) cells were plated as 2×10$^5$ cells/well in 96-well tissue culture plates (Nunc). Cells were then incubated with different combinations of stimuli for 5.5 hours. Culture supernatants were then collected and stored frozen (−80° C.) until assayed for cytokine production. All cytokine ELISAs were performed in 96-well MaxiSorp plates (Nalge Nunc International). Concentrations of human TNF-α protein in culture supernatants were determined by a solid phase sandwich ELISA. Plates were coated with purified mouse anti-human TNF-α antibody (Pharmingen). TNF-α in standards and samples was allowed to bind to the immobilized antibody. Biotinylated mouse anti-human TNF-α antibody (Pharmingen) was then added. Next, avidin-horseradish peroxidase conjugate (Pharmingen) and ABTS peroxidase substrate (Kirkegaard & Perry Laboratories) were added. After the reaction was stopped by adding peroxidase stop solution (Kirkegaard & Perry Laboratories), the absorbance was measured at 405 nm using a microplate reader (BMG Labtech). Cytokine DuoSet ELISA Development Kits (R&D Systems) were used for the cytokine quantification of mouse TNF-α, mouse IL-6, mouse IP-10 and mouse IL-1β according to the manufacturer's instructions. The absorbance was measured at 450 nm with wavelength correction set to 540 nm. Concentrations of mouse IFN-β in culture supernatants were determined as follows. Plates were coated with rabbit polyclonal antibody against mouse IFN-β (PBL Biomedical Laboratories). IFN-β in standards and samples was allowed to bind to the immobilized antibody. Rat anti-mouse IFN-β antibody (USBiological) was then added. Next, horseradish peroxidase (HRP) conjugated goat anti-rat IgG (H+L) antibody (Pierce) and a chromogenic substrate for HRP 3,3',5,5'-tetramethylbenzidine (TMB; Pierce) were added. After the reaction was stopped, the absorbance was measured at 450 nm with wavelength correction set to 540 nm. All cytokine values are presented as the means±SD of triplicate measurements, with each experiment being repeated three times.

Transfection and NF-κB activation assay. The day before transfection, HEK 293T wild type cells and HEK 293T cells stably transfected with human and murine TLR4/MD2/CD14 and human and murine TLR2 were plated in 96-well tissue culture plates (16,000 cells/well). The next day, cells were transiently transfected using PolyFect Transfection Reagent (Qiagen) with expression plasmids pELAM-Luc (NF-κB-dependent firefly luciferase reporter plasmid, 50 ng/well) (Chow et al., *J. Biol. Chem.*, 1999, 274, 10689-10692) and pRL-TK (*Renilla* luciferase control reporter vector, 1 ng/well; Promega) as an internal control to normalize experimental variations. The empty vector pcDNA3 (Invitrogen) was used as a control and to normalize the DNA concentration for all of the transfection reactions (total DNA 70 ng/well). Forty-four h post-transfection, cells were exposed to the stimuli in the presence of FCS to provide sCD14 for 4 h, after which cell extracts were prepared. The luciferase activity was measured using the Dual-Luciferase Reporter Assay System (Promega) according to the manufacturer's instructions and a combination luminometer/fluorometer microplate reader (BMG Labtech). Expression of the firefly luciferase reporter gene was normalized for transfection efficiency with expression of *Renilla* luciferase. The data are reported as the means±SD of triplicate treatments. The transfection experiments were repeated at least twice.

Data analysis. Concentration-response and inhibition data were analyzed using nonlinear least-squares curve fitting in Prism (GraphPad Software, Inc.). Concentration-response data were fit with the following four parameter logistic equation: $Y=E_{max}/(1+(EC_{50}/X)^{Hill\ slope})$, where Y is the cytokine response, X is logarithm of the concentration of the stimulus, $E_{max}$ is the maximum response and $EC_{50}$ is the concentration of the stimulus producing 50% stimulation. Inhibition data were fit with the following logistic equation: $Y=Bottom+(Top-Bottom)/(1+10^{(X-Log\ IC50)})$ where Y is the cytokine response, X is the logarithm of the concentration of the inhibitor and $IC_{50}$ is the concentration of the inhibitor that reduces the response by half.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. An isolated, synthetic lipid A derivative selected from the group consisting of compounds:

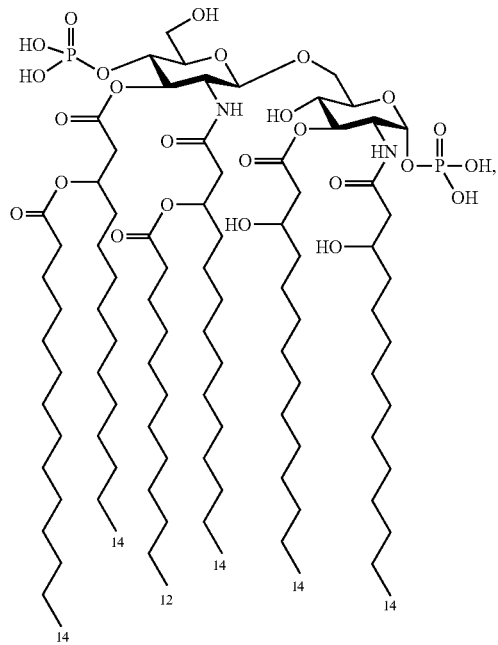

1

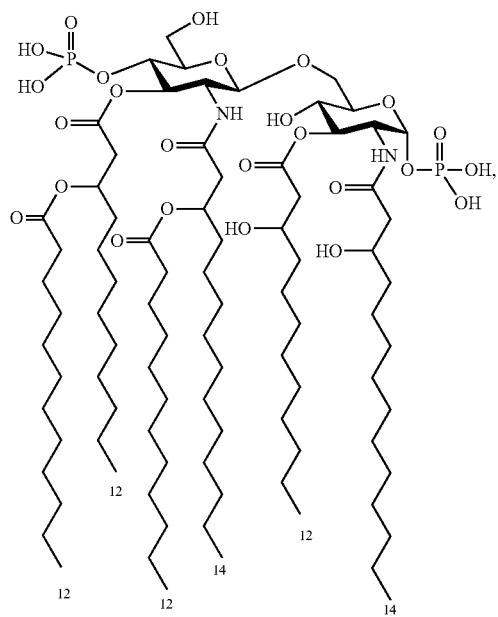

2

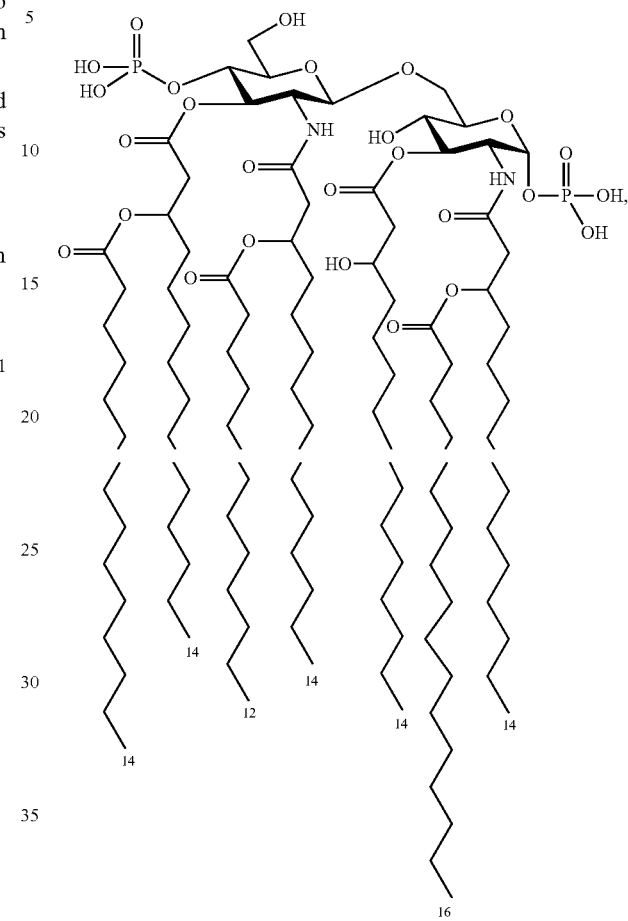

3

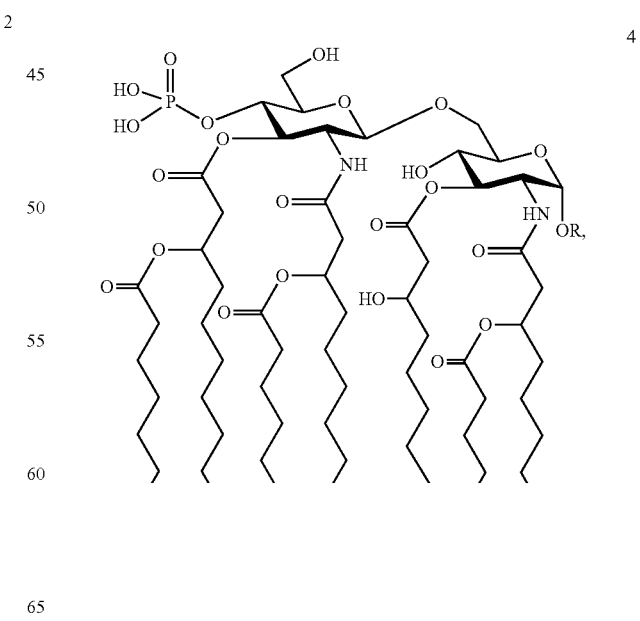

4

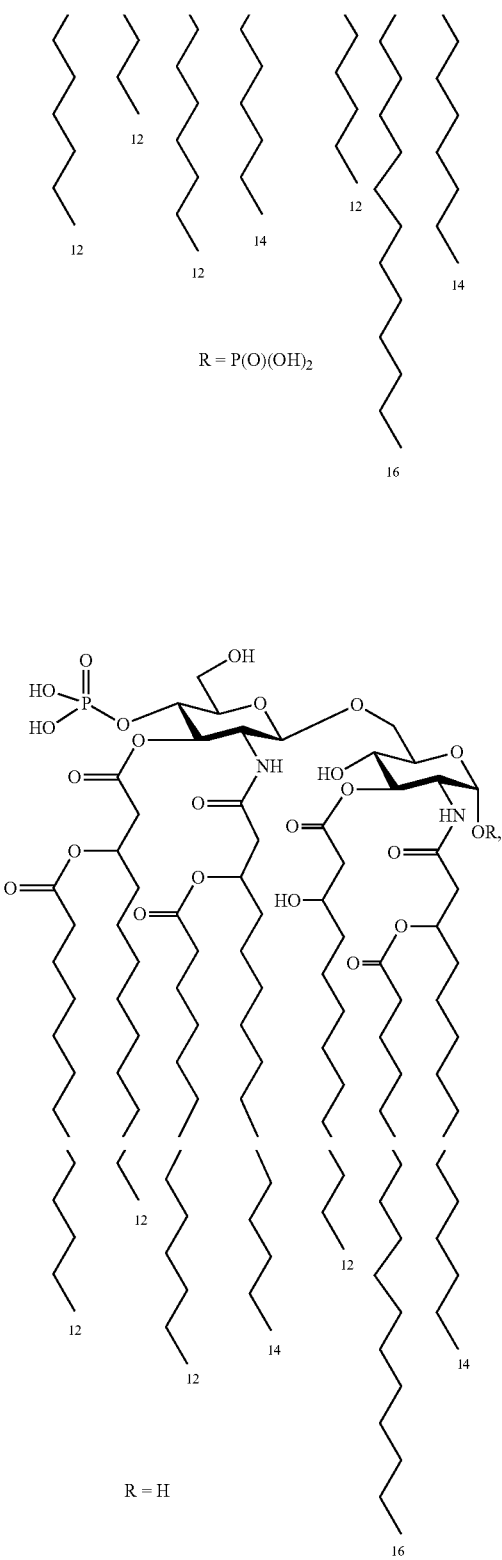
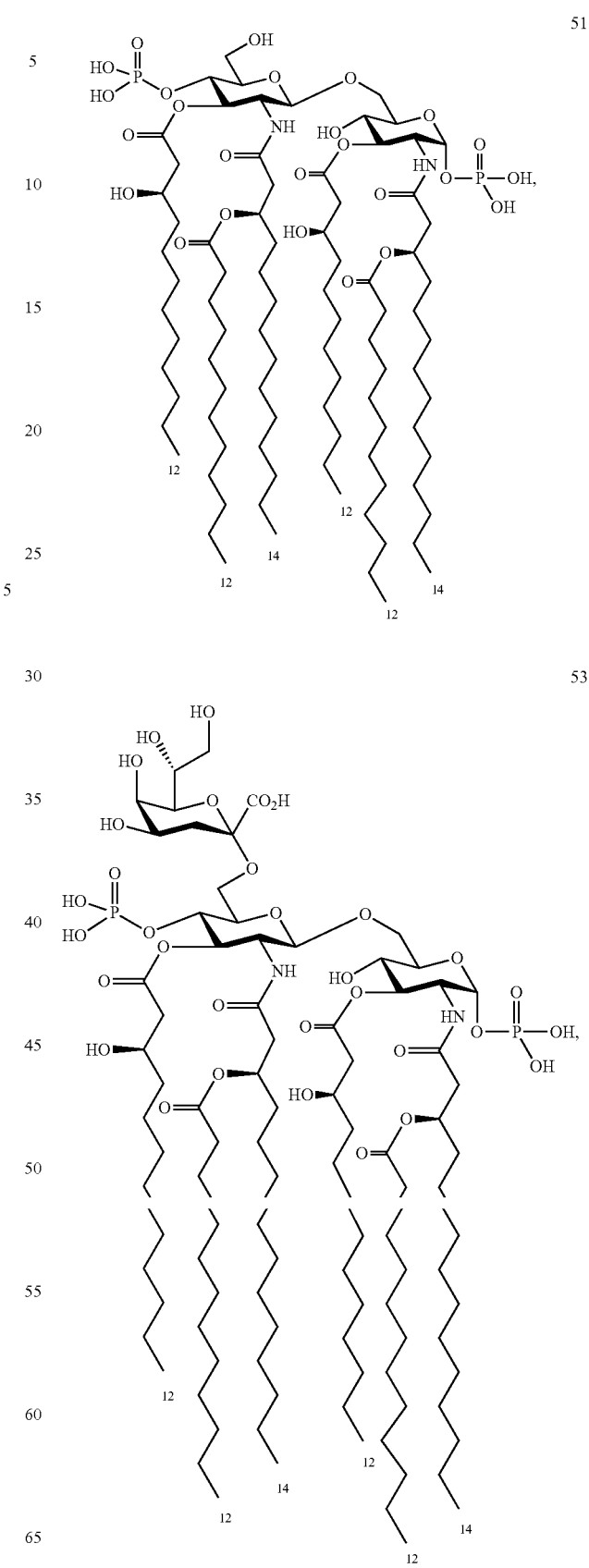

109
-continued
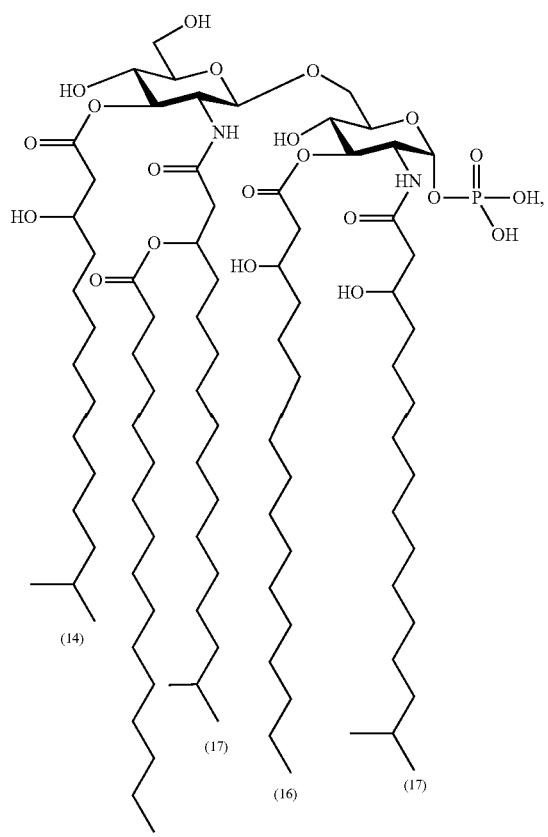
101
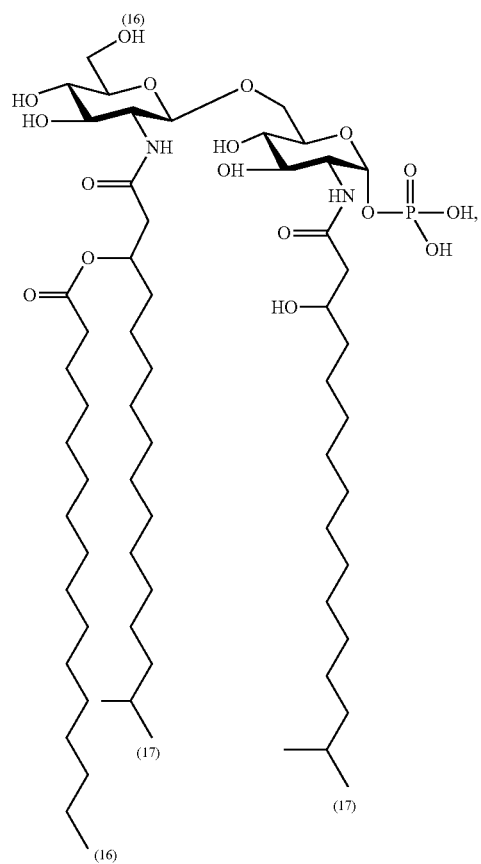
102
110
-continued
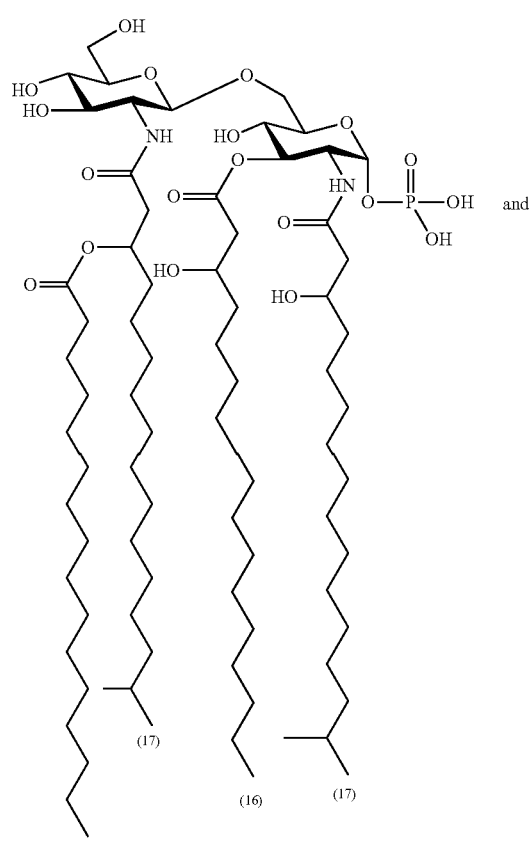 and
103
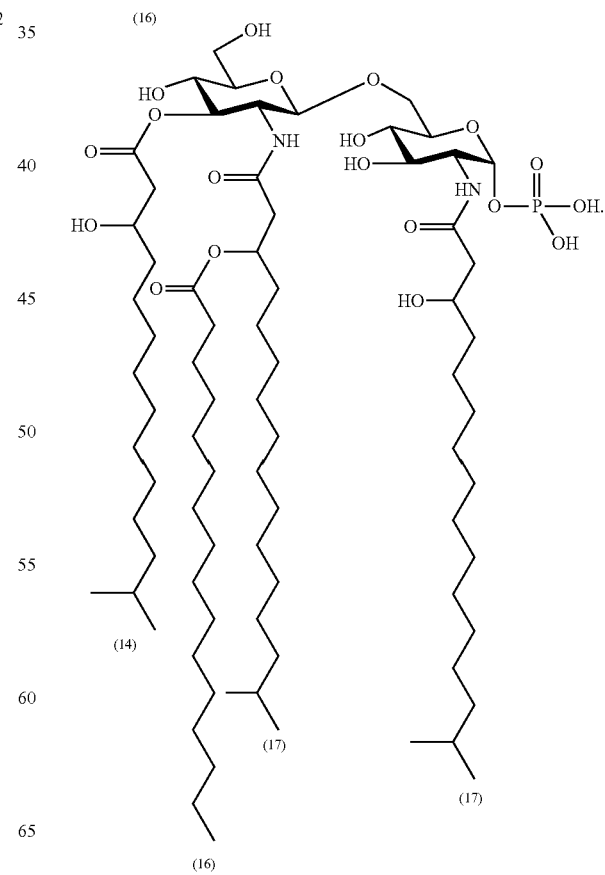
104

2. A pharmaceutical composition comprising:
an effective amount of a lipid A derivative of claim 1; and
a pharmaceutically acceptable carrier.

3. The pharmaceutical composition of claim 2 comprising:
a first component comprising an effective amount of an active agent;
a second component comprising a lipid A derivative of claim 1, wherein the lipid A derivative functions as an adjuvant; and
a pharmaceutically acceptable carrier.

4. The pharmaceutical composition of claim 3 wherein the active agent comprises an antigen or immunogen.

* * * * *